US012377219B2

(12) United States Patent
Kamen et al.

(10) Patent No.: US 12,377,219 B2
(45) Date of Patent: Aug. 5, 2025

(54) MEDICAL AGENT DISPENSING APPARATUSES, SYSTEMS, AND METHODS

(71) Applicant: DEKA Products Limited Partnership, Manchester, NH (US)

(72) Inventors: Dean Kamen, Bedford, NH (US); Richard J. Lanigan, Concord, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 784 days.

(21) Appl. No.: 17/566,818

(22) Filed: Dec. 31, 2021

(65) Prior Publication Data

US 2022/0273877 A1 Sep. 1, 2022

Related U.S. Application Data

(60) Provisional application No. 63/154,931, filed on Mar. 1, 2021.

(51) Int. Cl.
*A61M 5/24* (2006.01)

(52) U.S. Cl.
CPC ........ *A61M 5/2425* (2013.01); *A61M 5/2455* (2013.01); *A61M 2005/247* (2013.01);
(Continued)

(58) Field of Classification Search
CPC ......... A61M 2005/14252; A61M 2005/14256; A61M 2005/14272; A61M 2005/14506;
(Continued)

(56) References Cited

U.S. PATENT DOCUMENTS

| 3,048,171 A | 8/1962 | Grau |
| 3,539,455 A | 11/1970 | Clark, Jr. |

(Continued)

FOREIGN PATENT DOCUMENTS

| EP | 1301236 B1 | 10/2004 |
| EP | 1187653 B1 | 3/2010 |

(Continued)

OTHER PUBLICATIONS

International Search Report and Written Opinion dated Jun. 23, 2022 received in International patent application PCT/US2021/065818 from European Patent Office as International Searching Authority, European Patent Office, P.B. 5818 Patentlaan 2 NL—2280 HV Rijswijk (17pgs).

(Continued)

*Primary Examiner* — Nathan R Price
*Assistant Examiner* — John A Doubrava
(74) *Attorney, Agent, or Firm* — Kevin D. Mandro; Toohey Law Group, LLC

(57) ABSTRACT

An example agent administration device may comprise a housing. The device may further comprise a sharp assembly including a delivery sharp. The sharp assembly may be reciprocally displaceable along a guide channel of the housing. The device may further comprise an access port in fluid communication with the delivery sharp. The device may further comprise an actuation assembly configured drive the sharp assembly, via urging of a single bias member, from a storage state in which the delivery sharp is within the housing, through a first extended position in which the delivery sharp extends a maximum distance from the housing and to a partially retracted position in which the delivery sharp extends a lesser distance from the housing.

25 Claims, 63 Drawing Sheets

(52) U.S. Cl.
CPC .............. *A61M 2005/2477* (2013.01); *A61M 2202/0007* (2013.01)

(58) Field of Classification Search
CPC .... A61M 2005/247; A61M 2005/2477; A61M 2005/1585; A61M 2005/1586; A61M 2005/1587; A61M 2202/0007; A61M 39/04; A61M 2039/0276; A61M 5/14248; A61M 5/1456; A61M 5/148; A61M 5/2425; A61M 5/2455; A61M 5/1626; A61M 5/3298; A61M 5/46
See application file for complete search history.

(56) References Cited

U.S. PATENT DOCUMENTS

| | | | |
|---|---|---|---|
| 3,731,681 | A | 5/1973 | Blackshear et al. |
| 3,964,482 | A | 6/1976 | Gerstel et al. |
| 4,552,561 | A | 11/1985 | Eckenhoff et al. |
| 4,668,231 | A | 5/1987 | De Vries et al. |
| 4,772,263 | A | 9/1988 | Dorman et al. |
| 4,969,873 | A | 11/1990 | Steinbach et al. |
| 5,045,064 | A | 9/1991 | Idriss |
| 5,250,023 | A | 10/1993 | Lee et al. |
| 5,390,671 | A | 2/1995 | Lord et al. |
| 5,591,123 | A | 1/1997 | Sibalis et al. |
| 5,879,326 | A | 3/1999 | Godshall et al. |
| 5,957,895 | A | 9/1999 | Sage et al. |
| 5,983,136 | A | 11/1999 | Kamen |
| 6,132,755 | A | 10/2000 | Eicher et al. |
| 6,186,982 | B1 | 2/2001 | Gross et al. |
| 6,190,367 | B1 | 2/2001 | Hall |
| 6,280,148 | B1 | 8/2001 | Zengerle et al. |
| 6,334,856 | B1 | 1/2002 | Allen et al. |
| 6,358,239 | B1 | 3/2002 | Rake et al. |
| 6,360,888 | B1 | 3/2002 | McIvor et al. |
| 6,406,276 | B1 | 6/2002 | Normand et al. |
| 6,471,903 | B2 | 10/2002 | Sherman et al. |
| 6,533,949 | B1 | 3/2003 | Yeshurun et al. |
| 6,537,242 | B1 | 3/2003 | Palmer |
| 6,537,249 | B2 | 3/2003 | Kriesell et al. |
| 6,558,361 | B1 | 5/2003 | Yeshurun |
| 6,603,987 | B2 | 8/2003 | Whitson |
| 6,611,707 | B1 | 8/2003 | Prausnitz et al. |
| 6,656,147 | B1 | 12/2003 | Gertsek et al. |
| 6,743,211 | B1 | 6/2004 | Prausnitz et al. |
| 6,924,087 | B2 | 8/2005 | Yeshurun et al. |
| 7,025,774 | B2 | 4/2006 | Freeman et al. |
| 7,250,037 | B2* | 7/2007 | Shermer ........... A61M 5/14248 604/134 |
| 7,285,113 | B2 | 10/2007 | Yeshurun |
| 7,344,499 | B1 | 3/2008 | Prausnitz et al. |
| 7,588,552 | B2 | 9/2009 | Yeshurun et al. |
| 7,648,484 | B2 | 1/2010 | Yeshurun et al. |
| 7,985,203 | B2 | 7/2011 | Haueter et al. |
| 7,998,119 | B2 | 8/2011 | Yeshurun et al. |
| 8,007,466 | B2 | 8/2011 | Yeshurun et al. |
| 8,070,745 | B2 | 12/2011 | Gibson et al. |
| 8,162,901 | B2 | 4/2012 | Gonnelli et al. |
| 8,361,037 | B2 | 1/2013 | Gonnelli |
| 8,512,287 | B2 | 8/2013 | Cindrich et al. |
| 8,597,257 | B2 | 12/2013 | Modi |
| 8,684,968 | B2 | 4/2014 | Genosar |
| 8,696,619 | B2 | 4/2014 | Schnall |
| 8,784,383 | B2* | 7/2014 | Cole .................. A61M 5/158 604/164.12 |
| 8,795,230 | B2 | 8/2014 | Schoonmaker et al. |
| 8,858,498 | B2* | 10/2014 | West ................ A61M 5/3257 604/117 |
| 8,920,375 | B2 | 12/2014 | Gonnelli |
| 9,011,392 | B2 | 4/2015 | McAllister et al. |
| 9,017,289 | B2 | 4/2015 | Backes |
| 9,174,006 | B2 | 11/2015 | Vosseler et al. |
| 9,302,903 | B2 | 4/2016 | Park et al. |
| 9,375,529 | B2 | 6/2016 | Searle et al. |
| 9,415,198 | B2 | 8/2016 | McAllister |
| 9,445,762 | B2 | 9/2016 | Sullivan et al. |
| 9,693,894 | B2 | 7/2017 | Tai et al. |
| 10,350,289 | B2 | 7/2019 | Meyer et al. |
| 10,398,856 | B2 | 9/2019 | Clemenz et al. |
| 10,463,806 | B2 | 11/2019 | Hoffmann et al. |
| 10,549,079 | B2* | 2/2020 | Burton ............. A61M 37/0015 |
| 10,828,429 | B2 | 11/2020 | Admati et al. |
| 10,967,117 | B2 | 4/2021 | Lanigan |
| 11,964,121 | B2* | 4/2024 | Nawana ........... A61M 5/14248 |
| 11,986,624 | B2* | 5/2024 | McCullough ..... A61M 5/14248 |
| 2001/0053891 | A1 | 12/2001 | Ackley |
| 2002/0045907 | A1 | 4/2002 | Sherman et al. |
| 2003/0135166 | A1 | 7/2003 | Gonnelli |
| 2004/0098014 | A1 | 5/2004 | Flugeman et al. |
| 2005/0137536 | A1 | 6/2005 | Gonnelli |
| 2006/0051404 | A1 | 3/2006 | Yeshurun et al. |
| 2008/0015516 | A1 | 1/2008 | Lavi |
| 2008/0015522 | A1 | 1/2008 | Yeshurun et al. |
| 2008/0091226 | A1 | 4/2008 | Yeshurun et al. |
| 2008/0183144 | A1 | 7/2008 | Trautman et al. |
| 2009/0011158 | A1 | 1/2009 | Yeshurun |
| 2009/0012494 | A1 | 1/2009 | Yeshurun et al. |
| 2009/0048557 | A1 | 2/2009 | Yeshurun et al. |
| 2009/0054842 | A1 | 2/2009 | Yeshurun et al. |
| 2009/0099522 | A1 | 4/2009 | Kamen et al. |
| 2009/0157094 | A1 | 6/2009 | Yeshurun et al. |
| 2009/0198189 | A1 | 8/2009 | Simons et al. |
| 2009/0247953 | A1 | 10/2009 | Yeshurun et al. |
| 2009/0259176 | A1 | 10/2009 | Yairi |
| 2010/0179473 | A1 | 7/2010 | Genosar |
| 2010/0224590 | A1 | 9/2010 | Yeshurun et al. |
| 2011/0046557 | A1 | 2/2011 | Lee et al. |
| 2011/0054390 | A1* | 3/2011 | Searle ............... A61M 5/14248 604/151 |
| 2011/0213335 | A1 | 9/2011 | Burton et al. |
| 2011/0238038 | A1 | 9/2011 | Sefi et al. |
| 2011/0282298 | A1 | 11/2011 | Agian et al. |
| 2013/0041318 | A1* | 2/2013 | Vosseler ............ A61M 5/3293 604/117 |
| 2013/0110043 | A1 | 5/2013 | Levin |
| 2013/0110053 | A1 | 5/2013 | Yoshino et al. |
| 2013/0197438 | A1 | 8/2013 | Yang et al. |
| 2013/0296791 | A1 | 11/2013 | Segev et al. |
| 2014/0296708 | A1 | 10/2014 | Flaherty et al. |
| 2014/0350514 | A1 | 11/2014 | Levin |
| 2015/0011976 | A1 | 1/2015 | Vouillamoz et al. |
| 2015/0038911 | A1 | 2/2015 | Levin et al. |
| 2015/0151097 | A1 | 6/2015 | Carnahan et al. |
| 2016/0144137 | A1 | 5/2016 | Shapiro |
| 2016/0158514 | A1 | 6/2016 | Stoeber et al. |
| 2016/0184571 | A1 | 6/2016 | Admati |
| 2016/0199581 | A1 | 7/2016 | Cachemaille et al. |
| 2016/0296715 | A1* | 10/2016 | Clemenz ................ A61M 5/46 |
| 2016/0354589 | A1 | 12/2016 | Katsunori et al. |
| 2017/0043148 | A1 | 2/2017 | Baker et al. |
| 2017/0304604 | A1 | 10/2017 | Kato |
| 2018/0185623 | A1 | 7/2018 | Lesher et al. |
| 2018/0361132 | A1 | 12/2018 | Katsunori et al. |
| 2019/0111218 | A1 | 4/2019 | Beyers et al. |
| 2019/0160273 | A1 | 5/2019 | Baker et al. |
| 2019/0269895 | A1 | 9/2019 | Nguyen et al. |
| 2020/0078575 | A1 | 3/2020 | Mansoor et al. |
| 2021/0023354 | A1 | 1/2021 | Mansoor et al. |
| 2021/0045666 | A1* | 2/2021 | Simpson ........... A61B 5/14735 |
| 2021/0308439 | A1 | 10/2021 | Admati et al. |
| 2021/0330951 | A1 | 10/2021 | Kim |
| 2022/0273923 | A1 | 9/2022 | Zeira et al. |
| 2022/0273924 | A1 | 9/2022 | Kamen et al. |
| 2022/0273925 | A1 | 9/2022 | Zeira et al. |
| 2023/0009541 | A1* | 1/2023 | Agard ................. A61M 5/158 |
| 2023/0233824 | A1 | 7/2023 | Nawana et al. |
| 2023/0264006 | A1 | 8/2023 | Kamen et al. |
| 2023/0277759 | A1 | 9/2023 | Kamen et al. |
| 2024/0024566 | A1 | 1/2024 | Kamen et al. |
| 2024/0390661 | A1 | 11/2024 | Zeira et al. |
| 2024/0390662 | A1 | 11/2024 | Batchelder |

(56) References Cited

U.S. PATENT DOCUMENTS

FOREIGN PATENT DOCUMENTS

| | | | |
|---|---|---|---|
| EP | 2459267 B1 | 12/2017 | |
| EP | 3639873 A1 | 4/2020 | |
| JP | 2014 124434 A | 7/2014 | |
| JP | JP 2014 124434 A | 7/2014 | |
| WO | WO 2011/027586 A1 | 3/2011 | |
| WO | WO 2011/146166 A1 | 11/2011 | |
| WO | WO2020023804 A1 | 1/2020 | |
| WO | WO-2020097552 A1 * | 5/2020 | ........ A61M 25/0113 |
| WO | WO 2021/121589 A1 | 6/2021 | |
| WO | WO 2022/149833 A1 | 7/2022 | |

OTHER PUBLICATIONS

*6 VIPS Phase 1 Technical Note Compact Prefilled Auto-Disable Devices (CPADs)*. [online] Vaccine Innovation Prioritisation Strategy Vaccine Alliance Project, pp. 1-30. https://www.gavi.org/news/document-library/6-vips-phase-i-technical-note-compact-prefilled-auto-disable-devices-pdf (Retrieved May 6, 2021).
*Drug Delivery—Recent Developments in Microneedle Technology for Transdermal Drug Delivery & Vaccination* [online] Drug Development & Delivery, pp. 1-7. Jul./Aug. 2012. https://drug-dev.com/recent-developments-in-microneedle-technology-for-transdermal-drug-delivery-vaccination/.
*Intracutaneous Microneedle System*, [online] Zosano Pharma, pp. 1-2. https://www.zosanopharma.com/technology/ (Retrieved Jul. 15, 2021).
*Microneedle Coronavirus Vaccine Triggers Immune Response in Mice*, [online] NIH Research Matters, pp. 1-4. Apr. 14, 2020. https://www.nih.gov/news-events/nih-research-matters/microneedle-coronavirus-vaccine-triggers-immune-response-mice.
*Mimix Therapies* [online] Vaxess Technologies, pp. 1-9. https://www.vaxess.com/mimix-therapies (Retrieved Jul. 14, 2021).
*Solving the Challenges of Logistics, Infrastructure, and Manufacturing Capacity for COVID-19 Vaccines* [online] Vaxess Technologies pp. 1. https://www.vaxess.com/s/VAXESS-MIMIX-COVID-One-Page-12112020.pdf (Retrieved Jul. 14, 2021).
U. S. Food and Drug Administration. *FYs 2013-2017 GDUFA Science and Research Report: Transdermal Drug Products*. [online], pp. 1-15, https://www.fda.gov/industry/generic-drug-user-fee-amendments/fys-2013-2017-gdufa-science-and-research-report-transdermal-drugs-products. (Retrieved May 6, 2021).
*VAX-ID Accurate Intradermal Injection* [online], IDEVAX, pp. 1-2, https://idevax.com/wp-content/uploads/2021/02/Vax-ID_SpecSheet_version2021_01B_EN-gecomprimeerd.pdf (Retrieved May 7, 2021).
Bae, Won-Gyu, et al. "Snake Fang-Inspired Stamping Patch for Transdermal Delivery of Liquid Formulations." [online] *Science Translational Medicine*, vol. 11, No. 503, Jul. 31, 2019, pp. 1-12, doi:10.1126/scitranslmed.aaw3329.
Boopathy, Archana V., et al. "Enhancing Humoral Immunity via Sustained-Release Implantable Microneedle Patch Vaccination." [online] *Proceedings of the National Academy of Sciences of the United States of America*, vol. 116, No. 33, Jul. 29, 2019, pp. 16473-16478, doi: 10.1073/pnas.1902179116.
Briggaman, R. A., and C. E. Wheeler. "The Epidermal Dermal Junction." [online] *Journal of Investigative Dermatology*, vol. 65, No. 1, Jul. 1975, pp. 71-84, doi:10.1111/1523-1747.ep12598050.
Carter, Darrick, et al. "The Adjuvant GLA-AF Enhances Human Intradermal Vaccine Responses." [online] *Science Advances*, vol. 4, No. 9, Sep. 12, 2018, pp. 1-9, doi:10.1126/sciadv.aas9930.
Chanda, Arnab. "Biomechanical Modeling of Human Skin Tissue Surrogates." [online] *Biomimetics*, vol. 3, No. 3, Jul. 23, 2018, pp. 1-12, doi:10.3390/biomimetics3030018.
Chin, Sae Hoon, et al. "Selective Dermal Rejuvenation Using Intradermal Injection of Carbon Dioxide and Hyaluronic Acid for Facial Wrinkles." Annals of Plastic Surgery, vol. 70, No. 6, 2013, pp. 628-631, doi:10.1097/SAP.0b013e31823fa958.

Criscuolo, E., et al. "Alternative Methods of Vaccine Delivery: An Overview of Edible and Intradermal Vaccines." [online] *Journal of Immunology Research*, vol. 2019, Mar. 4, 2019, doi:10.1155/2019/8303648.
Das, Rakesh, et al. "Biomechanical Evaluation of Wasp and Honeybee Stingers." [online] *Nature: Scientific Reports*, vol. 8, Springer US, Oct. 8, 2018, pp. 1-13, doi:10.1038/s41598-018-33386-y.
Gallagher, A. J., et al. "Dynamic Tensile Properties of Human Skin." [online] *IRCOBI Conference Proceedings—International Research Council on the Biomechanics of Injury 2012 Sep. 12-14, 2012*, pp. 494-502. http://www.ircobi.org/wordpress/downloads/irc12/pdf_files/59.pdf (Retrieved May 6, 2021).
Gardeniers, Han J. G. E., et al. "Silicon Micromachined Hollow Microneedles for Transdermal Liquid Transport." [online] *Journal of Microelectromechanical Systems*, vol. 12, No. 6, Dec. 2003, pp. 855-862, doi:10.1109/JMEMS.2003.820293.
Hansen, Kris, et al. *Microneedle Enabled Intradermal Delivery of Biologics*. [Online] 3M Drug Delivery Systems, https://multimedia.3m.com/mws/media/1005621O/microneedle-enabled-intradermal-delivery-of-biologics.pdf (Retrieved Jul. 23, 2021).
Henry, Sebastien, et al. "Microfabricated Microneedles: A Novel Approach to Transdermal Drug Delivery." [online] *Journal of Pharmaceutical Sciences*, vol. 87, No. 8 Aug. 1, 1998, Abstract Only, Doi:10.1021/js980042+.
Hickling, JK, et al. "Intradermal Delivery of Vaccines: Potential Benefits and Current Challenges." [online] Bulletin of the World Health Organization, vol. 89, No. 3, Mar. 2011, pp. 221-226, doi:10.2471/BLT.10.079426.
Hickling, Julian, and Rebecca Jones. *Intradermal Delivery of Vaccines: A Review of the Literature and the Potential for Development for Use in Low- and Middle-Income Countries*. [online] Aug. 27, 2009. https://path.azureedge.net/media/documents/TS_opt_idd_review.pdf.
Hohlfelder, Robert J., et al. "Adhesion of Benzocyclobutene-Passivated Silicon in Epoxy Layered Structures." [online] *Journal of Materials Research*, vol. 16, No. 1, Jan. 2001, pp. 243-255, doi:10.1557/JMR.2001.0037.
Jain, Sunil M., et al. "Evaluation of Skin and Subcutaneous Tissue Thickness at Insulin Injection Sites in Indian, Insulin Naïve, Type-2 Diabetic Adult Population." [online] *Indian Journal of Endocrinology and Metabolism*, vol. 17, No. 5, Sep.-Oct. 2013, p. 864-870, doi:10.4103/2230-8210.117249.
Jarrahian, Courtney, et al. "Clinical Performance and Safety of the ID Adapter, a Prototype Intradermal Delivery Technology for Vaccines, Drugs, and Diagnostic Tests." [online] *Procedia in Vaccinology*, vol. 6, Available online May 2, 2012, pp. 125-133, doi:10.1016/j.provac.2012.04.017.
Jeewandara, Thamarasee. "Glassy Carbon Microneedles: A new transdermal drug delivery device" [online] Phys.org Science News, Jan. 3, 2019, https://phys.org/news/2019-01-glassy-carbon-microneedles-transdermal-drug.html.
Jeong, Hye-Rin et al. "Considerations in the Use of Microneedles: Pain, Convenience, Anxiety, and Safety" [online] *Journal of Drug Targeting*, vol. 25, No. 1, Published Online Jun. 30, 2016. Abstract Only, doi:10.1080/1061186X.2016.1200589.
Khanna, Maneesh et al. "Painless Intradermal Delivery of Insulin: The Novel Clicksoft Microinjection Device" [online] Drug Delivery Technology, vol. 9, No. 2, Feb. 2009, https://pkasofttouch.com/wp-content/uploads/2020/07/AdvancedDelivery-DDT-Feb09-Rd4-Finalweb.pdf.
Kim, Y. C., et al. "Delivery Systems for Intradermal Vaccination." [online] *Current Topics in Microbiology and Immunology*, vol. 351, Apr. 7, 2011, pp. 77-112, doi:https://doi.org/10.1007/82_2011_123.
Kram, Tim, et al. *High Barrier Multilayer Blow-Fill-Seal Containers : A Comparison of Four Different Analytical Methods for Oxygen Permeation*. [online] Rommelag, https://www.pharmaceuticalonline.com/doc/high-barrier-multilayer-blow-fill-seal-containers-a-comparison-of-four-different-analytical-methods-for-oxygen-permeation-0001 (Retrieved May 6, 2021).
Larrañeta, Eneko, et al. "Microneedle Arrays as Transdermal and Intradermal Drug Delivery Systems: Materials Science, Manufacture and Commercial Development." [online] *Materials Science*

(56) References Cited

OTHER PUBLICATIONS

*and Engineering R: Reports*, vol. 104, Available online Apr. 13, 2016, pp. 1-32, doi:10.1016/j.mser.2016.03.001.
Lee, Jeong Woo, and Mark R. Prausnitz. "Drug Delivery Using Microneedle Patches: Not Just for Skin." [online] *Expert Opinion on Drug Delivery*, vol. 15, No. 6, Taylor & Francis, May 7, 2018, pp. 541-543, doi:10.1080/17425247.2018.1471059.
Levin, Yotam, et al. "Intradermal Vaccination Using the Novel Microneedle Device MicronJet600: Past, Present, and Future." [online] *Human Vaccines and Immunotherapeutics*, vol. 11, No. 4, Published online May 1, 2015, pp. 991-997, doi:10.1080/21645515.2015.1010871.
Li, Yan, et al. "Fabrication of Sharp Silicon Hollow Microneedles by Deep-Reactive Ion Etching towards Minimally Invasive Diagnostics." [online] *Microsystems and Nanoengineering*, vol. 5, Aug. 26, 2019, pp. 1-11, doi:10.1038/s41378-019-0077-y.
Maiti, Raman, et al. "In Vivo Measurement of Skin Surface Strain and Sub-Surface Layer Deformation Induced by Natural Tissue Stretching." [online] *Journal of the Mechanical Behavior of Biomedical Materials*, vol. 62, Available online Jun. 5, 2016, pp. 556-569, doi:10.1016/j.jmbbm.2016.05.035.
Markarian, Jennifer. "Manufacturing Microneedle Array Patches for Vaccine Delivery." [online] *Pharmaceutical Technology*, vol. 44, No. 5, May 2, 2020, pp. 31-32.
Norman, James J., et al. "Reliability and Accuracy of Intradermal Injection by Mantoux Technique, Hypodermic Needle Adapter, and Hollow Microneedle in Pigs." [online] *Drug Delivery and Translational Research*, vol. 4, No. 2, Published Online Nov. 18, 2013, pp. 126-130, doi:10.1007/s13346-013-0184-5.
Oltulu, Pembe, et al. "Measurement of Epidermis, Dermis, and Total Skin Thicknesses from Six Different Body Regions with a New Ethical Histometric Technique." [online] *Turkish Journal of Plastic Surgery*, vol. 26, No. 2, Web Publication Apr. 13, 2018, pp. 56-61, doi:10.4103/tjps.tjps_2_17.
Pastore, Michael N., et al. "Transdermal Patches: History, Development and Pharmacology." [online] *British Journal of Pharmacology*, vol. 172, No. 9, Jan. 5, 2015, pp. 2179-2209, doi:10.1111/bph.13059.
Patel, Dipen, et al. "Transdermal Drug Delivery System: A Review." [online] *The Pharma Innovation Journal*, vol. 1, No. 4, Jun. 2012, pp. 66-75, https://www.thepharmajournal.com/vol1Issue4/Issue_june_2012/14.pdf.
Prausnitz, Mark R., and Robert Langer. "Transdermal Drug Delivery (Author Manuscript)" [online] *Nature Biotechnology*, Available in PubMed Central Jun. 23, 2009, https://www.ncbi.nlm.nih.gov/pmc/articles/PMC2700785/pdf/nihms121685.pdf.
Rodgers, Aoife M., et al. "Dissolving Microneedles for Intradermal Vaccination: Manufacture, Formulation, and Stakeholder Considerations." [online] *Expert Opinion on Drug Delivery*, vol. 15, No. 11, Taylor & Francis, Published online Sep. 19, 2018, pp. 1039-1043, doi:10.1080/17425247.2018.1522301.
Roxhed, Niclas. "A Fully Integrated Microneedle-Based Transdermal Drug Delivery System." [online] *Submitted to the School of Electrical Engineering KTH—Royal Institute of Technology*, Available from Sep. 10, 2007, http://www.diva-portal.org/smash/get/diva2:12495/FULLTEXT01.pdf.
Samel, Bjoern. "Novel Microfluidic Devices Based on a Thermally Responsive PDMS Composite." [online] *Submitted to the School of Electrical Engineering KTH—Royal Institute of Technology*, Available from Aug. 21, 2007, https://www.diva-portal.org/smash/get/diva2:12419/FULLTEXT01.pdf.
Shrestha, Pranav, and Boris Stoeber. "Fluid Absorption by Skin Tissue during Intradermal Injections through Hollow Microneedles." [online] *Nature: Scientific Reports*, vol. 8, Springer US, Sep. 13, 2018, pp. 1-13, doi:10.1038/s41598-018-32026-9.
Tsals, Izrail. "Usability Evaluation of Intradermal Adapters (IDA)." [Article in Press online] *Vaccine*, 2016, http://dx.doi.org/10.1016/j.vaccine.2016.07.036.
Tsals, Izrail, et al. "Clinical Performance and Safety of Adapters for Intradermal Delivery with Conventional and Autodisable Syringes." [Article in Press online] *Vaccine*, 2015, http://dx.doi.org/10.1016/j.vaccine.2015.04.095.
Vosseler, Michael, et al. "A Smart Interface for Reliable Intradermal Injection and Infusion of High and Low Viscosity Solutions." [online] *Pharmaceutical Research* vol. 28, No. 3, Nov. 23, 2010, pp. 647-661, doi:10.1007/s11095-010-0319-z.
Waghule, Tejashree, et al. "Microneedles: A Smart Approach and Increasing Potential for Transdermal Drug Delivery System." [online] *Biomedicine and Pharmacotherapy*, vol. 109. Available online Nov. 9, 2018, Elsevier, 2019, pp. 1249-1258, doi:10.1016/j.biopha.2018.10.078.
Weatherford, Greg "Once a coronavirus vaccine exists, a VCU researcher's mailable patch could deliver it to millions" [online] Virginia Commonwealth University News, May 13, 2020. https://news.vcu.edu/article/Once_a_coronavirus_vaccine_exists_a_VCU_researchers_mailable.
Yadav, Prateek Ranjan, et al. "Mathematical Modelling, Simulation and Optimisation of Microneedles for Transdermal Drug Delivery: Trends and Progress." [online] *Pharmaceutics*, vol. 12, No. 8, Jul. 22, 2020, pp. 1-31, doi:10.3390/pharmaceutics12080693.
Yang, Jian, et al. "Recent Advances of Microneedles for Biomedical Applications: Drug Delivery and Beyond." [online] *Acta Pharmaceutica Sinica B*, vol. 9, No. 3, Elsevier Ltd, Available online Apr. 4, 2019, pp. 469-483, doi:10.1016/j.apsb.2019.03.007.
Verapido Medical Administering Drugs Into the Skin. Verapido Medical—Hahn-Schickard, https://www.hahn-schickard.de/en/spin-off-companies/verapido-medical. (Retrieved Jan. 6, 2023).
Streicher, Jessica. "Verapido Medical GmbH: Small Needles with a Huge Effect." Healthcare Industry BW, BIOPRO Baden-Württemberg GmbH, Feb. 3, 2014, https://www.gesundheitsindustrie-bw.de/en/article/news/verapido-medical-gmbh-small-needles-with-a-huge-effect.
Path Case Study: Development and Use of the Uniject Device. Path, Nov. 2009, https://www.path.org/publications/files/OTP_uniject_cs.pdf.
Leach, Chris. Faster Insulin: Short and Sweet. Insulin Nation, Mar. 26, 2013, https://insulinnation.com/treatment/medicine-drugs/faster-insulin-short-and-sweet/.
"Injection into the Dermal Skin Layer." Intradermal Drug Delivery, Idevax, https://idevax.com/device/intradermal-injection/. (Retrieved Jan. 6, 2023).
Lips, Bram, and Robert Puers. "Three Step Deep Reactive Ion Etch for High Density Trench Etching." Journal of Physics: Conference Series, vol. 757, 2016, pp. 1-5., https://doi.org/10.1088/1742-6596/757/1/012005.
U.S. Appl. No. 18/087,058, filed Dec. 22, 2022.

\* cited by examiner

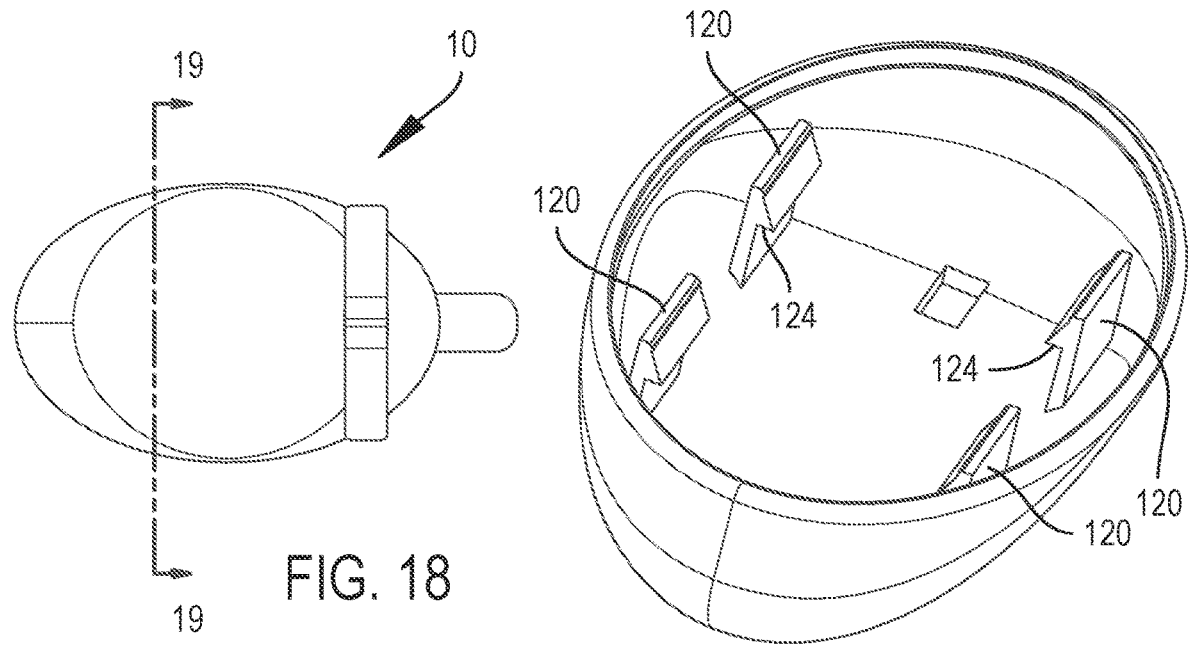
FIG. 18
FIG. 20
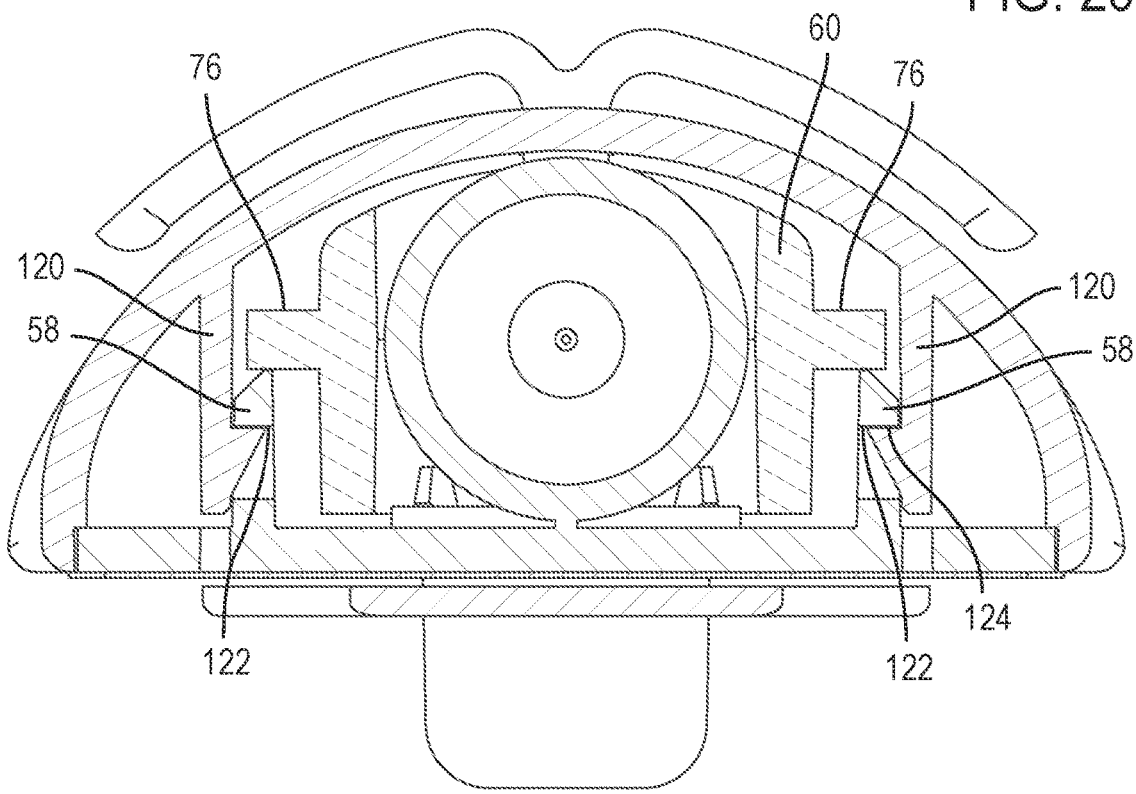
FIG. 19

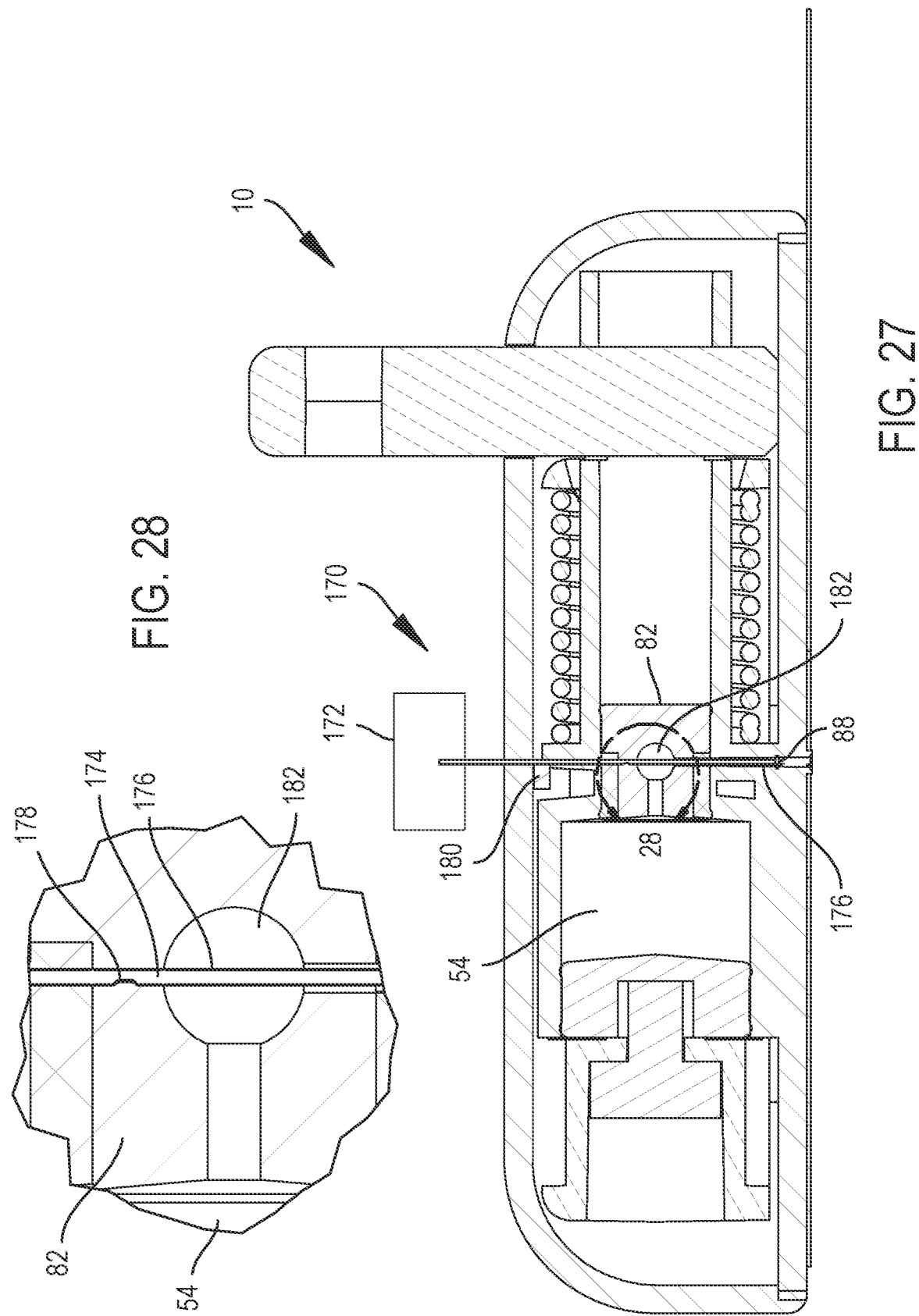

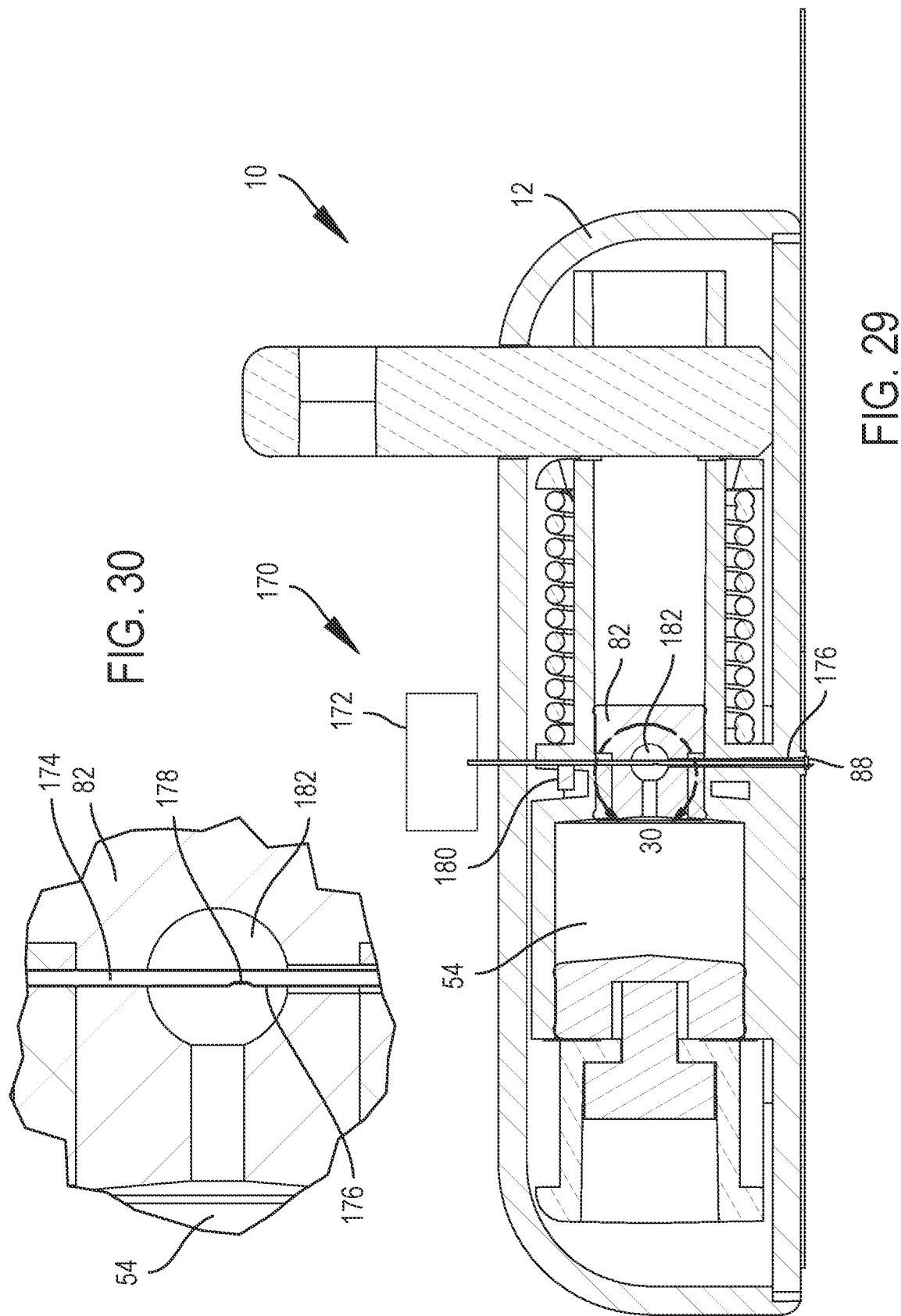

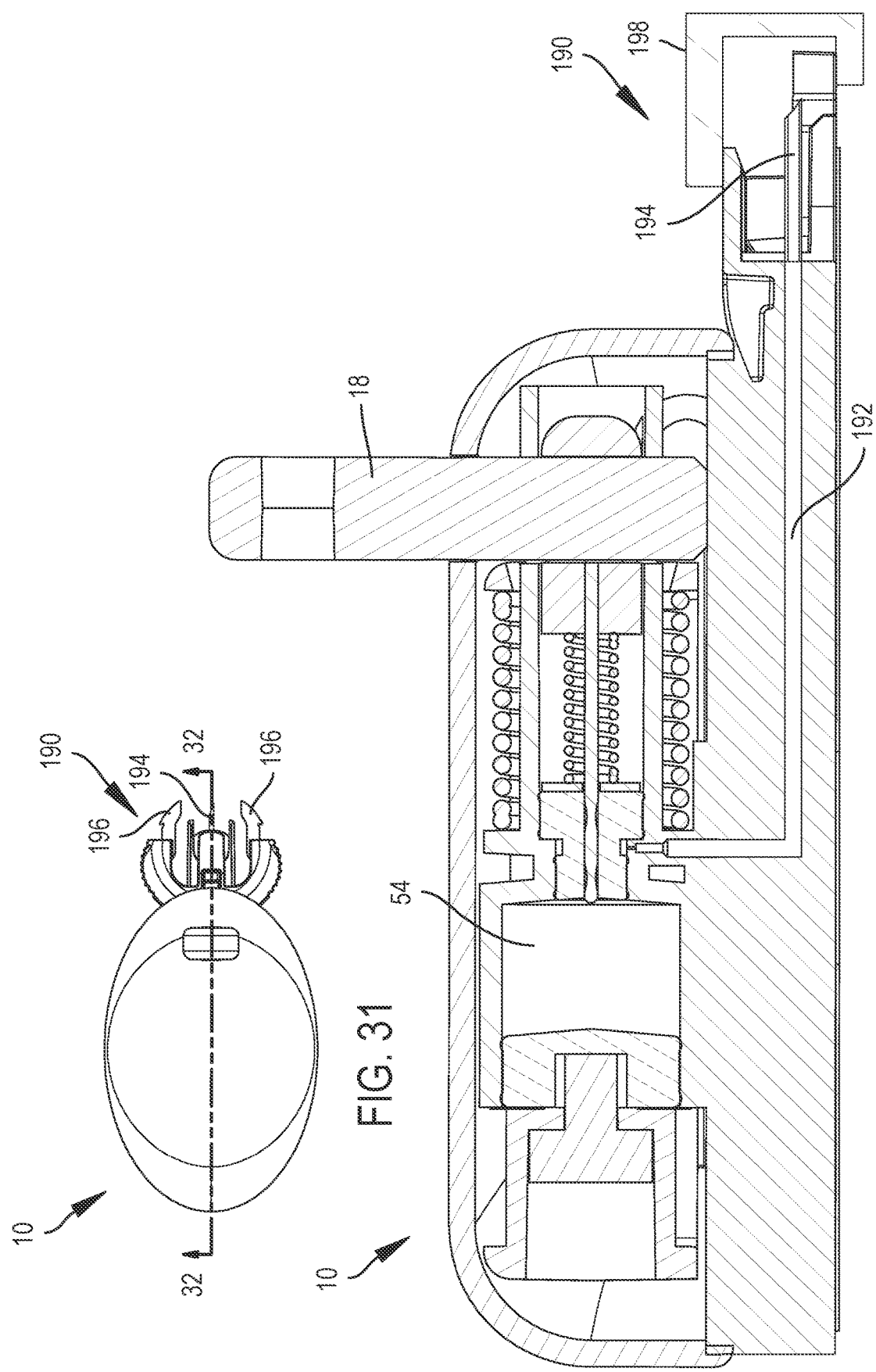

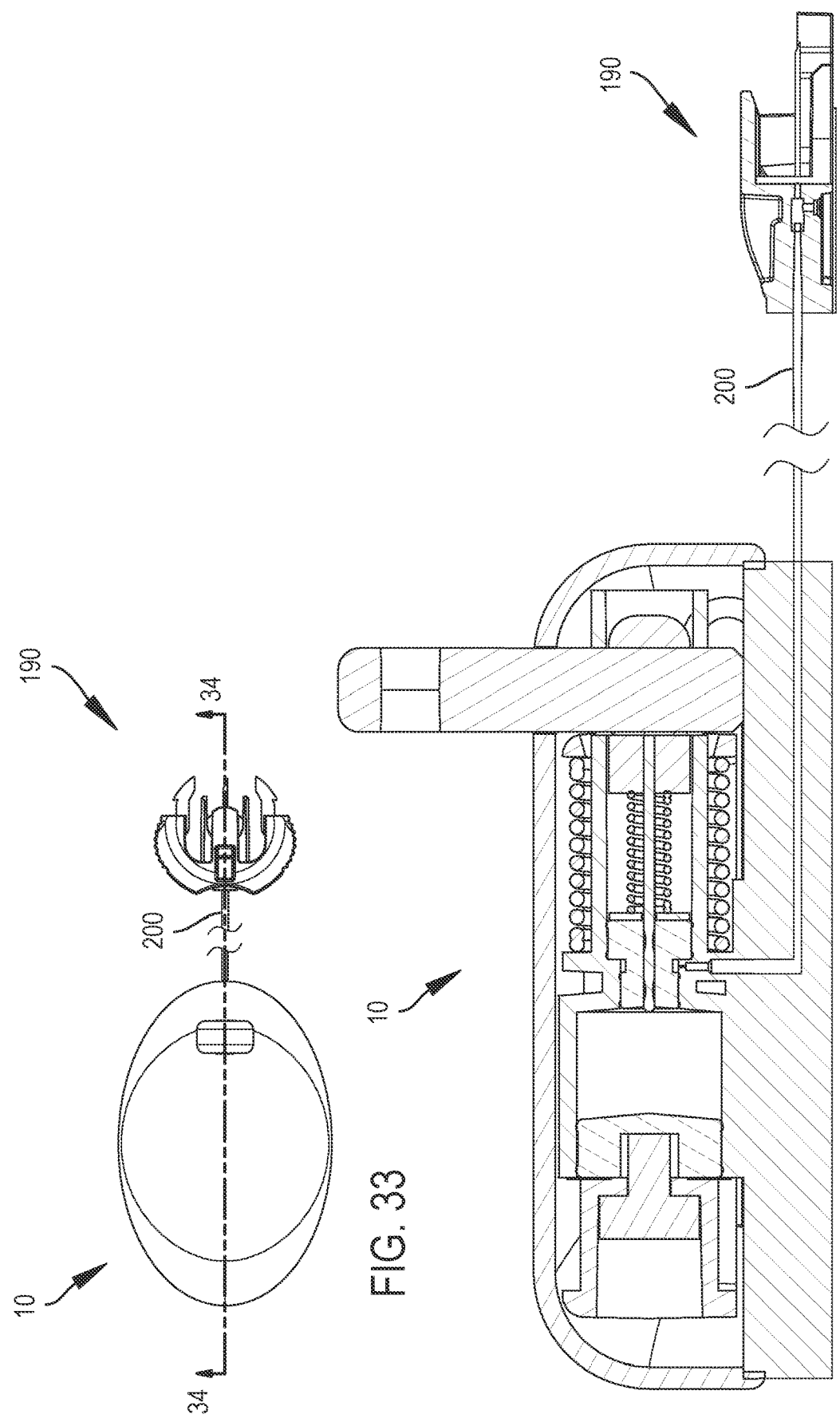

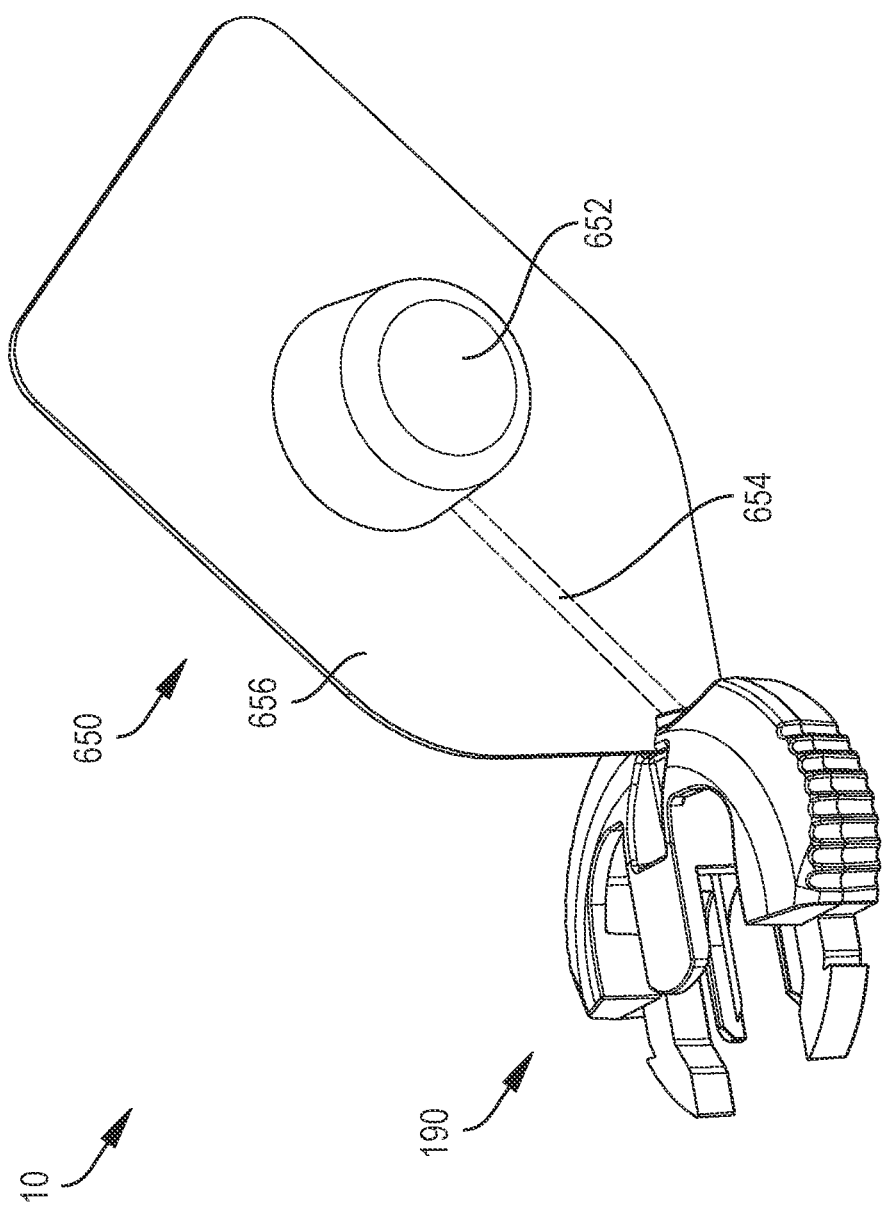
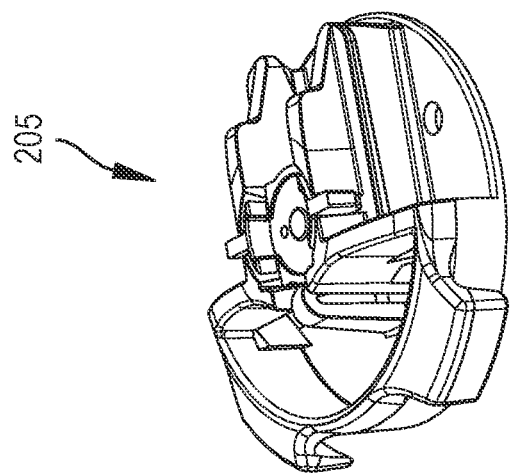
FIG. 36

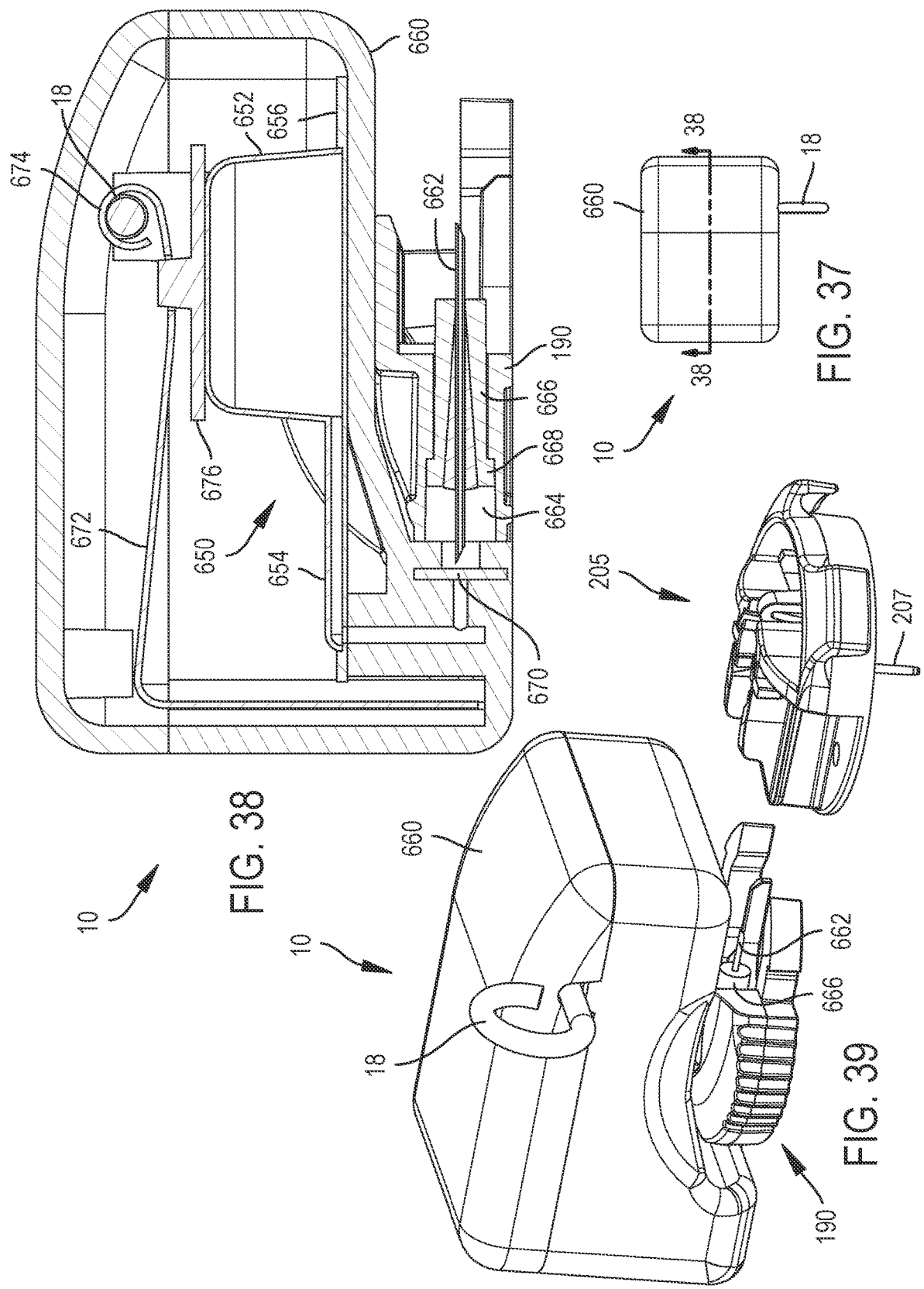

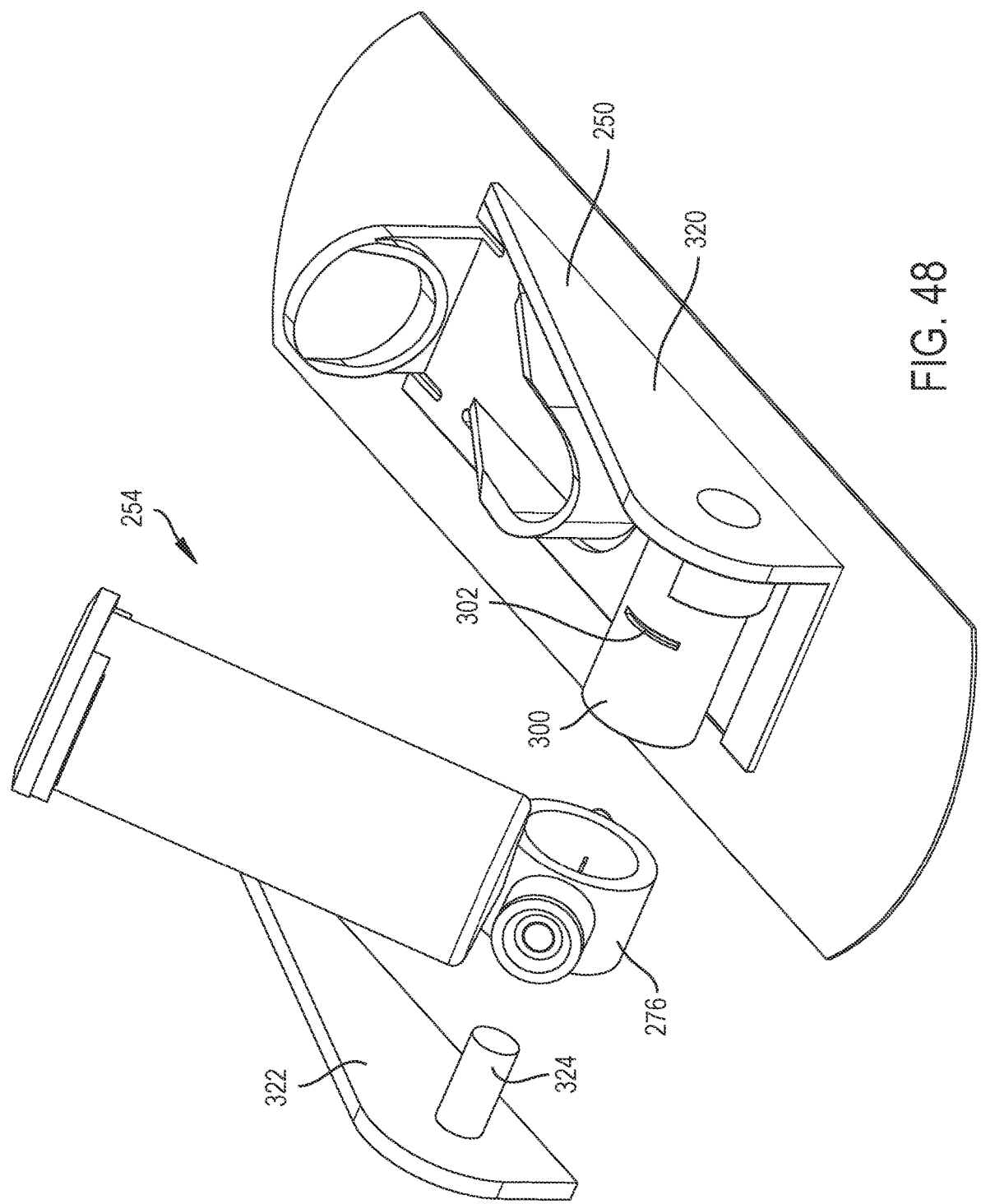

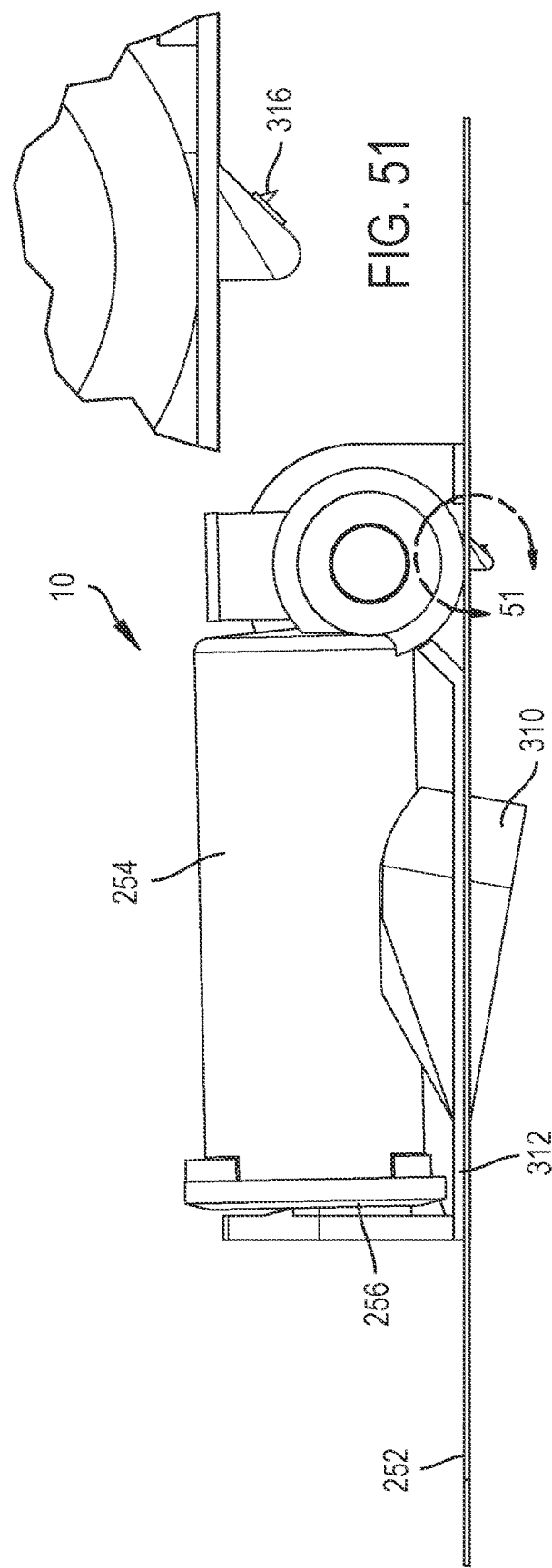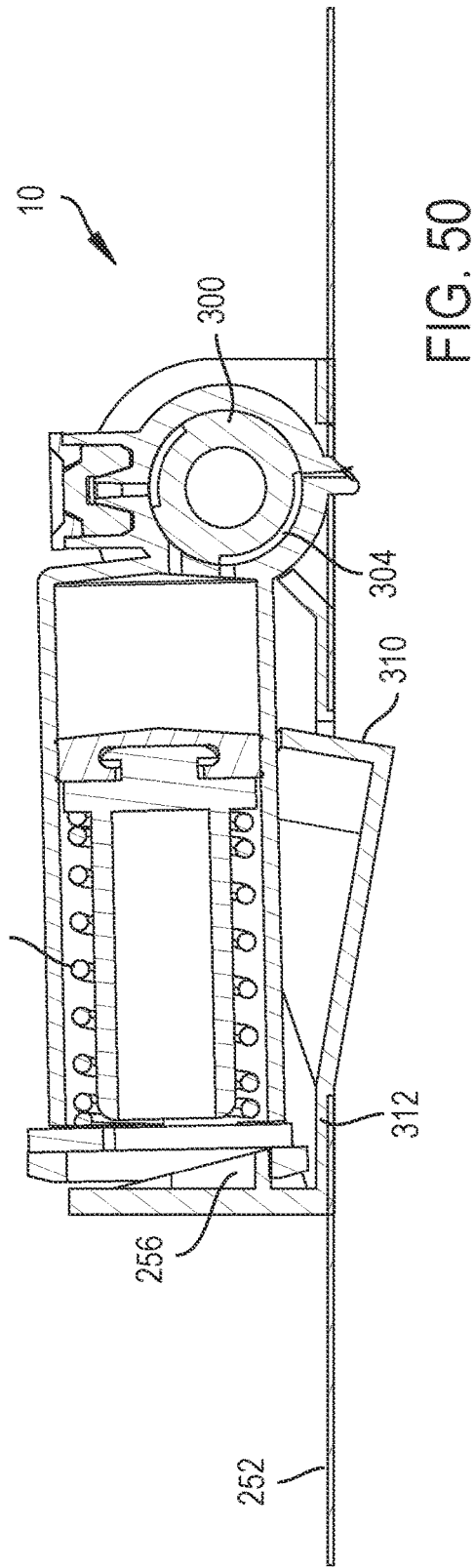

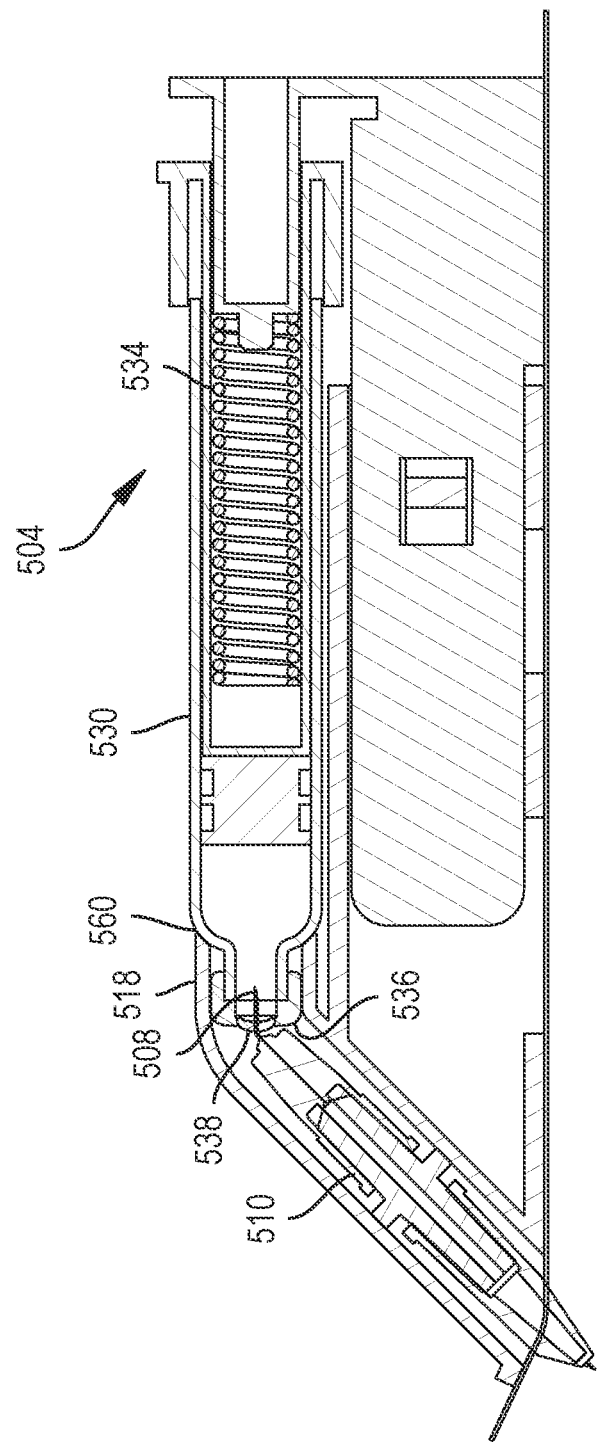

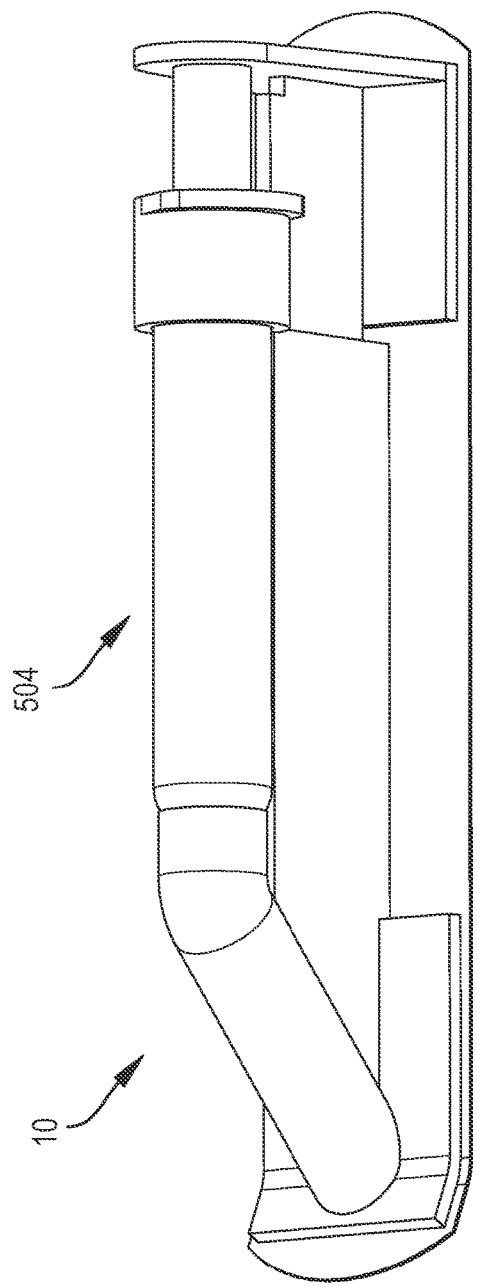
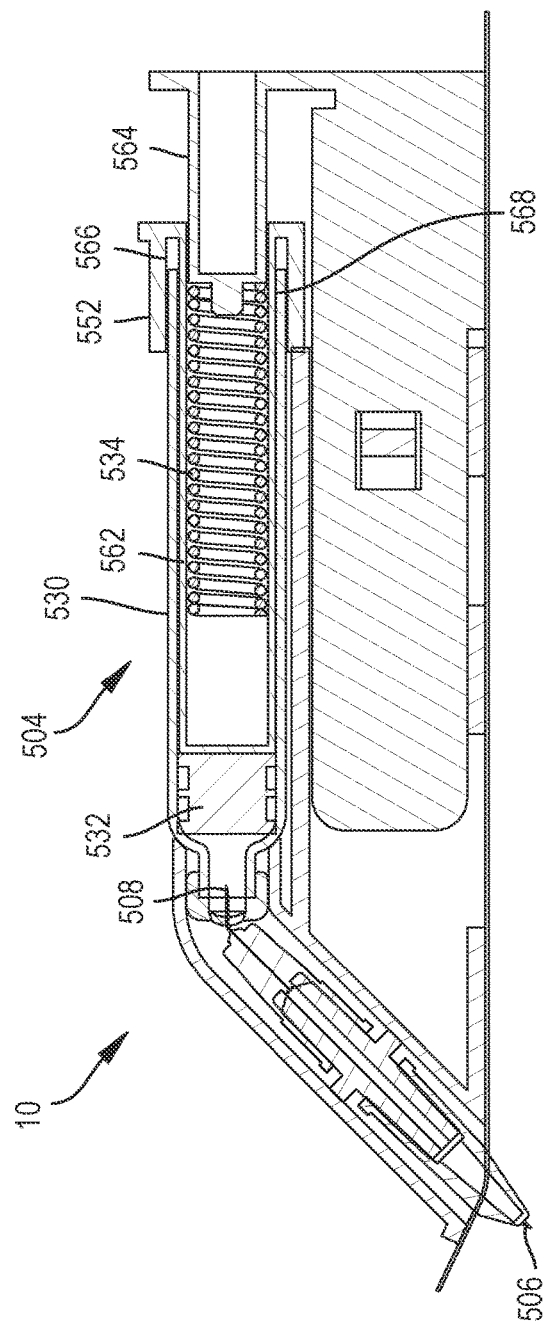

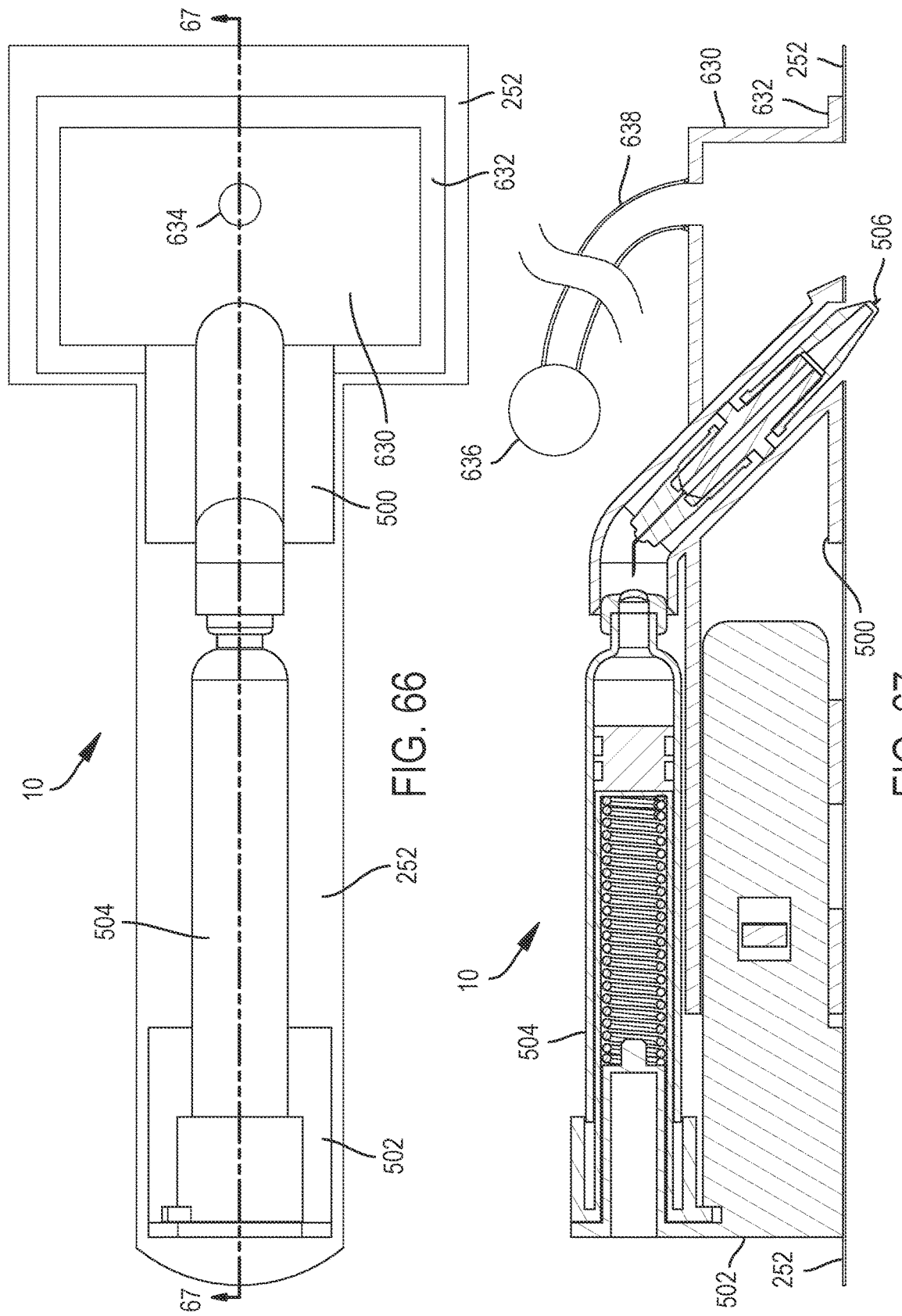

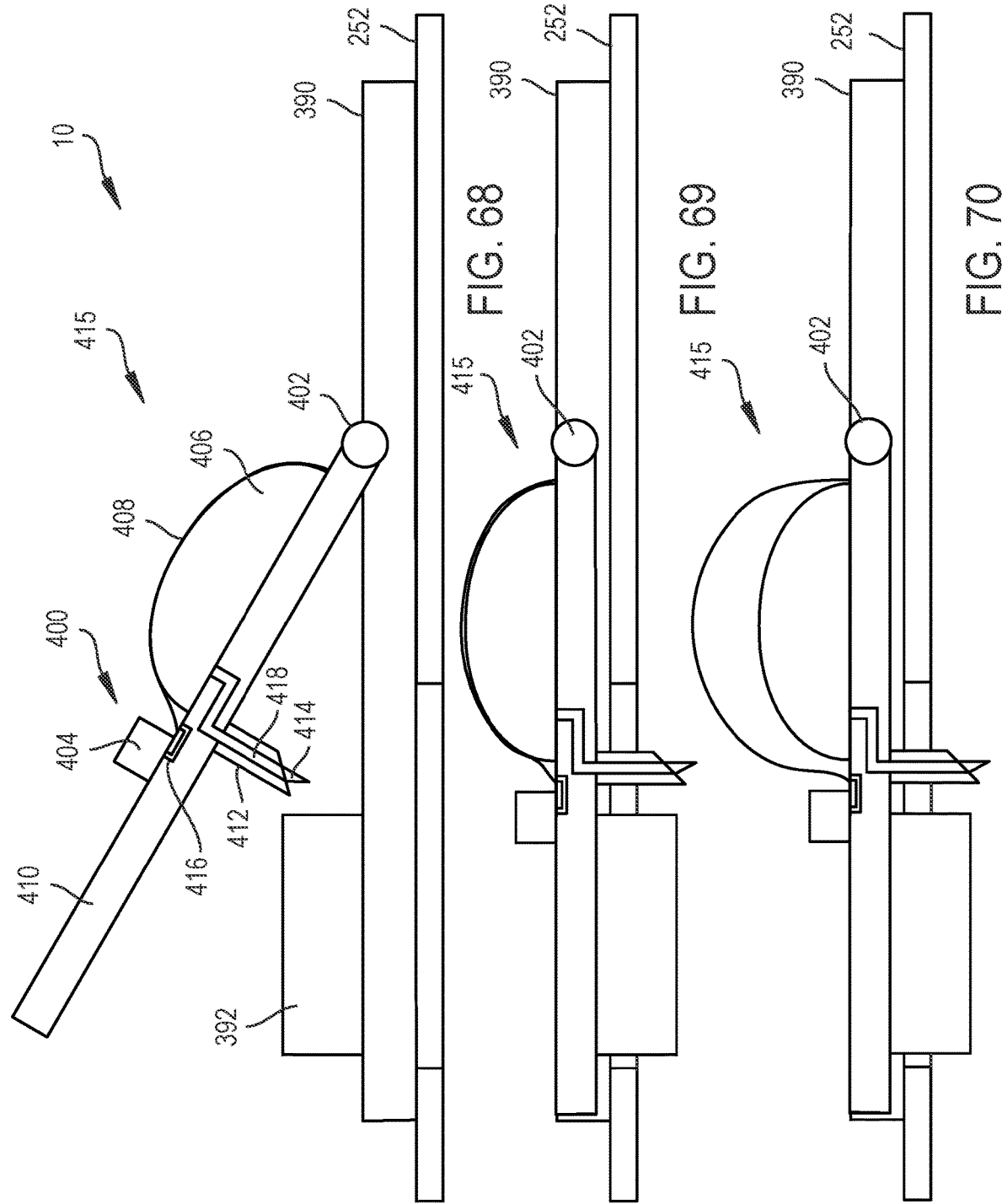

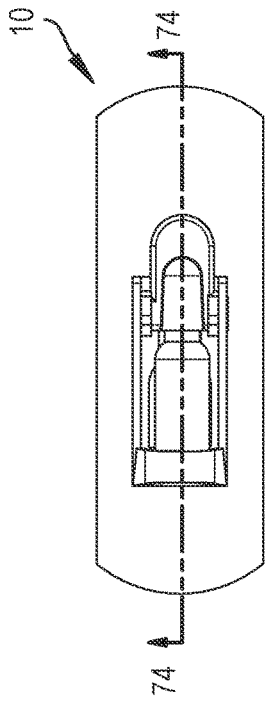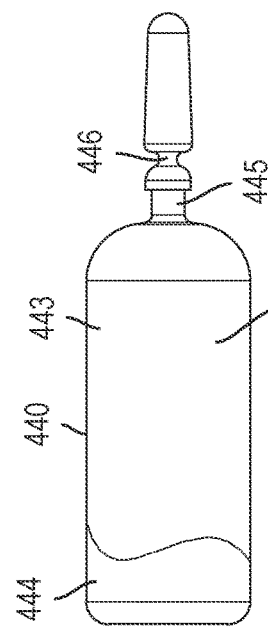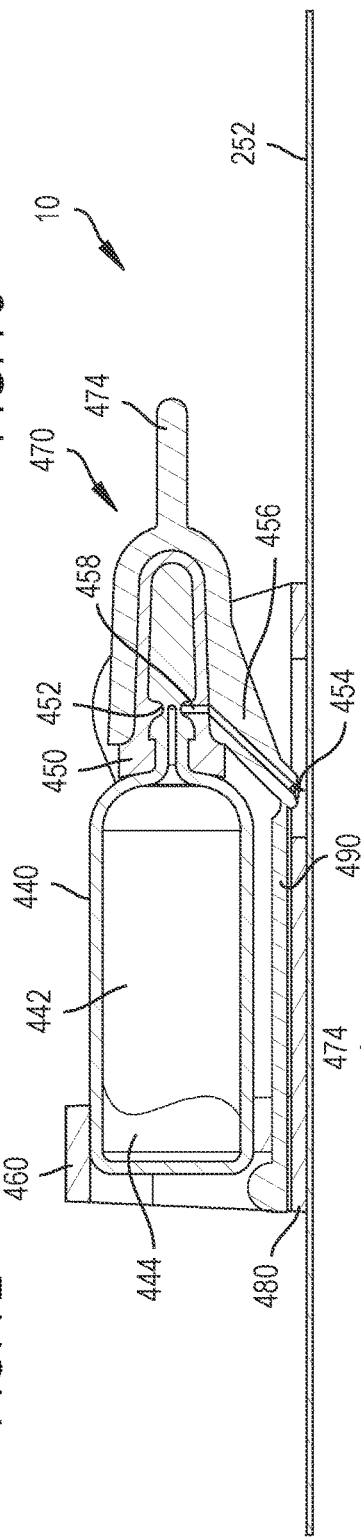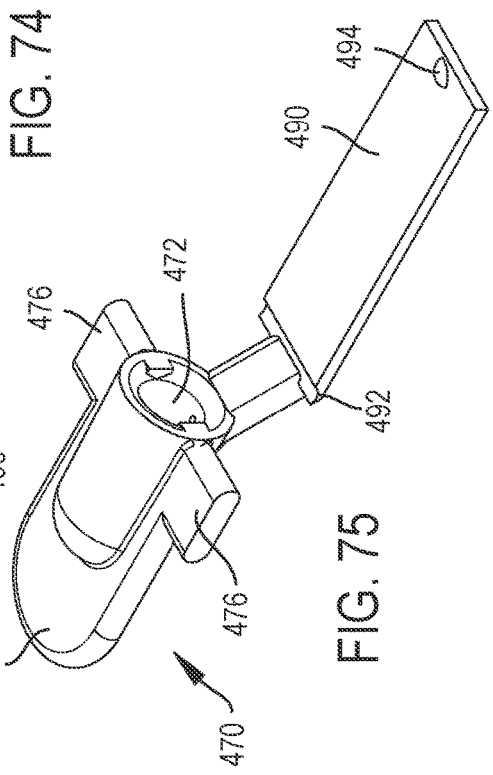

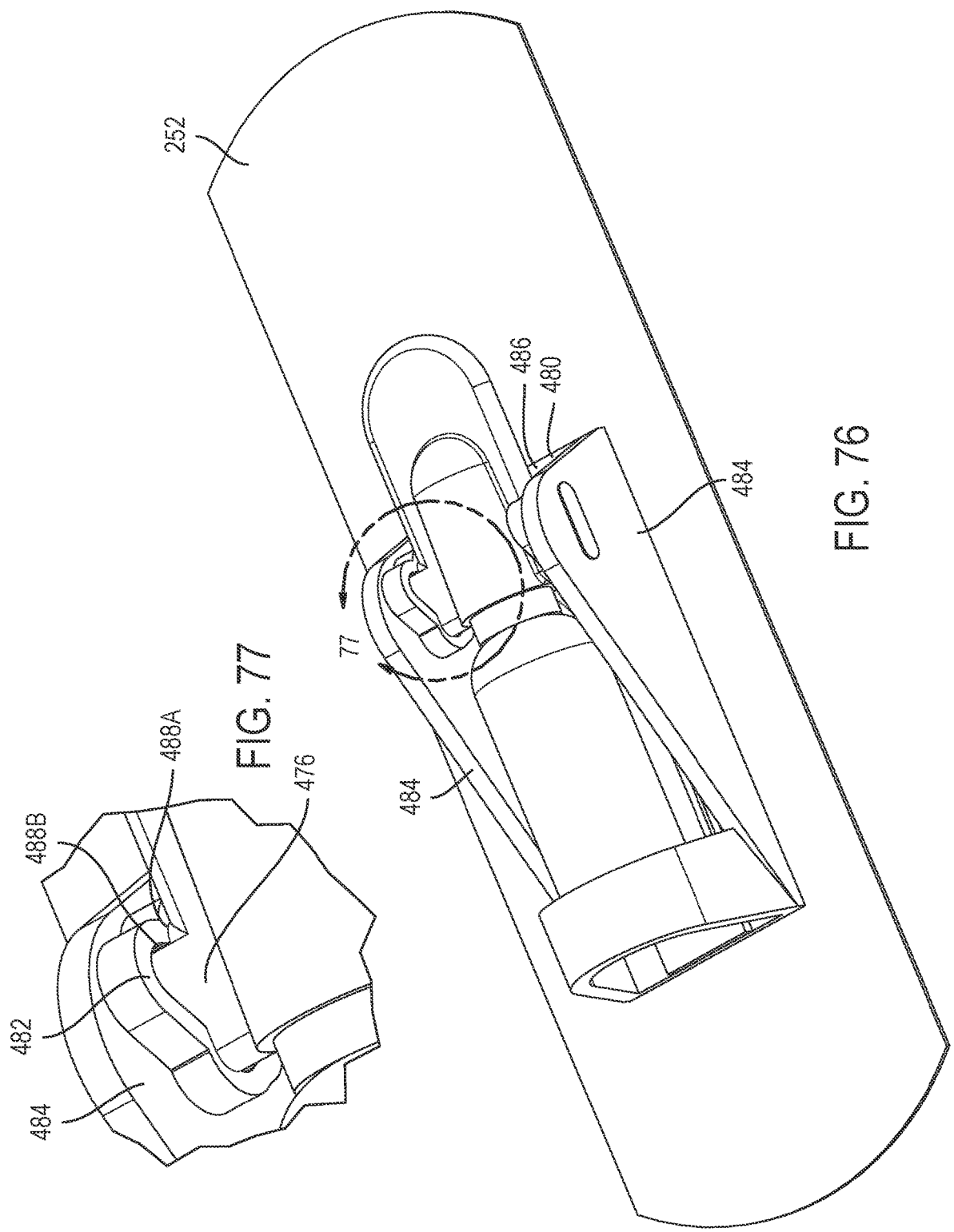

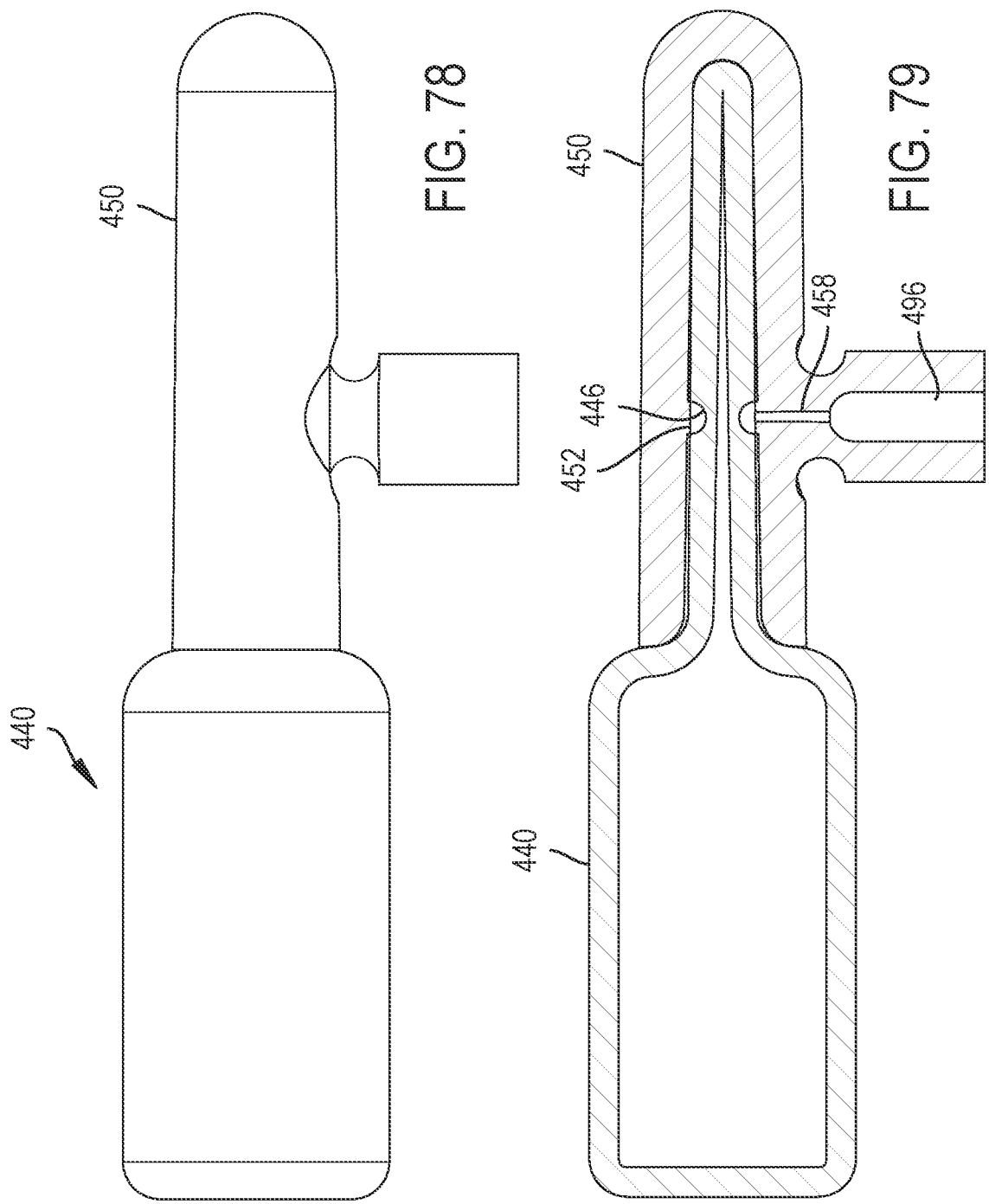

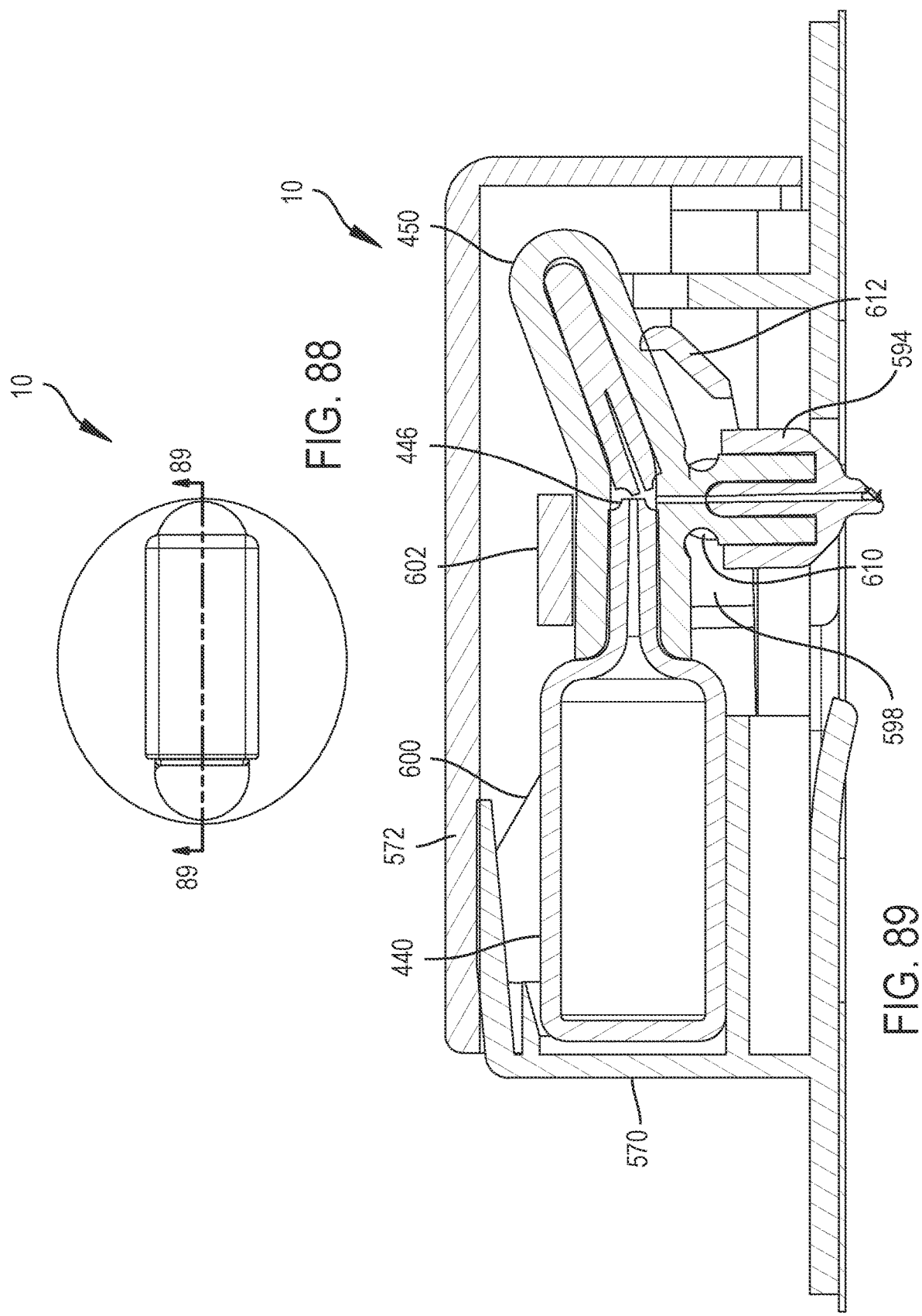

MEDICAL AGENT DISPENSING APPARATUSES, SYSTEMS, AND METHODS

CROSS-REFERENCE TO RELATED APPLICATIONS

The present application claims the benefit of U.S. Provisional Application Ser. No. 63/154,931, entitled Medical Agent Dispensing Apparatuses, Systems, and Methods, filed Mar. 1, 2021, which is incorporated herein by reference in its entirety.

STATEMENT REGARDING FEDERALLY SPONSORED RESEARCH OR DEVELOPMENT

This invention was made with Government support under Agreement W911NF-17-3-0003, awarded by ACC-APG-RTP. The Government has certain rights in the invention.

BACKGROUND

Field of Disclosure: This disclosure relates to medical agent delivery. More specifically, this disclosure relates to dispensers for therapeutic and other medical agents.

DESCRIPTION OF RELATED ART

Novel pathogens present a variety of public health challenges which are not simple to quickly overcome. From the medical perspective, existing preventive medicine infrastructure has not been and is not well suited to novel pathogens such as SARS, MERS, Zika, and COVID-19. Other pathogens for which herd immunity does not exist (e.g. Ebola), or highly dangerous pathogens which mutate quickly may present similar challenges. Vaccines typically take years to create and once a vaccine does exist, the prospect of rapidly generating billions of doses would almost certainly exceed current vaccine production capabilities. Without vaccination, other preventative measures such as, testing, contact tracing, and personal protective equipment (PPE) are of elevated importance. Again, however, these preventative measures can only provide as much benefit as relevant supply chains allow. Shortages of PPE and testing kits have plagued medical systems in the United States and elsewhere across the globe as they struggle to address the COVID-19 pandemic. In turn, this has hampered the potential to perform effective contact tracing which is already a vast undertaking due to the scale of the COVID-19 pandemic. Additionally, novel pathogens may refocus medical systems away from their typical functions. Secondary impacts often result when the medical community's attention is demanded by a widespread pandemic. This can take the form of delayed surgeries, elective procedures, routine doctor's office visits, etc., but secondary impacts can also be much worse. As has been pointed out by the Chief of Immunizations at UNICEF, for example, during efforts to control an Ebola outbreak in the Democratic Republic of the Congo in 2019 the number of deaths due to measles was double the death toll from Ebola.

Novel pathogens also present challenges that are more psychological in nature. Put simply, such pathogens scare people. Without readily available PPE and testing, people may elect to avoid visiting medical facilities or clinics for fear of exposure to disease. Even with readily available PPE, certain individuals, such as populations in high risk demographics for a particular pathogen, may still have misgivings about visiting such facilities. Additionally, as has been the case in the United States, some may fiercely object to usage of PPE for various reasons. This presents a further public health challenge to systems attempting to deal with pandemics. Solutions to novel pathogens should seek to address and work around these challenges in order to be effective.

SUMMARY

In accordance with an embodiment of the present disclosure a delivery device for administering a medical agent to a patient may comprise a housing cover. The delivery device may further comprise a base coupled to the housing cover. The base may include a first side with a skin adhering face and a second side including a reservoir portion and a guide portion. The delivery device may further comprise a plunger sled including a plunger portion and an aperture through which the guide portion extends. The plunger sled may be displaceable between a delivered position in which the plunger portion is adjacent an outlet of the reservoir portion and a retracted position in which the plunger is at an end of the reservoir portion opposite the outlet. The delivery device may further comprise at least one delivery sharp in fluid communication with a flow path in an insert at the outlet of the reservoir portion. The delivery device may further comprise a plug displaceable between a first position in which the plug blocks all flow through the insert and second position in which the plug blocks flow through a portion of the insert. The at least one delivery sharp may be in fluid communication with the reservoir portion via the insert when the plug is in the second position. The delivery device may further comprise a first bias member configured to urge the plug to the second position. The delivery device may further comprise a second bias member configured to urge the plunger sled to displace toward the delivered position. The delivery device may further comprise a removable locking member which blocks displacement of the plug and plunger sled until being removed from the delivery device.

In some embodiments, the plunger portion may be at least partially formed of elastomeric material. In some embodiments, the at least one delivery sharp may be selected from a group consisting of an intramuscular delivery needle and a subcutaneous delivery needle. In some embodiments, the at least one delivery sharp may comprise an array of delivery sharps. In some embodiments, the at least one delivery sharp may be a microneedle. In some embodiments, the at least one delivery sharp may be an array of microneedles. In some embodiments, the at least one delivery sharp may be oriented substantially perpendicular to the skin adhering face of the delivery device. In some embodiments, the at least one delivery sharp may be oriented at an acute angle to the skin adhering face of the base. In some embodiments, the at least one delivery sharp may have a length of no more than one millimeter. In some embodiments, the first and second bias member may be compression springs. In some embodiments, the insert may be at least partially elastomeric. In some embodiments, the plunger sled may be a rectilinear frame having a first end from which the plunger portion projects, an opposing second end in which the aperture is disposed, and side panels including guides. In some embodiments, the plunger sled may include at least one coupling lip configured to engage a drive element of a filling fixture. In some embodiments, the reservoir portion may be filled with a medical agent selected from a list consisting of a vaccine, an antiviral, a retroviral, a peptide, an endocrine disorder drug, insulin, a diagnostic agent, an allergen, an overdose intervention drug, and opioid antagonist, naloxone, and a tuberculosis testing agent. In some embodiments, the delivery device may further comprise a cover member coupled to the base and covering the at least one delivery sharp. In some embodiments, the locking member may include at least one portion which may be configured to displace from a stowed state against the housing cover to a second state where the at least one portion extends a greater distance from the housing cover compared to its position in the stowed state. In some embodiments, the delivery device may further comprise a flow limiter restriction upstream of the at least one delivery sharp. In some embodiments, the displacement of the second bias member which occurs as the plunger sled is displaced from the retracted position to the delivered position may be 10-20% of the total displacement range of the second bias member. In some embodiments, the plug and first bias member may be disposed within the guide portion and the second bias member may surround the guide portion. In some embodiments, the plug may include a head portion and a pin portion which extends from the head portion. In some embodiments, the locking member may extend through an orifice in the head portion when the locking member is installed within the delivery device.

In accordance with an embodiment of the present disclosure a delivery device for administering a medical agent to a patient may comprise a housing cover. The delivery device may further comprise a base coupled to the housing cover. The base may include a first side with a skin adhering face and a second side including a reservoir portion and a guide portion. The delivery device may further comprise a displaceable plunger sled including a plunger portion and an aperture through which the guide portion extends. Displacement of the plunger sled may cause displacement of the plunger portion toward an outlet of the reservoir. The delivery device may further comprise at least one delivery sharp in fluid communication with a flow path in an insert at the outlet of the reservoir portion. The delivery device may further comprise a displaceable plug configured to block all flow through the insert in a first position. The delivery device may further comprise a first bias member configured to urge the plug to a second position in which a flow path through the insert to the at least one delivery sharp is established. The delivery device may further comprise a second bias member configured to urge displacement of the plunger sled. The delivery device may further comprise a removable locking member which may block displacement of the plug and plunger sled until being removed from the delivery device.

In some embodiments, the plunger portion may be at least partially formed of elastomeric material. In some embodiments, the at least one delivery sharp may be selected from a group consisting of an intramuscular delivery needle and a subcutaneous delivery needle. In some embodiments, the at least one delivery sharp may comprise an array of delivery sharps. In some embodiments, the at least one delivery sharp may be a microneedle. In some embodiments, the at least one delivery sharp may be an array of microneedles. In some embodiments, the at least one delivery sharp may be oriented perpendicular to the skin adhering face of the delivery device. In some embodiments, the at least one delivery sharp may be oriented at an acute angle to the skin adhering face of the base. In some embodiments, the at least one delivery sharp may have a length of no more than one millimeter. In some embodiments, the first and second bias member may be compression springs. In some embodiments, the insert may be at least partially elastomeric. In some embodiments, the plunger sled may be a rectilinear frame having a first end from which the plunger portion projects, an opposing second end in which the aperture is disposed, and side panels including guides. In some embodiments, the plunger sled may include at least one coupling lip configured to engage a drive element of a filling fixture. In some embodiments, the reservoir portion may be filled with a medical agent selected from a list consisting of a vaccine, an antiviral, a retroviral, a peptide, an endocrine disorder drug, insulin, a diagnostic agent, an allergen, an overdose intervention drug, an opioid antagonist, naloxone, and a tuberculosis testing agent. In some embodiments, the delivery device may further comprise a cover member coupled to the base and covering the at least one delivery sharp. In some embodiments, the locking member may include a least one portion which is configured to displace from a stowed state against the housing cover to a second state where the at least one portion extends a greater distance from the housing cover compared to the its position in the stowed state. In some embodiments, the delivery device may further comprise a flow limiter restriction upstream of the at least one delivery sharp. In some embodiments, the displacement of the second bias member which occurs as the plunger sled is displaced along the reservoir portion to fully deliver the contents of the reservoir portion may be 10-20% of the total displacement range of the second bias member. In some embodiments, the plug and first bias member may be disposed within the guide portion and the second bias member surrounds the guide portion. In some embodiments, the plug may include a head portion and a pin portion which extends from the head portion.

In accordance with another embodiment of the present disclosure a delivery device for administering a medical agent to a patient may comprise a base including a first side with a skin adhering face and a second side including a reservoir portion. The delivery device may further comprise a housing cover coupled to the base. The delivery device may further comprise a plunger displaceable within the reservoir portion. The delivery device may further comprise at least one delivery sharp in fluid communication with a fluid pathway in an insert disposed at a reservoir outlet of the reservoir portion. The delivery device may further comprise a plug configured to block all flow through the insert in a first position. The delivery device may further comprise a first bias member configured to urge the plug to a second position in which a flow path through the insert to the at least one delivery sharp is established. The delivery device may further comprise a second bias member configured to urge the plunger toward the reservoir outlet. The delivery device may further comprise a lock which blocks displacement of the plug and plunger until the lock is actuated out a locking state.

In some embodiments, the plunger may be at least partly elastomeric. In some embodiments, the at least one delivery sharp may be selected from a group consisting of an intramuscular delivery needle and a subcutaneous delivery needle. In some embodiments, the at least one delivery sharp may comprise an array of delivery sharps. In some embodiments, the at least one delivery sharp may be a pyramid shaped, silicon crystal, microneedle. In some embodiments, the at least one delivery sharp may comprise an array of microneedles. In some embodiments, the at least one delivery sharp may be oriented perpendicular to the skin adhering face of the delivery device. In some embodiments, the at least one delivery sharp may be oriented at an acute angle to the skin adhering face of the base. In some embodiments, the at least one delivery sharp may have a length of no more than one millimeter. In some embodiments, the first and second bias member may be compression springs. In some embodiments, the insert may be at least partially elastomeric. In some embodiments, the plunger may be coupled to a frame having a first end from which the plunger projects, an opposing second end, and side panels including guides. In some embodiments, the frame may include at least one coupling lip configured to engage a drive element of a filling fixture. In some embodiments, the reservoir portion may be filled with a medical agent selected from a list consisting of a vaccine, an antiviral, a retroviral, a peptide, an endocrine disorder drug, insulin, a diagnostic agent, an allergen, an overdose intervention drug, an opioid antagonist, naloxone, and a tuberculosis testing agent. In some embodiments, the delivery device may further comprise a cover member coupled to the base and covering the at least one delivery sharp. In some embodiments, the lock may include at least one portion which is configured to displace from a stowed state against the housing cover to a second state where the at least one portion extends a greater distance from the housing cover compared to the its position in the stowed state. In some embodiments, the delivery device may further comprise a flow limiter restriction upstream of the at least one delivery sharp. In some embodiments, the displacement of the second bias member which occurs as the plunger is displaced to fully deliver the contents of the reservoir portion may be 10-20% of the total displacement range of the second bias member. In some embodiments, the plug and first bias member may be disposed within a guide portion of the base and the second bias member may surround the guide portion. In some embodiments, the plug may include a head portion and an occluder member.

In accordance with yet another embodiment of the present disclosure a delivery device for administering a medical agent to a patient may comprise a base including a first side with a skin adhering face and a second side including a reservoir portion. The delivery device may further comprise a housing cover coupled to the base. The delivery device may further comprise a plunger displaceable within the reservoir portion. The delivery device may further comprise at least one delivery sharp in fluid communication with a fluid pathway in an insert disposed at a reservoir outlet of the reservoir portion. The delivery device may further comprise an activation assembly configured to be actuated from an inactive state where flow from the reservoir portion is blocked and the plunger is inhibited from displacing to an activated state where a flow path through the insert to the delivery sharp is established and the plunger is free to displace. The delivery device may further comprise a bias member configured to urge the plunger toward the reservoir outlet.

In some embodiments, the activation assembly may include a lock which presents a mechanical interference to displacement of the plunger when the activation assembly is in the inactive state. In some embodiments, the activation assembly may include a displaceable plug. In some embodiments, the activation assembly may include a bias member disposed between a head of the plug and the insert. In some embodiments, the activation assembly may include a plug having a first position in which the plug blocks all flow through the insert and a second position in which a flow path through the insert to the at least one delivery sharp is established. In some embodiments, the activation assembly may include a plug bias member configured to urge the plug from the first position to the second position. The activation assembly may further comprise a lock which prevents displacement of the plug to the second position until the lock is actuated. In some embodiments, the at least one delivery sharp may be selected from a group consisting of an intramuscular delivery needle and a subcutaneous delivery needle. In some embodiments, the at least one delivery sharp may comprise an array of delivery sharps. In some embodiments, the at least one delivery sharp may be a pyramid shaped, silicon crystal, microneedle. In some embodiments, the at least one delivery sharp may be a pointed, silicon crystal, microneedle. In some embodiments, the at least one delivery sharp may comprise an array of microneedles. In some embodiments, the at least one delivery sharp may be oriented perpendicular to the skin adhering face of the delivery device. In some embodiments, the at least one delivery sharp may be oriented at an acute angle to the skin adhering face of the base. In some embodiments, the at least one delivery sharp may have a length of no more than one millimeter. In some embodiments, the at least one delivery sharp may have a length of about 0.6 millimeters. In some embodiments, the plunger may be coupled to a frame having a first end from which the plunger projects, an opposing second end, and side panels including guides. In some embodiments, the frame may include at least one coupling lip configured to engage a drive element of a filling fixture. In some embodiments, the reservoir portion may be filled with a medical agent selected from a list consisting of a vaccine, an antiviral, a retroviral, a peptide, an endocrine disorder drug, insulin, a diagnostic agent, an allergen, an overdose intervention drug, an opioid antagonist, naloxone, and a tuberculosis testing agent. In some embodiments, the delivery device may further comprise a cover member coupled to the base and covering the at least one delivery sharp. In some embodiments, the activation assembly may include a lock which presents a mechanical interference to displacement of the plunger when the activation assembly is in the inactive state. The lock may include a least one portion which is configured to displace from a stowed state against the housing cover to a second state where the at least one portion extends a greater distance from the housing cover compared to the its position in the stowed state. In some embodiments, the delivery device may further comprise a flow limiter restriction upstream of the at least one delivery sharp. In some embodiments, the displacement of the bias member which occurs as the plunger is displaced to fully deliver the contents of the reservoir portion is may be 10-20% of the total displacement range of the second bias member.

In accordance with an embodiment of the present disclosure a delivery device for administering a medical agent to a patient may comprise a base including a first side with a skin adhering face and a second side including a reservoir portion. The delivery device may further comprise a housing cover coupled to the base. The delivery device may further comprise a plunger. The delivery device may further comprise at least one delivery sharp. The delivery device may further comprise an activation assembly configured to be actuated between an inactive state where flow from the reservoir portion to the at least one delivery sharp is blocked and the plunger is inhibited from displacing to an activated state where a flow path to the delivery sharp is established and the plunger is free to displace. The delivery device may further comprise a bias member configured to urge the plunger toward the reservoir outlet.

In some embodiments, the activation assembly may include a lock which presents a mechanical interference to displacement of the plunger when the activation assembly is in the inactive state. In some embodiments, the activation assembly may include a displaceable plug. In some embodiments, the activation assembly may include a bias member disposed between a head of the plug and an insert disposed at an outlet of the reservoir portion. In some embodiments, the activation assembly may include a plug having a first position in which the plug blocks all flow through an insert disposed at an outlet of the reservoir portion and a second position in which a flow path through the insert to the at least one delivery sharp is established. In some embodiments, the activation assembly includes a plug bias member configured to urge the plug from the first position to the second position, the activation assembly further comprising a lock which prevents displacement of the plug to the second position until the lock is actuated. In some embodiments, the at least one delivery sharp may be selected from a group consisting of an intramuscular delivery needle and a subcutaneous delivery needle. In some embodiments, the at least one delivery sharp may comprise an array of delivery sharps. In some embodiments, the at least one delivery sharp may be a pyramid shaped, silicon crystal, microneedle. In some embodiments, the at least one delivery sharp may be a pointed, silicon crystal, microneedle. In some embodiments, the at least one delivery sharp may comprise an array of microneedles. In some embodiments, the at least one delivery sharp may be oriented perpendicular to the skin adhering face of the delivery device. In some embodiments, the at least one delivery sharp may be oriented at an acute angle to the skin adhering face of the base. In some embodiments, the at least one delivery sharp may have a length of no more than one millimeter. In some embodiments, the plunger may be coupled to a frame having a first end from which the plunger projects, an opposing second end, and side panels including guides. In some embodiments, the frame may include at least one coupling lip configured to engage a drive element of a filling fixture. In some embodiments, the reservoir portion may be filled with a medical agent selected from a list consisting of a vaccine, an antiviral, a retroviral, a peptide, an endocrine disorder drug, insulin, a diagnostic agent, an allergen, an overdose intervention drug, an opioid antagonist, naloxone, and a tuberculosis testing agent. In some embodiments, the delivery device may further comprise a cover member coupled to the base and covering the at least one delivery sharp. In some embodiments, the activation assembly may include a lock which presents a mechanical interference to displacement of the plunger when the activation assembly is in the inactive state. The lock may include a least one portion which is configured to displace from a stowed state against the housing cover to a second state where the at least one portion extends a greater distance from the housing cover compared to the its position in the stowed state. In some embodiments, the delivery device may further comprise a flow limiter restriction upstream of the at least one delivery sharp. In some embodiments, the displacement of the bias member which occurs as the plunger is displaced to fully deliver the contents of the reservoir portion may be 10-20% of the total displacement range of the second bias member.

In accordance with an embodiment of the present disclosure a delivery device for administering a medical agent to a patient may comprise a base including a first side with a skin adhering face and a second side including a reservoir portion. The delivery device may further comprise a housing cover coupled to the base. The delivery device may further comprise a plunger displaceable within the reservoir portion. The delivery device may further comprise an infusion set connector in fluid communication with a fluid pathway in an insert disposed at a reservoir outlet of the reservoir portion. The delivery device may further comprise an activation assembly configured to be actuated from an inactive state where flow from the reservoir portion is blocked and the plunger is inhibited from displacing to an activated state where a flow path through the insert to the delivery sharp is established and the plunger is free to displace. The delivery device may further comprise a bias member configured to urge the plunger toward the reservoir outlet.

In some embodiments, the activation assembly may include a lock which presents a mechanical interference to displacement of the plunger when the activation assembly is in the inactive state. In some embodiments, activation assembly may include a displaceable plug. In some embodiments, the activation assembly may include a bias member disposed between a head of the plug and an insert disposed at an outlet of the reservoir portion. In some embodiments, the activation assembly may include a plug having a first position in which the plug blocks all flow through an insert disposed at an outlet of the reservoir portion and a second position in which a flow path through the insert to the at least one delivery sharp is established. In some embodiments, the activation assembly may include a plug bias member configured to urge the plug from the first position to the second position, the activation assembly further comprising a lock which prevents displacement of the plug to the second position until the lock is actuated. In some embodiments, the infusion set connector may form a portion of the base and include a face which is coplanar with the skin adhering face of the base. In some embodiments, the infusion set connector may be coupled to the rest of the delivery device via an expanse of infusion tubing. In some embodiments, the infusion tubing may between an inch and a meter long. In some embodiments, the infusion tubing may be at least a meter long. In some embodiments, the infusion set connector may include a connector sharp configured to pierce a septum of an infusion set. In some embodiments, the infusion site connector may include at least one coupling projection. In some embodiments, the infusion site connector may include a removable cap member. In some embodiments, the infusion site connector may be configured to mate with an infusion set assembly. The reservoir portion may be placed into fluidic communication with a delivery destination in the patient via the infusion set assembly when the infusion site connector is mated to the infusion set assembly. In some embodiments, the plunger may be coupled to a frame having a first end from which the plunger projects, an opposing second end, and side panels including guides. In some embodiments, the frame may include at least one coupling lip configured to engage a drive element of a filling fixture. In some embodiments, the reservoir portion may be filled with a medical agent selected from a list consisting of a vaccine, an antiviral, a retroviral, a peptide, an endocrine disorder drug, insulin, a diagnostic agent, an allergen, an overdose intervention drug, an opioid antagonist, naloxone, and a tuberculosis testing agent. In some embodiments, the delivery device further comprises a cover member coupled to the base and covering the at least one delivery sharp. In some embodiments, the activation assembly may include a lock which presents a mechanical interference to displacement of the plunger when the activation assembly is in the inactive state. The lock may include a least one portion which is configured to displace from a stowed state against the housing cover to a second state where the at least one portion extends a greater distance from the housing cover compared to the its position in the stowed state. In some embodiments, the delivery device may further comprise a flow limiter restriction upstream of the at least one delivery sharp. In some embodiments, the displacement of the bias member which occurs as the plunger is displaced to fully deliver the contents of the reservoir portion may be 10-20% of the total displacement range of the second bias member.

In accordance with another embodiment of the present disclosure, a delivery device for administering a medical agent to a patient may comprise a base including a first side with a skin adhering face and a second side including a reservoir portion. The delivery device may further comprise a housing cover coupled to the base. The delivery device may further comprise a plunger displaceable within the reservoir portion. The delivery device may further comprise at least one delivery sharp which may be actuatable from a stowed position in the at least one delivery sharp is disposed in recessed relationship to the skin adhering face of the base to a deployed position in which at least a portion of the at least one delivery sharp extends proud of the skin adhering face of the base. The delivery device may further comprise an activation assembly configured to be actuated from an inactive state where flow from the reservoir portion is blocked and the plunger is inhibited from displacing to an activated state where a flow path through the insert to the delivery sharp is established and the plunger is free to displace. The delivery device may further comprise a bias member configured to urge the plunger toward the reservoir outlet.

In some embodiments, the activation assembly may include a lock which presents a mechanical interference to displacement of the plunger when the activation assembly is in the inactive state. In some embodiments, the activation assembly may include a displaceable plug. In some embodiments, the activation assembly may include a bias member disposed between a head of the plug and an insert disposed at an outlet of the reservoir portion. In some embodiments, the activation assembly ay include a plug having a first position in which the plug blocks all flow through an insert disposed at an outlet of the reservoir portion and a second position in which a flow path through the insert to the at least one delivery sharp is established. In some embodiments, the activation assembly includes a plug bias member configured to urge the plug from the first position to the second position. The activation assembly may further comprise a lock which prevents displacement of the plug to the second position until the lock is actuated. In some embodiments, the at least one delivery sharp may be selected from a group consisting of an intramuscular delivery needle and a subcutaneous delivery needle. In some embodiments, the at least one delivery sharp may comprise an array of delivery sharps. In some embodiments, the at least one delivery sharp may be a pyramid shaped, silicon crystal, microneedle. In some embodiments, the at least one delivery sharp may be a pointed, silicon crystal, microneedle. In some embodiments, the at least one delivery sharp may comprise an array of microneedles. In some embodiments, the at least one delivery sharp may be oriented perpendicular to the skin adhering face of the delivery device. In some embodiments, the at least one delivery sharp may be oriented at an acute angle to the skin adhering face of the base. In some embodiments, the at least one delivery sharp may have a length of no more than one millimeter. In some embodiments, the plunger may be coupled to a frame having a first end from which the plunger projects, an opposing second end, and side panels including guides. In some embodiments, the frame may include at least one coupling lip configured to engage a drive element of a filling fixture. In some embodiments, the reservoir portion may be filled with a medical agent selected from a list consisting of a vaccine, an antiviral, a retroviral, a peptide, an endocrine disorder drug, insulin, a diagnostic agent, an allergen, an overdose intervention drug, an opioid antagonist, naloxone, and a tuberculosis testing agent. In some embodiments, the delivery device may further comprise a cover member coupled to the base and covering the at least one delivery sharp. In some embodiments, the activation assembly may include a lock which presents a mechanical interference to displacement of the plunger when the activation assembly is in the inactive state. The lock may include a least one portion which is configured to displace from a stowed state against the housing cover to a second state where the at least one portion extends a greater distance from the housing cover compared to the its position in the stowed state. In some embodiments, the delivery device may further comprise a flow limiter restriction upstream of the at least one delivery sharp. In some embodiments, the displacement of the bias member which occurs as the plunger is displaced to fully deliver the contents of the reservoir portion may be 10-20% of the total displacement range of the second bias member.

In accordance with an embodiment of the present disclosure a method of delivering a medical agent may comprise applying a delivery device to a patient. The method may further comprise penetrating the skin of the patient with at least one delivery sharp of the delivery device. The method may further comprise actuating a lock of the delivery device. The method may further comprise driving a plug, via a plug driver, from a flow preventing position, to a second position in which a flow path from a reservoir portion of the delivery device to the at least one delivery sharp is established. The method may further comprise dispensing contents of the reservoir portion out of the at least one delivery sharp by driving a plunger sled, via plunger sled driver, from a retracted position to a delivered position in which a plunger on the plunger sled is adjacent an outlet of the reservoir portion.

In some embodiments, the plug driver and plunger sled driver may be coil springs. In some embodiments, the plug driver and the plunger sled driver may be compression springs. In some embodiments, driving the plunger sled from the retracted position to the delivered position may comprise displacing the plunger sled along a guide portion of a base of the delivery device. In some embodiments, the plunger sled may be a rectilinear frame having a first end from which the plunger extends, and an opposing end including an aperture and driving the plunger sled from the retracted position to the delivered position may comprise displacing the aperture along a guide portion of the base of the delivery device. In some embodiments, the plunger sled may further comprise side panels with guides and driving the plunger sled from the retracted position to the delivered position may comprise displacing the guides along a guide surface formed as part of the base. In some embodiments, dispensing the contents of the reservoir portion may comprise dispensing an agent selected from a list consisting of a vaccine, an antiviral, a retroviral, a peptide, an endocrine disorder drug, insulin, a diagnostic agent, an allergen, an overdose intervention drug, an opioid antagonist, naloxone, and a tuberculosis testing agent. In some embodiments, penetrating the skin with the at least one delivery sharp comprises puncturing the skin with a delivery sharp selected from a list consisting of a subcutaneous needle and an intramuscular needle. In some embodiments, penetrating the skin with the at least one delivery sharp may comprise penetrating the skin with a microneedle array. In some embodiments, penetrating the skin with the at least one delivery sharp may comprise penetrating the skin with a plurality of pyramid sharped, silicon crystal microneedles no longer than one millimeter in length. In some embodiments, penetrating the skin with the at least one delivery sharp may comprise penetrating at least the stratum corneum and epidermis with the at least one delivery sharp. In some embodiments, penetrating the skin with the at least one delivery sharp may comprise penetrating the skin with the at least one delivery sharp at an angle substantially perpendicular to the skin surface. In some embodiments, penetrating the skin with the at least one delivery sharp may comprise penetrating the skin with the at least one delivery sharp at an acute angle relative to the skin surface. In some embodiments, actuating the lock may comprise removing the lock from the delivery device. In some embodiments, actuating the lock comprises displacing a portion of the lock from a stowed state in which the portion is against a housing of the delivery device to a second state in which the portion projects a greater distance from the housing and removing the lock from the delivery device. In some embodiments, driving the plug to the second position may comprise urging the plug against a stop surface provided by an interior face of a portion of a housing for the delivery device. In some embodiments, displacing the plug to the second position may comprise displacing a pin of the plug along a portion of a flow path in an elastomeric insert disposed at the outlet of the reservoir. In some embodiments, the plunger sled driver may be a coil spring and driving the plunger sled from the retracted position to the delivered position may comprise relaxing the coil spring over 10-20% of its total displacement range. In some embodiments, the method may further comprise removing a cover member and an adhesive backing from the delivery device. In some embodiments, the method may further comprise limiting the flow rate of fluid out of the at least one delivery sharp with a flow limiting restriction in the flow path from the reservoir to the at least one delivery sharp. In some embodiments, penetrating the skin with the at least one delivery sharp may comprise actuating the at least on delivery sharp from a stowed state within the delivery device to an exposed state in which at least a portion of the at least one delivery sharp extends out of the delivery device.

In accordance with another embodiment of the present disclosure a method of delivering opioid antagonist to an overdose victim may comprise applying a delivery device to a patient. The method may further comprise penetrating the skin of the patient with at least one delivery sharp of the delivery device to at least subcutaneous tissue. The method may further comprise actuating a lock of the delivery device. The method may further comprise driving a plug, via a plug driver, from a flow preventing position, to a second position in which a flow path from a reservoir portion of the delivery device to the at least one delivery sharp is established. The method may further comprise dispensing the opioid antagonist from the reservoir portion out of the at least one delivery sharp by driving a plunger sled, via plunger sled driver, from a retracted position to a delivered position in which a plunger on the plunger sled is adjacent an outlet of the reservoir portion.

In some embodiments, the method may further comprise applying a second delivery device to the victim and dispensing the opioid antagonist from the reservoir portion to the user. The flow rate from the second delivery device being a faction of the flow rate from the first delivery device. In some embodiments, the plug driver and plunger sled driver may be compression springs. In some embodiments, the plug driver and plunger sled driver may be coil springs. In some embodiments, driving the plunger sled from the retracted position to the delivered position may comprise displacing the plunger sled along a guide portion of a base of the delivery device. In some embodiments, the plunger sled may be a rectilinear frame having a first end from which the plunger extends, and an opposing end including an aperture and driving the plunger sled from the retracted position to the delivered position comprises displacing the aperture along a guide portion of the base of the delivery device. In some embodiments, the plunger sled may further comprise side panels with guides and driving the plunger sled from the retracted position to the delivered position may comprise displacing the guides along a guide surface formed as part of the base. In some embodiments, dispensing the opioid antagonist from the reservoir portion may comprise dispensing naloxone from the reservoir portion. In some embodiments, penetrating the skin with the at least one delivery sharp may comprise puncturing the skin with a delivery sharp selected from a list consisting of a subcutaneous needle and an intramuscular needle. In some embodiments, penetrating the skin with the at least one delivery sharp may comprise penetrating the skin with an array of delivery sharps. In some embodiments, penetrating the skin with the at least one delivery sharp may comprise penetrating the skin with the at least one delivery sharp at an angle substantially perpendicular to the skin surface. In some embodiments, penetrating the skin with the at least one delivery sharp may comprise penetrating the skin with the at least one delivery sharp at an acute angle relative to the skin surface. In some embodiments, penetrating the skin with the at least one delivery sharp may comprise actuating the at least on delivery sharp from a stowed state within the delivery device to an exposed state in which at least a portion of the at least one delivery sharp extends out of the delivery device. In some embodiments, actuating the lock may comprise removing the lock from the delivery device. In some embodiments, actuating the lock may comprise displacing a portion of the lock from a stowed state in which the portion is against a housing of the delivery device to a second state in which the portion projects a greater distance from the housing and removing the lock from the delivery device. In some embodiments, driving the plug to the second position may comprise urging the plug against a stop surface provided by an interior face of a portion of a housing for the delivery device. In some embodiments, displacing the plug to the second position may comprise displacing a pin of the plug along a portion of a flow path in an elastomeric insert disposed at the outlet of the reservoir. In some embodiments, the plunger sled driver may be a coil spring and driving the plunger sled from the retracted position to the delivered position may comprise relaxing the coil spring over 10-20% of its total displacement range. In some embodiments, the method may further comprise removing a cover member and an adhesive backing from the delivery device. In some embodiments, the method may further comprise limiting the flow rate of fluid out of the at least one delivery sharp with a flow limiting restriction in the flow path from the reservoir to the at least one delivery sharp.

In accordance with an embodiment of the present disclosure a method of delivering a medical agent may comprise applying a delivery device to a patient. The method may further comprise coupling an infusion set connector to an infusion set base in the skin of the patient. The method may further comprise actuating a lock of the delivery device. The method may further comprise driving a plug, via a plug driver, from a flow preventing position, to a second position in which a flow path from a reservoir portion of the delivery device to the at least one delivery sharp is established. The method may further comprise dispensing contents of the reservoir portion out of the at least one delivery sharp by driving a plunger sled, via plunger sled driver, from a retracted position to a delivered position in which a plunger on the plunger sled is adjacent an outlet of the reservoir portion.

In some embodiments, the plug driver and plunger sled driver may be compression springs. In some embodiments, the plug driver and the plunger sled drive may be coil springs. In some embodiments, driving the plunger sled from the retracted position to the delivered position may comprise displacing the plunger sled along a guide portion of a base of the delivery device. In some embodiments, the plunger sled may be a rectilinear frame having a first end from which the plunger extends, and an opposing end including an aperture and driving the plunger sled from the retracted position to the delivered position comprises displacing the aperture along a guide portion of the base of the delivery device. In some embodiments, the plunger sled may further comprise side panels with guides and driving the plunger sled from the retracted position to the delivered position may comprise displacing the guides along a guide surface formed as part of the base. In some embodiments, dispensing the contents of the reservoir portion may comprise dispensing an agent selected from a list consisting of a vaccine, an antiviral, a retroviral, a peptide, an endocrine disorder drug, insulin, a diagnostic agent, an allergen, an overdose intervention drug, an opioid antagonist, naloxone, and a tuberculosis testing agent. In some embodiments, penetrating the skin with the at least one delivery sharp may comprise puncturing the skin with a delivery sharp selected from a list consisting of a subcutaneous needle and an intramuscular needle. In some embodiments, penetrating the skin with the at least one delivery sharp may comprise penetrating the skin with a microneedle array. In some embodiments, penetrating the skin with the at least one delivery sharp may comprise penetrating the skin with a plurality of pyramid sharped, silicon crystal microneedles no longer than one millimeter in length. In some embodiments, penetrating the skin with the at least one delivery sharp may comprise penetrating at least the stratum corneum and epidermis with the at least one delivery sharp. In some embodiments, penetrating the skin with the at least one delivery sharp may comprise penetrating the skin with the at least one delivery sharp at an angle substantially perpendicular to the skin surface. In some embodiments, penetrating the skin with the at least one delivery sharp may comprise penetrating the skin with the at least one delivery sharp at an acute angle relative to the skin surface. In some embodiments, actuating the lock may comprise removing the lock from the delivery device. In some embodiments, actuating the lock may comprise displacing a portion of the lock from a stowed state in which the portion is against a housing of the delivery device to a second state in which the portion projects a greater distance from the housing and removing the lock from the delivery device. In some embodiments, driving the plug to the second position may comprise urging the plug against a stop surface provided by an interior face of a portion of a housing for the delivery device. In some embodiments, displacing the plug to the second position may comprise displacing a pin of the plug along a portion of a flow path in an elastomeric insert disposed at the outlet of the reservoir. In some embodiments, the plunger sled driver may be a coil spring and driving the plunger sled from the retracted position to the delivered position may comprise relaxing the coil spring over 10-20% of its total displacement range. In some embodiments, the method may further comprises removing a cover member and an adhesive backing from the delivery device. In some embodiments, the method may further comprise limiting the flow rate of fluid out of the at least one delivery sharp with a flow limiting restriction in the flow path from the reservoir to the at least one delivery sharp. In some embodiments, penetrating the skin with the at least one delivery sharp may comprise actuating the at least one delivery sharp from a stowed state within the delivery device to an exposed state in which at least a portion of the at least one delivery sharp extends out of the delivery device.

In accordance with another embodiment of the present disclosure an agent administration device may comprise a housing. The device may further comprise a sharp assembly including a delivery sharp. The sharp assembly may be reciprocally displaceable along a guide channel of the housing. The device may further comprise an access port in fluid communication with the delivery sharp. The device may further comprise an actuation assembly configured drive the sharp assembly, via urging of a single bias member, from a storage state in which the delivery sharp is within the housing, through a first extended position in which the delivery sharp extends a maximum distance from the housing and to a partially retracted position in which the delivery sharp extends a lesser distance from the housing.

In some embodiments, the housing may include a base portion in which the guide channel is defined and the housing may include a cover portion. The access port may be included as part of the cover portion. In some embodiments, the guide channel may define an insertion angle of the delivery sharp. In some embodiments, the insertion angle may be 5°-45°. In some embodiments, the insertion angle may be no greater than 35°. In some embodiments, the access port may include a piercable septum. In some embodiments, the delivery sharp may be a needle of no larger than 30 gauge. In some embodiments, the bias member may be a torsion spring. In some embodiments, the delivery sharp may include a point which may be rotationally clocked to a 12 o'clock position. In some embodiments, the maximum distance may be sufficient to penetrate transcutaneously into a patient. In some embodiments, the lesser distance may correspond to a penetration depth in a patient suitable for intradermal administration of agent. In some embodiments, the agent may include at least one vaccine. In some embodiments, the agent may include at least one SARS-COV-2 vaccine. In some embodiments, the SARS-COV-2 vaccine may be selected from a group consisting of an attenuated live virus vaccine, inactivated virus vaccine, non-replicating viral vector vaccine, nucleic acid based vaccine, RNA based vaccine, mRNA based vaccine, saRNA based vaccine DNA based vaccine, DNA plasmid vaccine, recombinant protein vaccine, protein subunit vaccine, spike protein based vaccine, nanoparticle vaccine, and virus like particle vaccine. In some embodiments, the device may further comprise a removable lock member configured to hold the sharp assembly in the storage state when installed in the device. In some embodiments, the lock member may be coupled to a removable cover strip attached to the housing and covering the access port. In some embodiments, the actuation assembly may include the single bias member, a pivot pin pivotally retained in the housing, and a guide pin coupled to the pivot pin and the sharp assembly. In some embodiments, the housing may define a guide track, the guide pin being displaceable along the guide track.

In accordance with yet another embodiment of the present disclosure, an agent administration device may comprise a housing including a guide channel. The device may further comprise a sharp assembly including a delivery sharp. The sharp assembly may be reciprocally displaceable along the guide channel. The device may further comprise an access port in fluid communication with the delivery sharp. The device may further comprise an actuation assembly coupled to the sharp assembly and including a guide pin displaceable along an arcuate path from a first position to a stop. The sharp assembly may be displaced from a storage state in which the delivery sharp is within the housing, to an administration position in which the delivery sharp extends a target distance out of the housing as the guide pin displaces from the first position to the stop. The delivery sharp may extend a distance greater than the target distance as the guide pin is displaced along an intermediate portion of the path.

In some embodiments, the housing may include a base portion in which the guide channel is defined and the housing may include a cover portion. The access port may be included as part of the cover portion. In some embodiments, the guide channel may define an insertion angle of the delivery sharp. In some embodiments, the insertion angle may be 5°-45°. In some embodiments, the insertion angle may be no greater than 35°. In some embodiments, the access port may include a piercable septum. In some embodiments, the delivery sharp may be a needle of no larger than 30 gauge. In some embodiments, the delivery sharp may include a point which is rotationally clocked to a 12 o'clock position. In some embodiments, the distance greater than the target distance may be a distance sufficient to penetrate transcutaneously into a patient. In some embodiments, the target distance may correspond to a penetration depth in a patient suitable for intradermal administration of agent. In some embodiments, the agent may include at least one vaccine. In some embodiments, the agent may include at least one SARS-COV-2 vaccine. In some embodiments, the SARS-COV-2 vaccine may be selected from a group consisting of an attenuated live virus vaccine, inactivated virus vaccine, non-replicating viral vector vaccine, nucleic acid based vaccine, RNA based vaccine, mRNA based vaccine, saRNA based vaccine DNA based vaccine, DNA plasmid vaccine, recombinant protein vaccine, protein subunit vaccine, spike protein based vaccine, nanoparticle vaccine, and virus like particle vaccine. In some embodiments, the device may further comprise a removable lock member configured to hold the sharp assembly in the storage state when installed in the device. In some embodiments, the lock member may be coupled to a removable cover strip attached to the housing and covering the access port. In some embodiments, the actuation assembly may include a bias member, a pivot pin pivotally retained in the housing, the guide pin and a linkage coupling which couples the actuation assembly to the sharp assembly. In some embodiments, the housing may define a guide track within which a portion of the guide pin is disposed, the guide track defining the arcuate path.

In accordance with yet another embodiment of the present disclosure an agent administration device may comprise a housing. The device may further comprise a sharp assembly including a delivery sharp. The sharp assembly may be reciprocally displaceable along a guide channel of the housing. The device may further comprise an access port in fluid communication with the delivery sharp. The device may further comprise an actuation assembly including a guide pin coupled to the sharp assembly. The actuation assembly may be configured to drive the sharp assembly from a storage state in which the delivery sharp is within the housing, through a first extended position in which the delivery sharp extends a maximum distance from the housing and to a partially retracted position in which the delivery sharp extends a lesser distance from the housing via spring loaded displacement of the guide pin along an arcuate path.

In some embodiments, the housing may include a base portion in which the guide channel is defined and the housing may include a cover portion. The access port may be included as part of the cover portion. In some embodiments, the guide channel may define an insertion angle of the delivery sharp. In some embodiments, the insertion angle may be 5°-45°. In some embodiments, the insertion angle may be no greater than 35°. In some embodiments, the access port may include a piercable septum. In some embodiments, the delivery sharp may be a needle of no larger than 30 gauge. In some embodiments, the delivery sharp may include a point which is rotationally clocked to a 12 o'clock position. In some embodiments, the maximum distance may be a distance sufficient to penetrate transcutaneously into a patient. In some embodiments, the target distance may correspond to a penetration depth in a patient suitable for intradermal administration of agent. In some embodiments, the agent may include at least one vaccine. In some embodiments, the agent may include at least one SARS-COV-2 vaccine. In some embodiments, the SARS-COV-2 vaccine may be selected from a group consisting of an attenuated live virus vaccine, inactivated virus vaccine, non-replicating viral vector vaccine, nucleic acid based vaccine, RNA based vaccine, mRNA based vaccine, saRNA based vaccine DNA based vaccine, DNA plasmid vaccine, recombinant protein vaccine, protein subunit vaccine, spike protein based vaccine, nanoparticle vaccine, and virus like particle vaccine. In some embodiments, the device may further comprise a removable lock member configured to hold the sharp assembly in the storage state when installed in the device. In some embodiments, the lock member may be coupled to a removable cover strip attached to the housing and covering the access port. In some embodiments, the actuation assembly may include the guide pin, a bias member configured to assert a spring load on the guide pin, and a pivot pin pivotally retained in the housing and coupled to the guide pin. In some embodiments, the housing may define a guide track within which a portion of the guide pin is disposed. The guide track may define the arcuate path.

In accordance with yet another embodiment of the present disclosure an agent administration device may comprise a housing including a guide. The device may further comprise a sharp assembly including a delivery sharp. The sharp assembly may be reciprocally displaceable along the guide. The device may further comprise an access port in fluid communication with the delivery sharp. The device may further comprise an actuation assembly coupled to the sharp assembly and including a guide pin continuously displaceable along a path from a starting position to a stop. The sharp assembly may be displaced from a storage state as the guide pin displaces from the first position, to an administration state when the guide pin contacts the stop in which the delivery sharp extends a target distance out of the housing. The delivery sharp may extend a distance greater than the target distance as the guide pin is displaced along an intermediate portion of the path.

In some embodiments, the housing may include a base portion in which the guide is defined and the housing may include a cover portion. The access port may be included as part of the cover portion. In some embodiments, the guide may define an insertion angle of the delivery sharp. In some embodiments, the insertion angle may be 5°-45°. In some embodiments, the insertion angle may be no greater than 35°. In some embodiments, the access port may include a piercable septum. In some embodiments, the delivery sharp may be a needle of no larger than 30 gauge. In some embodiments, the delivery sharp may include a point which is rotationally clocked to a 12 o'clock position. In some embodiments, the distance greater than the target distance may be a distance sufficient to penetrate transcutaneously into a patient. In some embodiments, the target distance may correspond to a penetration depth in a patient suitable for intradermal administration of agent. In some embodiments, the agent may include at least one vaccine. In some embodiments, the agent may include at least one SARS-COV-2 vaccine. In some embodiments, the SARS-COV-2 vaccine may be selected from a group consisting of an attenuated live virus vaccine, inactivated virus vaccine, non-replicating viral vector vaccine, nucleic acid based vaccine, RNA based vaccine, mRNA based vaccine, saRNA based vaccine DNA based vaccine, DNA plasmid vaccine, recombinant protein vaccine, protein subunit vaccine, spike protein based vaccine, nanoparticle vaccine, and virus like particle vaccine. In some embodiments, the device may further comprise a removable lock member configured to hold the sharp assembly in the storage state when installed in the device. In some embodiments, the lock member may be coupled to a removable cover strip attached to the housing and covering the access port. In some embodiments, the actuation assembly may include the guide pin, a bias member configured to assert a bias force on the guide pin, and a pivot pin pivotally retained in the housing and coupled to the guide pin. In some embodiments, the housing may define an arcuate guide track within which a portion of the guide pin is disposed. The portion of the guide pin may displace along the arcuate track as the guide pin displaces along the path from the starting position to the stop.

In accordance with another embodiment of the present disclosure an agent administration device may comprise a housing including a guide. The device may further comprise a sharp assembly including at least one delivery sharp. The sharp assembly may be reciprocally displaceable along the guide. The device may further comprise an access port in fluid communication with the delivery sharp. The device may further comprise an actuation assembly coupled to the sharp assembly and including a guide pin. The sharp assembly may be displaced from a storage state to an administration state in which the at least one delivery sharp extends a target distance out of the housing as the guide pin displaces from a starting position to a stop in a single direction. The at least one delivery sharp may extend a distance greater than the target distance as the guide pin is displaced along an intermediate portion of the path.

In some embodiments, the single direction may be selected from a group consisting of a clockwise direction and a counterclockwise direction. In some embodiments, the single direction may be a direction of rotational motion. In some embodiments, the housing may include a base portion in which the guide is defined and the housing may include a cover portion. The access port may be included as part of the cover portion. In some embodiments, the guide may define an insertion angle of the delivery sharp. In some embodiments, the insertion angle may be 5°-45°. In some embodiments, the insertion angle may be no greater than 35°. In some embodiments, the access port may include a piercable septum. In some embodiments, the delivery sharp may be a needle of no larger than 30 gauge. In some embodiments, the delivery sharp may include a point which is rotationally clocked to a 12 o'clock position. In some embodiments, the distance greater than the target distance may be a distance sufficient to penetrate transcutaneously into a patient. In some embodiments, the target distance may correspond to a penetration depth in a patient suitable for intradermal administration of agent. In some embodiments, the agent may include at least one vaccine. In some embodiments, the agent may include at least one SARS-COV-2 vaccine. In some embodiments, the SARS-COV-2 vaccine may be selected from a group consisting of an attenuated live virus vaccine, inactivated virus vaccine, non-replicating viral vector vaccine, nucleic acid based vaccine, RNA based vaccine, mRNA based vaccine, saRNA based vaccine DNA based vaccine, DNA plasmid vaccine, recombinant protein vaccine, protein subunit vaccine, spike protein based vaccine, nanoparticle vaccine, and virus like particle vaccine. In some embodiments, the device may further comprise a removable lock member configured to hold the sharp assembly in the storage state when installed in the device. In some embodiments, the lock member may be coupled to a removable cover strip attached to the housing and covering the access port. In some embodiments, the actuation assembly may include the guide pin, a bias member configured to assert a bias force on the guide pin, and a pivot pin pivotally retained in the housing and coupled to the guide pin. In some embodiments, the housing may define an arcuate guide track within which a portion of the guide pin is disposed. The portion of the guide pin may displace along the arcuate track as the guide pin displaces along the path from the starting position to the stop.

In accordance with another embodiment of the present disclosure a drug delivery device may comprise a housing. The device may further comprise a sharp assembly including a delivery sharp. The sharp assembly may be displaceable through an actuation sequence from a storage state in which the delivery sharp is within the housing, through a first extended position in which the delivery sharp extends a maximum distance from the housing and to a second extended position in which the delivery sharp extends a lesser distance from the housing. The device may further comprise an access port in fluid communication with the delivery sharp. The device may further comprise an actuator assembly having a bias member, a guide pin configured for displacement along a guide track, and a linkage coupling the actuation assembly to the sharp assembly such that displacement of the guide pin engenders displacement of the sharp assembly. When the sharp assembly is in the storage state, the bias member may urge the guide pin to a terminus of the guide track. The sharp assembly may be displaced through the actuation sequence as the guide pin is displaced to the terminus via the linkage.

In accordance with yet another embodiment of the present disclosure a drug delivery device may comprise a housing including a base portion and a cover portion. The device may further comprise a sharp assembly displaceable along a guide channel and including a delivery sharp. The device may further comprise an access port in fluid communication with the delivery sharp. The device may further comprise an actuator assembly having a bias member, a guide pin configured for displacement along a guide track, and a linkage coupling the actuation assembly to the sharp assembly such that displacement of the guide pin engenders displacement of the sharp assembly. The device may further comprise a lock member including a portion that projects into the guide channel. The lock member may block displacement of the sled and may hold the bias member in a stressed state when the delivery sharp is in a storage state. Upon removal of the lock member, the bias member may be configured to restore to a less stressed state and urge the guide pin along the guide track to a terminus of the guide track. The sharp assembly displacing through a first extended position in which the delivery sharp extends a maximum distance from the housing and to a second extended position in which the delivery sharp extends a second distance from the housing as the guide pin displaces to the terminus of the guide track.

In accordance with another embodiment of the present disclosure an agent administration device may comprise a housing including a base body and a slide body displaceable relative to the base body from a first position to a second position. The slide body may include a cam. The device may further comprise an elastomeric housing and including a chamber. The device may further comprise a pressurized agent containing ampoule including a frangible which is disposed within the chamber. The elastomeric housing may form a seal against the ampoule upstream of the frangible. The device may further comprise an outlet assembly including a ram, a cam follower, and a nozzle portion having at least one microneedle in fluid communication with the chamber. The outlet assembly may be configured to displace from a storage state to a deployed state via interaction of the cam and cam follower as the slide body displaces from the first position to the second position. The ram may be configured to be driven into the elastomeric housing and break the frangible as the outlet assembly is displaced toward the deployed state.

In some embodiments, the elastomeric housing may include a port with a receptacle. The outlet assembly may include a portion which is coupled into the receptacle. In some embodiments, the base body may define a holster and at least a portion of the ampoule may be disposed within the holster. In some embodiments, the base body may include at least one guide track and the slide body may include at least one rail which moves along the guide track with displacement of the slide body. In some embodiments, the base body may include a latch configured for actuation between a first state and a second state. The latch may block displacement of the slide body when in the first state and permit displacement of the slide body in the second state. In some embodiments, the latch may be configured to resiliently deflect from the first state to the second state. In some embodiments, the slide body may comprise a pair of cams and a cross piece extending between the cams. In some embodiments, the slide body may further comprise a second cam and the outlet assembly may include a second cam follower. In some embodiments, the outlet assembly may be configured to pivot from the storage state to the deployed state. In some embodiments, the cam may include a ramped section and a plateau section. The ramped section may be configured to drive the cam follower towards a face of the base portion configured to be adhered to the skin of a patient as the slide body is displaced from the first position toward the second position. In some embodiments, when the slide body is in the second position, the cam follower may be in contact with the plateau portion and the plateau portion may inhibit further displacement of the cam follower. In some embodiments, the plateau portion may present a mechanical interference to further displacement of the cam follower. In some embodiments, the base portion may include a skin depressor. In some embodiments, the device may further comprise an injection port. The injection port may be disposed over a tail including a second frangible that extends from the ampoule. The device may further comprise an elastomeric sleeve surrounding a portion of the injection port, the tail, and a main body of the ampoule. In some embodiments, the injection port may be pivotally displaceable from a first position to a second position. The second frangible may be configured to break with displacement of the injection portion from the first position to the second position.

In accordance with yet another embodiment of the present disclosure an agent administration device may comprise a base body. The device may further comprise a slide body coupled to the base body and displaceable relative to the base body from a first position to a second position. The slide body may include a cam. The device may further comprise an elastomeric housing and including a chamber. The device may further comprise a pressurized agent containing ampoule including a frangible which is disposed within the chamber. The elastomeric housing may form a seal against the ampoule upstream of the frangible. The device may further comprise an outlet assembly including a ram, a cam follower, and a nozzle portion having at least one microneedle in fluid communication with the chamber. The outlet assembly may be configured to displace from a storage state to a deployed state via interaction of the cam and cam follower as the slide body displaces from the first position to the second position. The ram may be configured to be driven into the elastomeric housing and break the frangible as the outlet assembly is displaced toward the deployed state.

In some embodiments, the elastomeric housing may include a port with a receptacle. The outlet assembly may include a portion which is coupled into the receptacle. In some embodiments, the base body may define a holster and at least a portion of the ampoule may be disposed within the holster. In some embodiments, the base body may include at least one guide track and the slide body may include at least one rail which moves along the guide track with displacement of the slide body. In some embodiments, the base body may include a latch configured for actuation between a first state and a second state. The latch may block displacement of the slide body when in the first state and permit displacement of the slide body in the second state. In some embodiments, the latch may be configured to resiliently deflect from the first state to the second state. In some embodiments, the slide body may comprise a pair of cams and a cross piece extending between the cams. In some embodiments, the slide body may further comprise a second cam and the outlet assembly may include a second cam follower. In some embodiments, the outlet assembly may be configured to pivot from the storage state to the deployed state. In some embodiments, the cam may include a ramped section and a plateau section. The ramped section may be configured to drive the cam follower towards a face of the base portion configured to be adhered to the skin of a patient as the slide body is displaced from the first position toward the second position. In some embodiments, when the slide body is in the second position, the cam follower may be in contact with the plateau portion and the plateau portion may inhibit further displacement of the cam follower. In some embodiments, the base portion may include a skin depressor. In some embodiments, the ampoule may be constructed out of glass. In some embodiments, the device may further comprise an injection port. The injection port may be disposed over a tail including a second frangible that extends from the ampoule. The device may further comprise an elastomeric sleeve surrounding a portion of the injection port, the tail, and a main body of the ampoule. In some embodiments, the injection port may be pivotally displaceable from a first position to a second position. The second frangible may be configured to break with displacement of the injection portion from the first position to the second position.

In accordance with another embodiment of the present disclosure an agent administration device may comprise a pressurized agent containing ampoule including a frangible. The device may further comprise an elastomeric housing surrounding and forming a seal against a portion of the ampoule including the frangible. The device may further comprise an outlet assembly including a ram, a cam follower, and a nozzle portion having at least one microneedle in fluid communication with the chamber. The device may further comprise a housing including a displaceable body having a cam. The outlet assembly may be configured to displace from a storage state to a deployed state via interaction of the cam and cam follower as the displaceable body displaces from a first position to a second position relative to a base portion of the housing. The ram may be configured to be driven into the elastomeric housing and break the frangible as the outlet assembly is displaced toward the deployed state.

In some embodiments, the elastomeric housing may include a port with a receptacle. The outlet assembly may include a portion which is coupled into the receptacle. In some embodiments, the base body may define a holster and at least a portion of the ampoule may be disposed within the holster. In some embodiments, the base portion may include at least one guide track and the displaceable body may include at least one rail which moves along the guide track with displacement of the displaceable body. In some embodiments, the housing may include a latch configured for actuation between a first state and a second state. The latch may block displacement of the displaceable body when in the first state and may permit displacement of the displaceable body in the second state. In some embodiments, the latch may be configured to resiliently deflect from the first state to the second state. In some embodiments, the displaceable body may comprise a pair of cams and a cross piece extending between the cams. In some embodiments, the cross piece may be disposed over a portion of the ampoule downstream of the frangible when the displaceable body is in the first position and may be displaced over a portion of the ampoule upstream of the frangible as the displaceable body is displaced to the second position. In some embodiments, the outlet assembly may include a second cam follower and the displaceable body may further comprise a second cam configured to interact with the second cam follower as the displaceable body is displaced from the first position to the second position. In some embodiments, the outlet assembly may be configured to pivot from the storage state to the deployed state. In some embodiments, the cam may include a ramped section and a plateau section. The ramped section may be configured to drive the cam follower towards a face of the base portion configured to be adhered to the skin of a patient as the displaceable body is displaced from the first position toward the second position. In some embodiments, when the displaceable body is in the second position, the cam follower may be in contact with the plateau portion and the plateau portion may inhibit further displacement of the cam follower. In some embodiments, the housing may include a skin depressor. In some embodiments, the ampoule is constructed out of glass. In some embodiments, the device may further comprise an injection port. The injection port may be disposed over a tail including a second frangible that extends from the ampoule. The device may further comprise an elastomeric sleeve surrounding a portion of the injection port, the tail, and a main body of the ampoule. In some embodiments, the injection port may be pivotally displaceable from a first position to a second position. The second frangible may be configured to break with displacement of the injection portion from the first position to the second position.

In accordance with another embodiment of the present disclosure an agent administration device may comprise a pressurized agent containing ampoule including a frangible. The device may further comprise an elastomeric housing having a chamber surrounding and forming a seal against a portion of the ampoule that includes the frangible. The device may further comprise an outlet assembly pivotally displaceable between a storage state and a deployed state and including a ram, a cam follower, and a nozzle having at least one microneedle in fluid communication with the chamber. The device may further comprise a housing including a displaceable body having a cam. The cam may be configured to engender displacement of the cam follower and pivoting of the outlet assembly to the deployed state as the displaceable body is displaced from a first position to a second position on the housing. At least a portion of the elastomeric housing may be in a displacement path of the ram as the outlet assembly is pivoted to the deployed state. The ram may be configured exert a frangible breaking force on the ampoule as the ram is driven into the at least a portion of the elastomeric housing.

In some embodiments, the elastomeric housing may include a port with a receptacle. The outlet assembly may include a portion which may be coupled into the receptacle. In some embodiments, the housing may define a holster and at least a portion of the ampoule may be disposed within the holster. In some embodiments, the housing may include at least one guide track and the displaceable body may include at least one rail which moves along the guide track with displacement of the displaceable body. In some embodiments, the housing may include a latch configured for actuation between a first state and a second state. The latch may block displacement of the displaceable body when in the first state and may permit displacement of the displaceable body in the second state. In some embodiments, the latch may be configured to resiliently deflect from the first state to the second state. In some embodiments, the displaceable body may comprise a pair of cams and a cross piece extending between the cams. In some embodiments, the cross piece may be disposed over a portion of the ampoule downstream of the frangible when the displaceable body is in the first position and is displaced over a portion of the ampoule upstream of the frangible as the displaceable body is displaced to the second position. In some embodiments, the outlet assembly may include a second cam follower and the displaceable body may further comprise a second cam configured to interact with the second cam follower as the displaceable body is displaced from the first position to the second position. In some embodiments, the outlet assembly may be configured to pivot about a pivot axis which extends through a portion of the nozzle. In some embodiments, the cam may include a ramped section and a plateau section. The ramped section may be configured to drive the cam follower towards a face of the housing configured to be adhered to the skin of a patient as the displaceable body is displaced from the first position toward the second position. In some embodiments, when the displaceable body is in the second position, the cam follower may be in contact with the plateau portion and the plateau portion may inhibit further displacement of the cam follower. In some embodiments, the housing may include a skin depressor. In some embodiments, the ampoule may be constructed out of glass. In some embodiments, the device may further comprise an injection port. The injection port may be disposed over a tail including a second frangible that extends from the ampoule. The device may further comprise an elastomeric sleeve surrounding a portion of the injection port, the tail, and a main body of the ampoule. In some embodiments, the injection port may be pivotally displaceable from a first position to a second position. The second frangible may be configured to break with displacement of the injection portion from the first position to the second position.

In accordance with another embodiment of the present disclosure an agent administration device may comprise a pressurized agent containing ampoule including a frangible. The device may further comprise an elastomeric boot disposed on and sealing against a region of the ampoule that includes the frangible. The device may further comprise an outlet assembly including a ram, a cam follower, a nozzle in communication with the region via a flow path extending through the boot, and a delivery sharp extending from the nozzle. The device may further comprise a housing including a first portion and a second portion that includes a cam and is displaceable relative to the first portion from a first position to a second position. The cam may be configured to direct displacement of the outlet assembly from a storage state to a deployed state as the second portion is displaced to the second position and the cam is displaced over the cam follower. The ram may be configured exert a frangible breaking force on the ampoule through the boot as the outlet assembly is displaced to the deployed state.

In some embodiments, the boot may include a port with a receptacle. The outlet assembly may include a portion which is coupled into the receptacle. In some embodiments, the first portion of the housing may define a holster and at least a portion of the ampoule may be disposed within the holster. In some embodiments, the first portion of the housing may include at least one guide track and the displaceable body may include at least one rail which moves along the guide track with displacement of the displaceable body. In some embodiments, the housing may include a latch configured for actuation between a first state and a second state. The latch may block displacement of the displaceable body when in the first state and may permit displacement of the displaceable body in the second state. In some embodiments, the latch may be configured to resiliently deflect from the first state to the second state. In some embodiments, the second portion of the housing may comprise a pair of cams and a cross piece extending between the cams. In some embodiments, the cross piece may be disposed over a portion of the ampoule downstream of the frangible when the second portion of the housing is in the first position and is displaced over a portion of the ampoule upstream of the frangible as the second portion of the housing is displaced to the second position. In some embodiments, the outlet assembly may include a second cam follower and the second portion of the housing may further comprise a second cam configured to interact with the second cam follower as the second portion of the housing is displaced from the first position to the second position. In some embodiments, the outlet assembly may be configured to pivot from the storage state to the deployed state. In some embodiments, the cam may include a ramped section and a plateau section. The ramped section may be configured to drive the cam follower towards a face of the housing configured to be adhered to the skin of a patient as the second portion of the housing is displaced from the first position toward the second position. In some embodiments, when the second portion of the housing is in the second position, the cam follower may be in contact with the plateau portion and the plateau portion may inhibit further displacement of the cam follower. In some embodiments, the housing may include a skin depressor. In some embodiments, the ampoule may be constructed out of glass. In some embodiments, the device may further comprise an injection port. The injection port may be disposed over a tail including a second frangible that extends from the ampoule. The device may further comprise an elastomeric sleeve surrounding a portion of the injection port, the tail, and a main body of the ampoule. In some embodiments, the injection port may be pivotally displaceable from a first position to a second position. The second frangible may be configured to break with displacement of the injection portion from the first position to the second position.

In accordance with an embodiment of the present disclosure an agent administration device may comprise a housing including a base body and a slide body including a cam which displaces along a displacement path as the slide body is displaced from a first position to a second position. The device may further comprise a pressurized agent containing ampoule including a frangible. The device may further comprise an elastomeric housing covering and sealing against a portion of the ampoule and including a chamber. The frangible may be disposed in the chamber. The device may further comprise an outlet assembly including a nozzle portion having at least one microneedle and being in fluid communication with the chamber, a ram, and a cam follower at least partially disposed in the displacement path of the cam when the outlet assembly is in a storage state. The outlet assembly may be configured to pivot from the storage state to a deployed state in which the at least one microneedle is outside of the housing via interaction of the cam and cam follower as the slide body displaces from the first position to the second position. The ram may be driven into the elastomeric housing breaking the frangible as the outlet assembly is pivoted toward the deployed state.

In some embodiments, the elastomeric housing may include a port with a receptacle. The outlet assembly may include a portion which may be coupled into the receptacle. In some embodiments, the base body may define a holster and at least a portion of the ampoule may be disposed within the holster. In some embodiments, the base body may include at least one guide track and the slide body may include at least one rail which moves along the guide track with displacement of the slide body. In some embodiments, the housing may include a latch configured for actuation between a first state and a second state. The latch may block displacement of the displaceable body when in the first state and may permit displacement of the displaceable body in the second state. In some embodiments, the latch may be configured to resiliently deflect from the first state to the second state. In some embodiments, the slide body may comprise a pair of cams and a cross piece extending between the cams. In some embodiments, the cross piece may be disposed over a portion of the ampoule downstream of the frangible when the slide body is in the first position and may be displaced over a portion of the ampoule upstream of the frangible as the slide body is displaced to the second position. In some embodiments, the outlet assembly may include a second cam follower and the slide body may further comprise a second cam configured to interact with the second cam follower as the slide body is displaced from the first position to the second position. In some embodiments, the outlet assembly may be configured to pivot about a pivot axis which extends through a portion of the nozzle. In some embodiments, the cam may include a ramped section and a plateau section. The ramped section may be configured to drive the cam follower towards a face of the housing configured to be adhered to the skin of a patient as the slide body is displaced from the first position toward the second position. In some embodiments, when the slide body is in the second position, the cam follower may be in contact with the plateau portion and the plateau portion may inhibit further displacement of the cam follower. In some embodiments, the base body may include a skin depressor. In some embodiments, the ampoule may be constructed out of glass. In some embodiments, the device may further comprise an injection port. The injection port may be disposed over a tail including a second frangible that extends from the ampoule. The device may further comprise an elastomeric sleeve surrounding a portion of the injection port, the tail, and a main body of the ampoule. In some embodiments, the injection port may be pivotally displaceable from a first position to a second position. The second frangible may be configured to break with displacement of the injection portion from the first position to the second position.

In accordance with yet a further embodiment of the present disclosure an agent delivery device may comprise a reservoir assembly including a panel having an agent filled collapsible blister and a flow path extending from the blister. The device may further comprise an infusion site connector coupled to the panel and in fluid communication with the blister via the flow path. The infusion site connector may have a connector sharp and a pair of cantilevered arms flanking the connector sharp. Each of the arms may include a ledge configured to engage a retention catch of an infusion site assembly.

In some embodiments, the panel may be constructed of rigid material. In some embodiments, the reservoir assembly may include a check valve which inhibits flow of fluid along the flow path to the blister. In some embodiments, the infusion site connector may include at least one guard projection which extends alongside the connector sharp. In some embodiments, the agent may be a vaccine. In some embodiments, the agent may be a SARS-COV-2 vaccine. In some embodiments, the SARS-COV-2 vaccine may be selected from a group consisting of an attenuated live virus vaccine, inactivated virus vaccine, non-replicating viral vector vaccine, nucleic acid based vaccine, RNA based vaccine, mRNA based vaccine, saRNA based vaccine DNA based vaccine, DNA plasmid vaccine, recombinant protein vaccine, protein subunit vaccine, spike protein based vaccine, nanoparticle vaccine, and virus like particle vaccine.

In accordance with yet another embodiment of the present disclosure a delivery device may comprise a housing. The device may further comprise a reservoir assembly including a panel having an agent filled collapsible blister and a flow path extending from the blister. The device may further comprise a displaceable lock member. The device may further comprise a bias member configured to receive the lock member in a stressed state. The lock member may hold the bias member in the stressed state when received by the bias member. The bias member may be configured to transition to a less stressed state and exert a collapsing force on the blister upon displacement of the lock member to a disengaged state. The device may further comprise a septum. The device may further comprise an outlet assembly including a sharp displaceable from a first position to a second position. The sharp may pierce through the septum and establish fluid communication with the fluid path upon displacement to the second position.

In some embodiments, the outlet assembly may include an infusion site connector. The sharp may be mounted on a hub displaceable along a channel defined in the infusion site connector. In some embodiments, the hub may include a shoulder. The shoulder may abut a stop and prevent further displacement of the hub in at least one direction when the sharp is displaced to the second position. In some embodiments, the lock member may be a removable pin. In some embodiments, the lock member may include a button which extends through the housing. In some embodiments, the button may include at least one arm including a bar extending therefrom. The bias member may be configured to receive a portion of the bar. In some embodiments, the device may further comprise a pressure plate disposed against the blister and coupled to the bias member. The pressure plate may be urged against the panel upon transition of the bias member to the less stressed state. In some embodiments, the bias member may be a cantilevered spring. In some embodiments, the outlet assembly may include an infusion site connector having a pair of cantilevered arms flanking the sharp. Each of the arms may include a ledge configured to engage a retention catch of an infusion site assembly. In some embodiments, the reservoir assembly may include a check valve configured to prevent refilling of the blister. In some embodiments, the agent may be a vaccine. In some embodiments, the agent may be a SARS-COV-2 vaccine. In some embodiments, the SARS-COV-2 vaccine may be selected from a group consisting of an attenuated live virus vaccine, inactivated virus vaccine, non-replicating viral vector vaccine, nucleic acid based vaccine, RNA based vaccine, mRNA based vaccine, saRNA based vaccine DNA based vaccine, DNA plasmid vaccine, recombinant protein vaccine, protein subunit vaccine, spike protein based vaccine, nanoparticle vaccine, and virus like particle vaccine.

In accordance with another embodiment of the present disclosure a delivery device may comprise a base. The device may further comprise a main body displaceable relative to the base. The device may further comprise a reservoir having a variable interior volume. The reservoir may be defined by a convex surface on the main body and a membrane covering the convex surface which is sealed to the main body around the periphery of the convex surface. The membrane may be in a first stretched state against the convex surface to accommodate the shape of the convex surface when the reservoir is in an empty state. The membrane may be distensible away from the convex surface to a second stretched state to accommodate fluid when the reservoir is in a filled state. The device may further comprise a port in fluid communication with the reservoir. The device may further comprise an outlet in fluid communication with the reservoir. The outlet may include at least one delivery sharp and may be displaceable with the main body such that the at least one delivery sharp extends out of an aperture in the base when the main body is displaced against the base. Stretching of the membrane between the first stretched state and second stretched state may be over a steady pressure stretching range of the membrane.

In some embodiments, the at least one delivery sharp may include a microneedle. In some embodiments, the at least one delivery sharp may include a microneedle array. In some embodiments, the base may include a skin depressor. In some embodiments, the convex surface on the main body may be a spherical segment. In some embodiments, the membrane may be configured to assume a flat shape when unstressed. In some embodiments, the port may include a piercable septum. In some embodiments, the base and the main body may include cooperating retention features. The retention features may be configured to engage upon movement of the main body against the base to hold the main body against the base. In some embodiments, the device may further comprise a bandage mounted on the base for adhering the device to a patient. In some embodiments, the main body may be pivotally displaceable relative to the base body.

In accordance with still another embodiment of the present disclosure a delivery device may comprise a base. The delivery device may further comprise a main body displaceable relative to the base. The delivery device may further comprise a reservoir defined by a raised surface on the main body and a membrane covering the raised surface which is sealed to the main body around the periphery of the raised surface. The membrane may be in a first stretched state against the raised surface when the reservoir is in an empty state. The membrane may be distensible away from the raised surface to a second stretched state to accommodate fluid when the reservoir is in a filled state. The device may further comprise a filling port in fluid communication with the reservoir. The device may further comprise an outlet in fluid communication with the reservoir. The outlet may include at least one delivery sharp. Stretching of the membrane between the first stretched state and second stretched state may be over a steady pressure stretching range of the membrane.

In some embodiments, the at least one delivery sharp may include a microneedle. In some embodiments, the at least one delivery sharp may include a microneedle array. In some embodiments, the base may include a skin depressor. In some embodiments, the raised surface on the main body may be a round protuberance. In some embodiments, the membrane may be configured to assume a flat shape when unstressed. In some embodiments, the port may include a piercable septum. In some embodiments, the base and the main body may include cooperating retention features. The retention features may be configured to engage upon movement of the main body against the base to hold the main body against the base. In some embodiments, the device may further comprise a bandage mounted on the base for adhering the device to a patient. In some embodiments, the main body may be pivotally displaceable relative to the base body.

In accordance with another embodiment of the present disclosure a delivery device may comprise a base having a locking recess. The device may further comprise an outlet assembly including at least one delivery sharp and an access sharp on opposing ends of the outlet assembly. The access sharp may be in fluid communication with the at least one delivery sharp. The device may further comprise a reservoir assembly including a barrel having an outlet sealed by a septum, a plunger and an insert both displaceable within the barrel. The insert may have an end adjacent the plunger and a projection. The barrel may be displaceable from a sealed state to an accessed state in which the septum is pierced by the access sharp. The device may comprise a bias member configured to, when transitioned from a stressed state to a less stressed state, urge the reservoir assembly toward the accessed state. The bias member may be further configured to urge the insert and plunger toward the outlet once the barrel is in the accessed state. The bias member may be held in the stressed state when the projection of the insert is engaged with the locking recess.

In some embodiments, the at least one delivery sharp may include a microneedle. In some embodiments, the at least one delivery sharp may include an array of microneedles. In some embodiments, the at least one delivery sharp may be clocked such that the tip of the at least one delivery sharp is in a controlled orientation. In some embodiments, barrel may be constructed of an inert material. In some embodiments, the projection may be included on a cap portion of the insert. In some embodiments, the projection may be a radially extending flange. The insert may be rotatable about a long axis of the insert between a state in which the projection is in engagement with the recess and a state in which the projection is free of the recess when the barrel is in the sealed state. In some embodiments, the projection may be included on a second end of the insert opposite the end adjacent the plunger. In some embodiments, the septum may be crimped in place on the barrel. In some embodiments, the bias member may be a compression spring. In some embodiments, the insert may include a cap body on a second end of the insert opposite the end adjacent the plunger. The at least a portion of the cap body may be configured to displace over an exterior surface of the barrel as the insert and plunger are displaced toward the outlet. In some embodiments, the at least one delivery sharp may be surrounded by a pressure chamber operatively coupled to a pressure source. In some embodiments, the pressure source may be a negative pressure source.

In accordance with another embodiment of the present disclosure a delivery device may comprise a base having a locking recess. The device may further comprise an outlet assembly including at least one delivery sharp on a first end of the outlet assembly and an access sharp on an opposing end of the outlet assembly. The access sharp may be in fluid communication with the at least one delivery sharp. The device may further comprise a reservoir assembly including a barrel having an outlet sealed by a septum, a plunger displaceable along the barrel and having a first side proximal to the outlet and a second side distal to the outlet, and an insert displaceable within the barrel and having an end adjacent the second side of the plunger. The insert may further include a projection. The device may further comprise a bias member configured to urge the reservoir portion from a first position to a second position in which the septum is punctured by the access sharp. The bias member may further be configured to urge the insert and plunger toward the outlet once the reservoir assembly has been driven to the second position. The bias member may be held in a stressed state when the projection of the inserter is engaged with the locking recess.

In some embodiments, the at least one delivery sharp may include a microneedle. In some embodiments, the at least one delivery sharp may include an array of microneedles. The array may be a one dimensional or a two dimensional array of microneedles. In some embodiments, the at least one delivery sharp may be clocked such that the tip of the at least one delivery sharp is in a controlled orientation. In some embodiments, the barrel may be constructed of an inert material. In some embodiments, the projection may be included on a cap portion of the insert. In some embodiments, the projection may be a radially extending flange. The insert may be rotatable about a long axis of the insert between a state in which the projection is in engagement with the recess and a state in which the projection is free of the recess when the barrel is in the sealed state. In some embodiments, the projection may be included on a second end of the insert opposite the end adjacent the plunger. In some embodiments, the septum may be crimped in place on the barrel. In some embodiments, the bias member may be a compression spring. In some embodiments, the insert may include a cap body on a second end of the insert opposite the end adjacent the plunger. The at least a portion of the cap body may be configured to displace over an exterior surface of the barrel as the insert and plunger are displaced toward the outlet. In some embodiments, the at least one delivery sharp may be surrounded by a pressure chamber operatively coupled to a pressure source. In some embodiments, the pressure source may be a negative pressure source.

In accordance with yet another embodiment of the present disclosure a delivery device may comprise a base. The delivery device may further comprise an axel supported by the base and including an inlet flow channel and an outlet flow channel recessed into an outer face of the axel. The delivery device may further comprise a fluid handling portion. The fluid handling portion may comprise a port assembly. The fluid handling portion may further comprise a reservoir assembly including a barrel and a plunger within the barrel biased toward an outlet of the barrel. The fluid handling portion may further comprise an outlet assembly including at least one delivery sharp. The fluid handling portion may further comprise a hub body disposed and pivotally displaceable about the axel. Each of the port assembly, reservoir assembly, and outlet assembly may extend from the hub body. The fluid handling portion may be displaceable from a filling orientation in which the port assembly is in fluid communication with the barrel via the inlet flow channel to a delivery orientation in which the outlet assembly is in fluid communication with the barrel via the outlet flow channel.

In some embodiments, the at least one delivery sharp may include a microneedle. In some embodiments, the at least one delivery sharp may include an array of microneedles. In some embodiments, the base may include a stop. The outlet assembly may abut the stop when fluid handling portion is in the filling orientation. In some embodiments, the base may include a deflectable cradle configured to displace against the skin of a patient when the fluid handling portion is displaced from the filling orientation to the delivery orientation. In some embodiments, the cradle may be cantilevered from a main body of the base. In some embodiments, the delivery sharp may be configured to extend through an aperture in the base when the fluid handling portion is displaced from the filling orientation to the delivery orientation. In some embodiments, the base may include a catch. The catch may be configured to engage the reservoir portion when the fluid handling portion is displaced from the filling orientation to the delivery orientation. The catch may inhibit displacement of the fluid handling portion when engaged with the reservoir portion. In some embodiments, the port assembly may include a piercable septum. In some embodiments, the device may further comprise an inlet and an outlet. The inlet may be in communication with the inlet flow path when the fluid handling portion is in the filling orientation. The outlet may be in communication with the outlet flow path when the fluid handling portion is in the delivery orientation.

In accordance with an embodiment of the present disclosure a method for accessing a target delivery depth of a patient may comprise applying an administration device to a patient. The method may further comprise displacing a lock member from a locking state to a disengaged state. The method may further comprise propelling a guide pin along a displacement path. The method may further comprise transmitting, via a linkage, motion of the guide pin to a sharp assembly to extend at least one delivery sharp of the sharp assembly a first distance out of a housing of the administration device and retract the at least one delivery sharp to a delivery position in which the at least one delivery sharp extends a second distance out of the housing which is less than the first distance.

In some embodiments, the displacement path may be an arcuate displacement path. In some embodiments, propelling the guide pin may comprise exerting a bias force on the guide pin with a single bias member. In some embodiments, propelling the guide pin may comprise propelling the guide pin along the displacement path to a stop in a single direction along the guide path. In some embodiments, the single direction may be a single rotational direction. In some embodiments, propelling the guide pin along the displacement path may comprise displacing a portion of the guide pin along a guide track defined in the housing. In some embodiments, the first distance may correspond to a transcutaneous puncture depth in the patient. In some embodiments, the second distance may correspond to an intradermal puncture depth in the patient. In some embodiments, the method may further comprise constraining the at least one delivery sharp to displace at a predefined angle relative to a skin surface of the patient to which the administration device is adhered. In some embodiments, the predefined angle may be 5°-45°. In some embodiments, displacing the lock member may comprise removing a strip to which the lock member is attached from the delivery device. In some embodiments, displacing the lock member may comprise removing the lock member. In some embodiments, propelling the guide pin along the displacement path may comprise propelling the guide pin in a single fluid motion along the displacement path. In some embodiments, the delivery sharp may be a needle of no larger than 30 gauge. In some embodiments, the propelling the guide pin along the displacement track may comprise propelling the guide pin along a first portion of the displacement path in which the guide pin increases in proximity to a delivery sharp aperture in the housing and along a second portion of the displacement path shorter than the first portion in which the guide pin decreases in proximity to the delivery sharp aperture.

In accordance with another embodiment of the present disclosure an agent administration device may comprise a housing including a first portion that includes at least one guide surface and a rigid shelf. The housing may include a second portion displaceable relative to the first portion between a storage state and a delivery state. The second portion may have at least one guide projection which slides along and is directed by the at least one guide surface as the second portion is displaced between the storage and delivery states. The device may further comprise at least one delivery sharp extending from the second portion. The at least one delivery sharp may be within the housing in the storage state and extending out of the housing in the delivery state. The device may further comprise a pressurized agent containing ampoule including a frangible retained within the second portion. The device may further comprise an elastomeric boot disposed on and sealing against a region of the ampoule that includes the frangible. Displacement of the second portion from the storage state to the delivery state may be configured displace at least a portion of the ampoule into the rigid shelf and exert a frangible breaking force on the ampoule through the boot as the second portion is displaced to the deployed state.

In some embodiments, the boot may include a port with a receptacle. The second portion may include a flow pathway projection which is coupled into the receptacle. The flow pathway projection may include a flow channel which communicates with the at least one delivery sharp. In some embodiments, the second portion of the housing may define a holster clamshell with at least one foldable portion. The foldable portion may be displaceable between a molding configuration in which the holster clamshell is open and an assembly configuration in which the holster clamshell is closed. In some embodiments, the second portion of the housing may define a holster clamshell. The ampoule may be retained within the holster clamshell when the clamshell is in a closed state. In some embodiments, the first portion of the housing may include a ratcheting wall including a plurality of ratcheting interfaces. In some embodiments, the ratcheting interfaces may be recessed into a face of the ratcheting wall. In some embodiments, the ratcheting interfaces may be raised from a face of the ratcheting wall. In some embodiments, the second portion of the housing may include a foldable section coupled to a main portion of the second portion via a living hinge. In some embodiments, the foldable section may include a pawl projection and a clip. The ratcheting wall may be held between the clip and a remainder of the foldable section. The pawl projection may engage a first ratcheting interface when the second portion is in the storage state and a second ratcheting interface when the second portion is in the delivery state. In some embodiments, the foldable section may include a pawl projection and a clip. The ratcheting wall being held between the clip and a remainder of the foldable section. The foldable section may be configured to displace in a direction parallel to a plane of the ratcheting wall as the second portion is displaced between the storage state and the delivery state. In some embodiments, the agent administration device may further comprise a support means for inhibiting breakage of the ampoule at locations other than the frangible. In some embodiments, the at least one delivery sharp may include a microneedle. In some embodiments, the second portion may include a skin depressor. In some embodiments, the ampoule may be constructed out of glass. In some embodiments, at least a portion of the housing may include at least one foldable portion monolithically formed with the at least a portion of the housing. Each of the at least one foldable portion may be displaceable between a molding configuration and an assembly configuration. In some embodiments, the each of the at least one foldable portion may be coupled to the at least a portion of the housing via a living hinge. In some embodiments, the at least one foldable portion may include at least one latch projection and the at least a portion of the housing may include at least one retention slot configured to accept one of the at least one latch projection. In some embodiments, the device may further comprise an injection port. The injection port may be disposed over a tail including a second frangible that extends from the ampoule. The elastomeric boot may surround a portion of the injection port, the tail, and a main body of the ampoule. In some embodiments, the injection port may be pivotally displaceable from a first position to a second position. The second frangible may be configured to break with displacement of the injection port from the first position to the second position.

In accordance with another embodiment of the present disclosure a method of delivering an intradermal injection may comprise puncturing, with at least one delivery sharp, to an intradermal delivery destination. The method may further comprise dispensing a first fluid through the at least one delivery sharp to the delivery destination. The method may further comprise dispensing a second fluid through the at least one delivery sharp to the delivery destination. One of the first and second fluid may be a vaccine and the other of the first and second fluid is a gas.

In some embodiments, the at least one delivery sharp may comprise an array of microneedles. In some embodiments, the puncturing to an intradermal delivery destination may comprise driving the at least one delivery sharp to a first depth and subsequently retracting the at least one delivery sharp to the intradermal delivery destination. In some embodiments, driving the at least one delivery sharp to a first depth and subsequently retracting the at least one delivery sharp to the intradermal delivery destination may be executed in a single reciprocating fluid motion. In some embodiments, the at least one delivery sharp may comprise a needle of no greater than 30 gauge. In some embodiments, the method may further comprise stimulating blood flow in the vicinity of the intradermal delivery destination. In some embodiments, the gas is a gas selected to stimulate blood flow to the intradermal delivery destination.

BRIEF DESCRIPTION OF THE DRAWINGS

These and other aspects will become more apparent from the following detailed description of the various embodiments of the present disclosure with reference to the drawings wherein:

FIG. 1 depicts a perspective view of an example delivery device;

FIG. 2 depicts a perspective view of an example delivery device having a locking member which may be flexed to transition between a first state and a second state;

FIG. 3 depicts a bottom perspective view of an example delivery device and cover member;

FIG. 4 depicts a bottom perspective view of the delivery device of FIG. 3 with the cover member removed;

FIG. 5 depicts a perspective view of an example cover member;

FIG. 6 depicts a perspective view of an example delivery device with a portion of the housing exploded away from the remainder of the delivery device;

FIG. 7 depicts an exploded view of an example delivery device;

FIG. 8 depicts a top plan view of an example delivery device;

FIG. 9 depicts a cross sectional view of an example delivery device taken at the indicated cut plane of FIG. 8;

FIG. 10 depicts a cross-sectional view of an example insert which may be included in a delivery device;

FIG. 11 depicts a cross-sectional view of an example delivery device with a locking member of the delivery device being removed from the delivery device;

FIG. 12 depicts another cross-sectional view of another delivery device with a turnkey;

FIG. 13 depicts another cross-sectional view of another delivery device with a teethed locking member;

FIG. 14 depicts a cross-sectional view of an example delivery device with a plug of the delivery device being displaced against a stop surface included in the delivery device;

FIG. 15 depicts a cross-sectional view of an example delivery device in a partially dispensed state;

FIG. 16 depicts a cross-sectional view of an example delivery device in a fully dispensed state;

FIG. 17 depicts an enlarged view of the indicated portion of the cross-sectional view depicted in FIG. 9;

FIG. 18 depicts a top plan view of an example delivery device;

FIG. 19 depicts a cross-sectional view of an example delivery device taken at the indicated cut plane in FIG. 18;

FIG. 20 depicts a perspective view of a portion of a housing of a delivery device;

FIG. 21 depicts a cross-sectional view of a portion of a delivery device being filled via a filling implement;

FIG. 22 depicts a bottom perspective view of an example delivery device;

FIG. 23 depicts a perspective view of an example cover member for a delivery device;

FIG. 24 depicts a bottom perspective view of a delivery device with its cover member removed;

FIG. 25 depicts a detailed view of the indicated region of FIG. 24;

FIG. 27 depicts a cross-sectional view of an example delivery device including an actuatable delivery sharp where the actuatable delivery sharp is in a stowed state;

FIG. 28 depicts a detailed view of the indicated region of FIG. 27;

FIG. 29 depicts a cross-sectional view of an example delivery device including an actuatable delivery sharp where the actuatable delivery sharp is in a deployed state;

FIG. 30 depicts a detailed view of the indicated region of FIG. 29;

FIG. 31 depicts a top plan view of an example delivery device including an infusion site connector;

FIG. 32 depicts a cross-sectional view of an example delivery device including an infusion site connector taken at the indicated cut plane in FIG. 31;

FIG. 33 depicts a top plan view of an example delivery device which is connected to an infusion site connector via a run of infusion tubing;

FIG. 34 depicts a cross sectional view of an example delivery device taken at the indicated cut plane in FIG. 33;

FIG. 36 depicts another example delivery device including an infusion site connector;

FIG. 37 depicts a top down plan view of another example embodiment of a delivery device;

FIG. 38 depicts a cross-sectional view of the example delivery device of FIG. 37 taken at the indicated cut plane of FIG. 37;

FIG. 39 depicts a perspective view of an example delivery device and example infusion site assembly;

FIG. 48 depicts an exploded view of an example delivery device;

FIG. 49 depicts a side view of an example delivery device in a delivery state;

FIG. 50 depicts a cross-sectional view of the delivery device shown in FIG. 49 taken along a longitudinally extending mid plane of the delivery device shown in FIG. 49;

FIG. 51 depicts a detailed view of the indicated region of FIG. 49;

FIG. 63 depicts a cross-sectional view of the example delivery device shown in FIG. 62 taken along a longitudinally extending mid plane of the delivery device shown in FIG. 62;

FIG. 64 depicts another perspective view of an example delivery device embodiment;

FIG. 65 depicts a cross-sectional view of the example delivery device shown in FIG. 64 taken along a longitudinally extending mid plane of the delivery device shown in FIG. 65;

FIG. 66 depicts a top down plan view of yet another example embodiment of a delivery device;

FIG. 67 depicts a cross-sectional view of the delivery device shown in FIG. 66 taken at the indicated cut plane in FIG. 66;

FIGS. 68-70 depict a views of yet another example embodiment of a delivery device;

FIG. 72 depicts a view of an example ampoule;

FIG. 73 depicts a top down plan view of an example embodiment of a delivery device including an ampoule;

FIG. 74 depicts a cross-sectional view of the example delivery device of FIG. 73 taken at the indicated cut plane of FIG. 73;

FIG. 75 depicts a perspective view of an example activation assembly which may be included in a delivery device such as that shown in FIG. 74;

FIG. 76 depicts a perspective view of an example delivery device;

FIG. 77 depicts a detailed view of the indicated region of FIG. 76;

FIG. 78 depicts a view of another example ampoule and an elastomeric housing;

FIG. 79 depicts a cross sectional view of the example ampoule and elastomeric housing of FIG. 78;

FIG. 88 depicts a top down plan view of an example embodiment of a delivery device which is in a delivery state;

FIG. 89 depicts a cross-sectional view of the example delivery device of FIG. 88 taken at the indicated cut plane of FIG. 88;

DETAILED DESCRIPTION

Figure 1:
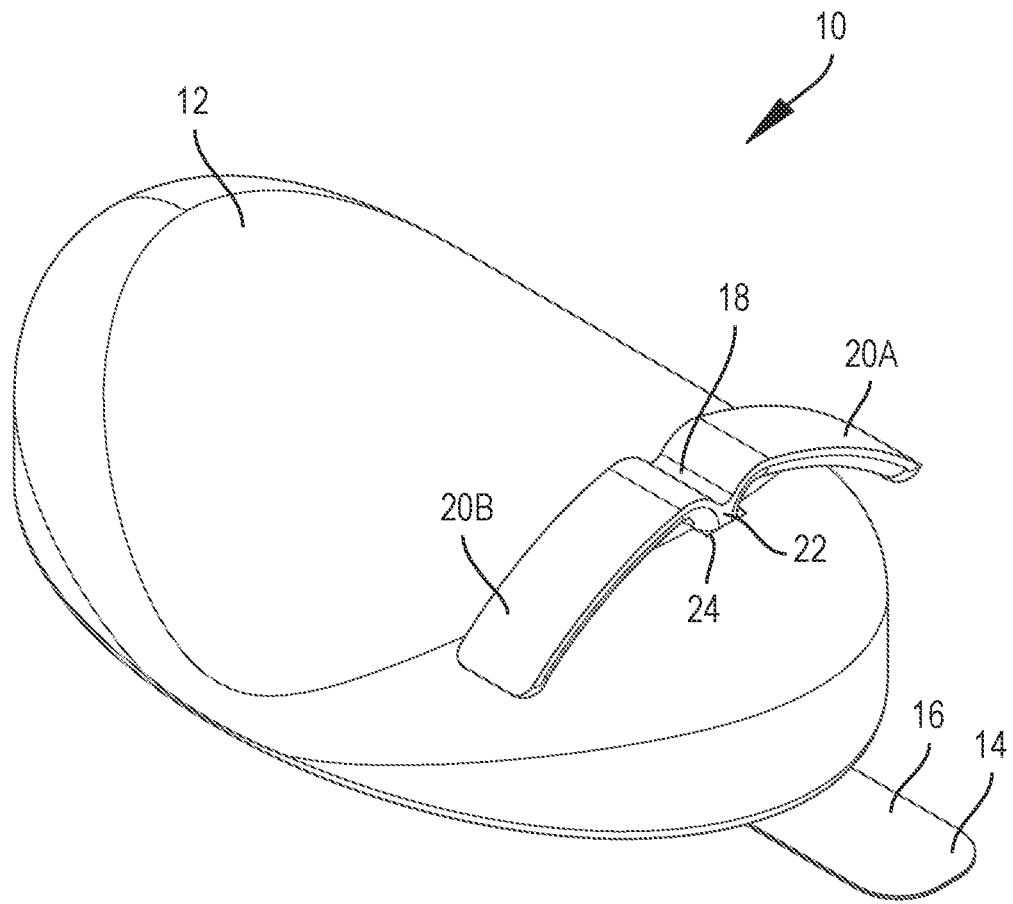

Referring to FIG. 1, an example delivery device 10 is depicted. The delivery device 10 may be a vaccine delivery device in certain example. The example delivery device 10 may be designed for patient or other untrained use. Thus, a medical caregiver would not be necessary to administer any contents of the delivery device 10. This would aid in the ability to rapidly perform a mass vaccination campaign, especially in scenarios where a medical care system is already stretched thinly. Additionally, it would help to free up caregivers to focus on other medical issues thus reducing secondary impacts of a pandemic. As the delivery device 10 may be designed for patient use, the delivery device 10 may significantly limit consumption of PPE related to vaccination. Moreover, it may aid in limiting opportunities for exposure as less interaction between various parties (some of which may elect not to use PPE when available) may be needed to administer vaccine from the delivery device 10.

Such a delivery device 10 may deliver any suitable vaccine, though may be particularly well suited to vaccines for novel pathogens (e.g. SARS-CoV-2) or for pathogens where herd immunity does not exist (e.g. Ebola). Additionally, such delivery devices 10 may be of particular usefulness in outbreaks of pathogens (such as measles for example) in communities which choose to forego typical vaccinations. For example, such delivery devices 10 could be distributed without requiring patients to congregate in hospitals or other shared spaces. This would mitigate concern for pathogen transmission related to vaccination programs and alleviate potential worries that could dissuade people from reporting to receive a vaccination. Instead, delivery devices 10 could be picked up and used by patients without breach of social distancing, gathering size recommendations, or other safety guidelines. Alternatively, such delivery devices 10 could be distributed directly to patients without requiring a patient to leave their domicile or requiring distribution personnel to interact with individuals who decline to utilize recommended PPE. Delivery devices 10 could be filled with a vaccine for a novel pathogen or could perhaps be filled with vaccines typical of a normal vaccination schedule. In the latter case, such a delivery device 10 could help to ensure that disruption of vaccination for known pathogens does not occur during a novel pathogen pandemic.

Vaccine may refer to any type of vaccine such as, though not limited to, attenuated live vaccines, inactivated virus vaccines, acellular vaccines, cellular vaccines, toxoid vaccines, heterotypic or Jennerian vaccines, monovalent vaccines, polyvalent vaccines, nucleic acid vaccines (e.g. DNA, plasmid vaccine, mRNA), virus like particle vaccines, recombinant vector vaccines (e.g. replicating, non-replicating), dendritic cell vaccines, T-cell receptor peptide vaccines, chimeric vaccines, subunit vaccines, nanoparticle vaccines, recombinant protein vaccines, polysaccharide vaccines, and conjugate vaccines. It should be noted that these are not necessarily mutually exclusive. For instance, a vaccine could be a recombinant protein nanoparticle vaccine or some other combination of the above. Vaccine may also refer to a combination vaccine (e.g. DTaP, MMR, MMRV, etc.) or a vaccination agent which targets a single pathogen or multiple strains of a single pathogen. Example vaccines may include, but are not limited to vaccines for various coronaviruses such as SARS-COV, SARS-COV-2, MERS-COV, HCoV-NL63, HCoV-229E, HCoV-OC43 and HKU1. Delivery devices 10 described herein are also not limited for use with humans. Such delivery devices 10 may be used for livestock, pets, services animals, in other veterinary applications, or in research settings. In such cases, these delivery devices 10 may be filled with a vaccine for at least one non-human pathogen.

Delivery devices 10, such as the example shown in FIG. 1 may also be advantageous in circumstances where the amount of available vaccine is limited. Evidence suggests that intradermal delivery of certain vaccines may provoke protective immune response with smaller amounts of vaccine antigen. As a result, dose sparing may be practiced allowing the same quantity of vaccine to be effective for immunizing a greater number of people. Alternatively or additionally, injection sparing may be possible. Intradermal administration with a delivery device 10 such as those shown herein may allow for a single injection protocol where other routes of administration may require multiple injections over some period of time. One or more adjuvants may be included in some vaccines to further aid in facilitating dose or injection sparing.

Particularly for new vaccines generated to combat an ongoing pandemic (e.g. a vaccine for SARS-CoV-2), the prospect of rapidly generating billions of doses would almost certainly exceed current vaccine production capabilities. Due to the injection and dose sparing potential of delivery devices 10 described herein, such delivery devices 10 may facilitate vaccination of large numbers of people even when a critically needed vaccine is in short supply. Additionally, as a consequence of potential dose and injection sparing, delivery devices 10 such as those shown and described herein may allow injections to be more cost effective. Moreover, due to the small volume of vaccine needed, delivery devices 10 may be made relatively small. This may simplify shipping and help to facilitate rapid distribution of vaccine to a population.

Additionally, some studies have suggested that intradermal administration may be particularly helpful in certain patient populations. For example, elderly populations may receive superior protection from vaccinations received intradermally than via other routes. That said, the Mantoux technique, which is typically used for intradermal administration, can pose reliability concerns and can be difficult to perform, especially without training. Per the World Health Organization, a large factor which has limited the use of intradermal vaccination has been the lack of a delivery platform.

Delivery devices 10, such as those shown and described herein, may provide an attractive delivery platform for intradermal vaccination. Consequentially, delivery devices 10 described and shown herein may help to give better protection to vulnerable populations and may help in meeting the large demand for vaccines to novel pathogens by leveraging dose/injection sparing possible with intradermal vaccination. Moreover, intradermal delivery devices 10 described herein may be painless or nearly pain free which may make the delivery devices 10 described herein user preferable over other types of injections. That said, delivery devices 10 described herein are not limited to delivery via the intradermal route. Delivery devices 10 may, for instance, be configured as transdermal (e.g. subcutaneous or intramuscular) delivery devices 10.

The example delivery devices 10 shown herein additionally are not limited to vaccine delivery devices. As explained elsewhere herein, such a delivery device 10 may fill a number of niches in the medical field. The delivery devices 10 shown and described herein may deliver any suitable therapeutic agent as a bolus or as a basal delivery depending on the embodiment. Such delivery devices 10 may, for example, be used to deliver medication for endocrine disorders. For instance, insulin may be delivered with some exemplary delivery devices 10.

Delivery devices 10 described and shown herein may also be well suited to deliver drugs for overdose intervention such as opioid antagonists (e.g. Naloxone). Delivery devices 10 such as that shown in FIG. 1 may be easily used at the site of an overdose by a non-medically trained bystander. Alternatively, delivery devices 10 may be used by emergency medical services (EMS) personnel responding to an overdose. Such delivery devices 10 may provide rapid access and delivery to, for instance, a subcutaneous space in the overdose victim. While absorption may be slower when delivered, e.g., subcutaneously, this may be balanced out by the fact that no time would be needed to attempt establishing an intravenous access (which may be especially difficult in intravenous drug users). Additionally, slower onset of the antagonist may blunt the onset of withdrawal symptoms. This may contribute to greater adoption in addict communities and may provide safety benefits for EMS personnel.

Other agents, for example, diagnostic or testing agents may also be supplied via certain example delivery devices 10. For instance, allergens or potential allergens may be administered via the delivery device 10. Tuberculosis testing agents may be delivered via the delivery device 10. Nutrients such as vitamins may also be delivered using delivery device 10 embodiments described herein. Additionally, the delivery devices 10 described herein may be arranged so as to be applied in serial fashion. For example, a first delivery device 10 may be configured to relatively rapidly supply a loading dose or bolus of an agent while a second, subsequently applied delivery device 10 may provide, for example, a basal injection of that agent or a different agent over a prolonged period of time (e.g. anywhere from 30-90 minutes or longer).

As shown in FIG. 1, a delivery device 10 may include a housing 12. The delivery device 10 may be sized so as to be handheld and easily applied to a variety of possible injection sites over a patient's body. The housing 12 may be ergonomically shaped so as to easily be held in the hand of a user. In the example embodiment, the housing 12 is contoured similarly to a computer mouse. Preferably, the delivery device 10 may be free from corners or edges which may catch on items such as clothing. The housing 12 may be formed of a rigid material which may be a polymer, metal, metal alloy, other material, or combination thereof.

The delivery device 10 may have a face which is intended to be adhered to the patient's skin. This face may be substantially planar or may be contoured or flexible to cooperate with the curvature of a desired patient injection site. This patient adhering face may be covered with a skin compatible adhesive. For example, an adhesive pad may be attached to the patient adhering face of the delivery device 10. The adhesive may be covered by a removable (e.g. peel off) backing 14. The adhesive backing 14 may include a protuberance 16 in certain examples. Such a protuberance 16 may facilitate removal of the backing 14 from the delivery device 10. In some embodiments, a portion of the adhesive bearing pad on the delivery device 10 may also project away from the rest of the delivery device 10 in the location of the backing protuberance 16. Thus, when the delivery device 10 is applied to a patient, the adhesive pad projection may be grasped by a user to facilitate removal of the delivery device 10.

In the example embodiment shown in FIG. 1, the delivery device 10 may also include a lock. The lock may be a locking member 18 or locking mechanism. The locking member 18 or mechanism may be included as part of an activation assembly of the delivery device 10. Such a locking member 18 or mechanism may inhibit delivery of therapeutic agent from a delivery device 10 until the locking member 18 or mechanism is acted on by a user. Thus, the locking member 18 or mechanism may prevent the delivery device 10 from inadvertently activating and delivering therapeutic agent during shipping, storage, preparation for use, etc. Upon actuation or displacement of the locking member 18 or mechanism, the delivery device 10 may transition to a usage state. For example, the delivery device 10 may begin dispensing of medication when the delivery device 10 is transitioned to the usage state. Alternatively, a delivery button or other interface may be made functional due to actuation or displacement of the locking member 18 or mechanism. Prior to actuation or displacement of the locking member 18 or mechanism, interaction with delivery button or other interface may have no effect.

As shown in the example embodiment depicted in FIG. 1, the delivery device 10 includes a removable locking member 18. The removable locking member 18 may include two arms 20A, B. The arms 20A, B may extend orthogonally to the longitudinal midplane of the delivery device 10 as shown in FIG. 1. The arms 20A, B may have a curvature which facilitates grasping by fingers of the user. In the example embodiment, each arm 20A, B is arcuate and bends downward toward the skin adhering face of the delivery device 10 as distance from the arm's 20A, B attachment point to the stem 22 increases. In other embodiments, locking members 18 may have alternative grasping features. In some examples, a locking member 18 may include one or more of a pull ring, flange, tab, nub, textured surface, etc. in place of or in addition to the arms 20A, B.

The exemplary locking member 18 may also include a stem portion 22 which may be installed into the delivery device 10 through an aperture 24 (best shown in FIG. 6) in the housing 12. In the example, the aperture 24 is disposed along the longitudinal midplane of the delivery device 10. The stem portion 22 may present a mechanical interference to displacement of internal components of the delivery device 10 active in dispensing of the contents of the delivery device 10. When the locking member 18 is disassociated with the delivery device 10, the mechanical interference may be removed allowing the interior components of the delivery device 10 to displace and cause delivery of therapeutic agent from the delivery device 10. Where a second button or other interface is used, removal of the locking member 18 may remove a mechanical interference which would otherwise block dispensing of drug when the button or other interface was actuated by a user. That is, when the locking member 18 is in place, the mechanical interference it presents may render the button or other interface impotent.

Figure 2:
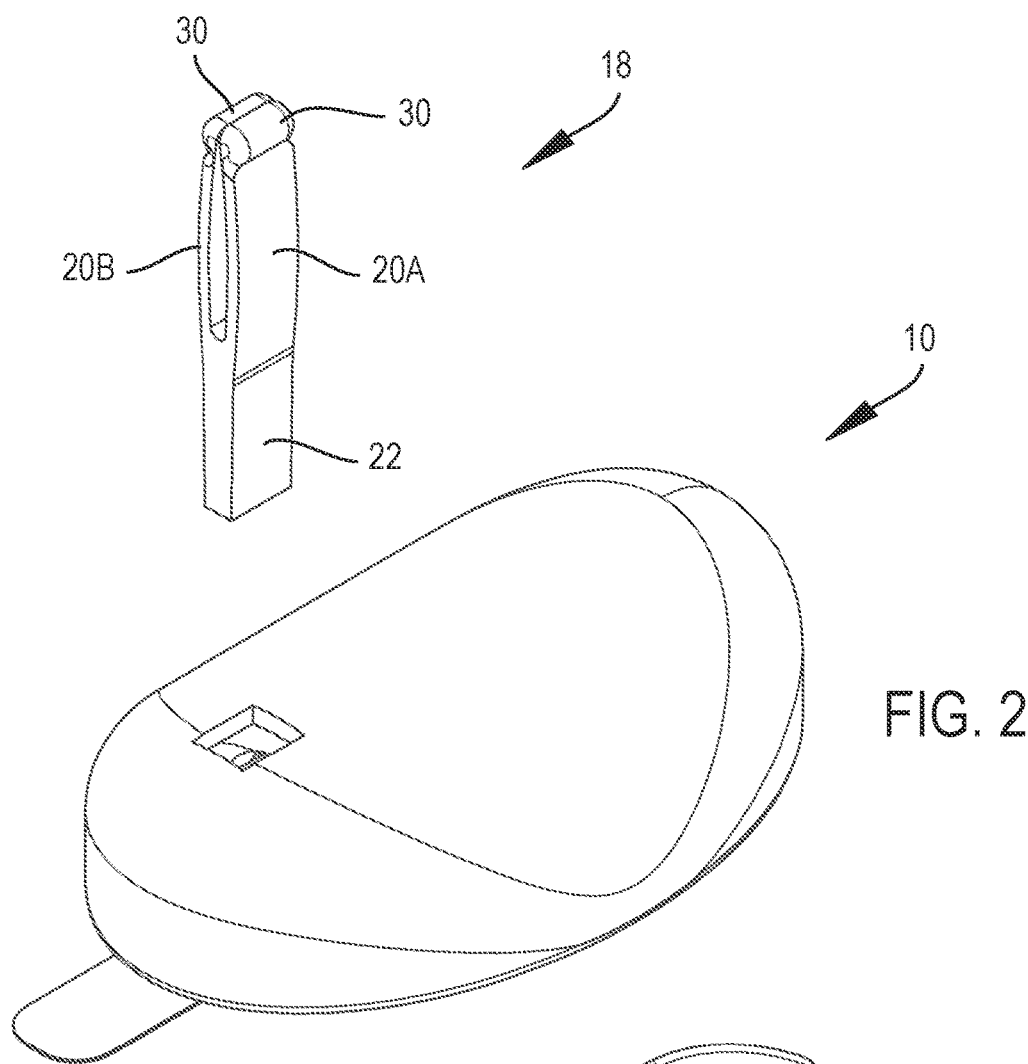

Referring now to FIG. 2, in certain embodiments, a locking member 18 may include one or more flexible component. In such embodiments, the locking member 18 may have a shipping or storage configuration. For use, the locking member 18 may be transitioned (e.g. via flexing or bending a portion of the locking member 18) from its storage configuration to a grasping configuration in which the locking member 18 may easily be grasped by a user. Using the example locking member 18 shown in FIG. 1, in some embodiments, the arms 20A, B may be at least partially flexible. For example, the arms 20A, B may be joined to the stem portion 22 via living hinges. To remove the locking member 18, the arms 20A, B may be displaced upward from their orientation in FIG. 1 (what would be the storage state for the arms 20A, B) to their position in FIG. 2. When in the graspable state the arms 20A, B may extend upward substantially parallel to the axis of the stem portion 22. Thus, the user may have a long surface over which to grasp the locking member 18. Additionally, the terminal ends of the arms 20A, B opposite their connection to the stem portion 22 may include nubs 30. The nubs 30 may further increase ease of removal of the locking member 18. Other embodiments may differ. For example, instead of arms 20A, B another suitable grasping element may be coupled to the stem portion 22. This grasping element may be close to (perhaps against) the housing 12 in its storage state and displaced to an easily graspable position during use. For instance, a pull ring which is folded against the housing 12 and hinged (e.g. via a living hinge) to the stem portion 22 may be used in some examples.

Use of a locking member 18 which has a storage state and grasping state may allow for the delivery device 10 to have a low profile when shipped and stored. As the locking member 18 may be transitioned into a state in which it protrudes a greater degree from the housing 12, ease of removal of the locking member 18 may not be sacrificed in order to make the delivery device 10 lower profile. Limiting the volume of packaged delivery devices 10 in the shipping state may help maximize the amount of delivery devices 10 which may be transported. This may be particularly useful in delivery devices 10 which require a cold chain type supply chain (e.g. delivery devices 10 loaded with heat labile vaccines). Many regions of the world may lack extensive cold chain infrastructure, thus a higher density of delivery devices 10 in a given storage volume may aid in limiting the demands on cold chain resources in these regions.

Figure 3:
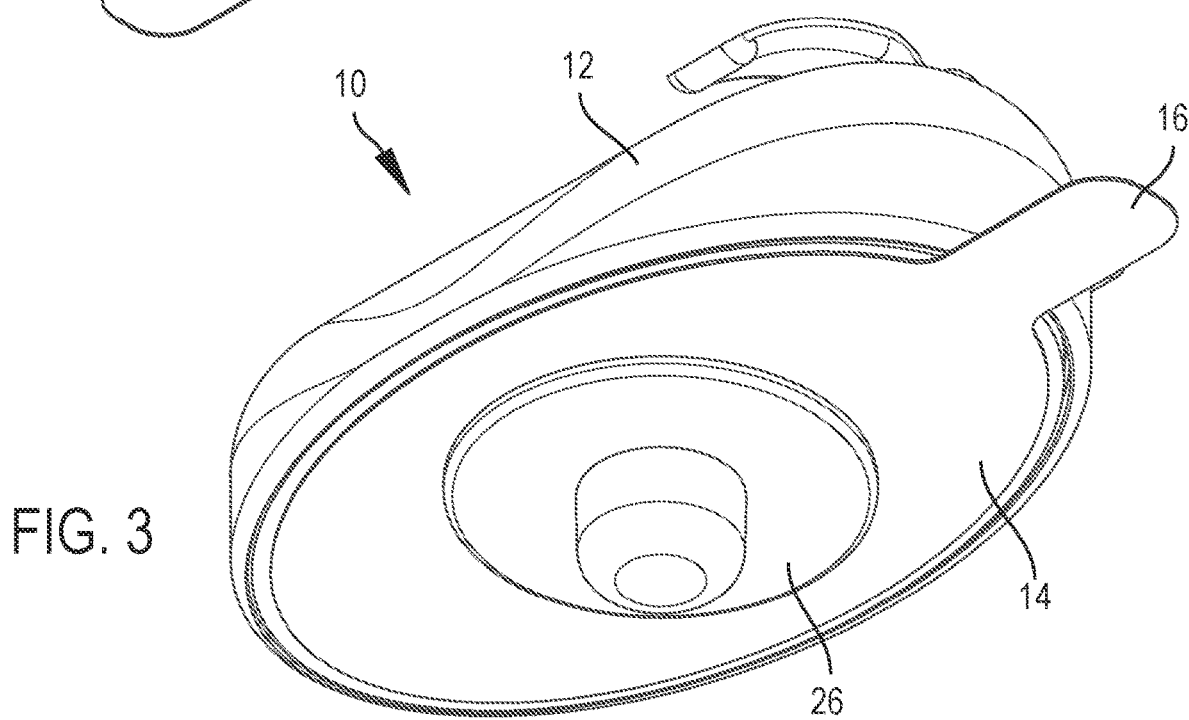

Referring now also to FIG. 3, a delivery device 10 may also include a cover member 26. A cover member 26 may engage with the housing 12 or another component of the delivery device 10 so as to be retained in place on the delivery device 10. The cover member 26 may act as a barrier which prevents the ingress of detritus, fingers, etc. into the interior of the delivery device 10. Where a fixed delivery sharp 88 (see, e.g. FIG. 4) is present in a delivery device 10, the cover member 26 may also inhibit inadvertent contact of the sharp 88 with a user and aid in maintaining sterility of the delivery sharp 88. In use, the cover member 26 may be removed and the delivery device 10 may be placed on the skin of the patient after removal of any adhesive backing 14. The locking member 18 or mechanism may be displaced or actuated to then begin delivery of therapeutic agent.

Figure 4:
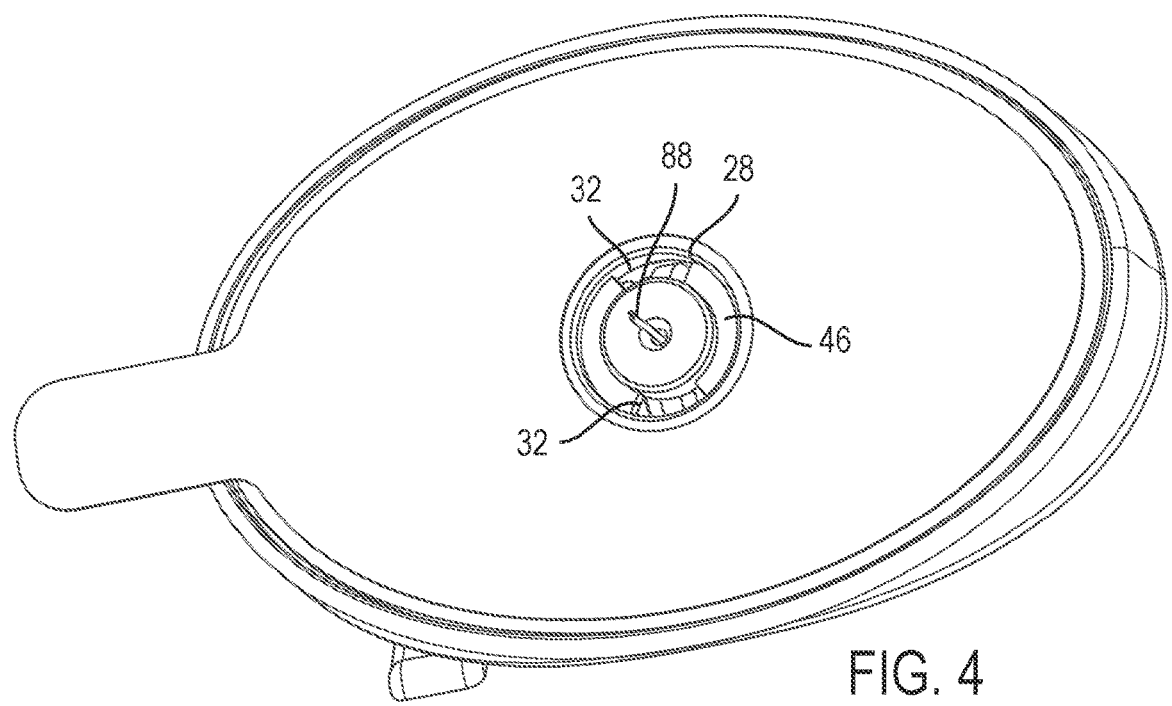
Figure 5:
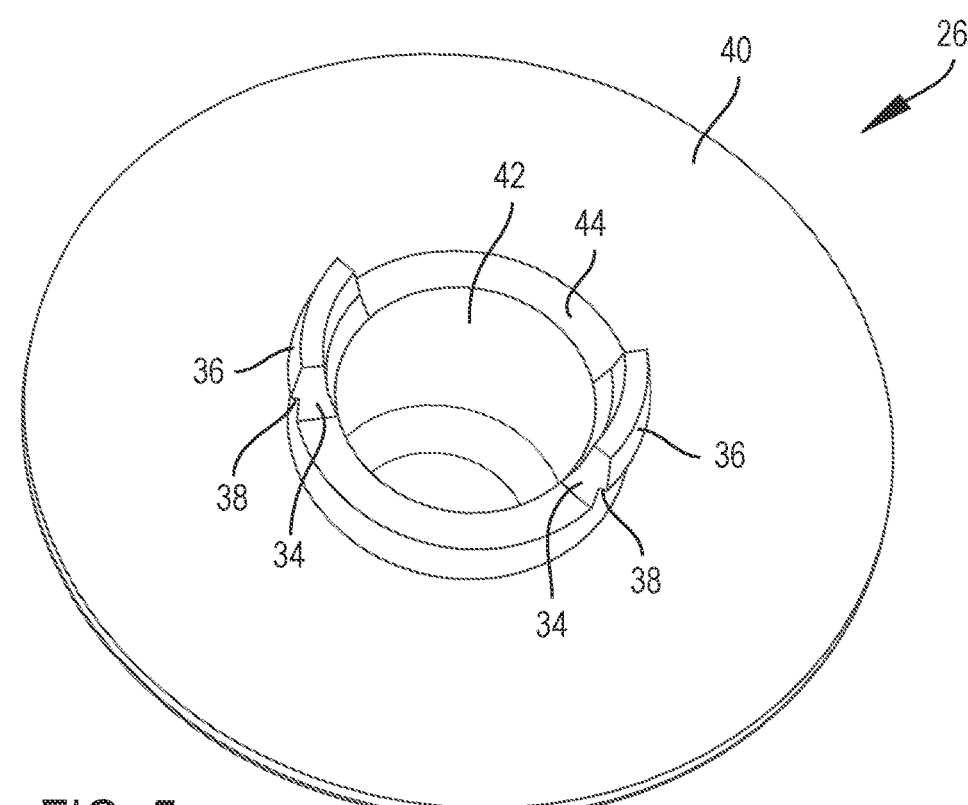

Referring primarily to FIGS. 4 and 5, the skin adhering face of the delivery device 10 may include a recess 28 through which at least one delivery sharp 88 may project. In the example embodiment, only one delivery sharp 88 is shown. The example delivery sharp 88 may be suitable for subcutaneous or intramuscular injection for example. In other embodiments, multiple delivery sharps 88 may be included. In some embodiments, the delivery device 10 may include a plurality of delivery sharps 88 in the form of a microneedle array (or alternatively a single microneedle). In such embodiments, the delivery device 10 may be suited to intradermal delivery of medication.

As shown, the example sharp 88 is oriented roughly perpendicular to the skin adhering face of the housing 12. In alternative embodiments, a sharp 88 or sharps 88 may be oriented at an angle other than a right angle. For example, in certain embodiments, the sharp 88 may be oriented at, e.g., 60°, 45°, or 30° with respect to the skin adhering face of the housing 12.

The adhesive and the adhesive backing 14 may include an interruption in the region where the recess 28 is present. The recess 28 may include at least one capture interface 32 which is configured to cooperate with a portion of the cover member 26 in order to retain the cover member 26 on the delivery device 10. In the example embodiment, the recess 28 includes a pair of fenestrations through the skin adhering face of the delivery device 10. The exemplary cover member 26 includes cooperating upstanding cantilevered projections 34. Each of the cantilevered projections 34 may include a ramped segment 36 at a terminal unsupported end thereof. The ramped segments 36 are included on the lateral faces of the cantilevered projections 34 in the example embodiment. The cantilevered projections 34 may further include a catch ledge 38 adjacent the ramped segments 36. To couple the cover member 26 to the delivery device 10, the cantilevered projections 34 may be pushed into the fenestrations. The ramped segments 36 may contact the edge wall of the fenestrations and facilitate deflection of the cantilevered projections 34 as the cover member 26 is advanced toward the rest of the delivery device 10. When the ramped segments 36 are advanced fully through the fenestrations, the cantilevered projections 34 may have a resiliency sufficient to cause the cantilevered projections 34 to return to an undeflected state. When the cantilevered projections 34 return to the undeflected state, the catch ledges 38 may rest on an interior facing side of the material in which the fenestrations are formed. Thus, cover member 26 may snap fit onto the delivery device 10 and the catch ledges 38 may inhibit inadvertent removal of the cover member 26.

As shown in FIGS. 3-5, the cover member 26 may include a flange 40 which surrounds a substantially centrally disposed well 42. The well 42 may accommodate the delivery sharp 88 or sharps 88. The well 42 may also provide a grasping surface for a user to aid in removal of the cover member 26. The flange 40 may provide a shield which helps to block a user's fingers from coming into contact with the delivery sharp(s) 88 during manipulation of the cover member 26. Additionally, as best shown in FIGS. 4 and 5, a raised rim 44 may be provided around the perimeter of the well 42. The cantilevered projections 34 may extend from the rim 44 in some embodiments. The recess 28 may have a trough 46 which corresponds with the rim 44. In the example embodiment, the well 42 is substantially circular and the trough 46 is substantially annular and includes the capture interfaces 32. The rim 44 and trough 46 may aid in alignment of the cover member 26 with the recess 28 during installation of the cover member 26 to the delivery device 10.

Though a snap fit engagement of the cover member 26 with the delivery device 10 is shown, any number of other retention arrangements may be used. For example, in some embodiments, the cover member 26 may couple to the delivery device 10 via an interference fit, threaded engagement, bayonet mount type engagement, adhesive, magnetic engagement, tape, etc. In some embodiments, the adhesive backing 14 may couple to the cover member 26 such that removal of the adhesive backing 14 will also remove the cover member 26.

Figure 6:
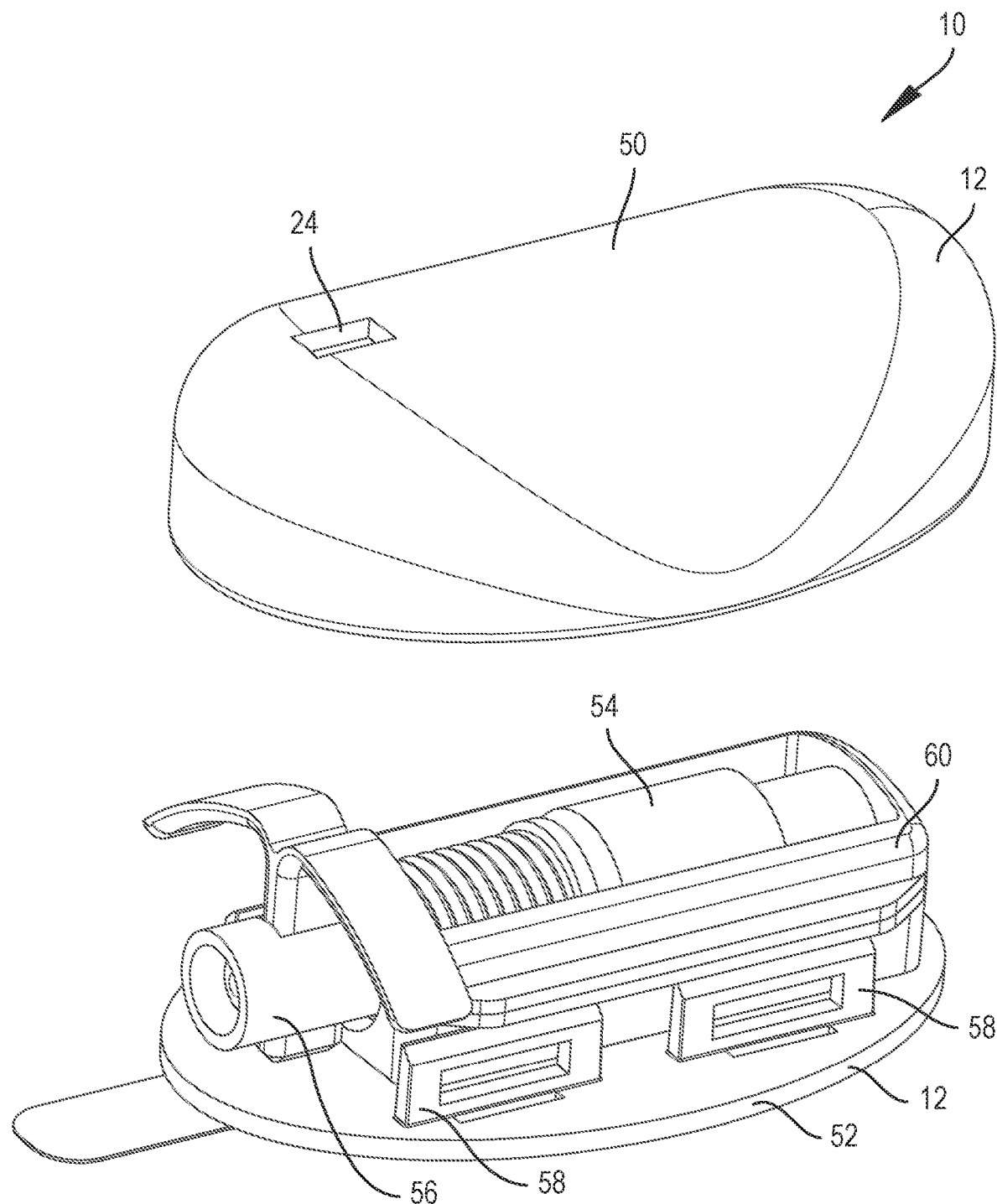
Figure 7:
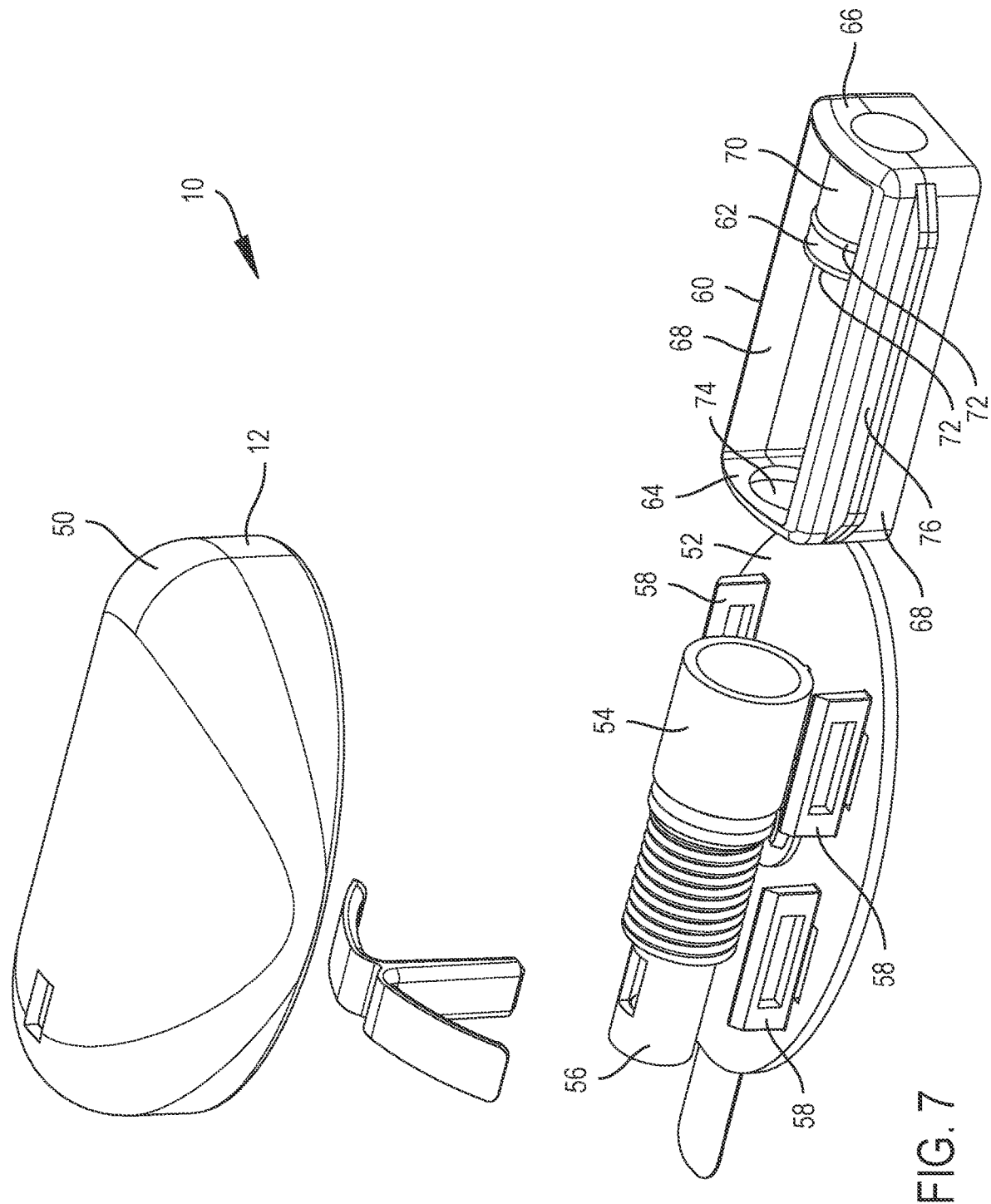

Referring now to FIG. 6 and FIG. 7, a partially exploded view and exploded view of an exemplary delivery device 10 are respectively depicted. As shown, the housing 12 of the delivery device 10 may include a first portion 50 and a second or base portion 52. The first portion 50 may couple to the second portion 52 and act as a housing cover or cap which encloses the internal components of the delivery device 10. The first portion 50 may be contoured for easy grasping. The second portion 52 of the housing 12, in the example embodiment, may include the skin adhering face of the delivery device 10. The second portion 52 may be substantially planar or may be at least partially flexible or contoured so as to accommodate placement against a cooperatively shaped section of a user's body.

The second portion 52 may also include stationary internal components of the delivery device 10. For example, the second portion 52 may also include a reservoir portion 54 and a guide portion 56. The reservoir portion 54 and guide portion 56 may be formed integrally with the second portion 52 of the housing 12 in certain embodiments. Thus, the reservoir portion 54, guide portion, and second portion 52 of the housing 12 may be constructed together as, for example, a single molded part. In other embodiments, one or more of the reservoir portion 54 and guide portion 56 may be discrete separate components which are assembled into place within a delivery device 10. For example, the reservoir portion 54 may be a separate component such as a syringe barrel which mates onto the second portion 52 of the housing 12. Housing retention members 58 may also be included and may, in some embodiments, be formed integrally with the second portion 52 of the housing 12. The housing retention members 58 may cooperate with features of the first portion 50 of the housing 12 so as to couple the first and second portions 50, 52 of the housing 12 together.

Still referring to FIGS. 6 and 7, a delivery device 10 may also include a plunger sled 60. The plunger sled 60 in the example embodiment has the form of a rectilinear frame with opposing first and second ends 64, 66 connected to one another via side panels 68. A plunger sled 60 may also be coupled to a plunger member 62. In the example embodiment, the plunger member 62 is included on the second end 66 of the plunger sled 60. The plunger member 62 may extend substantially perpendicularly from the interior face of the second end 66 and into the space surrounded by the plunger sled 60. The plunger member 62 may be constructed of or covered at least partially with an elastomeric material. In some embodiments, the elastomeric material of the plunger member 62 may be over molded onto a base body 70 of the plunger member 62. Alternatively, the terminal portion the plunger member 62 may be an elastomeric or partially elastomeric insert which is mounted (e.g. pressed into or onto and/or bonded or adhered to, see FIG. 9) to a base body 70 of the plunger member 62.

When the delivery device 10 is assembled, the plunger member 62 may be at least partially disposed within the reservoir portion 54 of the delivery device 10. The plunger member 62 may form a fluidic seal which inhibits fluid from passing out of the reservoir portion 54 and past the plunger member 62. Example plunger members 62 may include at least one radial rib 72 which extends proud of the side surface of the plunger member 62. The radial rib(s) 72 may compress against the interior wall of the reservoir portion 54 to aid in generating a robust fluid tight seal between the reservoir portion 54 and plunger member 62.

The first end 64 of the plunger sled 60 may include an aperture 74. The aperture 74 may be sized so as to accept the guide portion 56 of the delivery device 10. Thus, as the plunger sled 60 is displaced during operation, the aperture 74 may ride along the guide portion 56 helping to direct the displacement of the plunger sled 60 along a desired axis.

The side panels 68 of the plunger sled 60 may include protruding rails 76. These rails 76 may be disposed such that the rails 76 ride along the housing retention members 58 as the plunger sled 60 is displaced (best shown in FIG. 19). Again, this may aid in helping to constrain displacement of the plunger sled 60 to a desired path. Although the side panels 68 are shown as having protruding rails 76 in the example embodiment, in alternative embodiments, the side panels 68 may instead each include a groove or channel. In such embodiments, a projection or rail may be defined in one or more of the housing retention members 58 to guide the displacement of the plunger sled 60 during operation.

Figure 8:
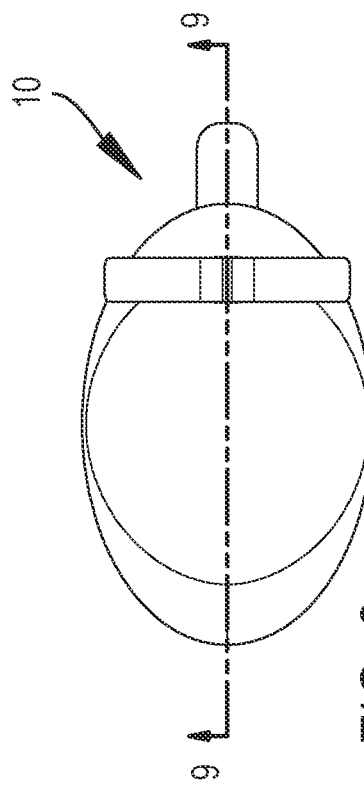
Figure 9:
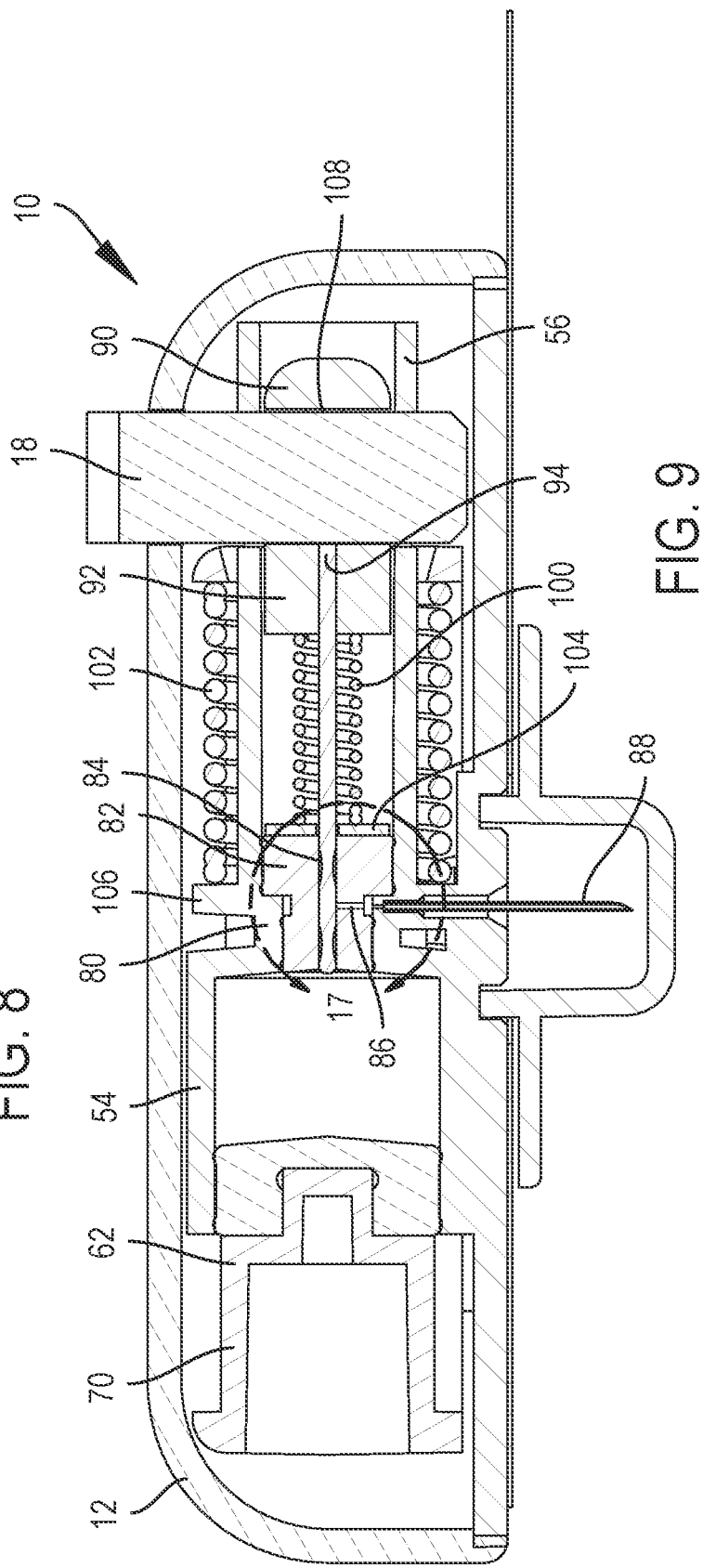

Referring now to FIG. 8 and FIG. 9, a top view of an example delivery device 10 and a cross section of a delivery device 10 are respectively shown. The cross section in FIG. 9 is taken at the cut plane indicated in FIG. 8. As shown, the delivery device 10 is in a locked state with its reservoir portion 54 in a fluid filled state. The plunger member 62 is disposed partially within the reservoir portion 54 of the delivery device 10 and forms a seal which prevents fluid from displacing past the plunger member 62 and out of the reservoir portion 54. Opposite the plunger member 62, the reservoir portion 54 includes a reservoir outlet 80.

Figure 10:
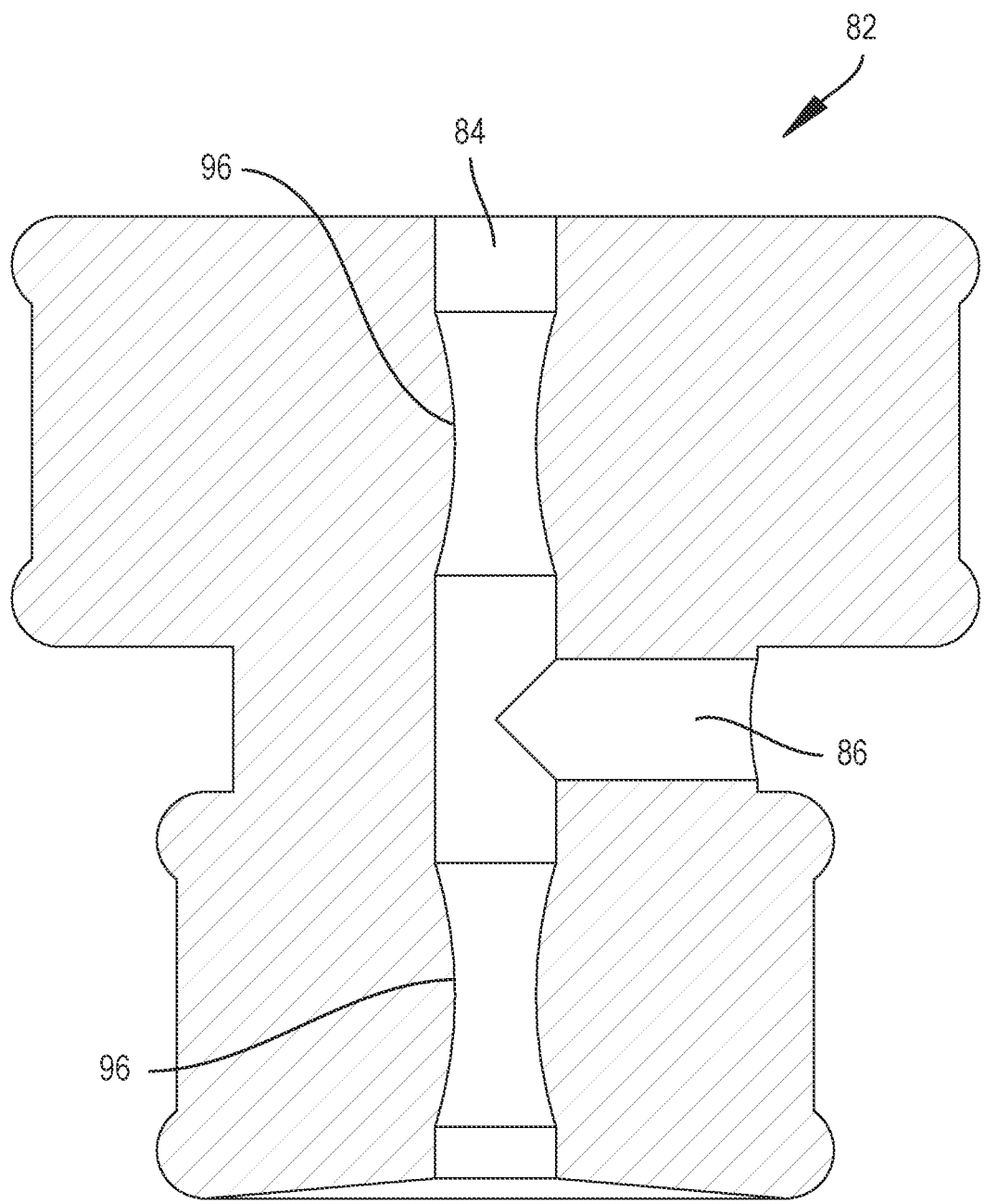

Referring now also to FIG. 10, an insert 82 (shown in cross-section in FIG. 10) is disposed within the reservoir outlet 80 in the example embodiment. Though referred to as an insert 82, the insert 82 may not necessarily be physically inserted into the reservoir outlet 80 during assembly. The insert 82 may be, for example, created in place as part of a molding operation or other manufacturing operation. The insert 82 may be constructed of a compliant material such as an elastomer. The insert 82 may include at least one fluid pathway 84, 86 defined therein. In the example embodiment, the insert 82 includes a fluid pathway 84 which extends through the insert 82 substantially along the longitudinal axis of the insert 82. The insert 82 also includes a second fluid pathway 86 which branches from the first fluid pathway 84. The second fluid pathway 86 may communicate with one or more fluid delivery sharp 88 (in this example a needle for subcutaneous delivery).

The delivery device 10 may include a plug 90. The plug 90 may include a head portion 92 from which an occluding member 94 may extend. The occluding member 94 may extend into a fluid pathway 84, 86 of the insert 82 and prevent flow from the reservoir portion 54 to the delivery sharp(s) 88 when disposed within the fluid pathway 84. In the example embodiment, the occluding member 94 is a pin which projects from the head portion 92 of the plug 90. The fluid pathway 84 of the insert 82 which interacts with the occluding member 94 may include one or more reduced diameter portions 96 (best shown in FIG. 10). The reduced diameter portions 96 may be arranged such that their diameter is less than that of the occluding member 94 ensuring that these segments of the fluid pathway 84 will be compressed against the exterior of the occluding member 94 when the occluding member 94 is present. This may aid in ensuring a robust fluid seal is formed when the occluding member 94 is in place within the fluid pathway 84. In the example embodiment, the fluid pathway 84 extending through the longitudinal axis of the insert 82 includes two reduced diameter sections 96. One of the reduced diameter sections 96 is disposed upstream of the branch fluid pathway 86 leading to the delivery sharp(s) 88. The other of the reduced diameter sections 96 is disposed downstream of the branch fluid pathway 86 leading to the delivery sharp(s) 88. The reduced diameter sections 96 may be included as stepwise changes in the diameter of the fluid pathway 84 or the fluid pathway 84 may have a continuous gradual change in diameter over the extent of the reduced diameter sections 96 as shown.

Referring primarily to FIG. 9, the delivery device 10 may include a plug driver and a plunger sled driver. In the example embodiment, the plug driver is shown as a first bias member 100 and the plunger sled driver is shown as a second bias member 102. Specifically, the exemplary bias members 100, 102 shown in FIG. 9 are compression springs. Any other suitable bias member such as other springs, gas bladders, compressible compliant members, etc. may be used. The first bias member 100 may be disposed between the head portion 92 of the plug 90 and the insert 82. Together with the locking member 18, the plug 90 and first bias member 100 may from an activation assembly of the delivery device 10. In some embodiments, a resilient body 104 (e.g. a washer or disk) may be disposed intermediate the inserter 82 and an end of the first bias member 100. The second bias member 102 may be disposed between the first end 64 of the plunger sled 60 and a radial flange 106 at an end of the guide portion 56 most proximal the reservoir portion 54 of the delivery device 10.

When the delivery device 10 is in a locked state, the first and second bias members 100, 102 may be in an energy storing state. The locking member 18 may be present and may extend at least partially through a receiving slot 108 in the head portion 92 of the plug 90. As the locking member 18 extends through the head portion 92 of the plug 90, the locking member 18 may block the plug 90 from displacing under restoring force supplied from the first bias member 100. The first end 64 of the plunger sled 60 may also be in contact with a face of the locking member 18. Thus, the locking member 18 may present a mechanical interference which prevents movement of the plunger sled 60 under restoring force supplied by the second bias member 102.

Figure 11:
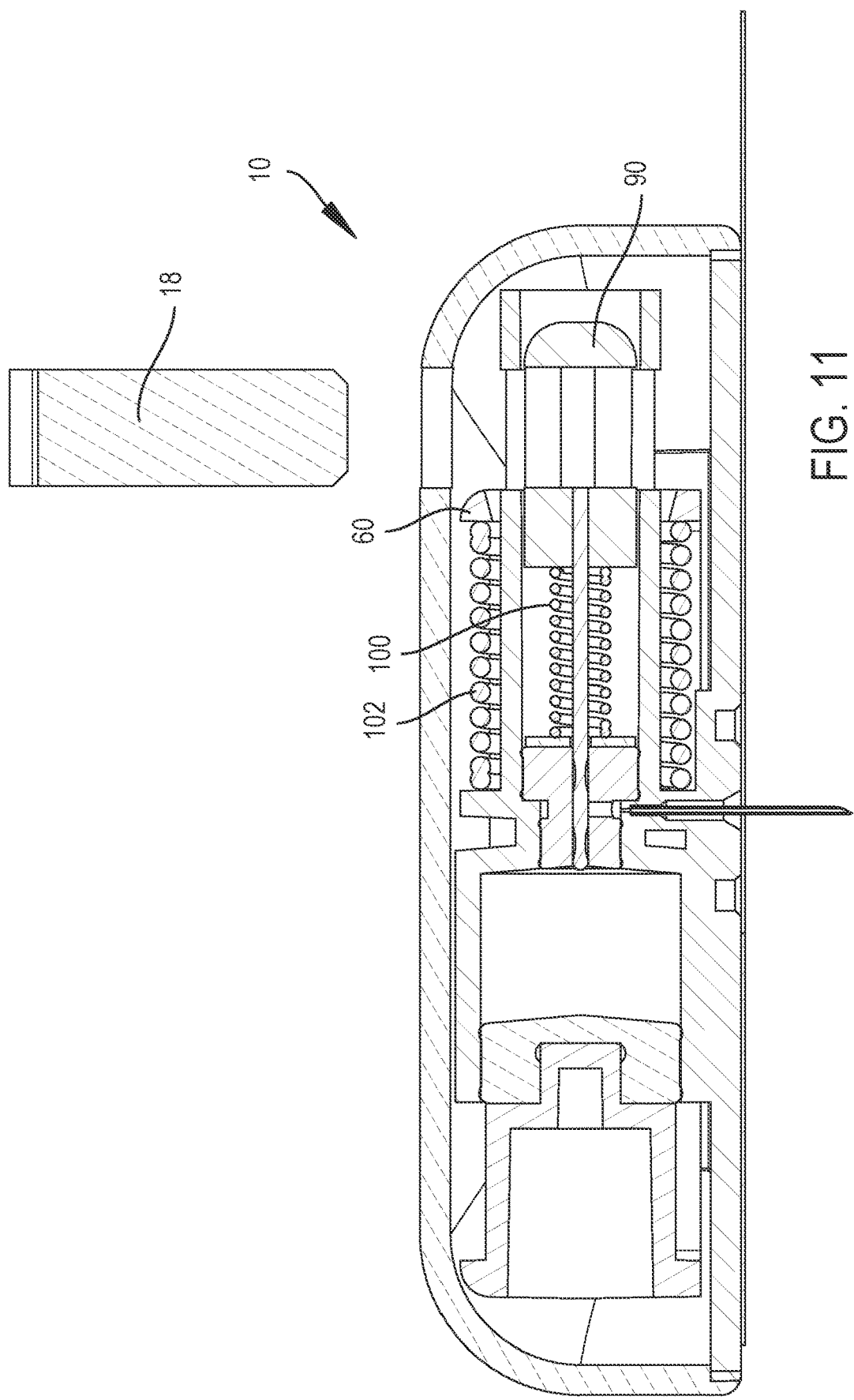

Referring now to FIG. 11, when a user is ready to deliver the contents of the delivery device 10 to a patient, the cover member 26 (see, e.g., FIG. 5) may be doffed and the locking member 18 may be displaced. With the locking member 18 displaced out of a locking state (in the example, fully removed from the delivery device 10), the plug 90 and the plunger sled 60 may be free to move under the urging of the first and second bias member 100, 102.

Figure 12:
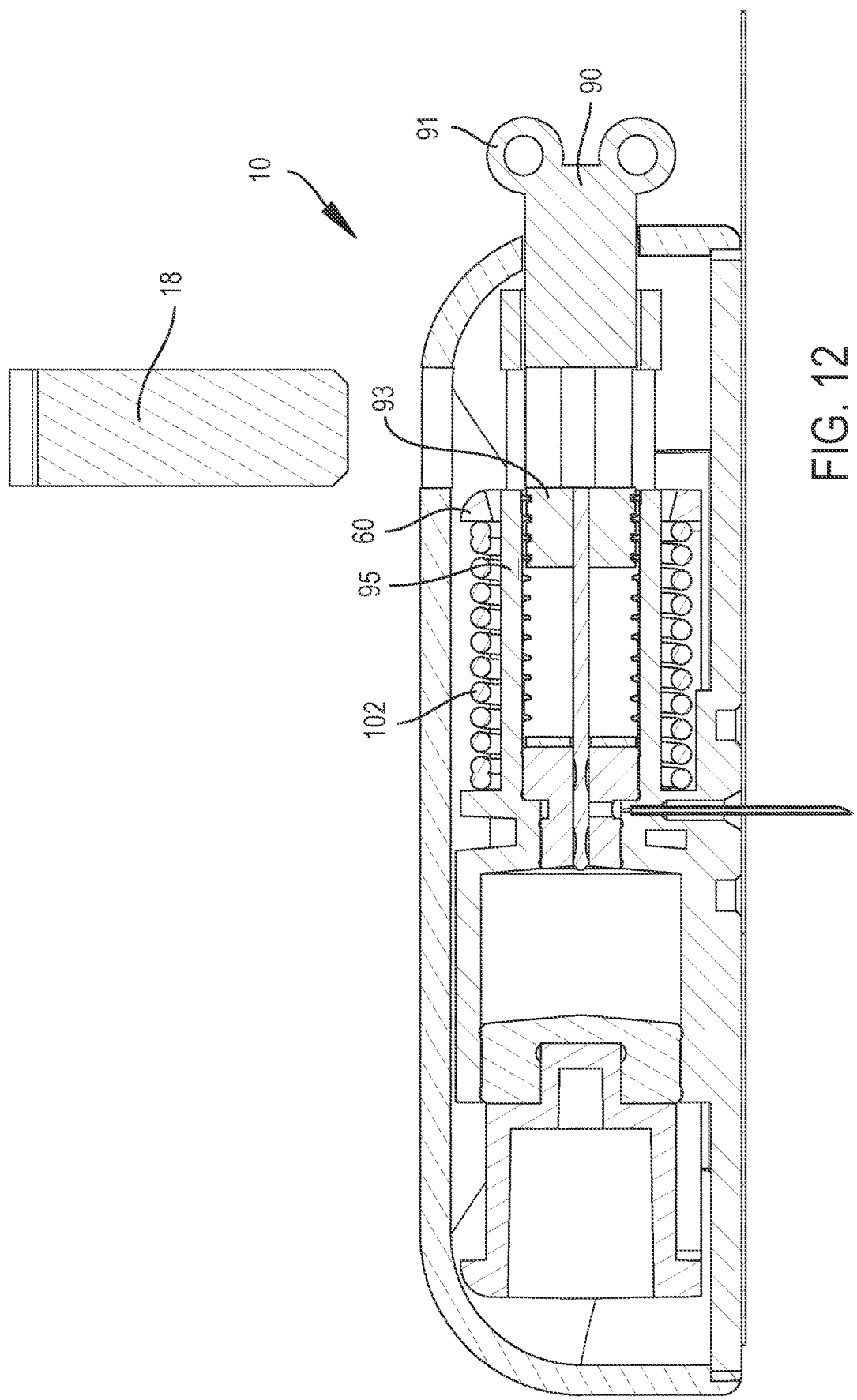

In some embodiments, and referring now to FIG. 12, the first bias member 100 may not be used. Instead, the plug 90 may be arranged to be manually extracted. In the example shown in FIG. 12, the plug 90 includes a turnkey portion 91 (which may be a knob, dial, lever, etc. in alternative embodiments) which is accessible via the exterior of the housing. The plug 90 also include a threaded section 93 which may interface with cooperating threads included in a receiving bore 95 of the guide portion 56. Rotation of the turnkey portion 91 may displace the plug 90. In other embodiments, a threaded section 93 may not be used. In such embodiments, the turnkey portion 91 may be replaced with a pull ring or other graspable interface and the plug 90 may be displaced by a manual pulling force exerted on the pull ring.

Figure 13:
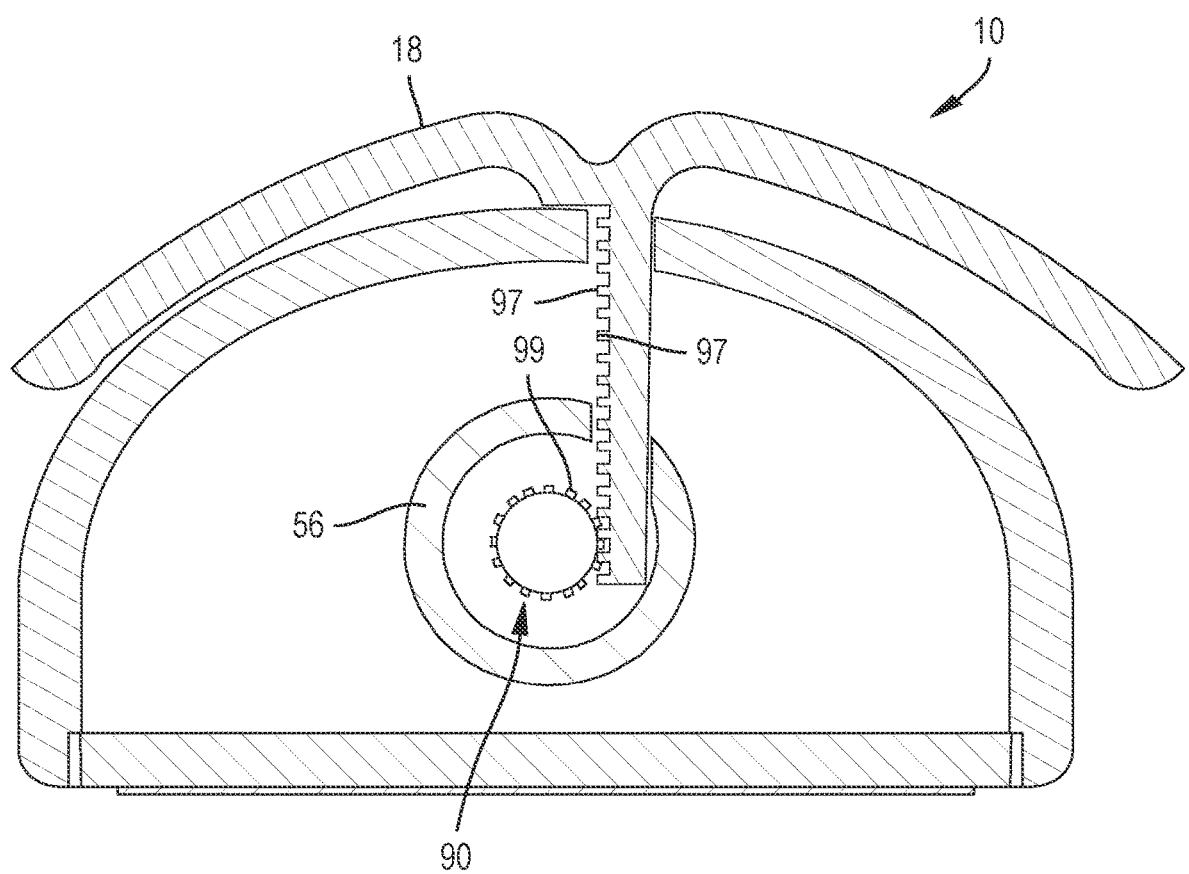

Referring now to FIG. 13, in other embodiments which do not include the first bias member 100, the lock member 18 may be teethed with at least one tooth 97. The plug 90, may include a pinion portion 99. When installed in the delivery device 10, the at least one tooth 97 of the lock member 18 may interdigitate with the teeth of the pinion portion 99 of the plug 90. As the lock member 18 is extracted, the teethed interface between the lock member 18 and pinion portion 99 of the plug 90 may convert translational displacement of the lock member 18 into rotation of the plug 90. As mentioned above, the plug 90 may include a threaded section 93 (see, e.g., FIG. 12). Thus, as the plug 90 is rotated, the plug 90 may translationally displace due to interaction between the threaded section 93 of the plug 90 and the cooperating threads of the receiving bore 95 of the guide portion 56. The pinion portion 99 of the plug 90 may have a length sufficient to accommodate this translational displacement. Thus the pinion portion 99 may not only rotate, but also slide across the at least one tooth 97 of the lock member 18 as the plug 90 is translationally displaced along the axis of the receiving bore 95 of the guide portion 56.

Figure 14:
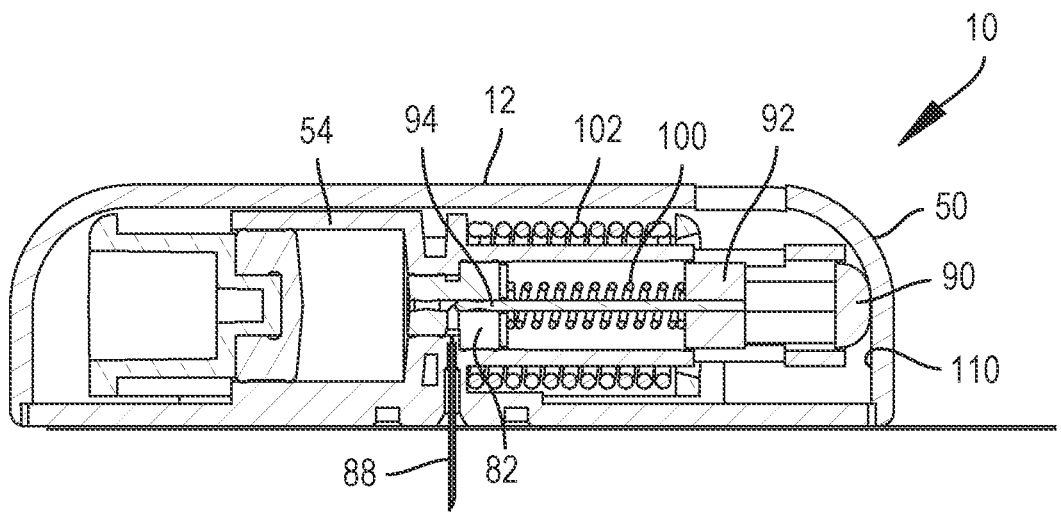

Referring now to FIG. 14, with the locking member 18 removed from the locking state, the bias members 100, 102 may begin to displace the plug 90 and the plunger sled 60. The first bias member 100 may quickly transition to a relaxed state and drive the plug 90 in a direction opposite the insert 82. In alternative embodiments, the plug 90 may be manually displaced (e.g. via a turnkey portion 91 of the plug 90, see, e.g., FIG. 12, via a rack and pinion arrangement between the plug 90 and lock member 18 see, e.g., FIG. 13, or any other suitable arrangement). As shown, the head portion 92 of the plug 90 may abut against a stop surface 110 on the interior face of the first portion 50 of the housing 12. The displacement distance of the plug 90 may be chosen such that the interior volume of the reservoir portion 54 may be placed into communication with the delivery sharp(s) 88 of the delivery device 10 when the plug 90 is driven into the stop surface 110. When the plug 90 is displaced against the stop surface 110, the occluding member 94 may be moved so as to establish a flow path through the insert 82 to the delivery sharp(s) 88, yet block fluid from passing fully through the first fluid pathway 84. Though the first bias member 100 is described as being in a relaxed state in FIG. 14, it should be understood that the first bias member 100 may not be fully restored to its unstressed configuration once the plug 90 is driven into the stop surface 110. This may be desirable as the plug 90 may be firmly held against the stop surface 110 if the first bias member 100 is still at least slightly stressed.

Figure 15:
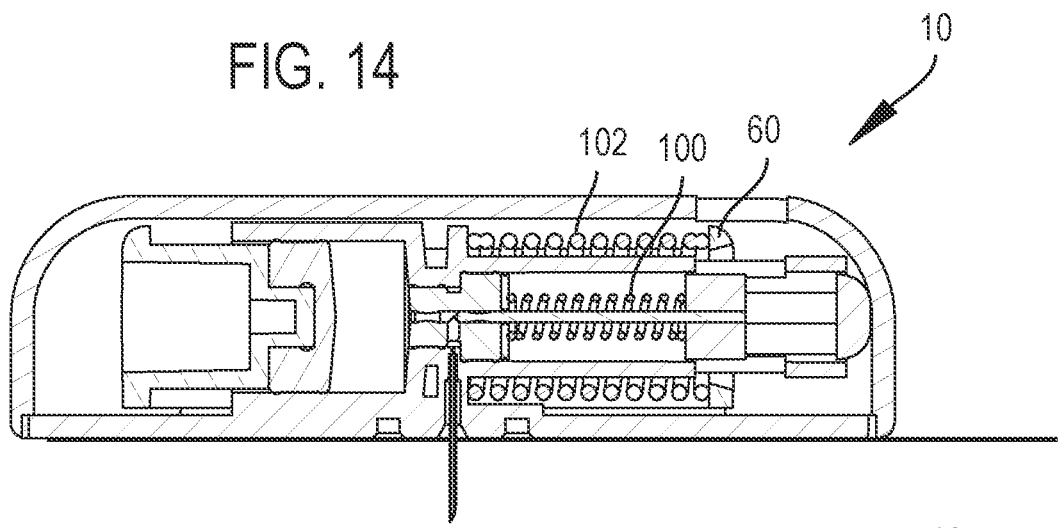
Figure 16:
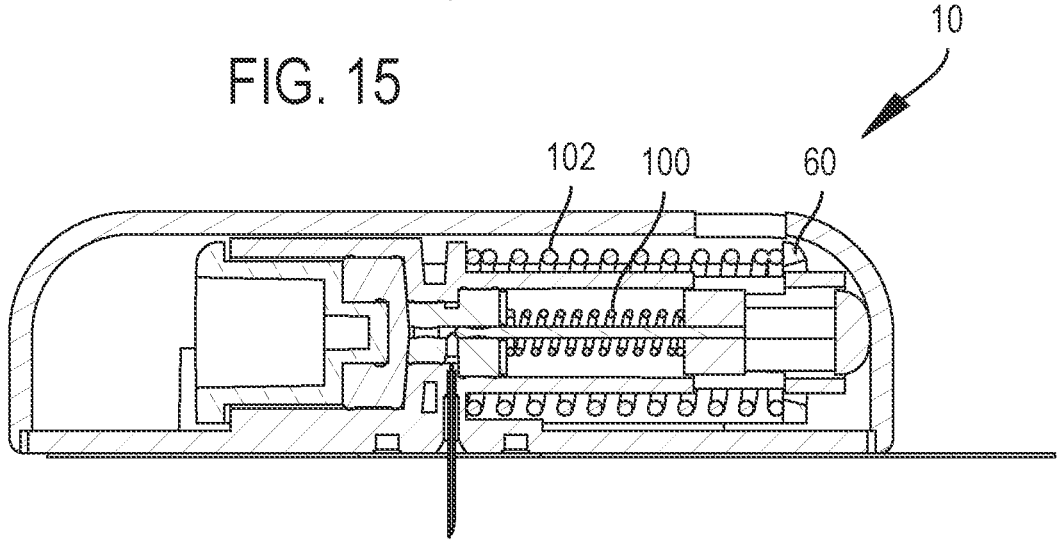

Referring now also to FIGS. 15 and 16, the second bias member 102, while free to transition to a more relaxed state when the locking member 18 is removed, may do so more slowly. This may be a result of any resistance to fluid flow from the reservoir portion 54 to the delivery sharp(s) 88.

In some examples, the second bias member 102 may be selected such that the relaxation of the second bias member 102 as the plunger sled 60 is driven from its position in FIG. 14 to its position in FIG. 16 only partially relaxes the second bias member 102. The displacement of the second bias member 102 as this relaxation occurs may be selected such that it occurs over a portion of the second bias member's 102 force v. displacement plot which has a characteristic of interest. For example, the displacement may be selected such that it occurs over a linear portion of the force v. displacement plot. Alternatively, the displacement may be selected to occur over a portion of the force v. displacement plot that is relatively constant. For example, the displacement of the second bias member 102 needed to deliver the contents of the reservoir portion 54 may be a small fraction (e.g. 10-15% or up to 20%) of the total spring displacement. The characteristic of interest for the force v. displacement plot may be selected to inform the flow rate of fluid from the delivery device 10 or its derivatives during operation.

Figure 17:
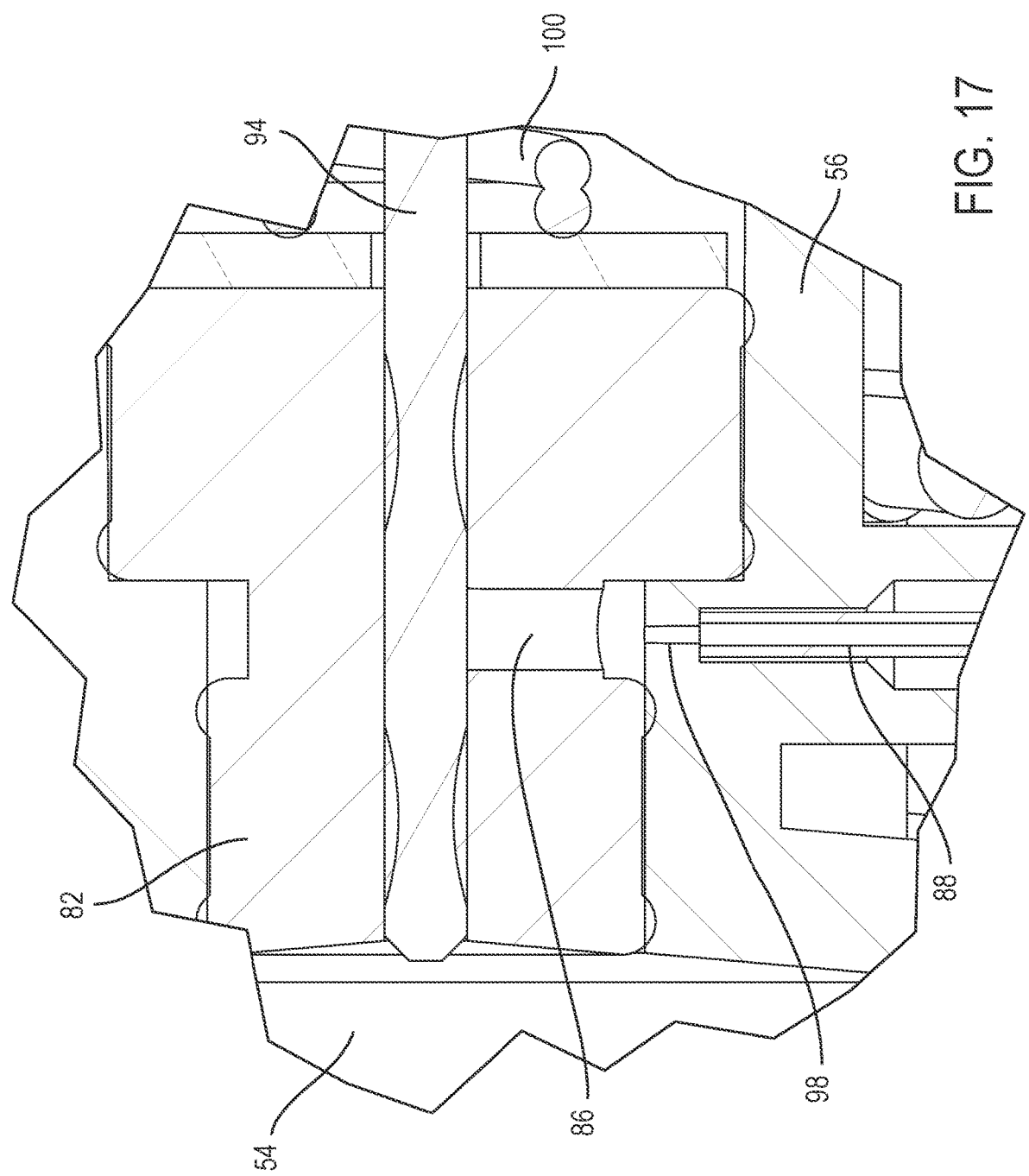

Referring now to FIG. 17, in certain embodiments, the resistance to fluid flow from the reservoir 54 may be manipulated to control the delivery rate from the delivery device 10. For example, in certain embodiments, a restriction 98 may be placed in the fluid flow path between the reservoir portion 54 and the delivery sharp(s) 88 to lower the flow rate. The length of the flow path between the reservoir portion 54 and the delivery sharp(s) 88 may also be altered to adjust the flow rate. Thus, delivery devices 10 may be constructed so as to support a bolus delivery of the contents of the reservoir portion 54 or a slower basal delivery of the reservoir portion 54 contents.

Referring now to FIGS. 18 and 19 a top down view of an example delivery device 10 and a cross section of a delivery device 10 taken at the indicated cut plane in FIG. 18 are respectively shown. As shown, during displacement of the plunger sled 60 the rails 76 of the plunger sled 60 may travel along a face of the housing retention members 58. In the example, the rails 76 travel along and may be guided by a face of the housing retention members 58 which is most distal to the main body of the second housing portion 52.

Referring now also to FIG. 20, the first housing portion 50 may include a number of coupling members 120. The coupling members 120 are shown as snap projections which are cantilevered from an interior face of the first housing portion 50 in the example embodiment. As the first housing portion 50 and second housing portion 52 are joined, the coupling members 120 may resiliently deflect around the housing retention members 58. As the first and second housing portions 50, 52 are further advanced toward one another, the coupling members 120 may reach a latch slot 122 in each of the housing retention members 58. The coupling members 120 may restore to their undeflected state upon reaching the latch slot 122. Upon restoring to their relaxed state, a ledge 124 on each coupling member 120 may abut against a wall of the latch slot 122 preventing inadvertent disassociation of the first and second housing portion 50, 52. As the coupling is inaccessible from the exterior of the delivery device 10, the connection between the first housing portion 50 and second housing portion 52 may be difficult for a user to disengage which may be desirable.

Figure 21:
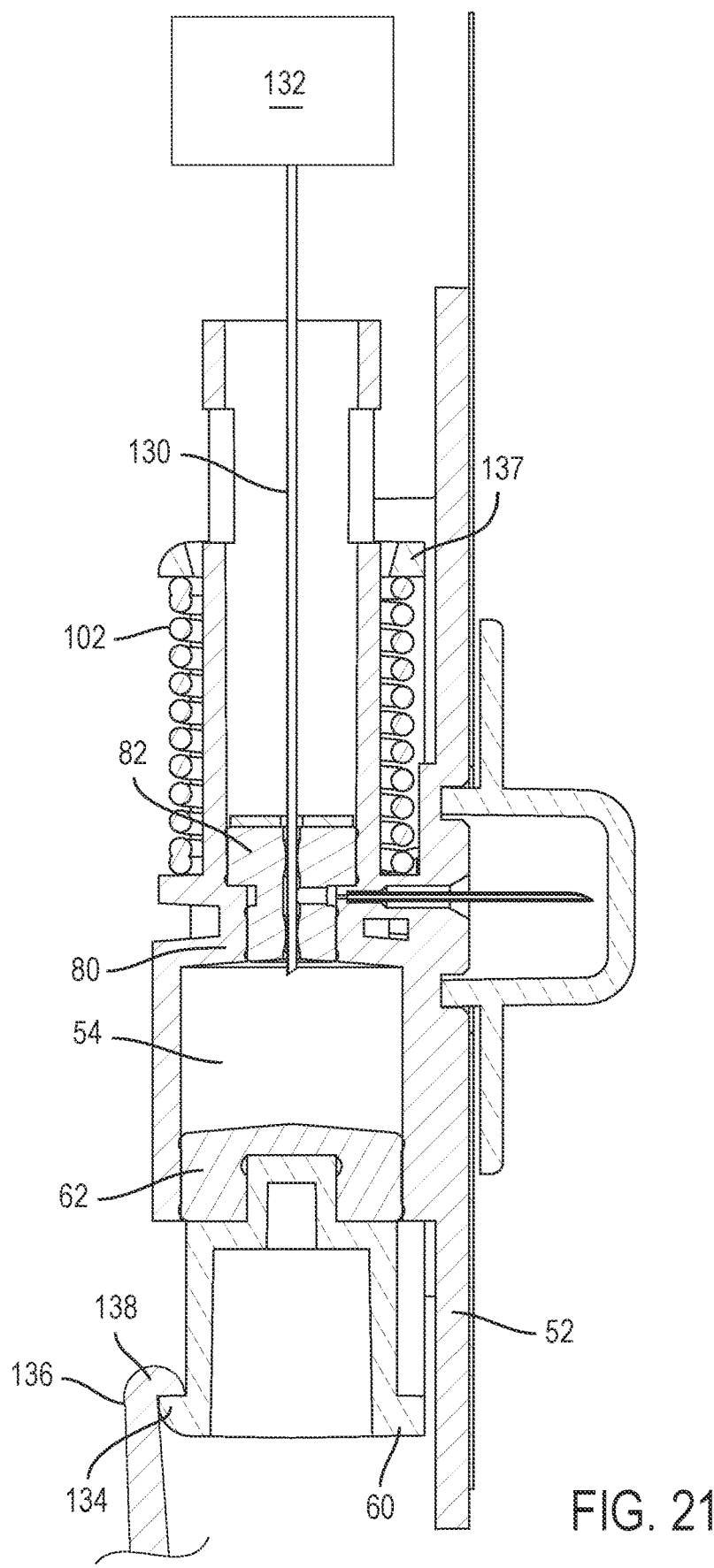

Referring now to FIG. 21, example delivery devices 10 may be filled in a variety of ways. For example, in certain examples, a filling implement 130 may be brought into fluid communication with the reservoir 54 via the insert 82. Fluid from a source 132 connected to the filling implement 130 may then be transferred into the interior volume of the reservoir portion 54. In certain embodiments, fluid from the source 132 may be driven into the reservoir portion 54 and the hydraulic pressure of the fluid may displace the plunger sled 60 and compress the second bias member 102 as needed to accommodate the fluid. In other examples, the plunger sled 60 may be driven so as to displace the plunger member 62 away from the outlet 80 of the reservoir portion 54 and compress the second bias member 102. In such embodiments, the negative pressure generated due to the displacement of the plunger member 62 within the reservoir portion 54 may draw fluid into the reservoir portion 54 through the filling implement 130. In still other embodiments, hydraulic pressure may force fluid into the reservoir portion 54 while the plunger sled 60 is be driven so as to suck fluid into the reservoir portion 54.

Where the plunger sled 60 is driven to aid in drawing of fluid into the reservoir portion 54, the plunger sled 60 may include at least one coupling 134 to which a drive element 136 may be coupled. Coupling 134 may, for example, be a hitch, hook, yoke, catch, or, as shown in FIG. 21, a lip. The drive element 136, which may be part of a filling fixture in a manufacturing setting, may be coupled to the plunger sled 60 via the coupling 134 and be actuated so as to displace the plunger sled 60 against the force exerted by the second bias member 102. In the example embodiment, the drive element 136 may include a protruding ridge 138 which may be brought into abutment with the lip 134 to pull back the plunger sled 60.

In alternative examples, the plunger sled 60 may be pushed so as to displace the plunger sled 60 against the force exerted by the second bias member 102. For example, a drive element 136 be press against a face 137 of the plunger sled 60 opposite the plunger 62. In such embodiments, the guide portion 56 may act as a locating projection which may help to position the drive element in place against the face 137 of the plunger sled 60.

After the reservoir portion 54 has been filled as desired, the plunger sled 60 may be held in position. As mentioned above, in some embodiments, the plunger sled 60 may include a coupling 134 which may engage with a portion of a filling fixture. This engagement may be used to hold the plunger sled 60 in position against the restoring force of the second bias member 102. While the plunger 60 is held in a withdrawn position, the first bias member 100 and plug 90 may be introduced into the delivery device 10 assembly. As shown in FIG. 9, the plug 90 may block flow through the outlet 80 of the reservoir portion 54. During filling the outlet 80 may be the highest portion of the reservoir portion 54 so as to prevent any egress of fluid prior to installation of the plug 90. A locking member 18 may be installed so as to block movement of the plug 90 and plunger sled 60. With the locking member 18 in a locking state, the plunger sled 60 may be disengaged from the drive element 136 of the filling fixture. The first portion 50 of the housing 12 may be coupled to the second portion 52 to enclose the internal components of the delivery device 10. As described in reference to FIG. 2, in certain examples, locking members 18 may be partially flexible. In the grasping configuration (see, e.g., FIG. 2) of such a locking member 18, the locking member 18 may be able to pass through the aperture 24 in the first portion 50 of the housing 12 as the first and second portions 50, 52 are coupled to one another.

Filling of the delivery device 10 and introduction of the plug 90 may occur in a tightly controlled environment. Once the plug 90 has been installed, the fluid paths of the delivery device 10 may be sealed or protected from the ambient environment (the cover member 26 may be present). Thus, remaining components of the delivery device 10 need not be provided in a sterile state. Additionally, such components may be assembled into place in a less stringently controlled environment.

Figure 22:
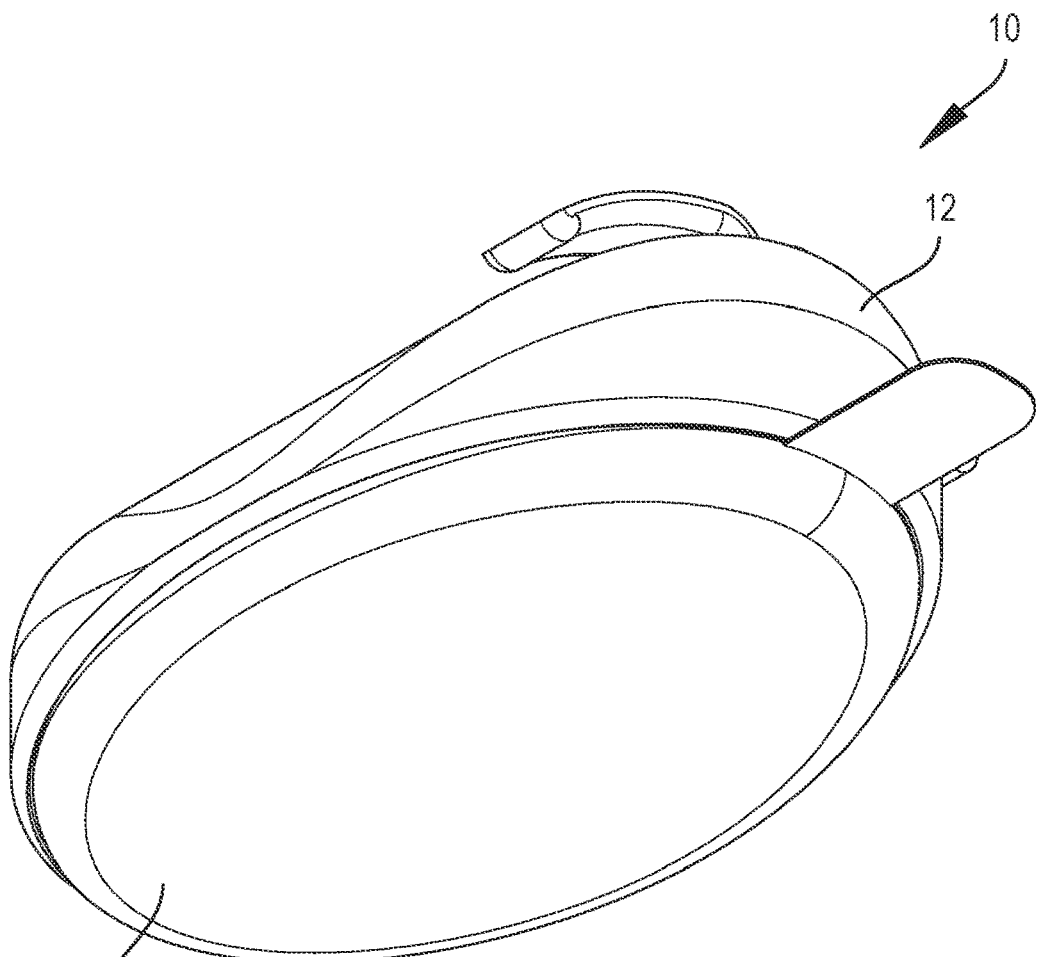
Figure 23:
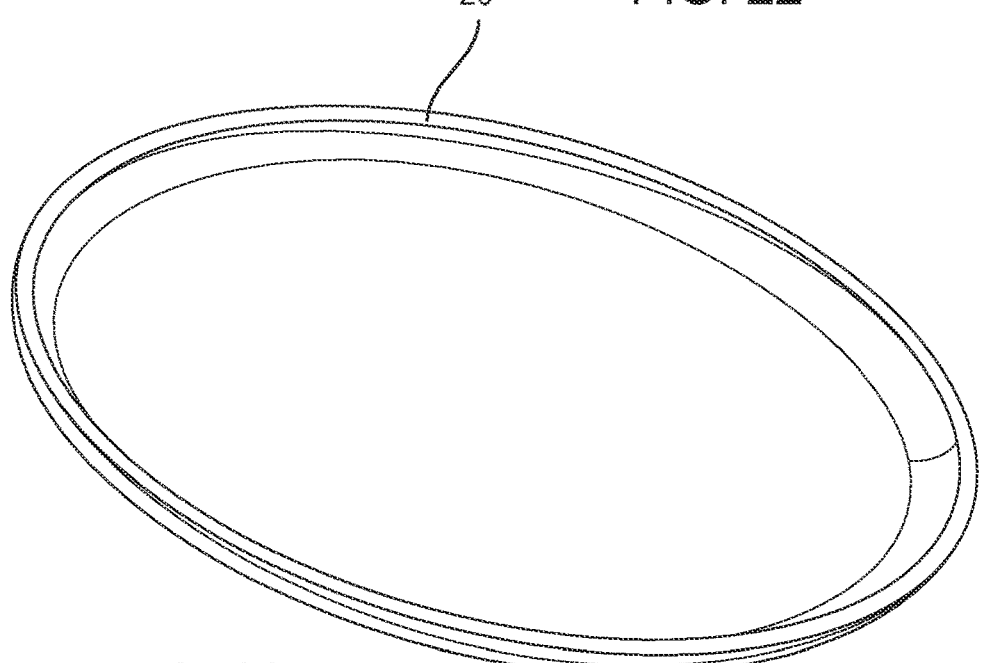

Referring now to FIG. 22, another exemplary embodiment of a delivery device 10 is depicted. The example delivery device 10 may be an intradermal delivery device 10 which is arranged to automatically deliver fluid to an intradermal location of a patient's body. As shown, the delivery device 10 includes a cover member 26. The cover member 26 may cover the majority or the entirety of the skin adhering surface of the delivery device 10. Referring now also to FIG. 23, the cover member 26 may have a concavely curved wall which forms a basin. When coupled to the housing 12 of the delivery device 10, the delivery sharp(s) 88 may be enclosed by the cover member 26.

Figure 24:
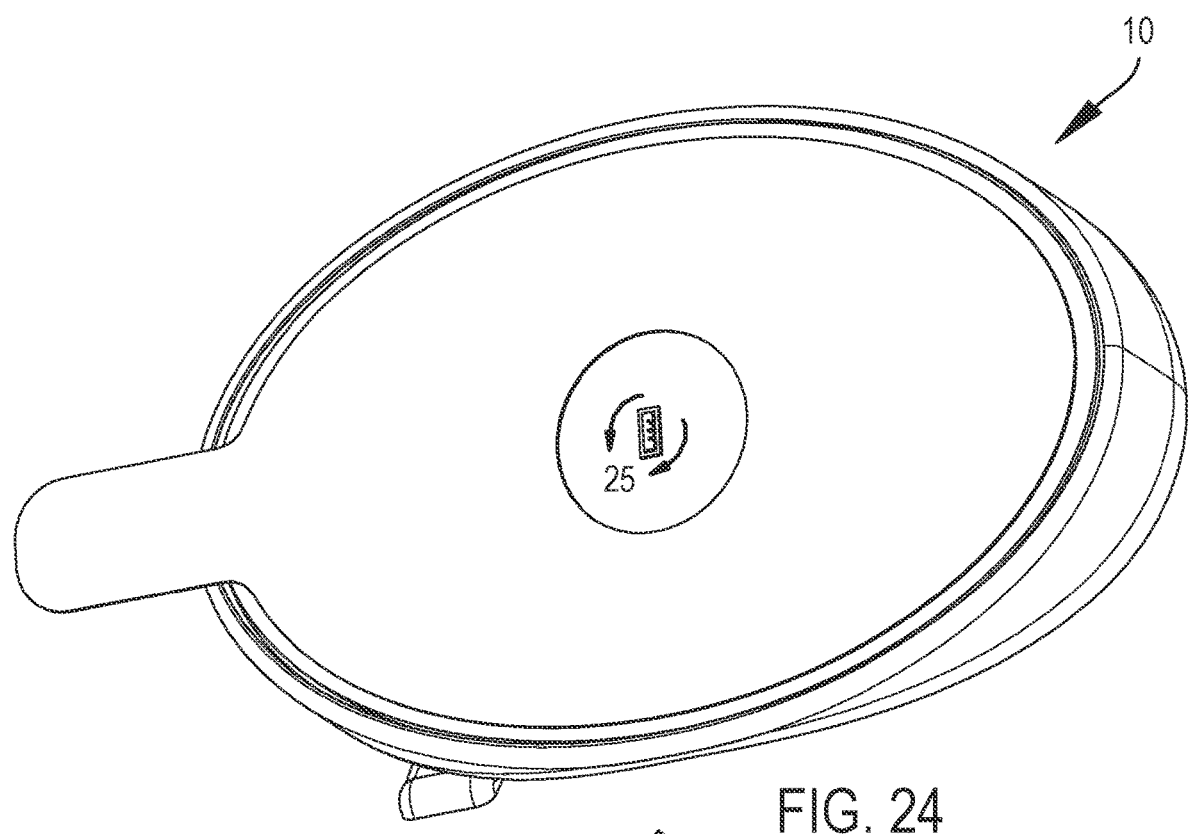
Figure 25:
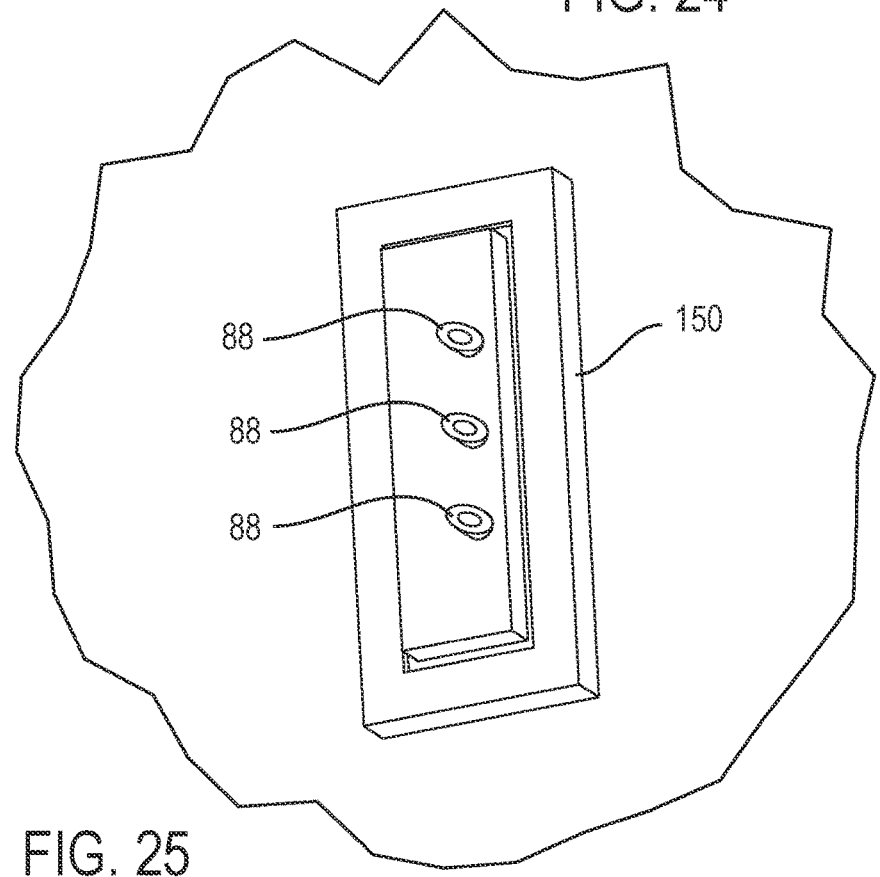

Referring now to FIGS. 24-25, the delivery device 10 may include an array of delivery sharps 88 which in the example embodiment are microneedles. In the example embodiment, an array of three microneedles is depicted for exemplary purposes. The three microneedles are arranged in a single row in the example. As with other embodiments described herein, any suitable number of microneedles may be included and in some examples a single microneedle may be included. Additionally, any suitable number of rows and/or columns or microneedles may be included where an array is used in an embodiment described herein. Preferably, the arrangement of microneedles may not produce a bed of nails type effect in which penetration of the skin is inhibited. The microneedles may be appropriately spaced in a spaced array to prevent this.

Microneedles included herein may be constructed of a biocompatible, non-ductile, high Young's modulus material with an indentation hardness sufficient to allow penetration into skin without breakage. The microneedles described herein may, in certain embodiments, be MEMS produced, polyhedral (e.g. pyramidal), silicon crystal microneedles. These microneedles may be no greater than 1 mm in height, e.g. 0.6 mm (though longer microneedles may also be used). At least some edges of the microneedles may be rounded or filleted, though such microneedles may still be considered polyhedral. In other embodiments, the microneedles may be conically shaped. Any suitable shape may be used. The points or tips of microneedles described herein may be solid and the flow lumens through the microneedles may be offset from the points or tips of the microneedles. Hollow tipped microneedles in which the flow lumen is extends to the tip of the microneedle may also be utilized. In some embodiments, the microneedles may be NanoPass hollow microneedles available from NanoPass Technologies Ltd. of 3 Golda Meir, Nes Ziona, Israel. It should be noted that microneedles described herein as constructed of silicon may have a surface layer of silicon dioxide which may, for example, form with exposure to air. In other embodiments, microneedles described herein may be constructed of glass (e.g. silica glass, borosilicate glass), ceramic (e.g. alumina, calcium sulfate dehydrate, calcium phosphate dehydrate, organically modified ceramics such as Ormocer), polymer, carbohydrate, or metal (e.g. stainless steel, titanium, palladium, nickel, alloys such as palladium cobalt alloys, etc.). Any suitable microneedle constructions including dissolvable microneedles may be used. Microneedles may be manufactured in one or more of, though are not limited to, a molding process, etching process, ablative process (e.g. laser ablation), or a material additive process (e.g. 3D printed).

Referring still to FIGS. 24-25, in the example, the microneedles are disposed substantially perpendicular to the skin adhering face of the delivery device 10. In alternative embodiments, the microneedles may extend at an acute angle (e.g. 30°, 45°, 60°) with respect to the skin adhering face of the delivery device 10. The microneedles may be provided on a portion of the delivery device 10 which is raised with respect the remainder of the skin adhering face of the delivery device 10. In the example embodiment, the microneedles are disposed on a platform 150. A platform 150 may not be used in all embodiments. For example, the delivery sharps 88 may be included on a portion of a convex bump raised from the skin adhering face. Disposing the delivery sharps 88 in raised relationship to the skin adhering surface of the delivery device 10 may ensure that pressure applied to the delivery device 10 when the delivery device 10 is placed on a patient's body is concentrated on the delivery sharps 88. Additionally, it may aid in stretching the skin at the puncture site. This may help to ensure that the delivery sharps 88 appropriately puncture into the patient's skin. Thus, the delivery device 10 may provide intradermal delivery access without need for a medical professional to utilize Mantoux technique. Additionally, the delivery device 10 may simply be applied to the skin obviating the need for a medical professional to hold an injection instrument at their estimate of a prescribed angle relative to the skin surface. Thus, intradermal injection via a delivery device 10 may be more precise and consistent.

Figure 26:
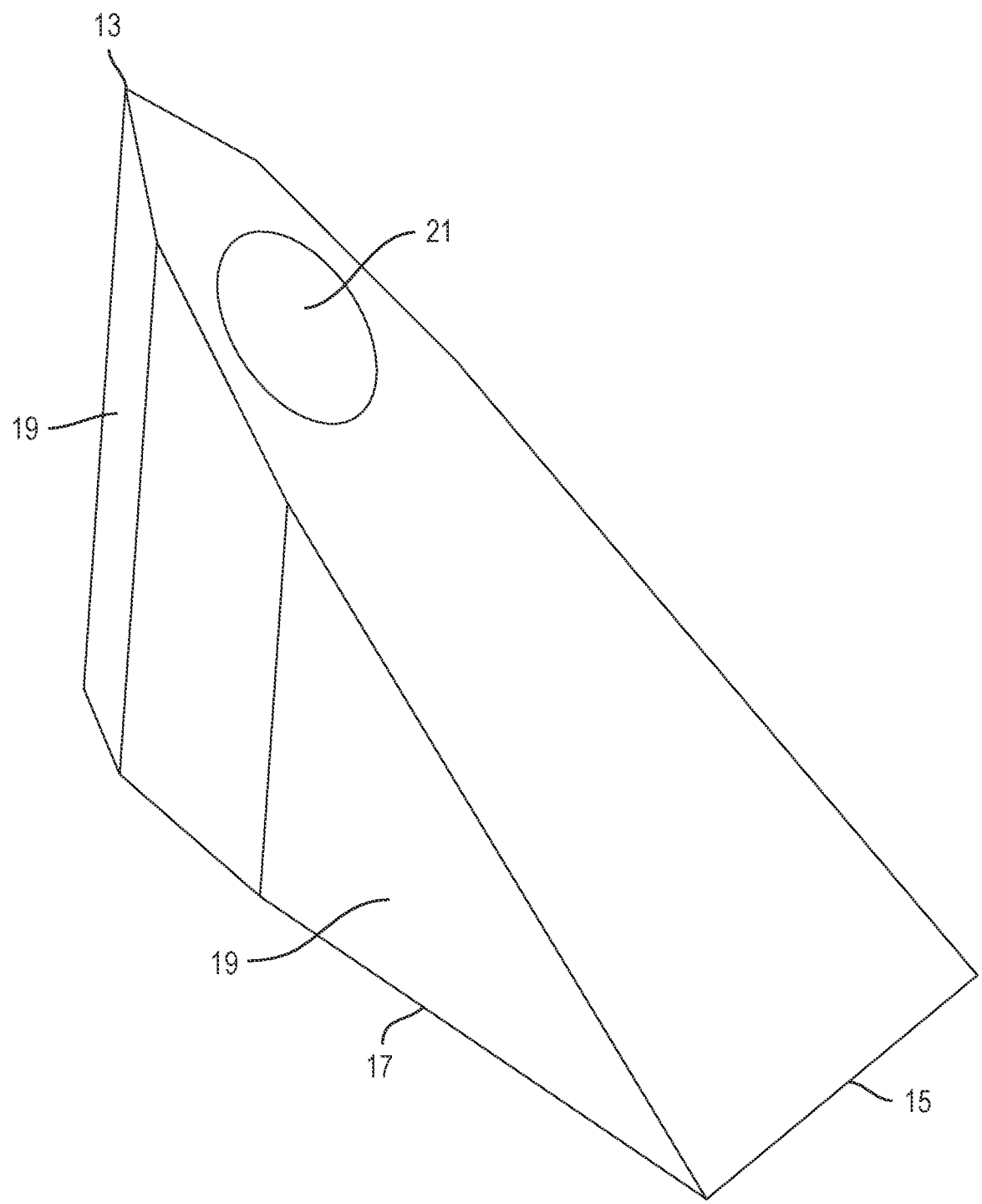
FIG. 26 depicts a view of an example microneedle.

Referring now to FIG. 26, another example microneedle is depicted. As shown, in some examples, the microneedles described herein may be generally in the shape of a heptagonal prism (in alternative embodiments the base shape may be a pentagonal, nonagonal, and so on type prism) which has been diagonally sected to form a heptagonal ramp or pointed wedge. In such embodiments, the heptagonal prism may be sected by a plane extending from a vertex 13 of the top face of the prism to the most distal side 15 of the base 17. At least two sides of the base of the microneedle may be parallel. The side walls 19 may extend substantially perpendicularly from the base 17. The microneedle may be substantially symmetric about a line of symmetry extending from the vertex 14 to a point above the center of the most distal side 15. The flow lumen 21 in the example embodiment is offset from the point of the microneedle and may thus be referred to a solid pointed microneedle.

Referring now again primarily to FIGS. 24-25, when the locking member 18 is removed from the delivery device 10 the second bias member 102 (see, e.g., FIG. 9) of the delivery device 10 may force fluid from a reservoir portion 54 (see, e.g., FIG. 9) out of the microneedle array of delivery sharps 88. No manual sustained pressure or other user interaction may be required as the delivery occurs. This may ensure that no medical personnel are needed to complete the delivery. This may be particularly desirable as the flow rate of fluid into the patient may be relatively slow due to the small apertures of the microneedles. Thus sustained manual pressure would be needed for a relatively long period of time to complete delivery if fluid was to be manually driven from the delivery device 10. From the perspective of the user, the user need only to wait a predefined period of time after applying the delivery device 10 and displacing the locking member 18 to effect the delivery.

Referring now to FIG. 27 and FIG. 28, another embodiment of an example delivery device 10 is shown. As shown, the delivery device 10 includes an actuatable delivery sharp assembly 170. The delivery sharp assembly 170 may include at least one delivery sharp 88. In some embodiments, a subcutaneous or intramuscular delivery sharp 88 may be included in the delivery sharp assembly 170. In other embodiments, the delivery sharp(s) 88 included in the deliver sharp assembly 170 may be a microneedle or microneedle array. In such delivery devices 10, the delivery device 10 may be applied to the injection site. The delivery sharp(s) 88 may be subsequently advanced from a stowed position inside the delivery device 10 to an extended position in which the delivery sharp(s) 88 establish fluid communication into the user's body. After injection, the delivery sharp(s) 88 may be actuated to a retracted state in which the tip(s) of the delivery sharp(s) 88 are recessed with respect to the skin adhering face of the delivery device 10. Thus, the delivery sharp(s) 88 may be substantially inaccessible to the user after the delivery device 10 has been used.

The delivery sharp assembly 170 may include a head 172 which may be disposed external to the housing 12 of the delivery device 10. The head 172 may be a nub, flange, or other surface against which a user may exert manual pressure. A flow lumen 174 may extend from the head 172. The flow lumen 174 may extend through the insert 82 and into a channel 176 which extends to the skin adhering face of the delivery device 10. The flow lumen 174 may terminate in a needle tip in some embodiments, or may have a terminal end coupled to a microneedle or microneedle array.

As best shown in FIG. 28, the flow lumen 174 may also include a side port 178. When the delivery sharp assembly 170 is in the stowed state, the side port 178 may be disposed in the elastomeric material of the insert 82. No flow path from the reservoir portion 54 of the delivery device 10 into the flow lumen 174 may be available with the delivery sharp assembly 170 in the stowed state.

Referring now to FIG. 29 and FIG. 30, the delivery sharp assembly 170 is depicted in an extended state. To actuate the delivery sharp assembly 170 to the extended state, a user may manually press the head 172 of the delivery sharp assembly 170 against the housing 12. The housing 12 may provide a stop surface for the nub 172 which prevents the delivery sharp(s) 88 from displacing past their desired penetration depth in the patient. As the delivery sharp assembly 170 is actuated to the extended state, the side port 178 of the flow lumen 174 may pass into fluid communication with an atrium 182 of the insert 82 which is in communication with the reservoir portion 54. Thus, a flow pathway from the reservoir portion 54 and into the patient may be established once the delivery sharp assembly 170 has been transitioned to the extended position. As mentioned above, after delivery has completed, the delivery sharp assembly 170 may be actuated to a retracted state in which the delivery sharp(s) 88 is/are withdrawn out of the skin and disposed within the delivery device 10. In some embodiments, the delivery sharp assembly 170 may include a stop projection 180 which inhibits the delivery sharp assembly 170 from being displaced beyond a predetermined amount.

This may prevent a user from removing the delivery sharp assembly 170 from the delivery device 10. In the example embodiment shown in FIG. 29-30, the delivery sharp 88 is shown as a microneedle. In certain embodiments, the delivery sharp 88 may instead be a conventional needle or a microneedle array.

Referring now to FIG. 31 and FIG. 32, another exemplary delivery device 10 is depicted. As shown, the delivery device 10 is delivery sharp 88 free. Instead, the example delivery device 10 depicted in FIG. 31 includes an infusion site connector 190. The delivery device 10 may include an internal flow channel 192 which extends from a branched fluid pathway 86 of the insert 82 to an inlet of the infusion site connector 190. The infusion site connector 190 may have a bottom face which is substantially even with the skin adhering face of the delivery device 10.

The infusion site connector 190 may include a connector sharp 194. The infusion site connector 190 may also include at least one coupling interface. In the example embodiment, the infusion site connector 190 includes a pair of cantilevered arms 196. The infusion site connector 190 may be docked with an infusion set assembly 205 (see, e.g. FIG. 35) which has been previously inserted into the skin of a user. The cantilevered arms 196 may have a ledge which snaps into place against a catch surface of the infusion set assembly 205 to maintain coupling of the infusion site connector 190 and the infusion set assembly 205. The infusion set assembly 205 may include a cannula 207 (see, e.g., FIG. 39) which extends into a desired delivery destination in the patient (e.g. subcutaneous tissue). During docking of the infusion site connector 190 with the infusion set assembly 205, the connector sharp 194 may puncture a barrier such as a septum in the infusion site assembly 205. This may place the outlet of the connector sharp 194 into sealed fluid communication with the cannula 207 of the infusion set assembly 205. The infusion site connector 190 may include guard projections which extend alongside the connector sharp 194 to inhibit contact of the connector sharp 194 with a user. The cantilevered arms 196 may help guard against contact with the connector sharp 194.

With fluid communication to the cannula 207 (see, e.g., FIG. 39) of the infusion set assembly 205 (see, e.g. FIG. 35) established, the locking member 18 of the delivery device 10 may be actuated and fluid may be delivered from the reservoir portion 54, through the insert 82 and interior flow channel 192, and into the cannula 207 via the connector sharp 192. Once the injection has completed, the coupling interfaces may be disengaged and the delivery device 10 along with the infusion site connector 190 may be discarded. In some embodiments, a cap member 198 may be placed over the infusion site connector 190 to prevent user interaction with the connector sharp 192. The infusion site assembly 205 may remain in place or may be removed if no longer needed.

The infusion site assembly 205 (see, e.g., FIG. 35) may be any suitable infusion site assembly 205. In some embodiments, the infusion site assembly 205 may be any of those shown and described in U.S. patent application Ser. No. 16/797,624, to Lanigan et al., entitled Infusion set and Inserter Assembly Systems and Methods, filed Feb. 21, 2020 incorporated herein by reference in its entirety. The infusion site assembly 205 may be installed on the user using any suitable inserter assembly. In some embodiments, an inserter assembly which lifts the skin from underlying tissue prior to triggering insertion may be used. Any inserter assembly described in the above mentioned U.S. patent application Ser. No. 16/797,624 may for example be used. Various infusion set connectors described in the above mentioned U.S. patent application Ser. No. 16/797,624 may be included as the infusion set connector 190 of delivery devices 10 described and shown herein.

Referring now to FIG. 33 and FIG. 34, another delivery device 10 embodiment which is delivery sharp 88 free is depicted. As shown, the delivery device 10 is connected to an infusion site connector 190 via an expanse of infusion tubing 200. The length of infusion tubing 200 may be anywhere from a few inches to a meter or more. As in the above described embodiment, the infusion site connector 190 may couple to an infusion site assembly 205 (see, e.g., FIG. 35) which may include a cannula 207 (see, e.g., FIG. 39) that extends into a delivery destination in a patient. The infusion tubing 200 may allow a user to place the infusion site assembly 205 in a wider variety of locations over a patient's body. The delivery device 10 may be applied to a different location on the patient's body. Alternatively, the delivery device 10 may be placed in a pocket, handbag, on a desk, tray, or other surface, etc. as the fluid is delivered from the delivery device 10 and into the patient through the infusion set assembly 205. Though described in relation to the delivery device 10 embodiment shown in FIG. 1, infusion site connectors 190 and/or infusion tubing 200 may be included on any of the delivery devices 10 described and shown herein. Thus any of the delivery devices 10 shown or described herein may be constructed as delivery sharp 88 free devices which may deliver to an external infusion site assembly 205.

Figure 35:
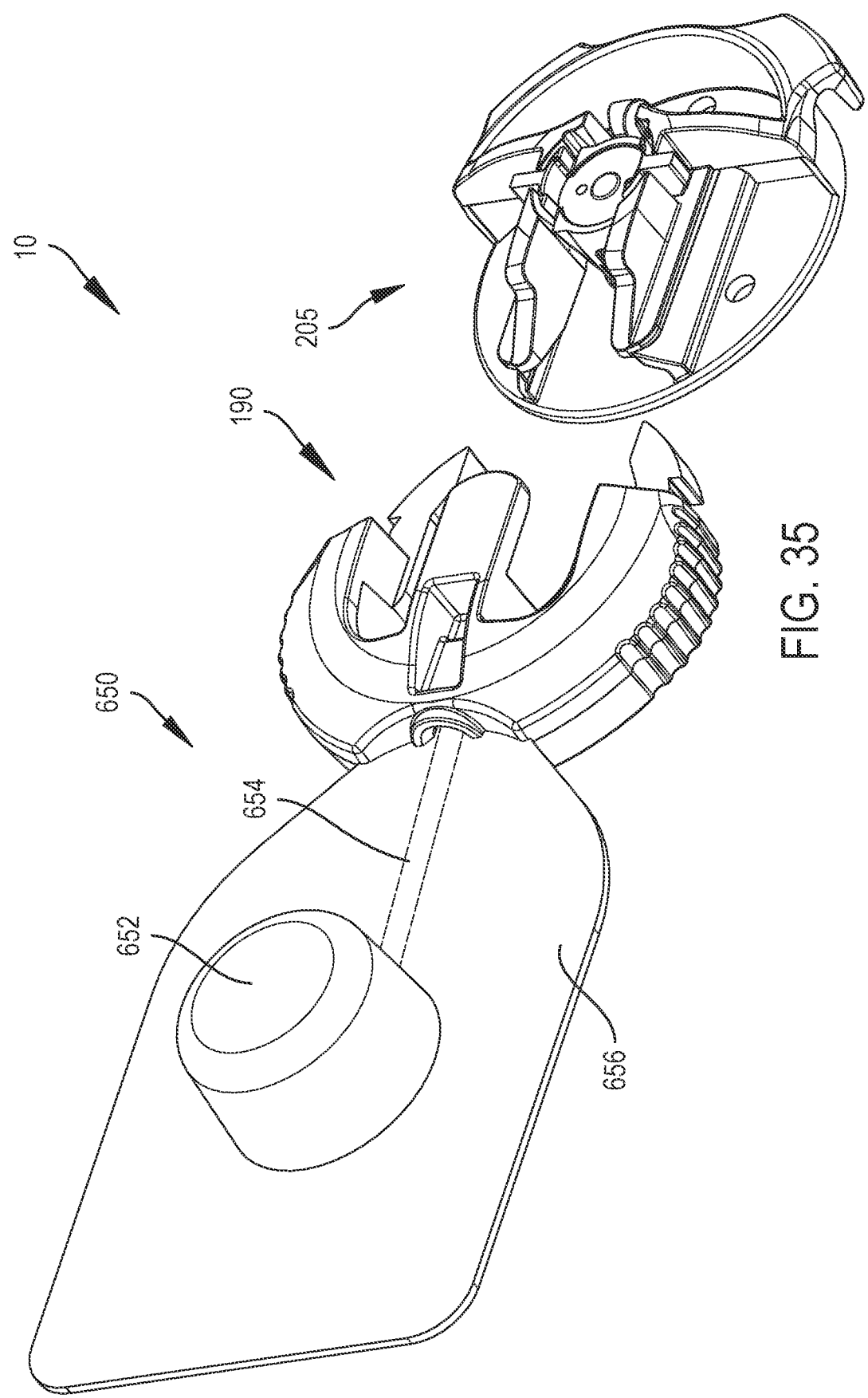
FIG. 35 depicts an example delivery device including an infusion site connector.

Referring now to FIG. 35 and FIG. 36, two additional exemplary embodiments of a delivery devices 10 including an infusion site connector 190 which may couple to an infusion site assembly 205 are shown. As shown, the infusion site connector 190 may be coupled to a reservoir assembly 650. The reservoir assembly 650 may include an agent filled collapsible blister 652. The agent filled blister 652 may be included on a panel 656 of material which may include a flow path 654 therein. The material forming the panel 656 may be rigid. In various examples the reservoir assembly 650 may also include a check valve to prevent refilling of the blister 652 once the delivery device 10 is used. The panel 656 may be provided in a variety of orientations. For example, the panel 656 may define a plane which is generally parallel to the skin (see FIG. 35). Alternatively, the panel 656 may define a plane which is transverse to the skin surface (e.g. substantially perpendicular as shown in FIG. 36). Once the infusion site connector 190 is coupled to the infusion site assembly 205, a user may manually press against the blister 652 to drive fluid out of the blister 652 and into the patient via the cannula 207 (see, e.g., FIG. 39) of the infusion site assembly 205. The infusion site connector 190 may be decoupled from the infusion site assembly 205 once the blister 652 has been fully collapsed and the infusion site connector 190 and reservoir assembly 650 may be discarded.

Referring now to FIG. 37 and FIG. 38 (a cross-section at the indicated plane of FIG. 37) another example delivery device 10 is depicted. As shown, the delivery device 10 may include a housing 660. The delivery device 10 may further include an infusion site connector 190. The infusion site connector 190 may couple to an infusion site assembly 205 as described elsewhere herein. The infusion site connector 190 is depicted as connected to the housing 660 in the example embodiment, though may alternatively be connected to the housing 660 via tubing 200 (see, e.g., FIG. 34). In alternative embodiments, the outlet of the delivery device 10 may be a delivery sharp (e.g. conventional needle, microneedle, microneedle array) which delivers agent directly to the patient instead of via an infusion site assembly 205.

As shown best in FIG. 38, a reservoir assembly 650 may be contained within the housing 660. The reservoir assembly 650 may include an agent containing collapsible blister 652. The blister 652 may be included on a panel 656. The interior volume of the blister 652 may be placed into communication with the infusion site connector 190 via a flow path 654 provided from the blister 652 along a portion of the panel 656. As shown, the infusion site connector 190 may include a connection sharp 662. The connection sharp 662 may be displaceable between a first position and a second position. In the example embodiment, the connection sharp 662 is mounted in a hub 666 which may displace within a channel 664 of the infusion site connector 190. The hub 666 may include a shoulder portion 668 which may limit travel of the hub 666 within the channel 664. The connection sharp 662 may include a needle point on each of the opposing ends of the connection sharp 662. During coupling of the infusion site connector 190 to an infusion site assembly 205, the hub 666 and connection sharp 662 may be displaced toward and through a septum 670. The connection sharp 662 may be in the second position when the connection sharp 662 has been displaced through the septum 670. The septum 670 may prevent fluid communication from the blister 652 to the connection sharp 662 until the septum 670 has been punctured by the connection sharp 662. When the connection sharp 662 is in the second position, the connection sharp 662 may be in fluid communication with the blister 652.

Still referring to FIG. 38, the delivery device 10 may include an actuator 672. The actuator 672 may be coupled to a pressure plate 676 which may be positioned atop the blister 652. In the example embodiment, the actuator 672 is depicted as a bias member which is provided in a stressed state. Specifically, a cantilevered spring is depicted with the pressure plate 676 being coupled to the spring near the unsupported end of the spring. The actuator 672 also includes a locking member interface 674. The locking member interface 674 may be a loop of material, slot, or other receptacle for a locking member 18. Referring now also to FIG. 38, in the example embodiment, the locking member 18 is depicted as a removable pin which may be received in the locking member interface 674 of the actuator 672. With the infusion site connector 190 coupled to an infusion site assembly 205 and the septum 670 breached by the connection sharp 662, the locking member 18 may be removed (e.g. pulled out in the example embodiment). The actuator 672 may resiliently restore to an unstressed state (or at least less stressed state) with the locking member 18 removed or displaced to a state in which it is disengaged from the actuator 672. This in turn may urge the pressure plate 676 against the blister 652 and toward the panel 656 so as to drive fluid from the blister 652 through the delivery device 10 and into the patient via the infusion site assembly 205. The reservoir assembly 650 may include a check valve which may prevent refilling of the reservoir assembly 650 in order to prevent reuse.

Figures 40, 41, 42:
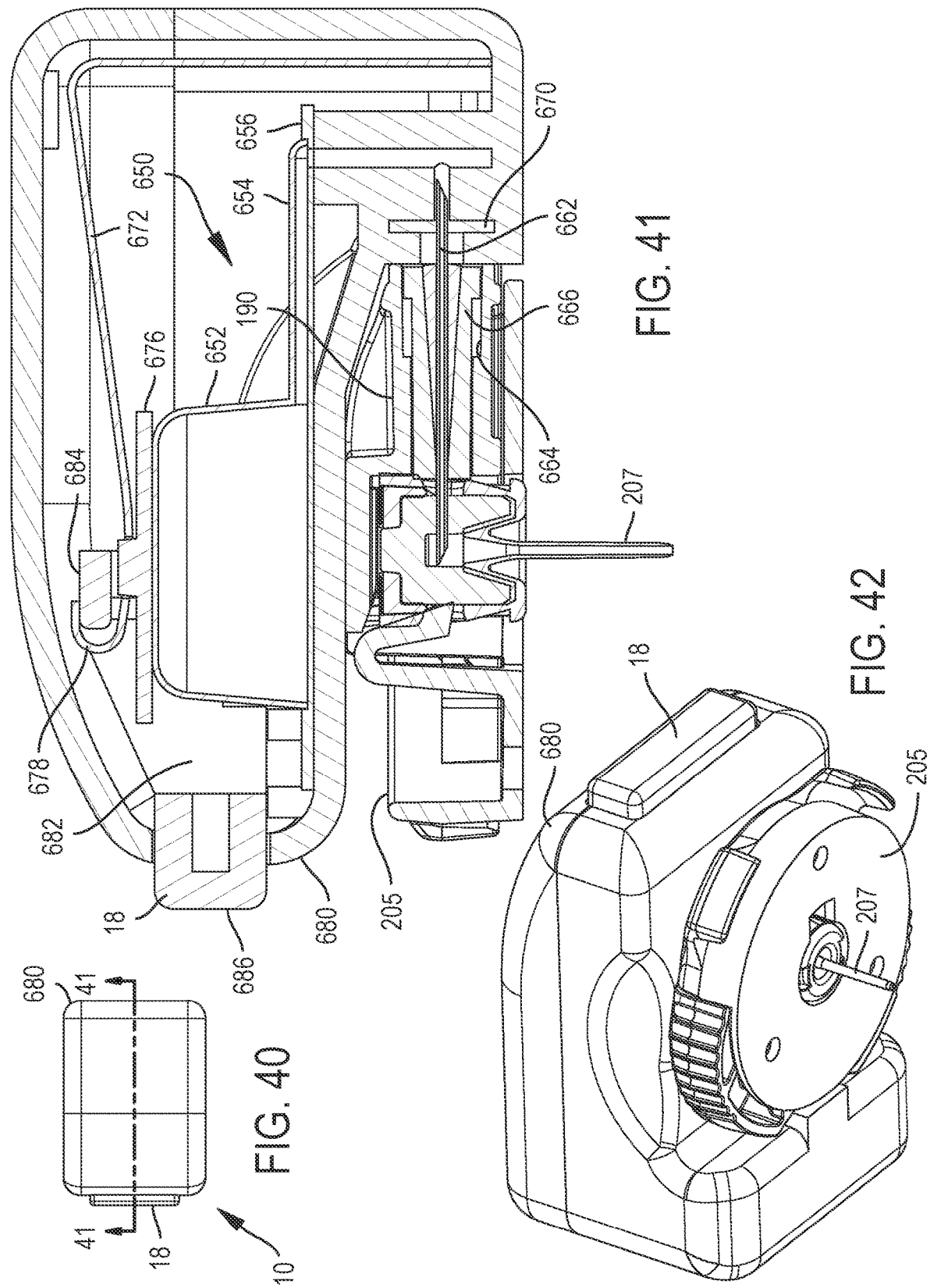
FIG. 40 depicts a top down plan view of another example embodiment of a delivery device.
FIG. 41 depicts a cross-sectional view of the example delivery device of FIG. 40 taken at the indicated cut plane of FIG. 40.
FIG. 42 depicts a perspective view of an example delivery device.

Referring now to FIGS. 40-42, another exemplary delivery device 10 similar to that depicted in FIGS. 37-39 is shown. As shown, the delivery device 10 may include a housing 680. The delivery device 10 may further include an infusion site connector 190. As shown, the infusion site connector 190 may couple to an infusion site assembly 205 which may provide access to a delivery destination in a patient via a cannula 207 for example. The infusion site connector 190 is depicted as connected to the housing 680 in the example embodiment, though may alternatively be connected to the housing 680 via tubing 200 (see, e.g., FIG. 34). The delivery device 10 may include a reservoir assembly 650 including a collapsible agent filled blister 652 on a panel 656. A flow path 654 may lead from the blister 652 to the infusion site connector 190. As the infusion site connector 190 is depicted coupled to an infusion site assembly 205, the connection sharp 662 and hub 666 have been driven along the channel 664 of the infusion site connector 190 such that the septum 670 is breached by the connection sharp 662.

As in FIGS. 37-39, the actuator 672 in the embodiment of FIGS. 40-42 may be a bias member such as a cantilevered spring which is provided in a stressed state. A pressure plate 676 may be coupled to the actuator 672 near the unsupported end of the actuator 672. The actuator 672 of the delivery device 10 may include a hook 678 which may interface with a locking member 18. In the example shown in FIGS. 40-42, the locking member 18 is depicted as a button 686 which includes a portion that is accessible from the exterior of the housing 680. The button 686 may include at least one arm 682 which may be attached to a bar 684. The bar 684 may be captured by the hook 678 and when engaged with the hook 678 may prevent the actuator 672 from restoring from its stressed state. A user may depress the button 686 to drive the bar 684 out of engagement with the hook 678. This may allow the actuator 672 to resiliently restore toward an unstressed state. As the actuator 672 restores, the pressure plate 676 may be forced against the blister 652 driving fluid from the blister 652 and into the patient via the cannula 207. The reservoir assembly 650 may include a check valve which may prevent refilling of the reservoir assembly 650 in order to prevent reuse.

Figure 43:
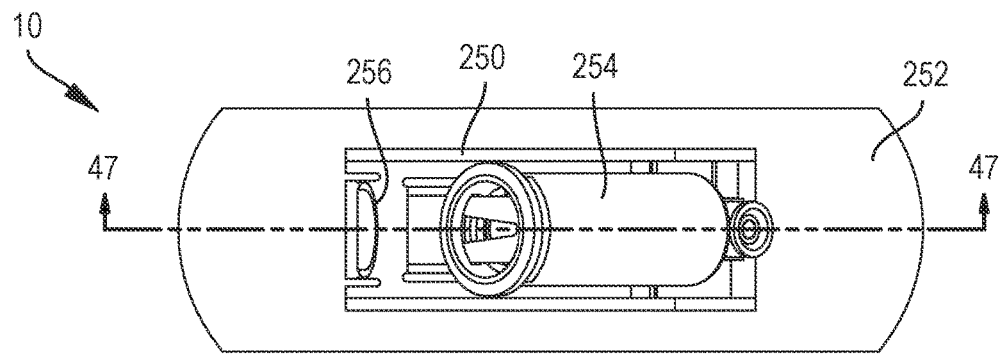
FIG. 43 depicts another top down plan view of another example embodiment of a delivery device.
Figure 44:
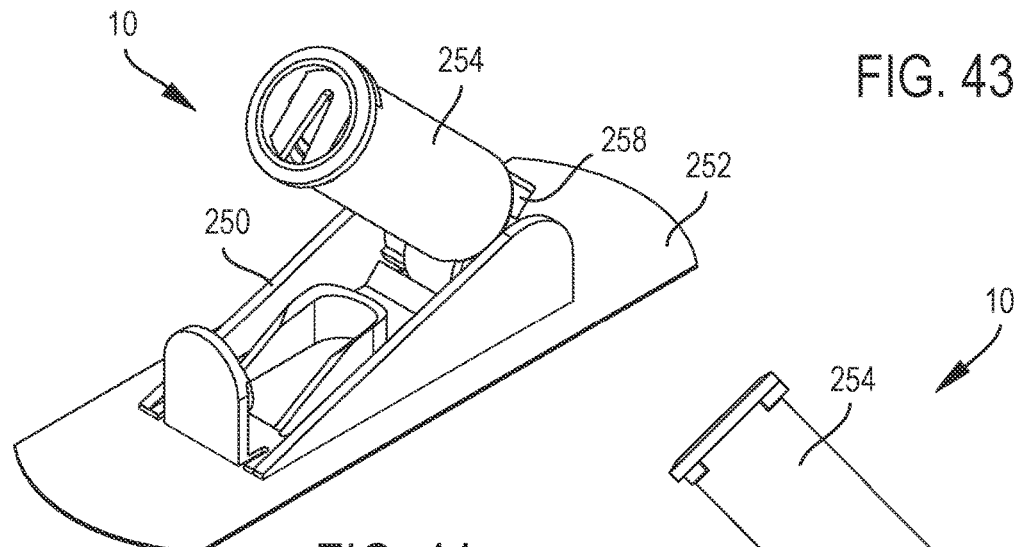
FIG. 44 depicts a perspective view of an example delivery device.
Figure 45:
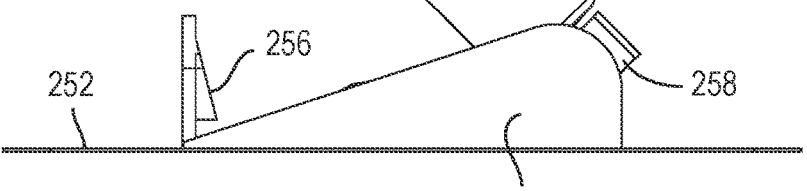
FIG. 45 depicts a side view of an example delivery device.
Figure 46:
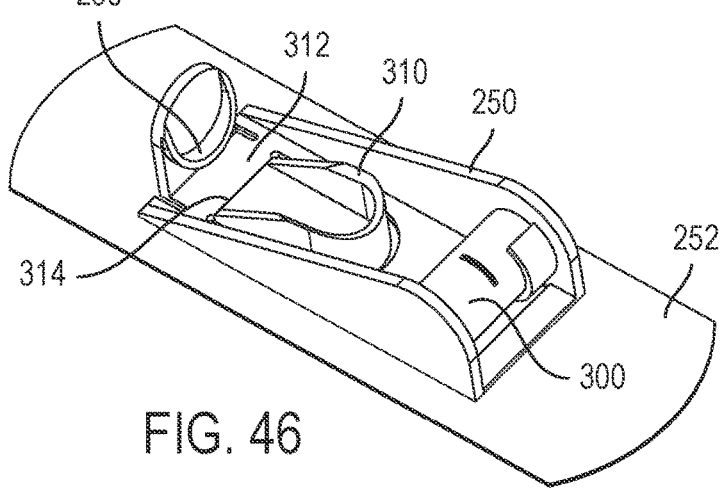
FIG. 46 depicts a perspective view of a delivery device with a fluid handling portion of the delivery device removed.

Referring now to FIGS. 43-44, another embodiment of an example delivery device 10 is depicted. The example delivery device 10 may include a base portion 250. The base portion 250 may be constructed of plastic material and may be mounted on an adhesive member 252. The adhesive member 252 may be a bandage or Band-Aid type member with the gauze portion omitted. As shown, the base portion 250 may be attached to a fluid handling portion 254. The fluid handling portion 254 may be pivotally attached to the base portion 250 in certain examples. The fluid handling portion 254 may be displaceable from a loading position (shown) to a delivery position (see, e.g. FIG. 49). The delivery device 10 may be shipped with the fluid handing portion 254 in the delivery position to minimize size of the delivery device 10. During filling, the fluid handling portion 254 may be in the loading position and rotated away from the base portion 250. Once the fluid handling portion 254 has been filled, the fluid handling portion 254 may be rotationally displaced toward the base portion 250. Referring now to FIG. 46, a perspective view of an example base portion 250 is depicted. The base portion 250 may include a flat member 312. The flat member 312 may be constructed of a plastic. The plastic chosen may be slightly flexible so as to allow the flat member 312 to bend with the adhesive member 252 to conform to various contours of a user's body. As shown, the base portion 250 may include a catch 256 which may capture the fluid handling portion 254 once the fluid handling portion 254 has been rotated against the base portion 250. Any suitable catch may be used. In the example, the catch 256 is defined on a body which extends upward from the flat member 312 at a substantially perpendicular angle. The base portion 250 may also include a projection 310 which may extend upward from the flat member 312. The projection 310 may be contoured so as to form a cradle against which part of the fluid handling portion 254 of the delivery device 10 may rest. In the example embodiment, the projection 310 is included on a portion of the flat member 312 which is hinged with respect to the rest of the flat member 312. As shown, the portion of the flat member 312 including the projection 310 is attached to the remainder of the flat member 312 via a living hinge 314.

Figure 47:
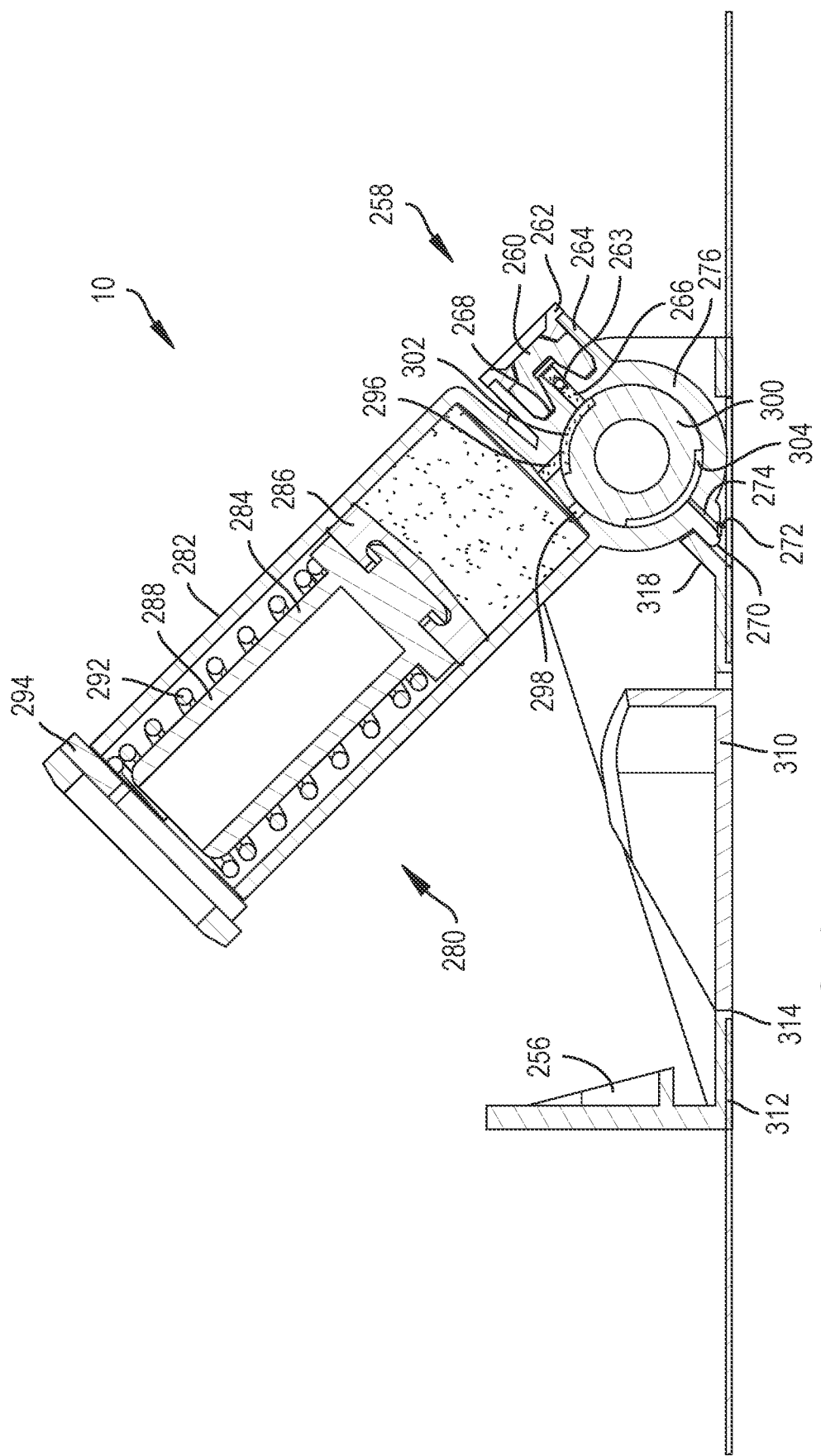
FIG. 47 depicts a cross-sectional view of the delivery device depicted in FIG. 43 at the cut plane indicated in FIG. 43.

Referring now primarily to FIG. 47, a cross-sectional view taken at the indicated cut plane in FIG. 43 is shown. As shown, the fluid handling portion 254 of the delivery device 10 may include a port assembly 258. The port assembly 258 may be used to access an interior volume of a reservoir portion 280 of the fluid handling portion 254. As shown, the port assembly 258 may include a septum 260 which may be constructed of an elastomeric material which may be punctured and self-seal upon removal of a filling implement (e.g. needle of a syringe). Alternatively, any suitable barrier may be used. Some embodiments may include a luer lock fitting and split septum for example. In the exemplary embodiment, the port assembly 258 may also include a septum retainer 262 which may be attached to a port wall 264 that surrounds a well 268 in which the septum 260 is located. The septum retainer 262 may sandwich the septum 260 between a face of the septum retainer 262 and a bottom of the well 268. A flow channel 266 of the port assembly 258 may also be included and may extend to the bottom face of the well 268. In certain examples, a check valve 263 may be included to prevent removal of fluid from the delivery device 10. Such a check valve 263 may also relieve pressure on the septum 260 when the delivery device 10 is filled.

The fluid handling portion 254 of the delivery device 10 may also include an outlet assembly 270. The outlet assembly 270 may include an outlet flow channel 274 which extends to a micro needle 272, an array of microneedles 272, or other delivery sharp. As shown in FIG. 47, the outlet assembly 270 may be in abutment with a stop projection 318 of the base portion 250 when the fluid handing portion 254 is in the loading position. This may present a mechanical interference which inhibits rotation of the fluid handling portion 254 beyond the loading position.

The reservoir portion 280 is depicted as a syringe type reservoir. The reservoir portion 280 includes a barrel portion 282. Within the barrel 282, a plunger 284 may be included. The plunger 284 may include an elastomeric member 286 which may be molded to or attached to a head portion of the plunger 284. The elastomeric member 286 may aid in generating a robust fluid seal against the interior wall of the barrel 282. The plunger 284 may include a plunger stem 288 which extend away from the head portion of the plunger 284. A bias member 292 may be included in the reservoir portion 280. The bias member 292 may store energy which tends to drive fluid out of the reservoir portion 280 by urging the plunger 284 to advance toward an outlet 296 of the barrel 282. Any suitable bias member 292 such as gas bladders, compressible elastomer, various springs, etc. may be used. In the example embodiment, the bias member 292 is depicted as a coil spring which surrounds the stem 288 of the plunger 284. The bias member 292 may be captured between the head portion of the plunger 284 and a rear of the barrel 282. In the example embodiment a clip 294 is installed at the rear of the barrel 282 to capture the bias member 292 and plunger 284 within the barrel 282.

Referring now to FIG. 47 and FIG. 48, in the example embodiment, the port assembly 258, outlet assembly 270, and the reservoir portion 280 may also be included as features which extend from an exterior face of a hub body 276. The hub body 276 may be round and may be coaxial with and rotate about an axel 300. In the example embodiment, the hub body 276 is generally cylindrical. The axel 300 may be supported by the base portion 250 and may be included as a part of the base portion 250. As shown, the base portion 250 may include a first section 320 and a second section 322. The first section may include the axel 300. The fluid handling portion 254 may be installed on the axel 300 and the second portion 322 may then be joined to the first portion 320 of the base portion 250 to retain the fluid handing portion 254 in place in the delivery device 10. In the example embodiment, the second portion 322 includes a pin 324 which may couple into a receptacle of the axel 300 via interference fit. Other coupling schemes may be used in other embodiments. For example, a snap fit, adhesive, solvent bonding, welding, fasteners, etc. may be used to couple the first and second portion 320, 322 together during assembly. In alternative embodiments, the first portion 320 and second portion 322 may be molded together as a monolithic part. In such embodiments, a living hinge may be present between the first portion 320 and second portion 322. The second portion 322 may be folded via bending at the living hinge during assembly.

The axel 300 may include a number of fluid flow channels. The fluid flow channels may be formed as troughs which are recessed into an outer or external face of the axel 300. In the example embodiment, a filling or inlet flow channel 302 and a delivery flow channel 304 are included. A gasket member may be included in certain embodiments as well. The filling flow channel 302 and delivery flow channel 304 may be stationary with respect to the fluid handling portion 254 of the delivery device 10. When the fluid handling portion 254 of the delivery device 10 is in the loading position (shown in FIG. 47) the flow channel 266 of the port assembly 258 may be in fluid communication with an inlet 298 of the reservoir portion 280 via the filling flow channel 302. Fluid may be loaded into the reservoir portion 280 via delivery of fluid (e.g. vaccine, opioid antagonist, or other types of medical agents depicted as stippling in FIG. 47) into the port assembly 258 (e.g. via syringe or other filling implement). As the reservoir portion 280 is filled, the plunger 284 may be pushed toward the rear of the barrel 282 to allow the volume of fluid dispensed into the port assembly 258 to be accommodated. This may also cause the bias member 292 to become stressed and store energy which may be used to drive later delivery of the fluid.

Referring now to FIGS. 49-50, once the reservoir portion 280 has been filled, the fluid handling portion 254 of the delivery device 10 may be displaced to the delivery state. As the reservoir portion 280 is displaced toward the base portion 250 the reservoir portion 280 may contact the projection 310. The reservoir portion 280 may contact the projection 310 at an intermediate position and prior to the fluid handling portion 254 of the delivery device 10 reaching its delivery position. As the reservoir portion 280 continues to pivot toward the flat member 312 of the base portion 250, the section of the flat member 312 including the projection 310 may begin to deflect about the living hinge 314 connecting it to the remainder of the flat member 312. This deflection may continue until the fluid handling portion 254 reaches its delivery state and is captured by the catch 256 on the base portion 250. The deflection of the section of the flat member 312 including the projection 310 may press against the skin of a user. In turn, this may cause stretching of the skin in the area where the section of the flat member 312 including the projection contacts the skin. As shown, pivotal displacement of the fluid handing portion 254 of the delivery device 10 toward the delivery state may also cause the microneedle(s) 316 (other embodiments may be outfitted with different delivery sharps) to be pivoted into the patient's skin. The bandage 252 may include apertures for the section of the flat member 312 including the projection 310 and the outlet assembly 270. Stretching of the skin as the microneedle(s) 316 is/are advanced into contact with the skin may facilitate consistent penetration into the intradermal space. Once the fluid handling portion 254 of the delivery device 10 reaches the delivery position, the interior volume of the reservoir may be placed into communication with the microneedle(s) 316 via the outlet flow channel 304 of the axel 300. The bias member 292 may then relax over a period of time forcing fluid from the reservoir portion 280 into the intradermal space of the patient. The patient may wait a predetermined period of time for the delivery to complete and then the delivery device 10 may be removed and discarded.

Figure 52:
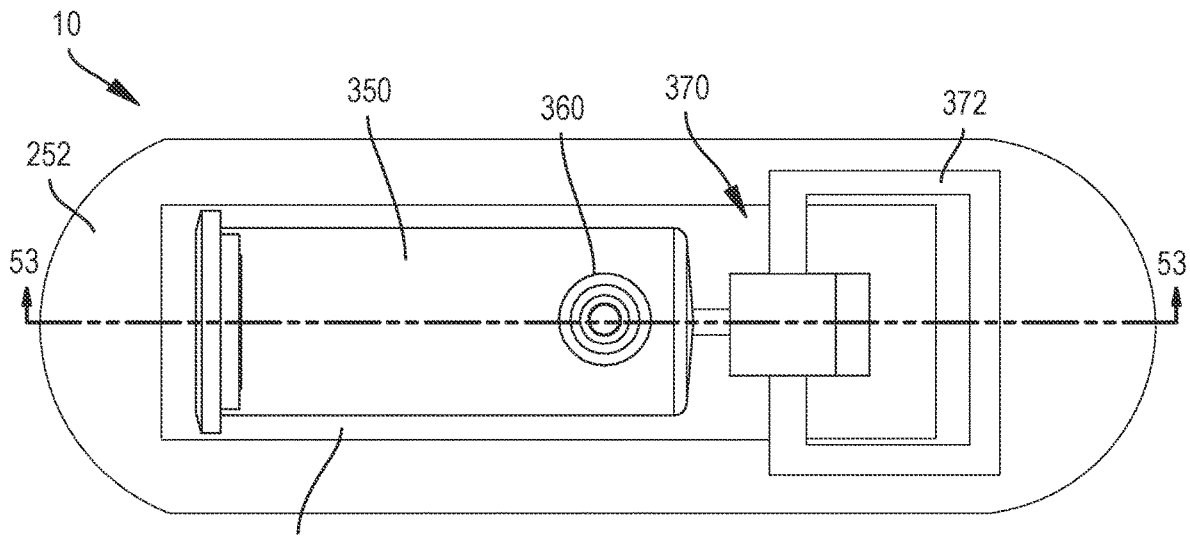
FIG. 52 depicts a top down plan view of another example delivery device.

Referring now to FIG. 52, a top down view of another example embodiment of a delivery device 10 is depicted. As shown, the delivery device 10 may include a reservoir portion 350. The reservoir portion 350 may include a port assembly 360. Any suitable port assembly 360 may be used. The port assembly 360 may be similar to that shown in FIG. 47 and may include a septum through which the interior volume of the reservoir portion 350 may be accessed for filling of the reservoir portion 350. The reservoir portion 350 may be attached to the bandage 252 via a base member 352 coupled to the reservoir portion 350 in some embodiments.

Figure 53:
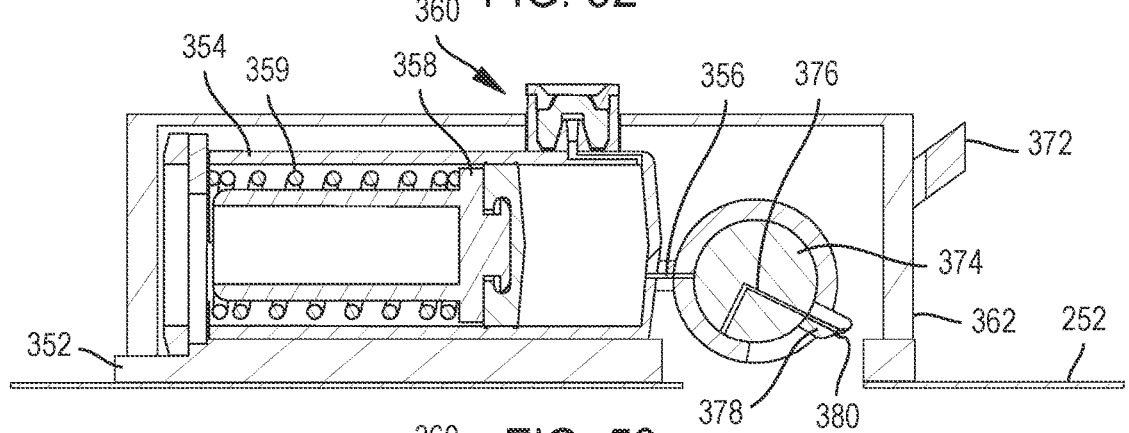
FIG. 53 depicts a cross-sectional view of the example delivery device of FIG. 52 taken at the cut plane superimposed over FIG. 52.
Figure 54:
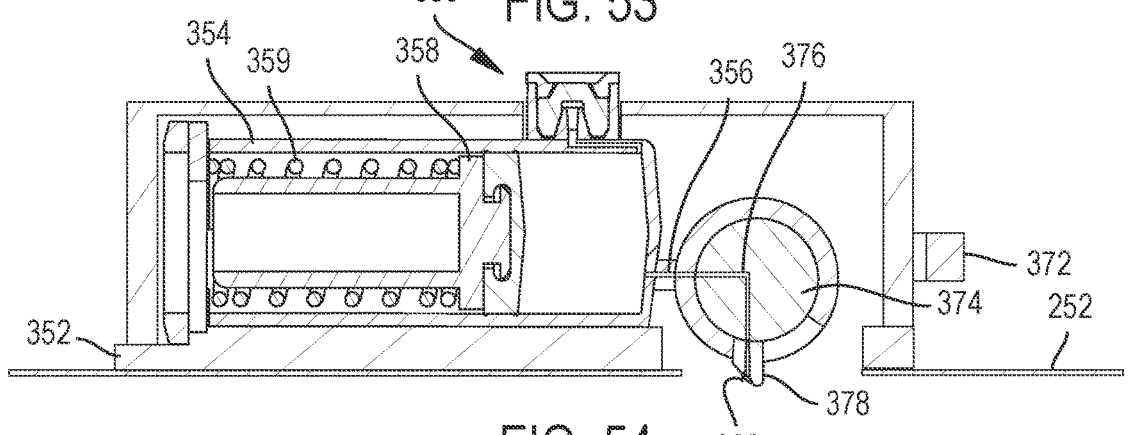
FIG. 54 depicts another cross-sectional view of the example delivery device of FIG. 52 where the delivery device has been transitioned into a delivery state.

Referring now also to FIG. 53 and FIG. 54, the delivery device 10 may include a stopcock assembly 370. The stopcock assembly 370 may include a lever 372. The lever 372 may be connected to the spindle 374 of the stopcock assembly 370. During loading of the reservoir portion 350 the bore 376 through the spindle 374 may be out of communication with the outlet 356 of the reservoir portion 350. The reservoir portion 350 shown in FIGS. 53-54 includes a barrel 354 with a plunger 358 therein. As with the embodiment described in relation to FIG. 47, during loading of the reservoir portion 350, a bias member 359 may become stressed when fluid is loaded into the interior volume of the reservoir portion 350 via the port assembly 360.

When the user is ready to deliver fluid from the delivery device 10, the lever 372 may be displaced to rotate the spindle 374. In the example embodiment, the lever 372 may be displaced toward the skin. As the spindle 374 rotates in response to displacement of the lever 372, the bore 376 may be brought into fluid communication with the outlet 356 of the reservoir portion 350. Additionally, during displacement of the lever 372, an outlet assembly 378 include a microneedle 380 or microneedle array may be driven into the skin of the user to access an intradermal space of the user. The bias member 359 may begin to relax and force fluid out of the reservoir portion 350 and into the intradermal space of the user.

The delivery device 10 may also include a cover 362. The cover 362 may seat over the reservoir portion 350 and stopcock assembly 370 and may include an aperture through which the port assembly 360 may extend. The lever 372 may also extend outside of the cover 362 so as to allow operation via a hand of the user.

Figure 55:
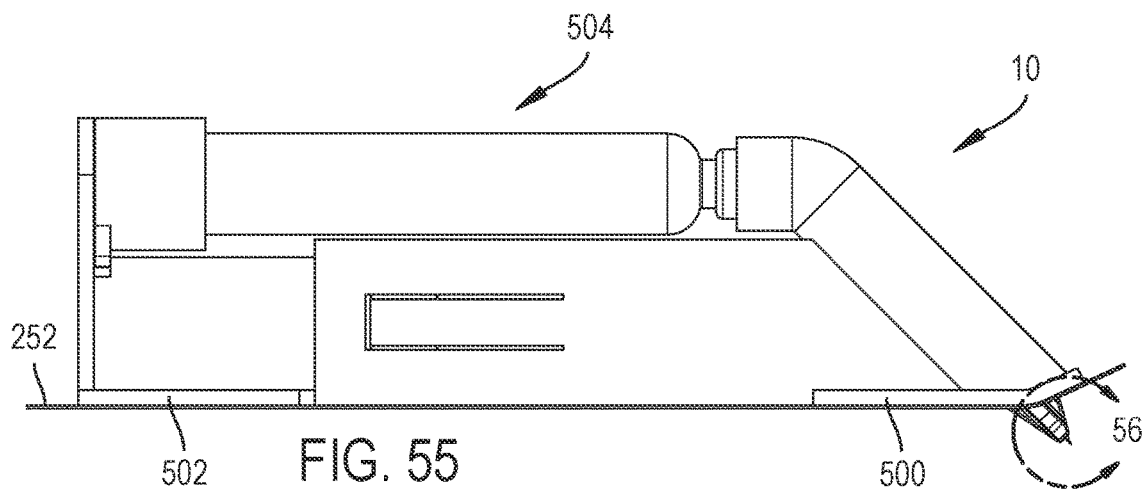
FIG. 55 depicts a side view of an example embodiment of yet another delivery device.
Figure 56:
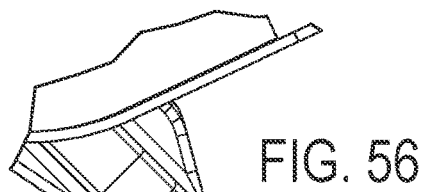
FIG. 56 depicts a detailed view of the indicated region of FIG. 55.

Referring now to FIG. 55-56, another example embodiment of a delivery device 10 is depicted. The example delivery device 10 may include a first base portion 500 and a second base portion 502. The base portions 500, 502 may be constructed of plastic material and may be mounted on an adhesive member 252. The adhesive member 252 may be bandage or a Band-Aid type member with the gauze portion omitted. As shown, the base portions 500, 502 may accept a reservoir portion 504 which may be included as part of a fluid handling portion 254 of the delivery device 10. The fluid handling portion 254 may be actuatable from a storage state (shown) to a delivery state (see, e.g. FIG. 65). The delivery device 10 may be shipped with the fluid handing portion 254 in the storage state and may be prefilled (e.g. via a manufacturer or at a pharmacy) in certain examples. As shown, the example delivery device 10 is depicted with a microneedle 506 or microneedle array. In alternative embodiments, transcutaneous delivery sharps such as subcutaneous or intramuscular needles may be included.

Figure 57:
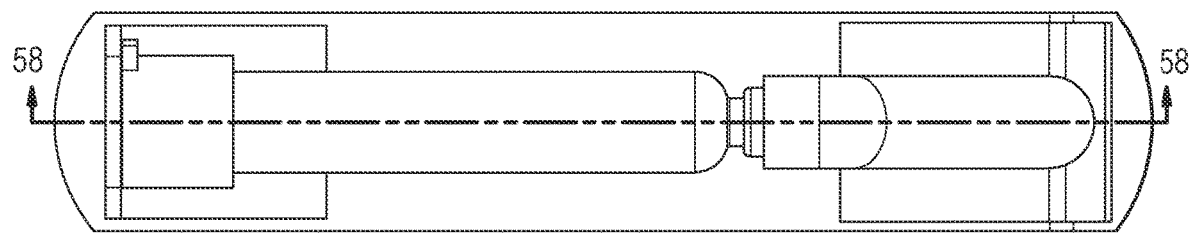
FIG. 57 depicts a top down plan view of an example delivery device embodiment.
Figure 58:
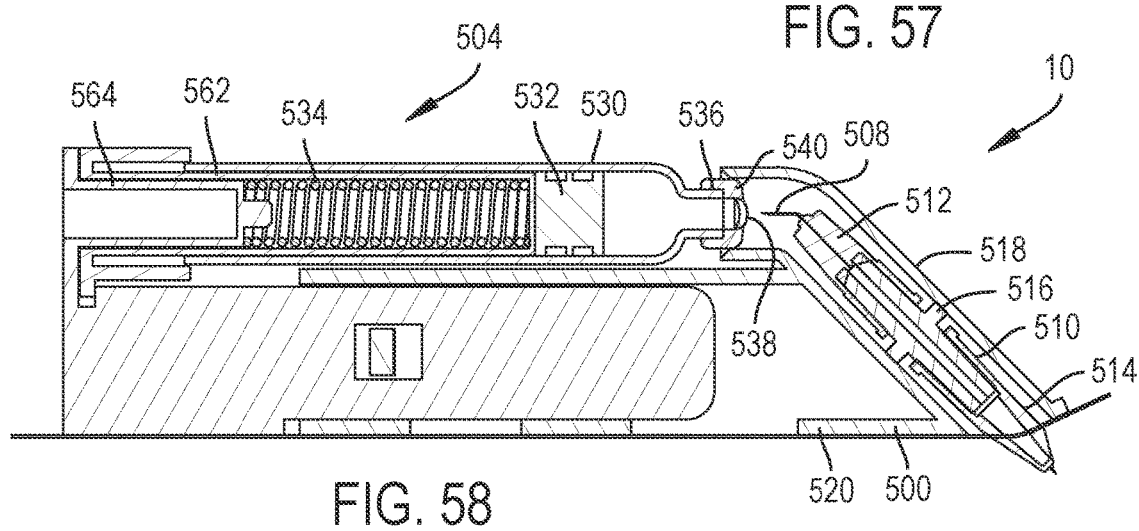
FIG. 58 depicts a cross-sectional view of the example delivery device depicted in FIG. 57 taken at the indicated cut plane in FIG. 57.

Referring now to FIGS. 57-58, the first base portion 500 may include an outlet assembly 510 which may form part of the fluid handling portion 254 of the delivery device 10. The outlet assembly 510 may include the microneedle 506 or microneedle array (or other delivery sharp(s)). The outlet assembly 510 may also include a reservoir access sharp 508 which may be disposed on an end of the outlet assembly opposite the microneedle(s) 506. The reservoir access sharp 508 and microneedle 506 may each be included on respective support bodies 512, 514 or hubs and may be in fluid communication with one another via a coupler 516 and flow channels in the support bodies 512, 514. As shown, each of the support bodies 512, 514 includes a female mating interface which couples to respective male interfaces on opposing sides of the coupler 516. In alternative embodiments, each support body 512, 514 may include a male interface which mates into a respective female mating interface of the coupler 516. In certain embodiments, a coupler 516 may be omitted and the support bodies 512, 514 may be formed as a single monolithic component. The outlet assembly 510 may be included within a housing receptacle 518 which extends from a flat member 520 of the first base portion 500. The outlet assembly 510 may be fixedly retained within the housing receptacle housing 518. For example, the outlet assembly 510 may be fixedly retained within the housing receptacle housing 518 via adhesive, solvent bonding, snap fit, interference fit, etc. In some examples, the receptacle housing 518 may be keyed such that the outlet assembly 510 may only be installed within the receptacle housing 518 in a particular orientation. This may ensure that the microneedle(s) 506 are clocked to a prescribed orientation once assembled into the delivery device 10.

Still referring primarily to FIG. 58, the reservoir assembly 504 may include a barrel 530. The reservoir assembly 504 may further include a plunger head 532 and a bias member 534 which may urge the plunger 532 toward an outlet 536 of the reservoir assembly 504. The bias member 534 may be disposed within an insert 562 to which the plunger head 532 may be mounted. The bias member 534 may be captured between a wall of the insert 562 adjacent the plunger head 532 and a bias member locating projection 564 included on the second base portion 502. The bias member locating projection 564 may aid in keeping the bias member 534 in proper position during assembly and operation. In the example embodiment, the bias member 534 is depicted as a coil type compression spring, though other suitable bias members 534 including other types of springs, gas bladders, etc. may be utilized in alternative embodiments.

In the example embodiment, the outlet 536 of the reservoir portion 504 is depicted as a vial closure. The example vial closure includes a septum 538 and a retainer 540 (e.g. a crimp) which retains the septum 538 in place on the outlet end of the barrel 530. In certain embodiments, the barrel 530 may be constructed of an inert material. The barrel 530 may, for example, be a glass vial with an open end opposite the outlet 536. As shown, the outlet of the barrel 530 is sealed from communication with the outlet assembly 510. Translational displacement of the reservoir assembly 504 or at least a portion including the outlet 536 (e.g. the barrel 530) may cause the reservoir access sharp 508 to puncture through the septum 538 and establish a flow path from the outlet 536 of the reservoir assembly 504 to the microneedle (s) 506.

Figure 59:
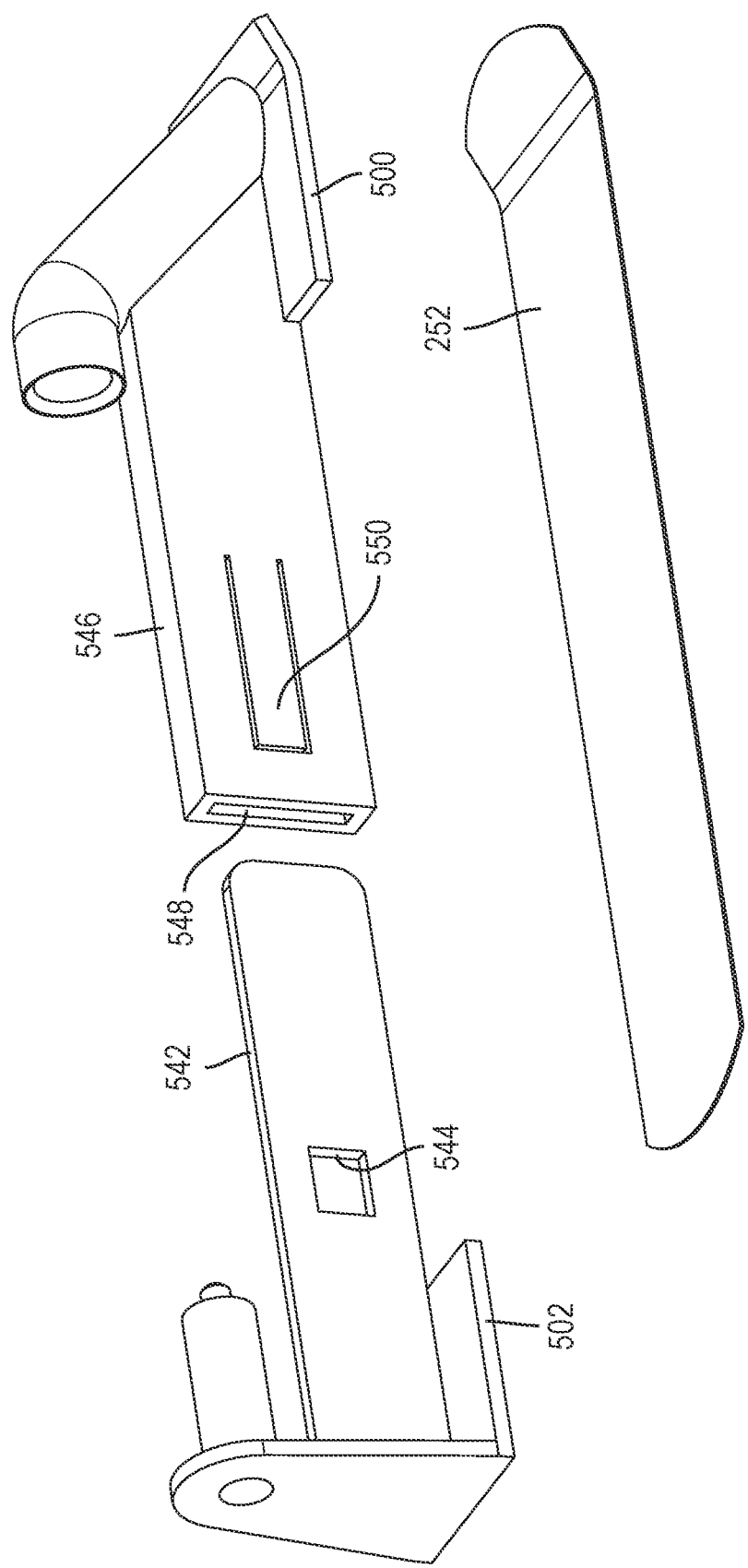
FIG. 59 depicts an exploded view of an example delivery device.

Referring now to FIG. 59, an exploded view of the base portions 500, 502 of an example delivery device 10 is depicted. As shown, the second base portion 502 of the delivery device 10 may include a projection 542 with a fenestration 544 or alternatively a recess. The first base portion 500 may include a protruding member 546 which includes a slot 548 therein. The slot 548 may be sized to accept the projection 542 of the second base portion 502. In the example embodiment, the protruding member 546 of the first base portion 500 includes a cantilever arm 550 which forms a portion of the wall of the slot 548. The cantilevered arm 550 may include a coupling interface (e.g. catch, nub, hook, etc.) which extends into the slot 548. As the projection 542 is introduced to the slot 548, the slot 548 may contact the coupling interface and the cantilevered arm 550 may deflect so as to allow further advance of the projection 542 into the slot 548. Once the projection 542 is fully advanced into the slot 548, the fenestration 544 may be in alignment with the coupling interface of the cantilevered arm 550. The cantilevered arm 550 may then snap into engagement with the fenestration 544 so as to retain the projection 542 within the slot 548 and hold the first and second base portion 500, 502 together.

Figure 60:
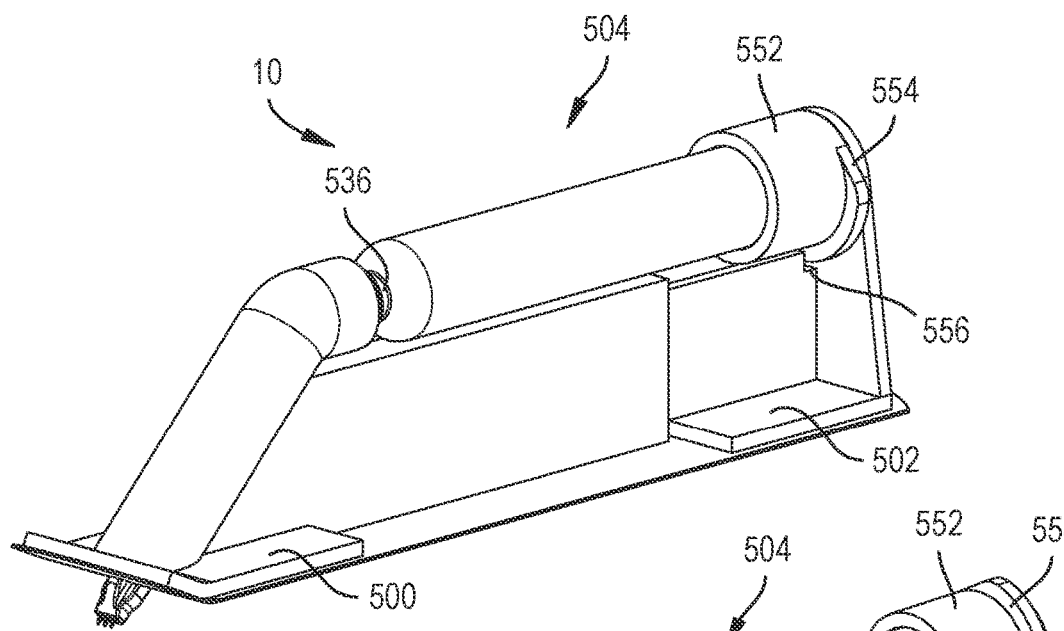
FIG. 60 depicts a perspective view of an example delivery device in a storage state.

Referring now to FIG. 60, the insert 562 (see, e.g., FIG. 58) may include a cap body 552 on an end of the insert 562 opposite the outlet 536. The cap body 552 may include a flange 554. As shown, the cap body 552 includes a radially extending flange 554 which is present around a portion of the exterior of the cap body 552. The second base portion 502 may include a notch or recess 556 within which the flange 554 may be located. With the flange 554 disposed within the recess 556, components attached or coupled to the cap body 552 may be prevented from displacing.

Figure 61:
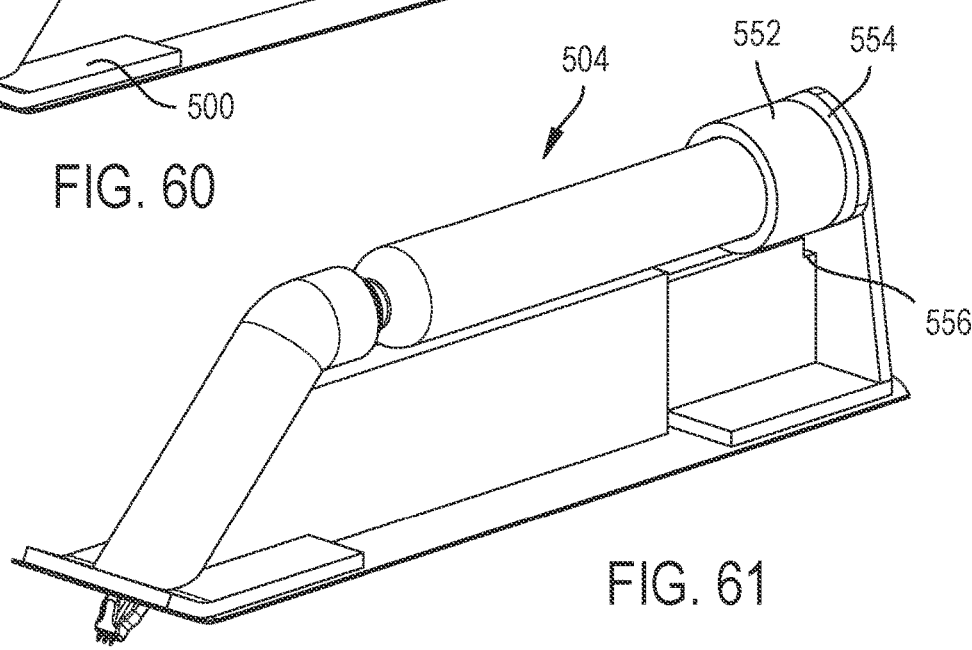
FIG. 61 depicts a perspective view of an example delivery device which has been unlocked such that it may be transitioned out of a storage state.
Figure 62:
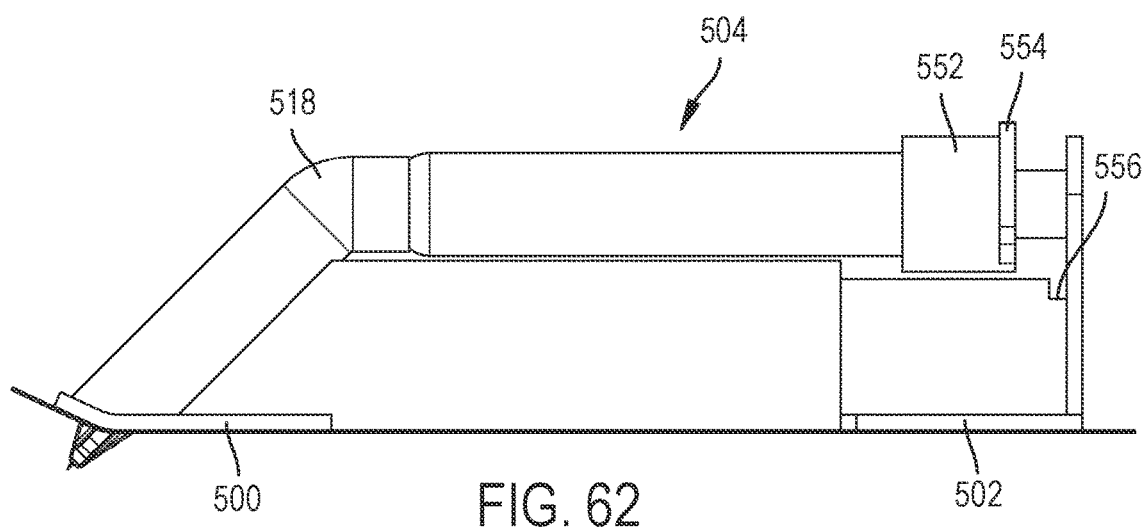
FIG. 62 depicts a side view of an example delivery device in a delivery state.

Referring now to FIG. 61 and FIG. 62, the reservoir assembly 504, insert 562, or at least the cap body 552 may be rotatable about the longitudinal axis of the reservoir assembly 504. As shown, this may allow the cap body 552 to be rotated such that the flange 554 may be displaced from a state in which it is in engagement with the recess 556 to a state in which it is free of the recess 556 in the second base portion 502. As shown, once the flange 554 is released from the recess 556, the reservoir portion 504 may be driven toward the receptacle housing 518 via urging of the bias member 534.

Referring now to FIG. 63, with the reservoir portion 504 free to displace, the reservoir portion 504 may advance, under urging of the bias member 534, into abutment with a wall 560 of the receptacle housing 518. This may cause the outlet 536 of the reservoir assembly 504 to be accessed via the reservoir access sharp 508. In the example embodiment, the reservoir access sharp 508 may access the interior volume of the reservoir via a septum 538. Further displacement of the barrel 530 of the reservoir portion 504 may be inhibited by the interference presented by the wall 560 of the receptacle housing 518. Thus, the reservoir portion 504 may be driven via the bias member 534 (in this case a coil spring) from a sealed state into an accessed state.

Referring now to FIG. 64 and FIG. 65, actuation of the delivery device 10 may be a two stage process. As shown, once the reservoir portion 504 has reached the accessed state, fluid contained within the reservoir portion 504 may be able to be driven out of the reservoir portion 504 through the access sharp 508 and into the patient via the microneedle(s) 506. The bias member 534 may urge the insert 562 and plunger head 532 toward the outlet 536 to force fluid out of the reservoir portion 504 over a delivery stage of actuation. At the conclusion of this stage, the delivery device 10 may be in a delivered state and the plunger head 532 may be at its most proximal to the outlet 536. The bias member 534 is shown in its compressed state for ease of illustration. In practice, and as would be understood by one of skill in the art, the bias member 534 would expand during actuation.

As shown, the cap body 552 may include a recess 566 in which a terminal end of the barrel 530 may be disposed. During the delivery stage, the recess 566 may displace over a segment of the terminal end of the barrel 530. In some embodiments, this may serve as an indicator of delivery progress. In some examples, the portion of the barrel 530 to be covered received in the recess 566 may include graduations, markings, coloration, or various indicia that indicate delivery progress. This may facilitate communication to a user that the delivery has completed and the delivery device 10 may be removed and discarded.

Referring now to FIGS. 66-67, in some embodiments, the injection site may be pressurized as agent in a delivery device 10 is dispensed. As shown, a delivery device 10 may include a chamber 630. When the delivery device 10 is applied to a patient, the chamber 630 may cover and surround the delivery site and the microneedle(s) 506 (or other delivery sharp or sharps). The chamber 630 may include a peripheral flange 632 which may be attached to a portion of the bandage 252. The peripheral flange 632 and bandage 252 surrounding the chamber 630 may aid in creating a seal against the skin of the patient. Also as shown, the chamber 630 may include a port 634. The port 634 may be provided with a mating interface (luer lock, barbed fitting, etc.) which may couple to a pressure source 636 or tubing 638 extending therefrom. In various embodiments, the pressure source 636 may include a pump, manual squeeze bulb, pressure reservoir, combination thereof and any associated check valves or other valving. The pressure source 636 may be operated to bring the chamber 630 to a negative pressure. The chamber 630 may also be outfitted with a relief valve (not shown) to ensure pressure does not drop below a predefined cracking pressure of the relief valve. Negatively pressurizing the chamber 630 may aid in drawing fluid out of the microneedle(s) 506 and into an intradermal space. Though shown in relation to the delivery device 10 depicted in FIGS. 55-65, such a pressure chamber 630 may be included in other varieties of delivery devices 10 depicted herein. For example, delivery devices 10 including ampoules 440 or the delivery device 10 described in relation to FIGS. 68-70 may include a chamber 630 which may be pressurized during delivery of agent to the patient. Any other delivery device 10 described herein may similarly include a pressure chamber 630 which may seal around an injection site so as to allow pressurization (positive or negative) of the injection site.

Referring now to FIG. 68, another example embodiment of a delivery device 10 is depicted. As shown, the delivery device 10 may include a base portion 390. The base portion 390 may be coupled to a bandage 252. The base portion 390 may be constructed of a plastic which may be rigid or slightly flexible so as to allow the delivery device 10 to adapt to contours of a user's body. The base portion 390 may include a displaceable section 392. The displaceable section 392 may be coupled to the rest of the base portion 390 at a hinge or may be integral with the rest of the base portion 390 and hinged via a living hinge. Alternatively, the displaceable section 392 may be arranged to displace substantially translationally. In such embodiments, the displaceable section 392 may include flanges on opposing edges. The flanges may overhang a channel within which the displaceable section 392 is configured to displace. At least one of these flanges may be flexible such that it may deflect as the displaceable section 392 is pressed into the channel during assembly. This flange would then restore to an undeflected state such that the displaceable section 392 cannot be removed without exertion of significant force. The displaceable section 392 may have a thickness which is thicker than the rest of the base portion 390.

The delivery device 10 may also include a fluid handling portion 400. The fluid handling portion 400 may be coupled to the base portion 390 at a hinge 402. The fluid handling section 400 may include a port assembly 404. The port assembly 404 may be any suitable port assembly such as port assembly 258 described in relation to FIG. 47. The fluid handling section 400 may also include a reservoir 415. In the example embodiment, the fluid handling section 400 includes a raised protuberance 406. In the example embodiment, the raised protuberance 406 is shown as a round or convex bump which provides a convex surface on the fluid handling section 400. In some embodiments, this convex surface presented by the raised protuberance 406 may be hemispherical or some other spherical segment. Other convex surfaces such as those presented by round raised protuberances 406 with egg-like, elliptical, oval, obround, etc. type footprints may also be included in alternative embodiments. The convex surface provided by the raised protuberance 406 may be covered via a membrane 408 which is fluidically sealed to a main body 410 of the fluid handling portion 400 at the periphery of the raised protuberance 406. In some embodiments, a retention ring may be attached to the main body 410 (ultrasonic welded, laser welded, adhered with adhesive, etc.) compressing the membrane 408 into sealing relationship with the main body. The membrane 408 may have an unstressed shape which differs from the shape of the raised protuberance 406. In various embodiments, the membrane 408 may be flat in its unstressed state. Thus, when in place over the raised protuberance 406, the membrane 408 may be said to be in a pre-stressed state as it may be stretched to accommodate the contour of the convex surface of raised protuberance 406. A fluid flow path 416 from the port assembly 404 to the sealed space between the membrane 408 and the raised protuberance 406 may be included. The space between the surface of the raised protuberance 406 and the membrane 408 may function as the reservoir 415 and the membrane 408 may stretch as fluid is loaded into the reservoir 415 to allow for filling of the reservoir 415.

The fluid handling portion 400 may also include an outlet assembly 412. The outlet assembly 412 may extend from a face of the main body 410 opposing that on which the raised protuberance 406 is included. The outlet assembly 412 in the example embodiment includes a microneedle 414 or an array of microneedles 414 (other delivery sharps such as subcutaneous or intramuscular needles may be used in alternative embodiments). A fluid flow path 418 from the sealed space between the membrane 408 and the raised protuberance 406 to the microneedle(s) 414 may be included.

The fluid handling portion 400 may be pivotal about the hinge 402 from a withdrawn position shown in FIG. 68 to a deployed position shown in FIGS. 69 and 70. The delivery device 10 may be applied to a user with the fluid handling portion 400 in the withdrawn position. In the withdrawn position, the fluid handling portion 400 may be raised with respect to the base portion 390. The fluid handling portion 400 may then be displaced to the deployed position. As the fluid handling portion 400 is displaced to the deployed position, the main body 410 (which may be rigid) may contact the displaceable portion 392 of the base portion 390. Further displacement of the fluid handling portion 400 toward the deployed position may cause the displaceable portion 392 to displace against the skin of the user. Thus the displaceable portion 392 may act as a skin depressor. This may cause the skin near the displaceable portion 392 to be stretched. Other embodiments described herein may include translationally displaceable skin depressors like that shown in FIGS. 68-70. The microneedle(s) 414 of the fluid handling portion 400 may puncture the stretched skin gaining access to an intradermal space in the user as the fluid handling portion 400 is fully displaced into the deployed position. In various embodiments, the fluid handling portion 400 and base portion 390 may include cooperating retention features which allow the fluid handling portion 400 to be retained in the deployed position once the fluid handling portion 400 has been fully rotated against the base portion 390. For example, the fluid handling portion 400 may snap into place on the base portion 390 upon displacement to the deployed position.

With the fluid handling portion 400 in the deployed position, a user may load fluid into the delivery device 10. The space between the raised protuberance 406 and the membrane 408 may function as a reservoir and may be variable in volume due to stretching of the membrane 408. As shown in FIG. 70, the membrane 408 may stretch to accommodate a volume of medical agent. As this stretching may stress the membrane 408, the membrane 408 may exert a pressure on the fluid which forces fluid into the patient through the fluid flow path 418 and microneedle(s) 414. The amount of pressure exerted by the membrane 408 may be related to the volume contained in the reservoir 415 defined by the membrane 408 and convex surface of the raise protuberance 406.

Figure 71:
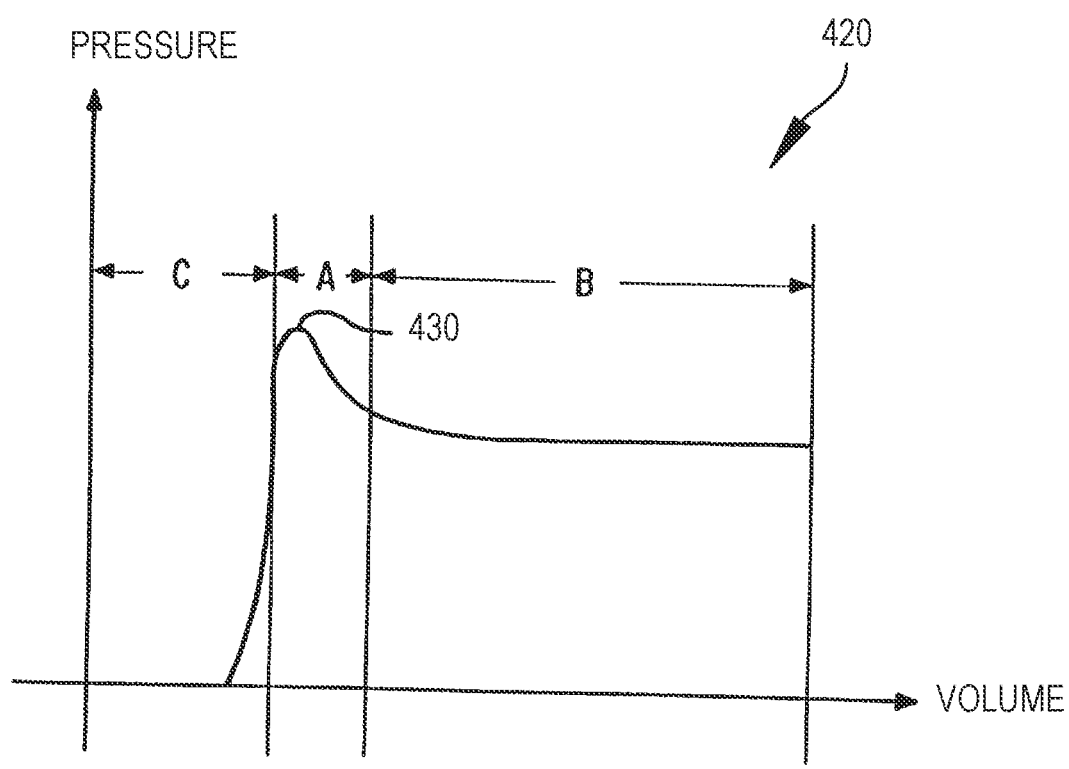
FIG. 71 depicts example plot depicting pressure versus volume characteristics of an example stretchable membrane based reservoir.

Referring now to FIG. 71, an example plot 420 depicting pressure versus volume characteristics of a stretchable membrane based reservoir is shown. As fluid is initially loaded into the reservoir, the reservoir may begin to balloon out through an initial stretching range of the reservoir. A relatively large pressure build up (see regions C and A) is required to begin stretching the membrane to accommodate the change in volume over the initial stretching range. There is a point at which the first derivative of pressure over volume becomes zero for the first time (430 in FIG. 71). Once the initial stretching has been completed, the pressure tends to remain relatively constant as further increase in volume occurs (see region B). Stretching of the membrane that occurs here may be said to occur over a steady pressure stretching range of the membrane.

Referring now also to FIGS. 68-70, the membrane 408 may be attached to the delivery device 10 over the raised protuberance 406 in a pre-stressed or a first stressed state. When the membrane 408 is snug against the raised protuberance 406, the volume of the reservoir 415 may be substantially zero and the reservoir 415 may be in an empty state. The membrane 408 may, however, be stretched to assume a shape which, absent the raised protuberance 406, would correspond to a volume in region B of the plot 420. Thus, as the reservoir 415 increases in volume as it is brought to a filled state, the pressure exerted by the membrane 408 on the fluid contained in the reservoir 415 may remain relatively stable. In certain embodiments, a change in pressure may be less than 10% or less than 5% may occur as the reservoir is brought to a filled state. As a result, delivery out of the delivery device 10 may occur at a substantially constant rate. This may be particular desirable where the delivery device 10 is used to deliver a fluid to a user at a basal delivery rate. In alternative embodiments, the raised protuberance 406 may be omitted. In such embodiments, the pressure may change, perhaps significantly, over the course of filling and delivery.

Referring now to FIG. 72, in certain embodiments, a delivery device 10 may include a breakable or fracturable reservoir which contains a medical agent. For example, delivery devices 10 may include a glass or plastic ampoule 440 which serves as the reservoir for the medical agent 442 (e.g. vaccine). Glass may be advantageous as it is inert and may lessen the amount of compatibility testing needed for the delivery device 10. This may help a delivery device 10 to be made available for a vaccine quickly which may be of particular interest where the delivery device 10 is intended to deliver a vaccine for a novel pathogen and time is of the essence. The ampoule 440 or other fracturable reservoir may be pressurized such that upon rupture, the pressure in the ampoule 440 may deliver fluid through the delivery device 10 and into the patient. In certain embodiments, the ampoule 440 may be pressurized with a volume of inert gas 444 (e.g. to 10 psi). The ampoule 440 may include a frangible 446 which may be thinned and/or scored (as shown) to provide a weak point in the ampoule 440 and allow the ampoule 440 to be cleanly snapped open. In the example embodiment, the ampoule 440 includes a neck portion 445 which extends from a main body 443 of the ampoule 440. The frangible 446 is located in the neck portion 445 in the example embodiment.

Referring now to FIG. 73 and FIG. 74 (a cross-section taken at the indicated plane of FIG. 73), when installed in a delivery device 10, the portion of the ampoule 440 including the frangible 446 may be contained in an elastomeric boot or housing 450. The elastomeric housing 450 may include a chamber 452 in which the frangible 446 is disposed. The chamber 452 may include a port 458 via which the chamber 452 is in communication with a microneedle 454 or array of microneedles 454 included as part of an outlet assembly 456. Alternatively, a conventional delivery sharp (e.g. needle) may be used. The elastomeric housing 450 may from a fluid and pressure tight seal around the exterior of another portion of the ampoule 440 upstream of the frangible 446. Additionally, in some embodiments, the ampoule 440 may include a step or notch which aids in ensuring that the elastomeric housing 450 is retained in place on the ampoule 440 and cannot easily be removed. As shown, the ampoule 440 may be placed in a holster 460 formed in a base portion 480 of the delivery device 10. The base portion 480 may be coupled to a bandage 252 which may be applied to the skin of a user. In some embodiments, a delivery device 10 may be packaged separate from the ampoule 440 (and perhaps elastomeric housing 450). The ampoule 440 (and perhaps elastomeric housing 450) may be inserted into the delivery device 10 prior to use (e.g. by a pharmacy, clinician, trained vaccination staff, user). Alternatively, the delivery device 10 may come with the ampoule 440 pre-assembled and ready for use.

Referring now to FIG. 74 and FIG. 75, the elastomeric housing 450 may seat into a receptacle 472 of an activation assembly 470. The activation assembly 470 may include a tab 474 which surrounds the receptacle 472. The tab 474 may be configured so as to be easily grasped by a user. In operation, the user may grasp the tab 474 and displace the tab 474 upward. Thus, the activation assembly 470 may be actuated from an inactive state to an active state. During this transition, the frangible 446 may be ruptured and a fluid flow path from the interior volume of the ampoule 440 to the microneedle(s) 454 may be established. As the ampoule 440 may be pressurized, agent disposed within the ampoule 440 may be driven out of the ampoule 440 and out of the delivery device 10 to the patient.

Referring now also to FIG. 76 and FIG. 77 (depicting a detailed view of the indicated region of FIG. 76), the activation assembly 470 may also include a number of wings 476. The wings 476 may be disposed within detent interfaces 482 included on walls 484 extending from a main body 486 of a base portion 480 of the delivery device 10. As shown, the detent interfaces 482 may be configured to allow the wings 476 to be locked in a first position and a second position. In the example embodiment shown in FIG. 76, the wings 476 are locked in the first position. The wings 476 may be in the first position when the activation assembly 470 is in an inactive state. Upon transition of the activation assembly 470 to the active state, the wings 476 may snap out of a first detent 488A of the detent interfaces 482 and snap into a second detent 488B of the detent interfaces 482. The wings 476 may be firmly retained in the second detent 488B maintaining the delivery device 10 in the active state.

Referring again primarily to FIG. 74 and FIG. 75, upon transition of the activation assembly 470 to the active state, a tail member 490 of the activation assembly 470 may be displaced forward. The tail member 490 may be hingedly connected to the rest of the activation assembly 470. In the example embodiment, the tail member 490 may be molded integrally with the rest of the activation assembly 470 and may be connected to the rest of the activation assembly via a living hinge 492. In alternative embodiments, a physical hinge may be used. As the tab 474 is displaced upward and the outlet assembly 476 pivots into the skin, the tail member 490 may translationally displace toward the forward end of the delivery device 10. As shown, the tail member 490 may include at least one raised portion 494 (e.g. a ramp, nub, bump, etc.). As the tail member 490 translationally displaces, the raised portion 494 may abut against a stationary portion of the delivery device 10. In the example embodiment, the raised portion 494 may abut against a bottom of the holster 460. Further displacement of the tail member 490 may force the tail member 490 downward toward the skin. The tail member 490 may press against a portion of the main body 486 of the base portion 480 which is hinged (e.g. connected via living hinge) with respect to the rest of the base portion 480. This portion may be pressed against the skin causing the skin in the vicinity to be stretched. This may facilitate puncture of the stratum corneum and access to an intradermal space of the user via the microneedle(s) 454.

In certain alternative embodiments, the ampoule 440 may be replaced by a biased plunger. In such embodiments, a reservoir portion similar to reservoir portion 280 shown in FIG. 47 may be used, however, the end of the reservoir portion 280 may be terminated in a closed frangible seal as described above. Embodiments of delivery devices 10 shown in FIGS. 80-89 and FIGS. 98-103 may similarly include such a biased plunger and reservoir in place of an ampoule 440. The plunger may begin to advance when the frangible is broken and a flow path to the patient is established. In other embodiments, the entire ampoule 440 may be encased in an elastomeric housing 450. In such embodiments, the entire ampoule 440 may be smashed within the elastomeric housing 450 and the pressure stored in the ampoule 440 may serve to drive fluid into the patient.

Use of microneedles may be attractive in embodiments with frangible seals as the microneedles may have a very small aperture through which agent is dispensed. These apertures may effectively act as filters which prevent any pieces of glass generated during fracture of the frangible from passing to the patient. Thus, a microneedle array may double as a filter assembly. Various delivery devices 10 may also include other filter elements for this purpose as well.

Referring now to FIGS. 78-79, another example ampoule 440 and elastomeric housing 450 are depicted. The ampoule 440 may be pressurized (e.g. with inert gas) such that upon rupture, the pressure in the ampoule 440 may cause the medicinal agent (e.g. a vaccine) in the ampoule 440 to be expelled. The ampoule 440 may include a frangible 446 which may be thinned and/or scored (as shown) to provide a weak point in the ampoule 440 and may allow the ampoule 440 to be cleanly snapped open at a prescribed location. The portion of the ampoule 440 including the frangible 446 may be contained in an elastomeric housing 450. The elastomeric housing 450 may include a chamber 452 in which the frangible 446 is disposed. The chamber 452 may include a port 458 via which the chamber 452 may fluidically communicate with an outlet assembly 594 (see, e.g. FIG. 83). The elastomeric housing 450 may from a fluid and pressure tight seal around the exterior of another portion of the ampoule 440 upstream of the frangible 446 (or the ampoule 440 may be complete encased in an elastomeric housing). Additionally, in some embodiments, the ampoule 440 may include a step or notch which engages a corresponding feature of the ampoule 440. This may aid in ensuring that the elastomeric housing 450 is retained in place on the ampoule 440 and cannot easily be removed. The elastomeric housing 450 may also include a receptacle 496 which may receive an outlet assembly. The receptacle may be in fluid communication with the port 458. As the elastomeric housing 450 may be made of a flexible material, the receptacle 496 may bend or flex relative to the remainder of the elastomeric housing 450.

Figure 80:
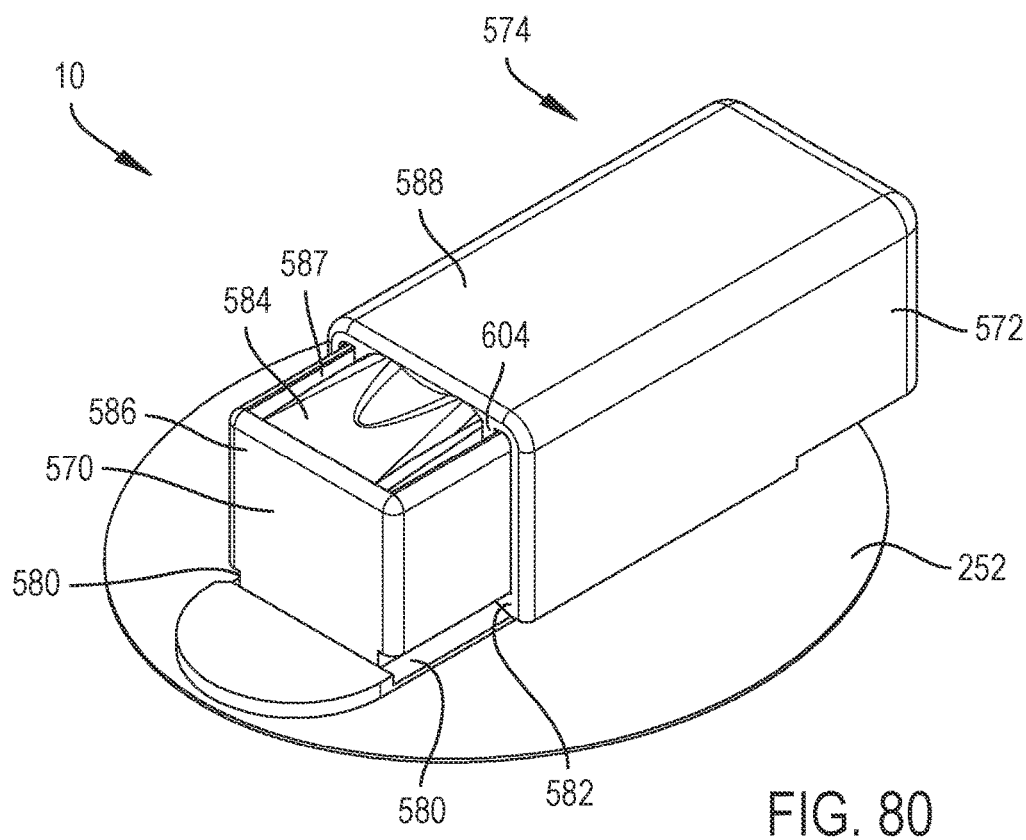
FIG. 80 depicts a perspective view of yet another example delivery device embodiment.
Figure 81:
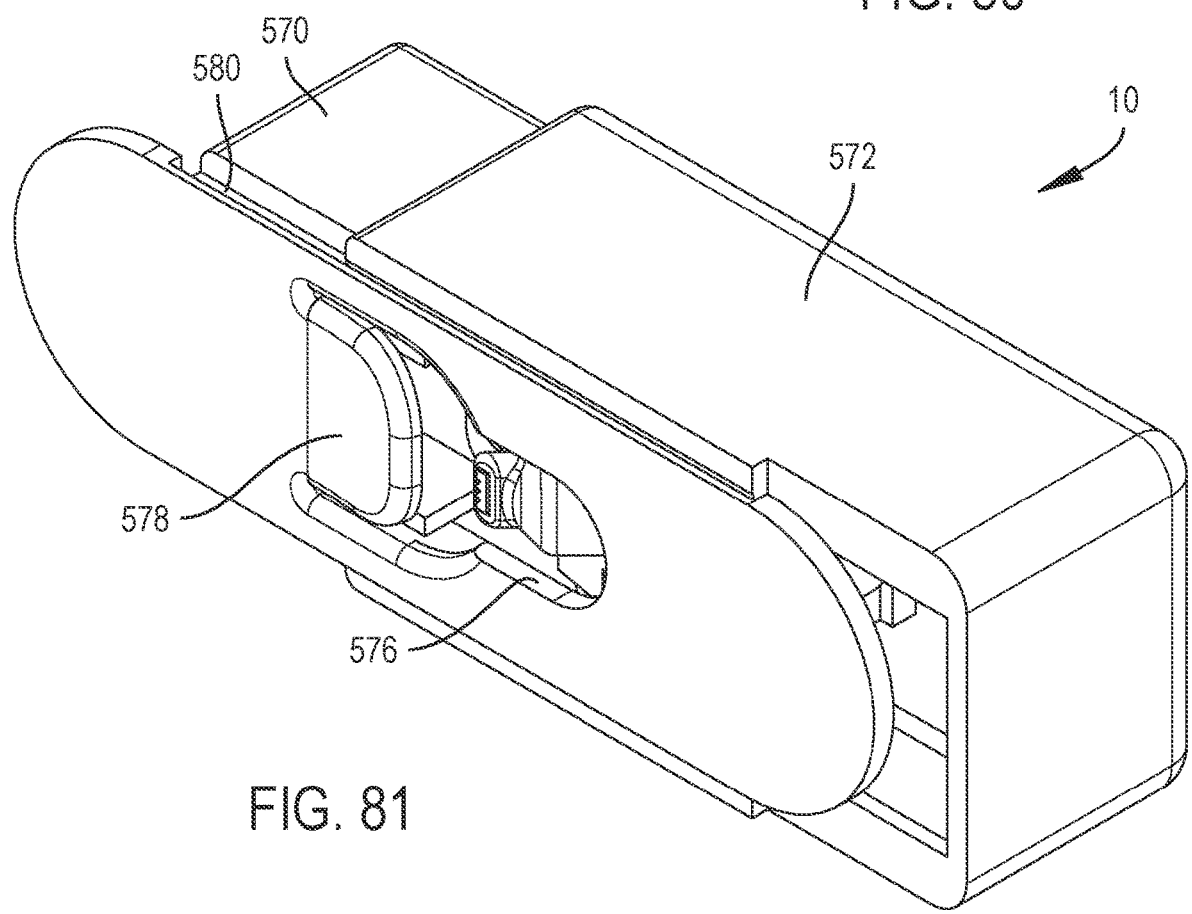
FIG. 81 depicts a perspective view of an example delivery device.

Referring now to FIGS. 80-81 another example delivery device 10 is depicted. The example delivery device 10 may accept and deliver fluid from an ampoule 440 as described in relation to FIGS. 78 and 79 in certain embodiments. As shown, the example delivery device 10 may include a base 570 and a slide body 572. The base 570 and slide body 572 may cooperate to form a housing 574 for the delivery device 10. As shown in FIG. 80, the base 570 may be mounted on a bandage 252 (omitted in FIG. 81). When shipped or in storage, portions of the bandage 252 outside the footprint of the housing 574 may be folded up against the sides of the housing 574 to minimize the size of the delivery device 10 during shipping. As shown, the base 570 (and bandage 252) may include an aperture 576. The aperture 576 may allow for displacement of at least one delivery sharp (e.g. microneedle, transcutaneous delivery sharp, etc.) from the interior of the housing 574 and into the skin of a patient.

As shown, the base 570 may also include a skin depressor 578. The skin depressor or stretcher 578 may be pressed against the skin of a patient as the delivery device 10 is applied to a patient. In certain examples, the skin depressor 578 may be molded so as to be cantilevered and have at least a portion which extends below a face of the base 570 to which the bandage 252 is attached. In the example embodiment, the unsupported end of the skin depressor 578 may be most distal to the face of the base 570 to which the bandage 252 is attached. Thus, when the delivery device 10 is in place on a patient, the skin depressor 578 may resiliently deflect and exert a restoring force against the patient's skin. Alternatively, the skin depressor 578 may be sufficiently rigid to displace skin without deflection. This may cause the skin aligned with the aperture 576 to be stretched when the delivery device 10 is coupled to a user. Other delivery devices 10 described herein may include such a skin depressor 578.

The base 570 and the slide body 572 may include cooperating guide interfaces. As shown, the base 570 of the delivery device 10 may include a set of tracks 580. These tracks 580 may accept guide projections 582 included in the slide body 572. The tracks 580 may act as guides which direct displacement of the slide body 572 via interaction with guide projections 582 on the slide body 572. In alternative embodiments, the base 570 may include guide projections 582 (e.g. rails) and the slide body 572 may include tracks 580. The slide body 572 may be displaceable from a first position (shown in FIGS. 80-81) to a second position (see, e.g., FIG. 86). The slide body 572 may be in the first position when the delivery device 10 is in a shipping or storage state. The delivery device 10 may be in a delivery state when the slide body 572 is displaced to the second position.

In certain embodiments, the tracks 580 may include a stop which may prevent displacement of the slide body 572 from the first position to a position in which the slide body 572 would be more distal to the second position. As shown, the base 570 may also include a latch 584. The latch 584 may prevent displacement of the slide body 572 toward the second position until actuation of the latch 584. In the example embodiment, the latch 584 is flanked by slots 587 such that the latch 584 is cantilevered from a side wall 586 of the base 570. To actuate the latch 584, a user may press the latch 584 out of a blocking position to an actuated position in which the slide body 572 may pass by the latch 584. The latch 584 would resiliently bend at its attachment point to the side wall 586 of the base 570 such that the latch 584 would be entirely below a top wall 588 of the slide body 572 in the example embodiment. In this position, the slide body 572 would be free to pass over that latch 584 as displacement toward the second position occurs. The resiliency of the latch 584 may help to prevent inadvertent actuation of the latch 584. The slide body 572 may include one or more stop projections 604 which may abut the side wall 586 of the base 570 to prevent displacement of the slide body 572 beyond the second position.

Figure 82:
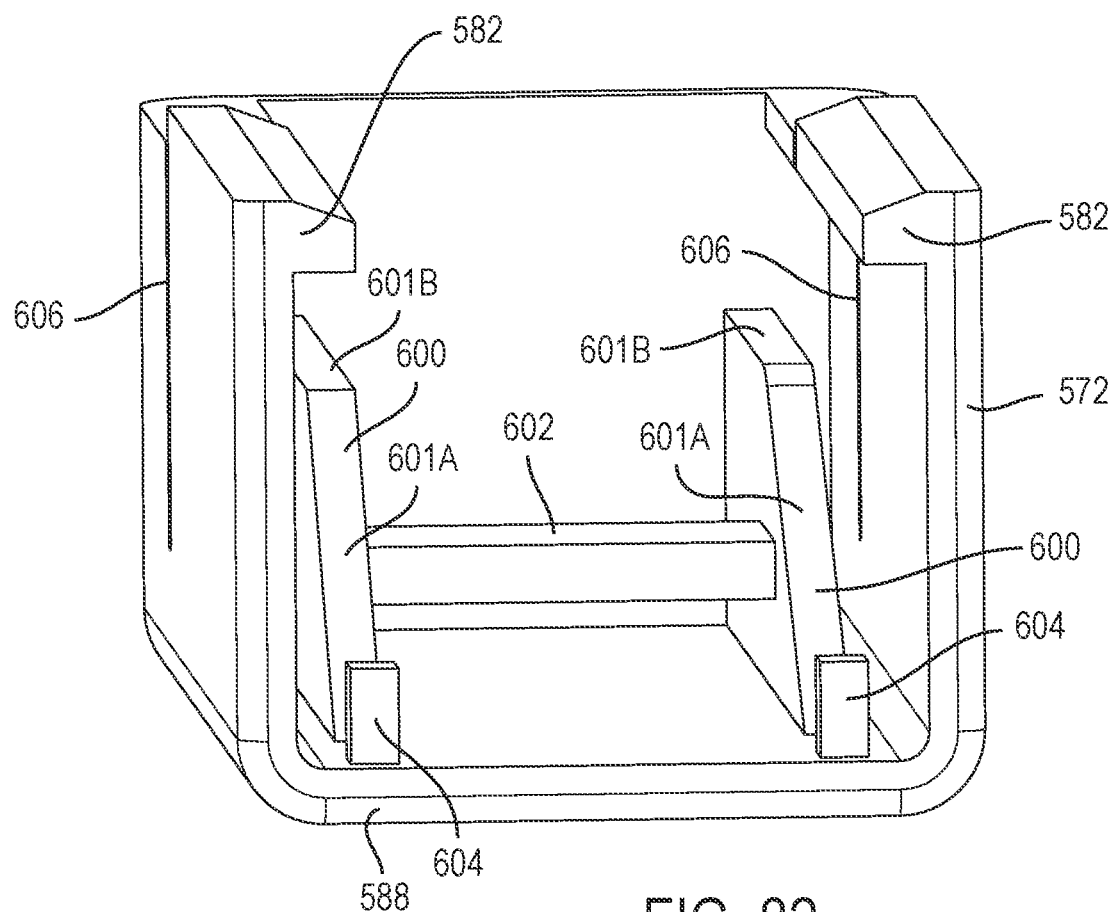
FIG. 82 depicts a perspective view of a slide body which may be included in an example delivery device such as that shown in FIG. 80.

Referring now to FIG. 82, a perspective view of an example slide body 572 is depicted. The slide body 572 may include a number of ramp section 600. In the example embodiment, the ramp section 600 may include a sloped portion 601A and a plateau portion 601B which may be substantially flat. A cross piece 602 may extend between the two ramp segments 600. Additionally, the slide body 572 may include a set of stop projections 604 (described above in relation to FIG. 80). Notches 606 may be cut into the slide body 572 to allow portions of the walls of the slide body 572 to deflect around the base 570 during assembly. In the example embodiment, the notches 606 may allow the portions of the slide body 572 including the guide projections 582 to deflect around a portion of the base 570 and snap into the tracks 580 as the delivery device 10 is assembled. As shown, the guide projections 582 may include ramped or sloped faces to aid in deflecting the walls as the delivery device 10 is assembled.

Figure 83:
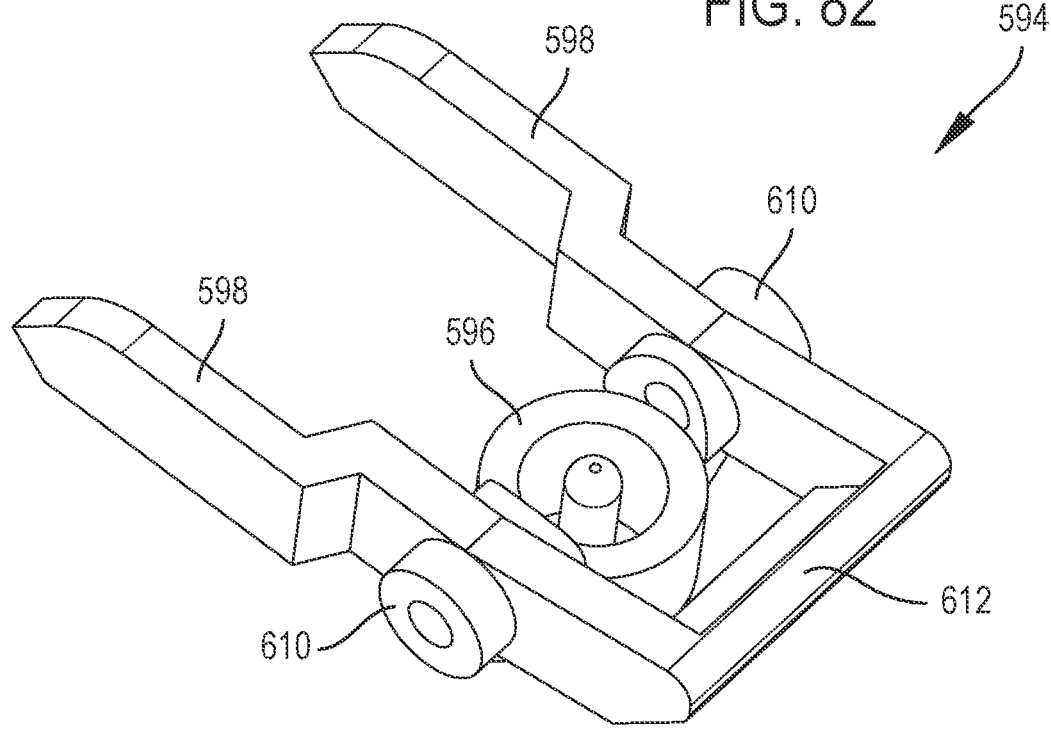
FIG. 83 depicts a perspective view of an outlet assembly which may be included in an example delivery device such as that shown in FIG. 80.

Referring now to FIG. 83, a perspective view of an example outlet assembly 594 is depicted. As shown, the outlet assembly 594 includes a nozzle 596 which may include one or more microneedle 592 (see, e.g., FIG. 85). The example outlet assembly 594 also includes a pair of actuation members 598. The actuation members 598 in the example embodiment are arm like projections which extend from pivot bearings 610 of the outlet assembly 594. In some embodiments, only a single actuation member 598 may be included. The outlet assembly 594 may also include a ram body 612. In the example embodiment, the ram body 612 extends from the pivot bearings 610. The nozzle 596 may be disposed between the pivot bearings 610.

Figure 84:
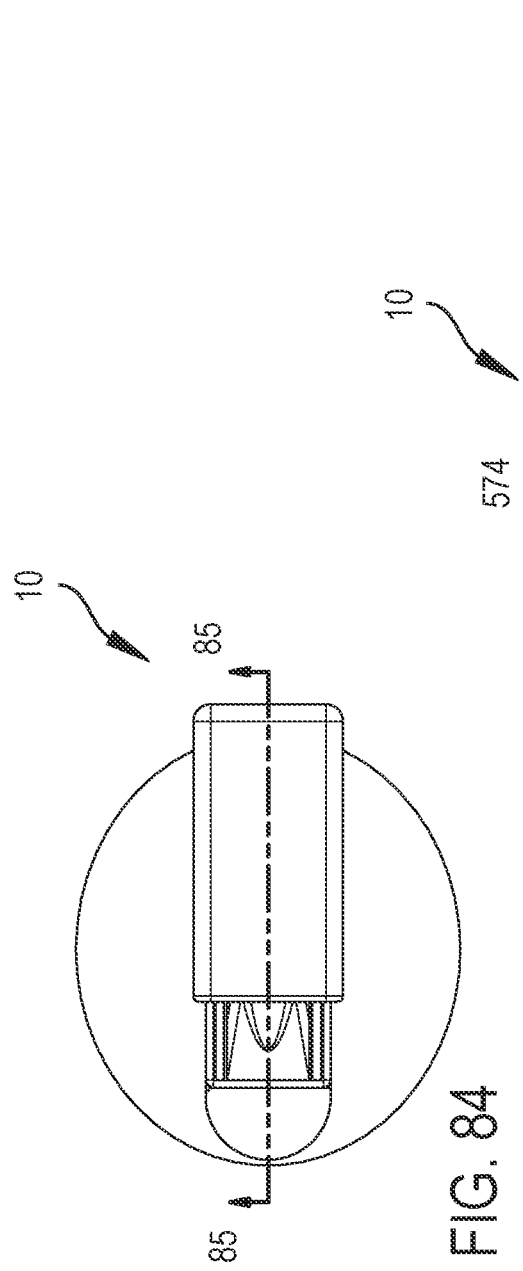
FIG. 84 depicts a top down plan view of an example delivery device.
Figure 85:
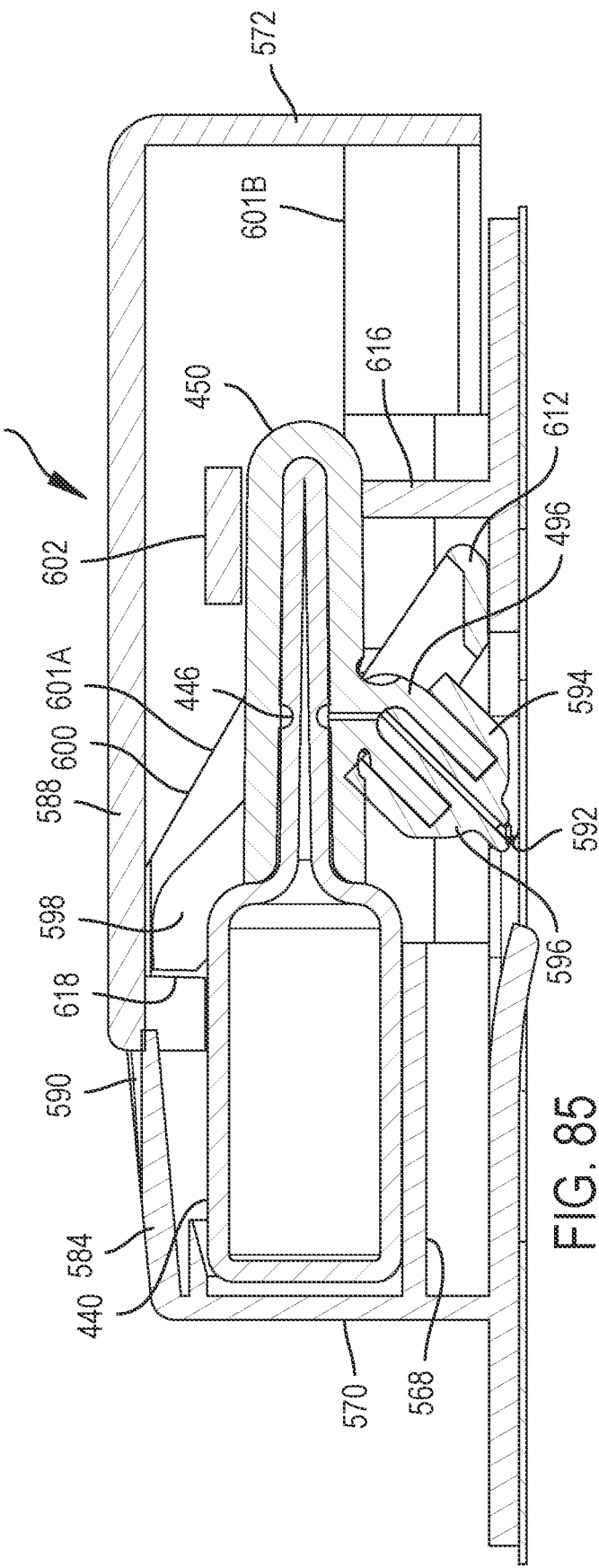
FIG. 85 depicts a cross-sectional view of the example delivery device shown in FIG. 84 taken at the indicated cut plane of FIG. 84.
Figure 86:
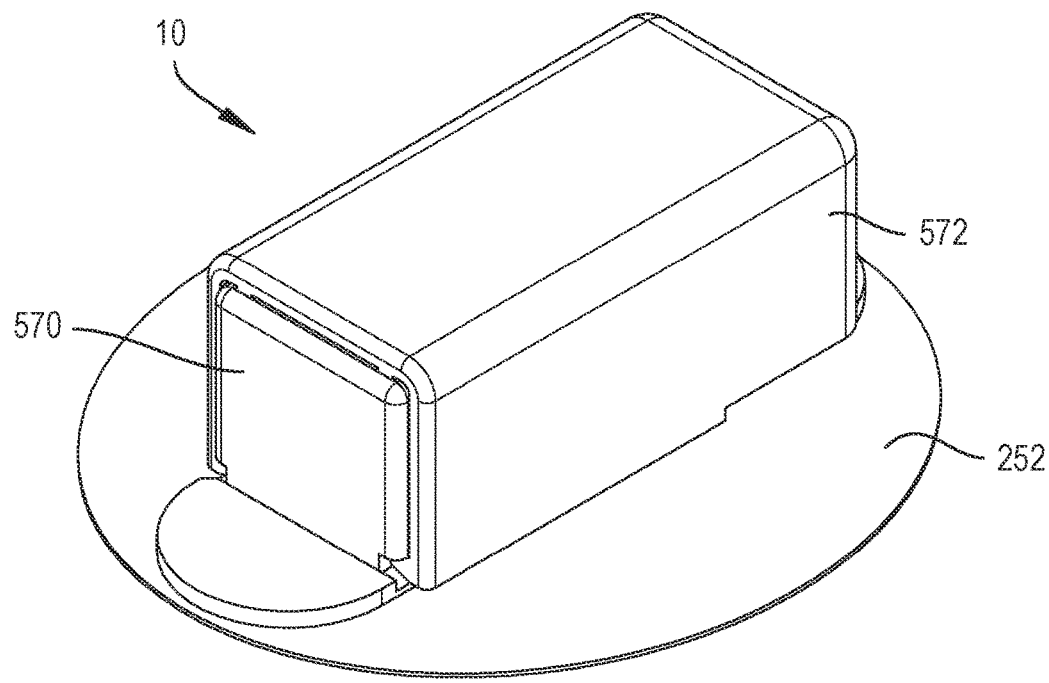
FIG. 86 depicts a perspective view of yet another example embodiment of a delivery device.
Figure 87:
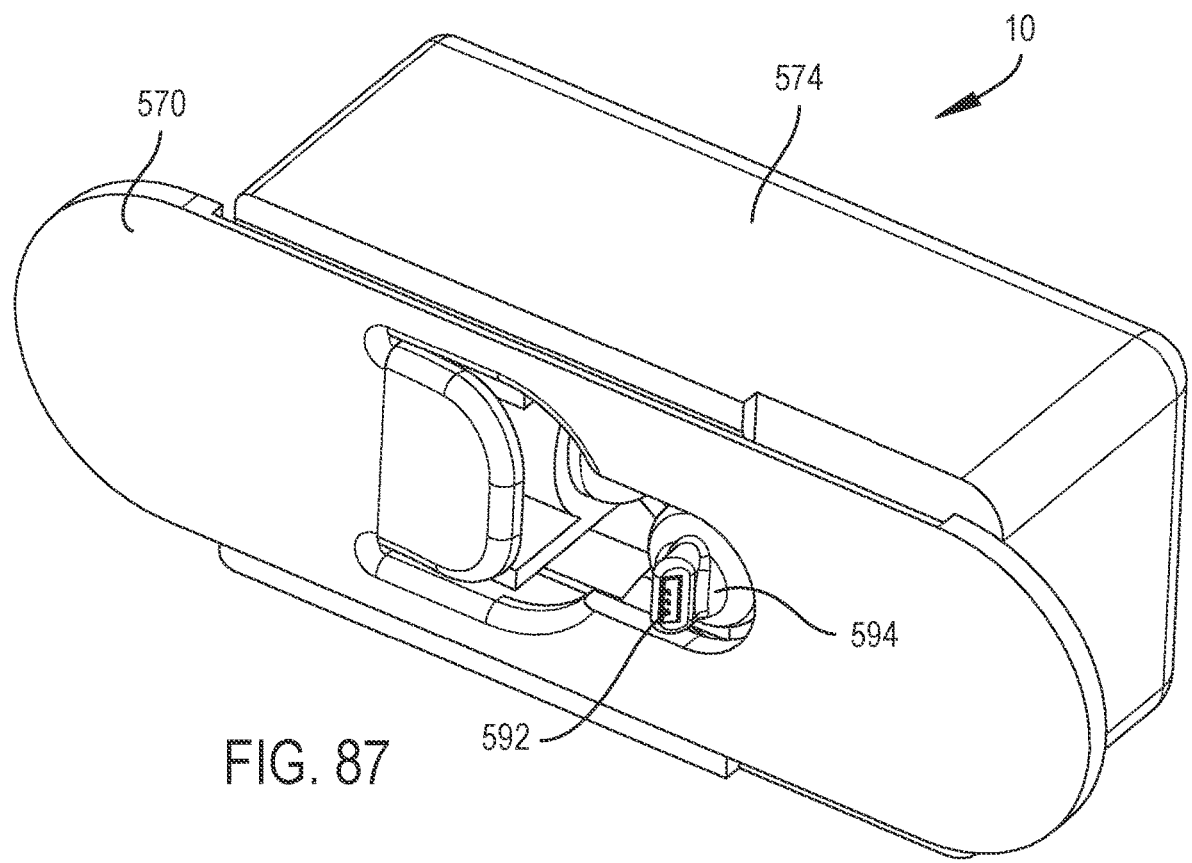
FIG. 87 depicts another perspective view of an example embodiment of a delivery device.

Referring now to FIGS. 84 and 85 (a cross-section taken at the indicated cut plane of FIG. 84), an example delivery device 10 is shown with the slide body 572 in the first position. As shown, the latch 584 may include at least one raised section which may catch against the top wall 588 of the slide body 572 inhibiting displacement toward the second position. With the slide body 572 in the first position, a microneedle or microneedles 592 (though other embodiments may use alternative delivery sharps described elsewhere herein) of the delivery device 10 may be disposed within the housing 574 of the delivery device 10.

The ampoule 440 may be located at least partially within a holster 568 defined in the base 570. The holster 568 may hold the ampoule 440 in place within the delivery device 10. The base 570 may also include a support rest 616. A side of the tip of the elastomeric housing 450 may seat on the support rest 616. Additionally, the cross piece 602 of the slide body 572 may be disposed slightly above the opposing side of the elastomeric housing 450. The support rest 616 and the cross piece 602 may help to ensure that the frangible 446 of the ampoule 440 is protected from breakage during storage or shipping.

The microneedle(s) 592 may form part of an outlet assembly 594. As mentioned above, the outlet assembly 594 may include a nozzle 596. The nozzle 596 may mate into the receptacle 496 of the elastomeric housing 450. The nozzle 596 may be retained in the receptacle 496 via friction fit, adhesive, or any other suitable manner. In some embodiments, the nozzle 596 may include a stepped region or barb which may aid in holding the nozzle 596 in place within the receptacle 496. The nozzle 596 may be coupled to at least one actuation member 598 which forms a portion of the outlet assembly 594. The at least one actuation member 598 may interact with a portion of the slide body 572 as the slide body 572 is displaced to the second position so as to displace (e.g. rotate) the nozzle 596 toward the skin and displace the microneedle(s) 592 into the patient.

In the example embodiment shown in FIG. 85, when the delivery device 10 is in the shipping or storage state, the outlet assembly 594 may be prevented from displacing. As shown, the ram body 612 may rest against an interior face of the base 570. As the base 570 is in the way, the base 570 may block rotation of the outlet assembly 594 in a first direction since the ram body 612 cannot displace through the base 570 material. Additionally, the ends of the actuation members 598 most distal to the pivot bearings 610 may be adjacent an interior side wall 618 of the slide body 572. This may prevent rotation of the outlet assembly 594 in a second direction opposite the first direction as the actuation members 598 may not pass through the solid side wall 618. Thus, the outlet assembly 594 may be rotationally locked when the delivery device 10 is in the shipping/storage state. When in the storage state, the microneedle(s) 592 may be within the housing 574 of the delivery device 10 and protected from inadvertent contact with a user.

When the slide body 572 is displaced toward the second position (see, e.g., FIG. 86) the ramp sections 600 of the slide body 572 may contact the actuation members 598. The ramp sections 600 may interact with the actuation members 598 to cause displacement of the outlet assembly 594 as the slide body 572 is displaced. The actuation members 598 may, for instance, act as cam followers and the ramp sections 600 may present a cam which may direct displacement of the actuation members 598 as the slide body 572 is displaced. Translational displacement of the slide body 572 may result in rotational displacement of the outlet assembly 594 through this interaction.

As the slide body 572 is displaced, the interior side wall 618 of the slide body 572 may also be displaced out of the outlet rotation preventing position described above as the slide body 572 is displaced. With the interior side wall 618 out of the rotation preventing position, further displacement of the slide body 572 may cause the actuation members 598 to displace as the ramp segments 600 are driven into the actuation members 598. Over the course of the displacement of the slide body 572 to the second position, the interaction of the ramp segments 600 and the actuation members 598 may cause the outlet assembly 594 to displace to a deployed position in which the microneedle(s) 592 extend out of the housing 574 and puncture into communication with an intradermal space of the patient.

Referring now to FIGS. 86-89, an example delivery device 10 is depicted with the slide body 572 in the second position. As best shown in FIG. 89, as the outlet assembly 594 is rotated during displacement of the slide body 572, the ram body 612 may be driven into the elastomeric housing 450 and exert a breaking or snapping force on the ampoule 440. As this occurs, the ampoule 440 may be snapped open at the location of the frangible 446. To aid in ensuring the ampoule 440 breaks at the frangible 446, the cross piece 602 may be displaced to a location upstream of the frangible 446 as the slide body 572 is moved to the second position. Thus, the cross piece 602 may provide support to this portion of the ampoule 440 as the ram body 612 is driven into the unsupported end of the ampoule 440 downstream of the frangible 446. This may help to ensure that any break in the ampoule 440 occurs at the location of the frangible 446. With the frangible 446 broken, the interior volume of the ampoule 440 may be placed into communication with the microneedle(s) 592 and the pressure within the ampoule 440 may drive the contents of the ampoule 440 into the patient via the microneedle(s) 592.

Referring now also to FIG. 82, with the slide body 572 in the second position, the plateau regions 601B of the ramp segments 600 on the slide body 572 may be positioned against at least a portion of the actuation members 598. This may block any additional rotation of the outlet assembly 594 about the pivot bearings 610 as the plateau regions 601B may present a mechanical interference to such rotation. Thus, once transitioned to the deployed state, the outlet assembly 594 may be locked in position such that the microneedle(s) 592 are robustly held in place within the patient.

Figure 90:
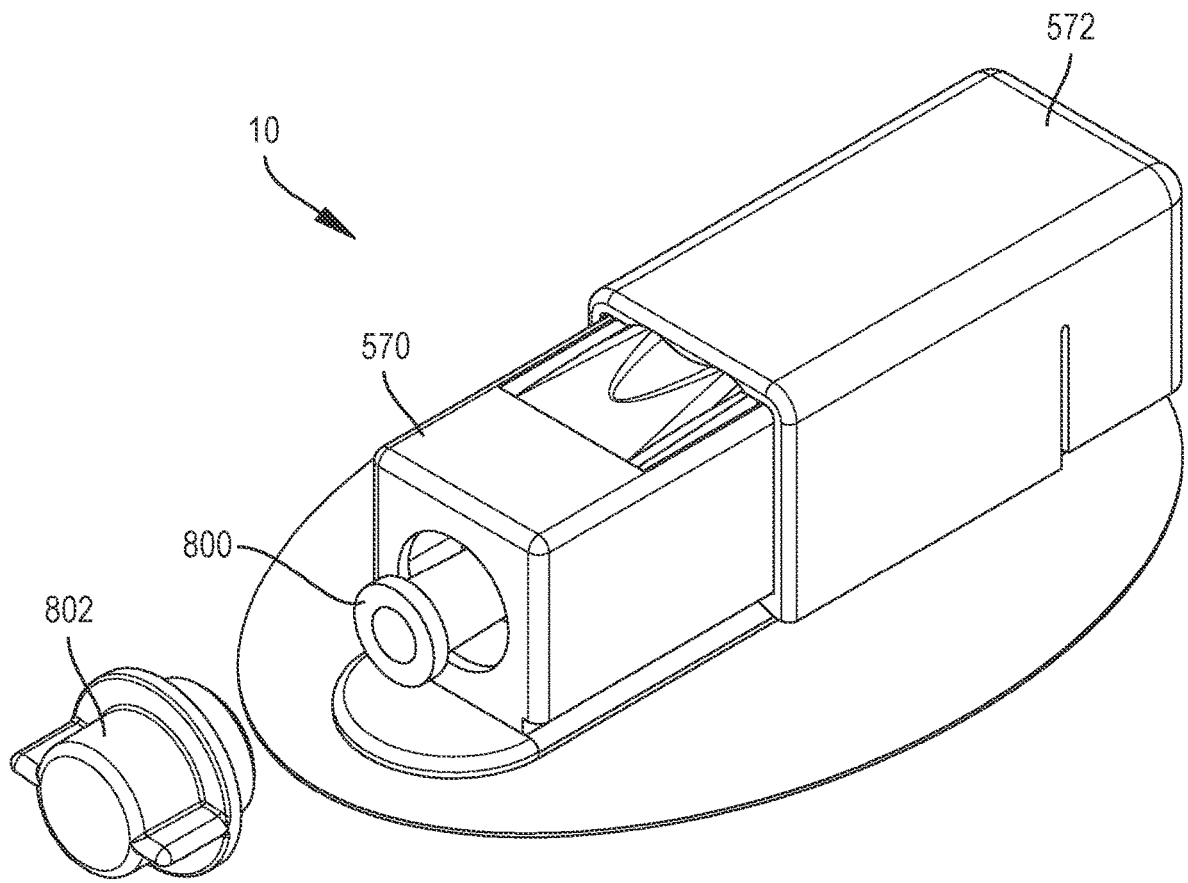
FIG. 90 depicts a perspective view of yet another embodiment of a delivery device which includes an injection port.
Figure 91:
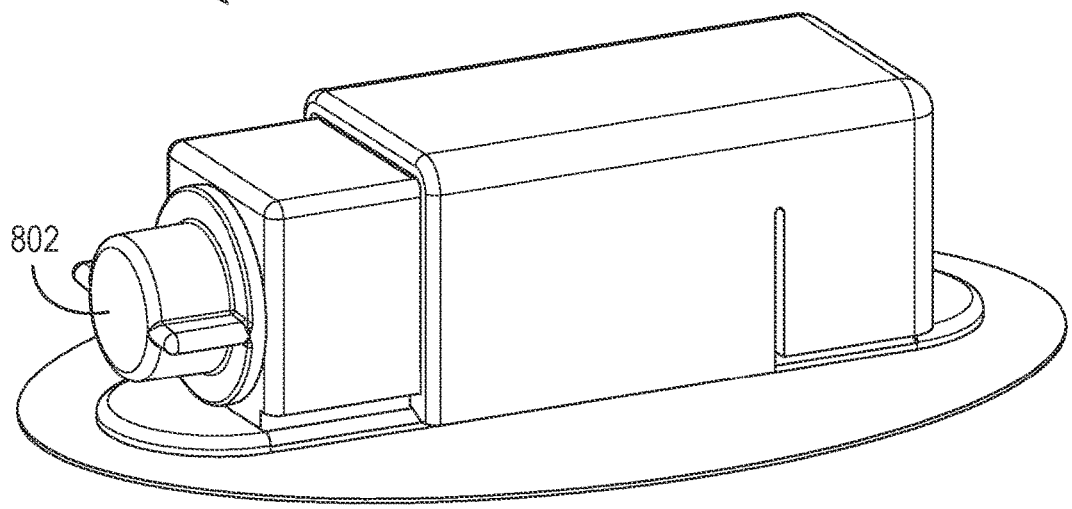
FIG. 91 depicts another perspective view of an embodiment of a delivery device including an injection port.
Figure 92:
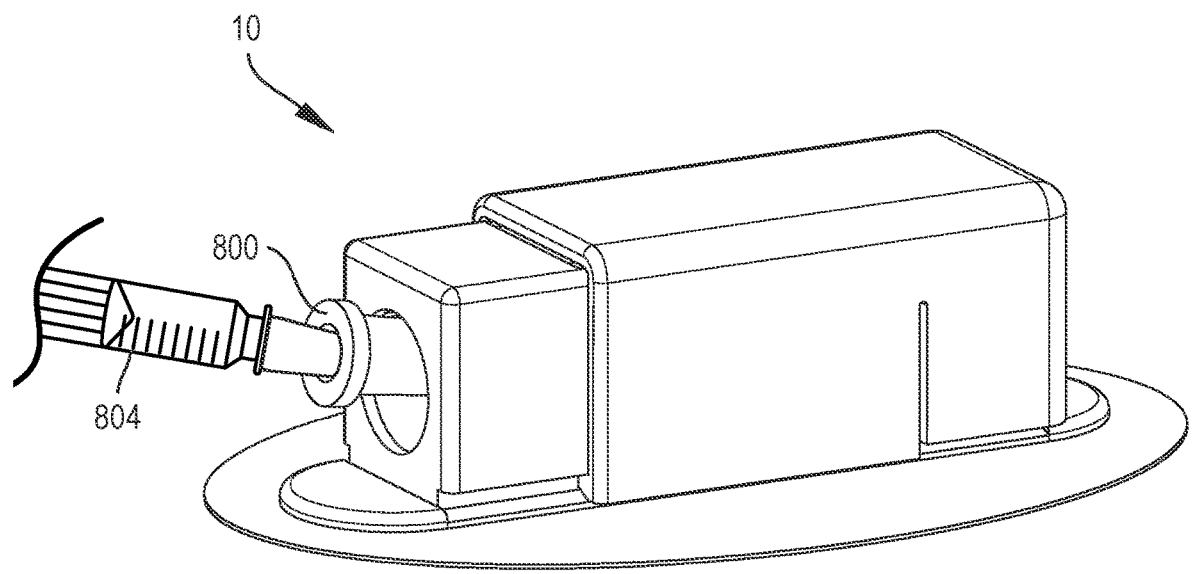
FIG. 92 depicts a perspective view of an embodiment of a delivery device with a syringe introducing fluid into the delivery device via an injection port included in the delivery device.

Referring now to FIGS. 90, 91, and 92, an alternative embodiment of the delivery device 10 shown in FIGS. 80-89 is depicted. The delivery device 10 may include an additional injection port 800. The injection port 800 may be covered by a removable cap 802 (exploded away from injection port 800 in FIG. 90). The injection port 800 may allow for a user to deliver fluid manually from a fluid administration implement 804 (e.g. syringe, injection pen, etc.) into the patient via the delivery device 10. In some embodiments, the outlet assembly 594 of the delivery device 10 may be in communication with the injection port 800 via tubing. Alternatively, the injection port 800 be used to access the interior volume of the ampoule 440.

The injection port 800 may be utilized to deliver a second agent to a patient after a first agent contained in the ampoule 440 in the delivery device 10 has already been expelled. Alternatively, the injection port 800 may allow for the ampoule 440 to be repressurized with a gas (e.g. via a syringe or other implement). Thus, in the event that agent remains in the delivery device 10 after actuation, pressure may be manually applied to drive the remaining agent from the ampoule 440.

Figure 93:
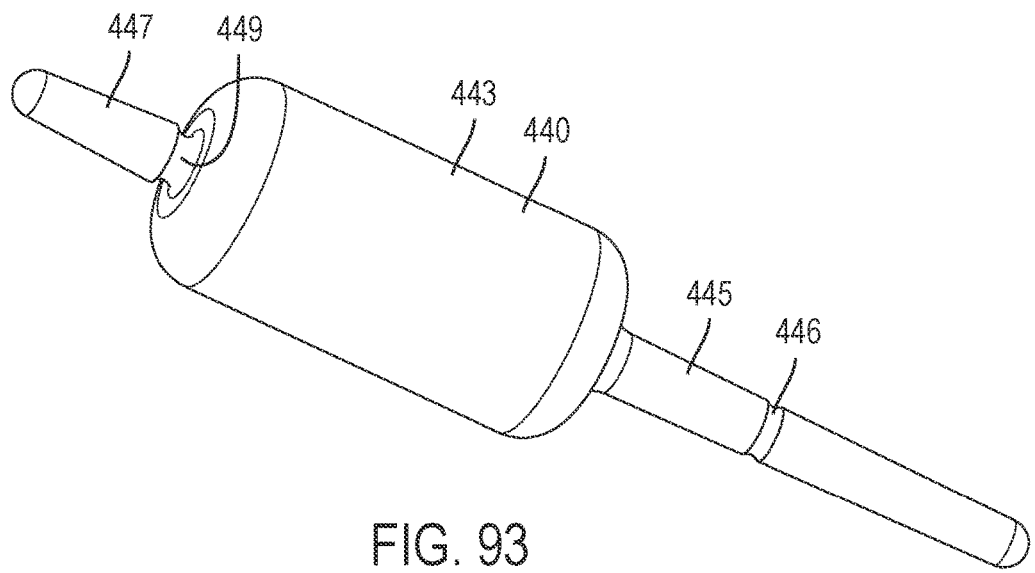
FIG. 93 depicts a view of an exemplary ampoule which may be included in certain delivery device embodiments including an injection port.

Referring now to FIG. 93 an example ampoule 440 which may be used in a delivery device 10 including an injection port 800 is depicted. As with other ampoules 440 described herein, the ampoule 440 may include a neck portion 445 which extends from the main body 443 of the ampoule 440. This neck portion 445 may include a frangible 446 which may be broken to establish fluid communication from the interior volume of the ampoule 440 to an outlet of a delivery device 10. The example ampoule 440 shown in FIG. 93 may further include a tail portion 447. The tail portion 447 may be disposed on an end of the main body 443 of the ampoule 440 which is opposite that from which the neck portion 445 extends. A tail frangible 449 may be included in the tail portion 447 of the ampoule 440. The tail frangible 449 may be a weakened and/or scored area of the tail portion 447 which may facilitate breaking of the tail portion 447 at the location of the tail frangible 449.

Figure 94:
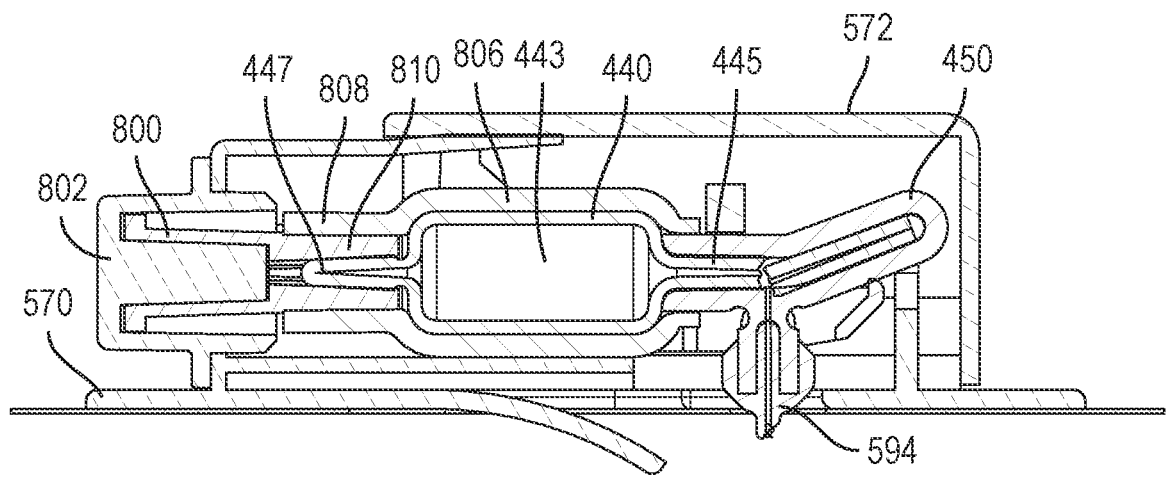
FIG. 94 depicts a cross-sectional view of an example delivery device including an injection port where the injection port is covered with a cap member.
Figure 95:
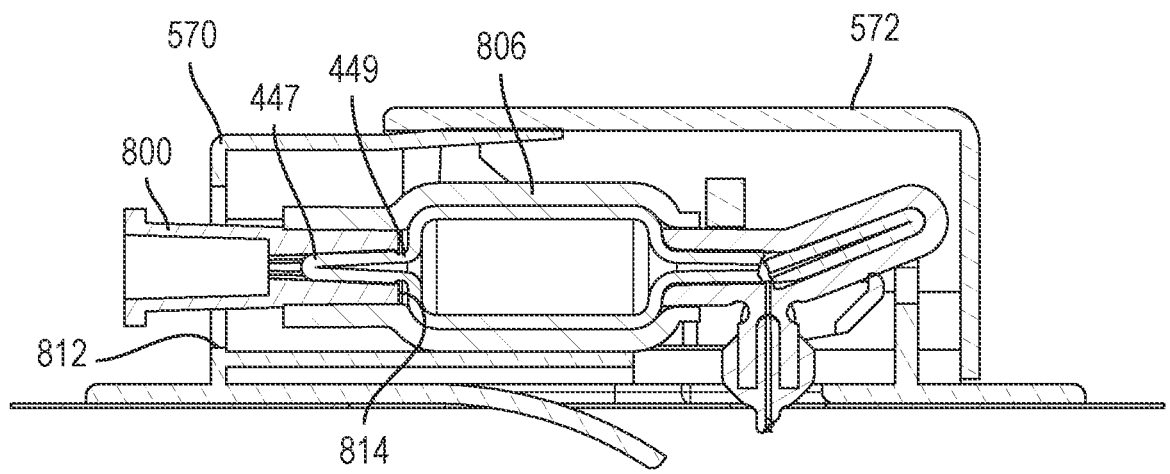
FIG. 95 depicts a cross-sectional view of an example delivery device including an injection port with the cap member removed.
Figure 96:
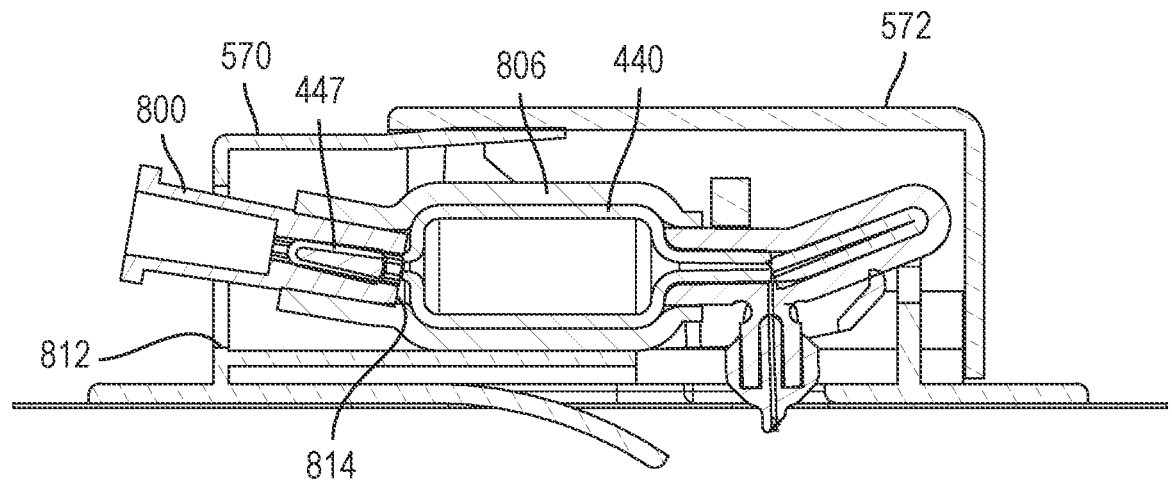
FIG. 96 depicts a cross-sectional view of an example delivery device including an injection port which has been displaced so as to break a frangible of an ampoule disposed in the delivery device in order to access the interior of the ampoule of the delivery device.

Referring now to FIGS. 94-96 a number of cross sectional view of an example delivery device 10 including an injection port 800 and the ampoule 440 of FIG. 93 are shown. As shown, the delivery device 10 is depicted with the slide body 572 in the second position. As the slide body 572 is in the second position, the outlet assembly 594 is displaced to a deployed state and the frangible 446 (see, e.g., FIG. 79) of the ampoule 440 has been broken. The neck portion 445 of the ampoule 440 is covered by an elastomeric housing 450 like that shown in FIG. 79. The ampoule 440 may also be housed in an elastomeric sleeve 806 which surrounds the remainder of the ampoule 440. In the example embodiment, the elastomeric housing 450 and elastomeric sleeve 806 are depicted as separate components. In alternative embodiments, the elastomeric housing 450 and the elastomeric sleeve 806 may be a single elastomeric article which is created as a monolithic component. The elastomeric sleeve 806 may surround the main body 443 of the ampoule 440. The elastomeric sleeve 806 may also contact and establish a seal against the elastomeric housing 450 (where the elastomeric sleeve 806 and elastomeric housing 450 are not a monolithic component).

As shown, the injection port 800 may include a tail receptacle 810. The tail portion 447 of the ampoule 440 may seat within the tail receptacle 810 when the delivery device 10 is assembled. The elastomeric sleeve 806 may include an injection port receiver portion 808. The injection port receiver portion 808 may surround the tail portion 447 of the ampoule 440 and the tail receptacle 810. The injection port receiver portion 808 may form a fluid tight seal against the tail receptacle 810.

In use, the slide body 572 of the delivery device 10 may be displaced to the second position on the base body 570 (as shown). This may break the frangible 446 of the ampoule 440 and cause the outlet assembly 594 to displace into a deployed state. Pressure in the ampoule 440 may drive the agent contained in the ampoule 440 into the patient through the outlet assembly 594. If desired, the cap 802 (which may protect the injection port 800 from contamination) on the injection port 800 may then be doffed from the injection port 800 (see FIG. 95) so that the ampoule 440 may be repressurized or another agent may be delivered. With the cap 802 removed from the delivery device 10, an agent dispensing implement 804 (see, e.g. FIG. 92) may be introduced to the injection port 800. In some embodiments, the injection port 800 may include a fitting such as a luer lock, bayonet mount, threaded fitting, etc. which may mate with an agent dispensing implement 804.

A user may pivot the agent dispensing implement 804 once it is introduced to the injection port 800. Pivoting of the agent dispensing implement 804 may cause the injection port 800 to pivot in tandem with the agent dispensing implement 804. The base body 570 may include an aperture 812 through which the injection port 800 extends. The aperture 812 may surround the injection port 812 and may present a stop which limits pivoting of the injection port 800 beyond a certain amount. The elastomeric sleeve 806 may bend to accommodate the pivoting of the injection port 800. The interior end 814 of the injection port 800 may be aligned with the tail frangible 449. Consequentially, stress on the tail portion 447 of the ampoule 440 (which may be constrained from moving within the delivery device 10) due to pivoting of the injection port 800 may be concentrated at the tail frangible 449. Thus, pivoting of the injection port 800 may cause the tail frangible 449 to break. With the tail frangible 449 broken, fluid communication with the interior of the main body 443 of the ampoule 440 may be established via the injection port 800. Fluid (e.g. repressurization gas or a second agent) may then be delivered into the delivery device 10 via the injection port 800.

Figure 97:
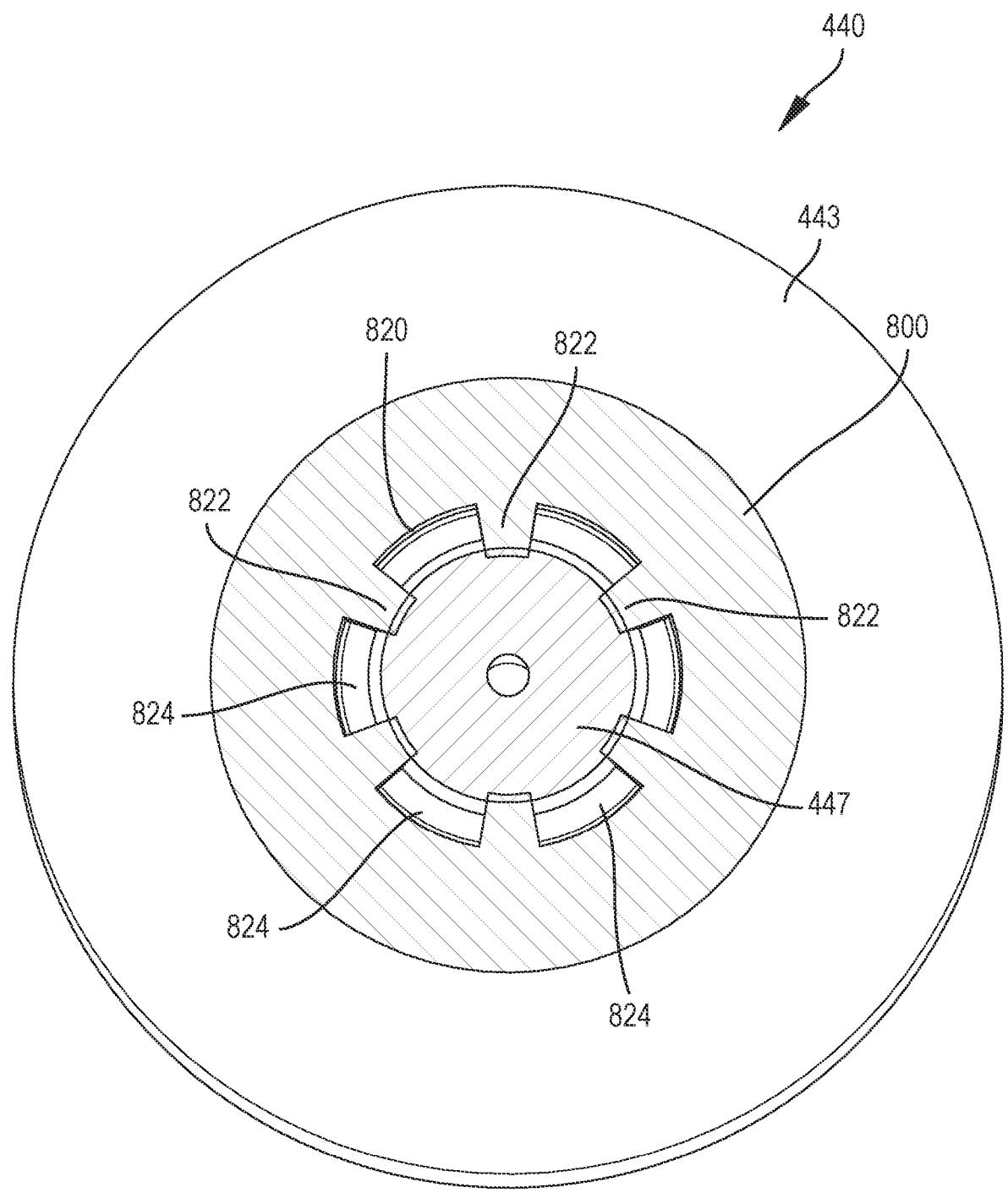
FIG. 97 depicts a cross-sectional view of an example injection port and a portion of an example ampoule.

Referring now to FIG. 97, a cross section through an injection port 800 and tail portion 447 of an ampoule 440 is depicted. As shown, the injection port 800 may include an interior channel 820 within which the tail portion 447 is received. The interior channel 820 may include a number of protrusions 822 which project radially inward from the wall of the interior channel 820. The protrusions 822 may be spaced at regular or irregular intervals about the interior channel 820. In the example embodiment, six protrusions 822 are included and are spaced at regular angular intervals (every 60° in the example) about the interior channel 820. The number of protrusions 822 may differ in alternative embodiments. The protrusions 822 may abut against the tail portion 447. In some embodiments, the protrusions 822 may be slightly compressed against the tail portion 447 establishing an interference fit. As shown, when the injection port 800 is installed over the tail portion 447 the gaps between protrusions 822 may provide flow pathways 824 between the tail portion 447 and wall of the interior channel 820. The protrusions 822 may also ensure that upon breakage of the tail portion 447 at the tail frangible 449 (see, e.g., FIG. 96) the tail portion 447 is held in a prescribed position relative to the injection port 800. This may ensure that when the tail frangible 449 is broken a flow path through the injection port 800 into the interior of the main body 443 of the ampoule 440 remains patent.

Figure 98:
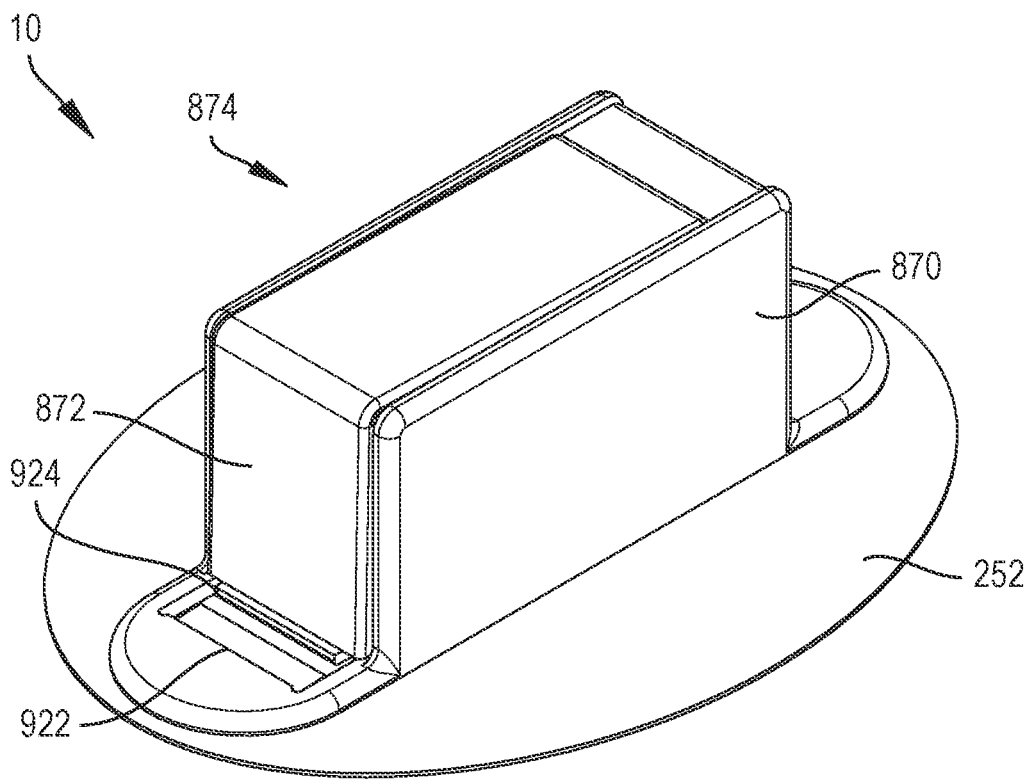
FIG. 98 depicts a perspective view of yet another example embodiment of a delivery device.
Figure 99:
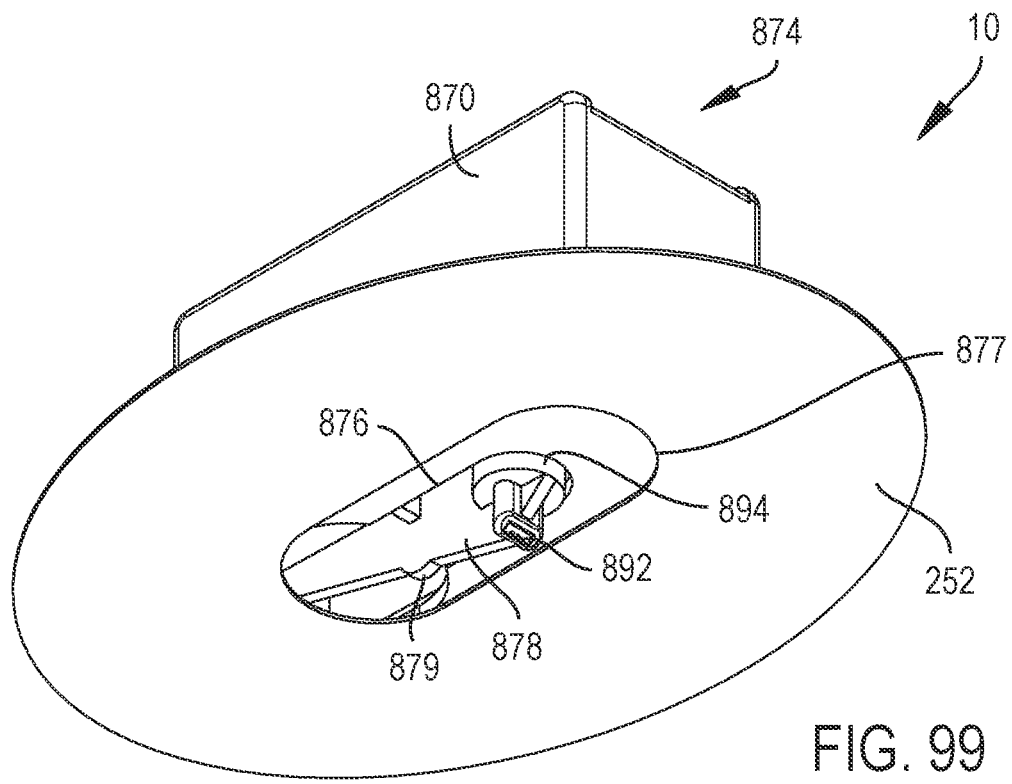
FIG. 99 depicts another perspective view of an example embodiment of a delivery device.

Referring now to FIGS. 98-99, another exemplary embodiment of a delivery device 10 is depicted. The example delivery device 10 may accept and deliver fluid from an ampoule 440 such as those described elsewhere herein. As shown, the example delivery device 10 may include a base 870 and a slide body 872. The base 870 and slide body 872 may cooperate to form a housing 874 for the delivery device 10. As shown, the base 870 may be mounted on a bandage 252. When shipped or in storage, portions of the bandage 252 outside the footprint of the housing 874 may be folded up against the sides of the housing 874 to minimize the size of the delivery device 10 during shipping. As shown, the base 870 may include an aperture 876. The bandage 252 may also include a bandage aperture 877 which surrounds the aperture 876 of the base 870. The aperture 876 may allow for displacement of at least one delivery sharp 892 (e.g. microneedle, transcutaneous delivery sharp, etc.) from the interior of the housing 874 and into the skin of a patient.

The example delivery device 10 may be transitioned from a storage state (see, e.g., FIG. 104) to a delivery state. This may be accomplished by displacing the slide body 872 from a first position to a second position relative to the base body 870. The delivery device 10 is depicted in a delivery state in FIGS. 98-99. In the delivery state, at least a portion of an outlet assembly 894 may protrude from the housing 874 such that microneedles 892 (or any other delivery sharp) extend into skin of a patient to access an intradermal space of the patient. As shown, a skin depressor or stretcher 878 may be included and also extends out of the housing 874 via the aperture 876 when the delivery device 10 is in the delivery state. In the example, the skin depressor 878 is included as part of the slide body 872 and extends to a point adjacent the microneedles 894 on the outlet assembly 892. The skin depressor 878 may also double as a support rib which buttresses the outlet assembly 894.

The skin depressor or stretcher 878 may be pressed against the skin of a patient as the delivery device 10 is transitioned from a storage/shipping state to a delivery state. This may cause stretching of the skin at the puncture location of the microneedle(s) 894 facilitating access to an intradermal space of the patient. In certain examples, the skin depressor 878 may include one or more projection 879 on the skin contacting side of the skin depressor 878. Such a projection 879 may further aid in causing stretching of the skin. Other skin depressors described herein may include similar projections for this purpose. In the example, the projection 879 is depicted as a bump though ribs or ridges may be used in alternative embodiments. In some examples, the projection 879 may be a tooth or barb which may catch on skin and aid in tugging on the skin as the delivery device 10 is transitioned into a delivery state. Multiple projections 879 may be included in alternative examples.

Figure 100:
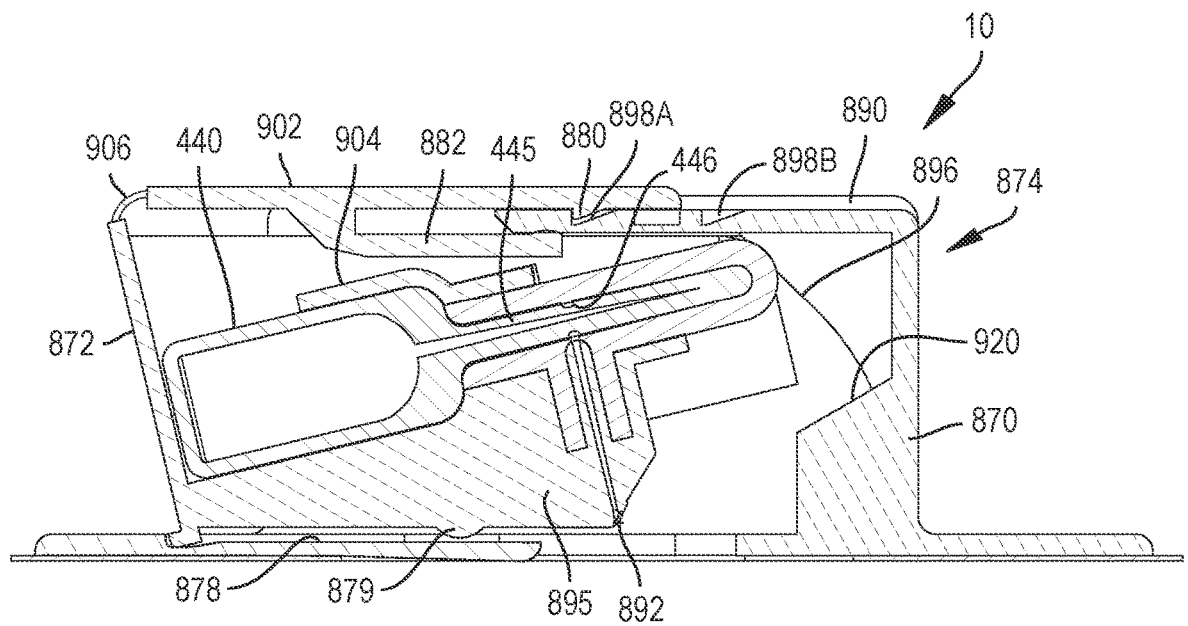
FIG. 100 depicts a cross-sectional view of an exemplary delivery device where the delivery device is in a storage state.
Figure 101:
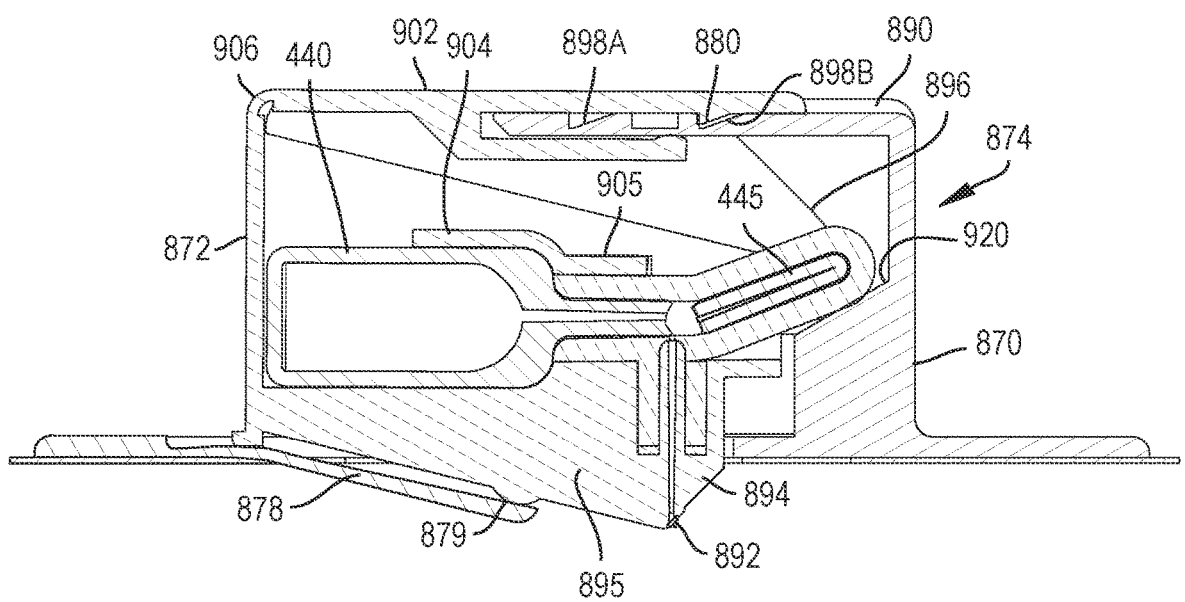
FIG. 101 depicts a cross-sectional view of an example delivery device where the delivery device is in a delivery state.

In alternative examples, and referring now to FIGS. 100 and 101, a cantilevered skin depressor or stretcher 878 may be included. Such a skin depressor 878 may, for example, be cantilevered from a portion of the base 870. The skin depressor or stretcher 878 may be deflected so as to be pressed against the skin of a patient as the delivery device 10 is transitioned from a storage/shipping state to a delivery state. This may cause stretching of the skin at the puncture location of the microneedle(s) 894 facilitating access to an intradermal space of the patient. In the example, the slide body 872 may include a support rib 895 which buttresses the outlet assembly 894. The support rib 895 may include a projection 879 thereon. The projection 879 may contact the skin depressor 878 as the delivery device 10 is transitioned to the delivery state and concentrate a deflecting force on an unsupported end of the skin depressor 878 to facilitate deflection of the skin depressor 878 against the skin. In the example embodiment, the projection 879 is shown as a rounded bump though any suitable shape (e.g. pin, rib, ridge, pointed tooth, etc.) may be used in other examples.

Figure 102:
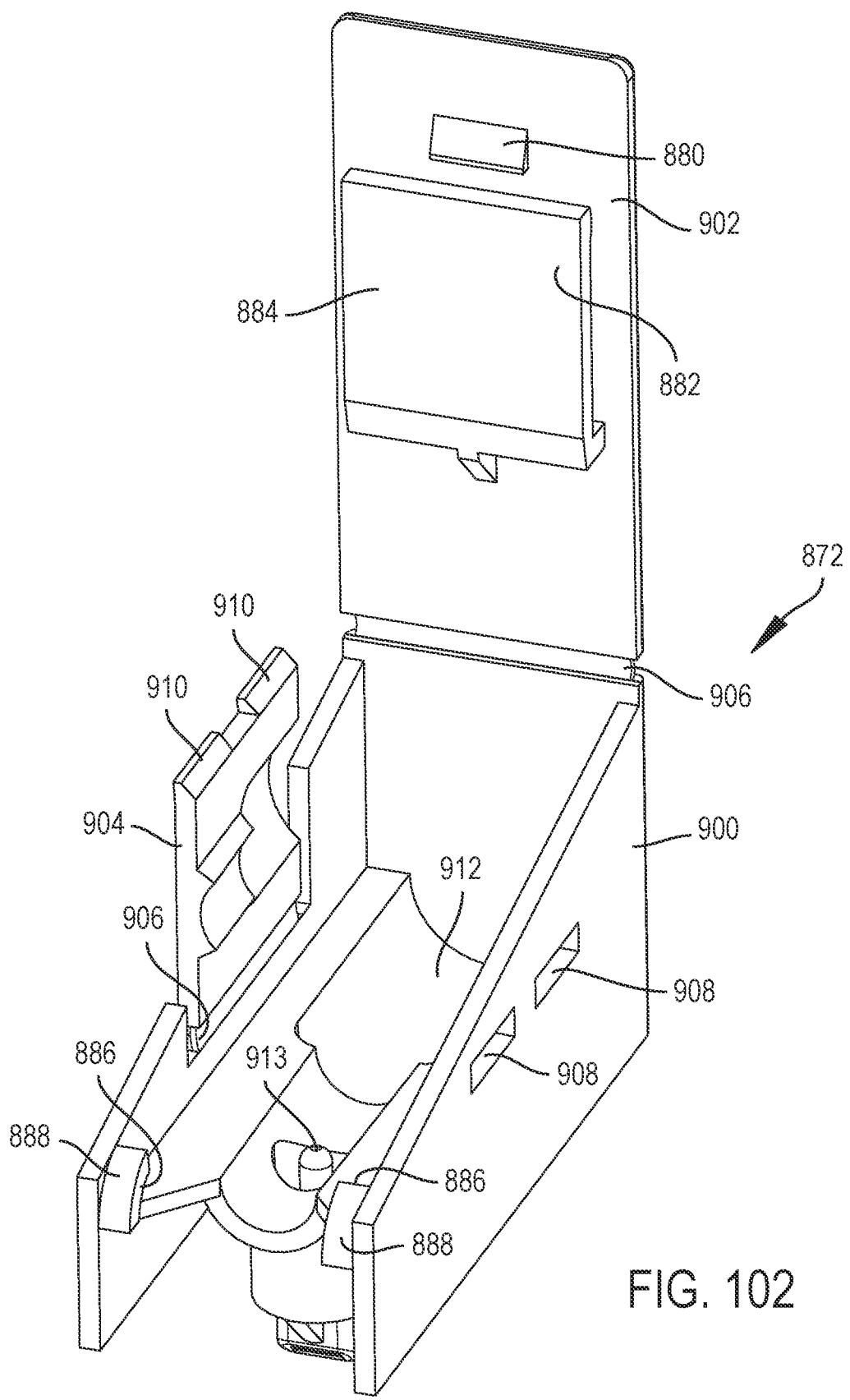
FIG. 102 depicts a view of an exemplary slide body which may be included in an example delivery device such as that shown in FIG. 98, the slide body being in a molding configuration.
Figure 103:
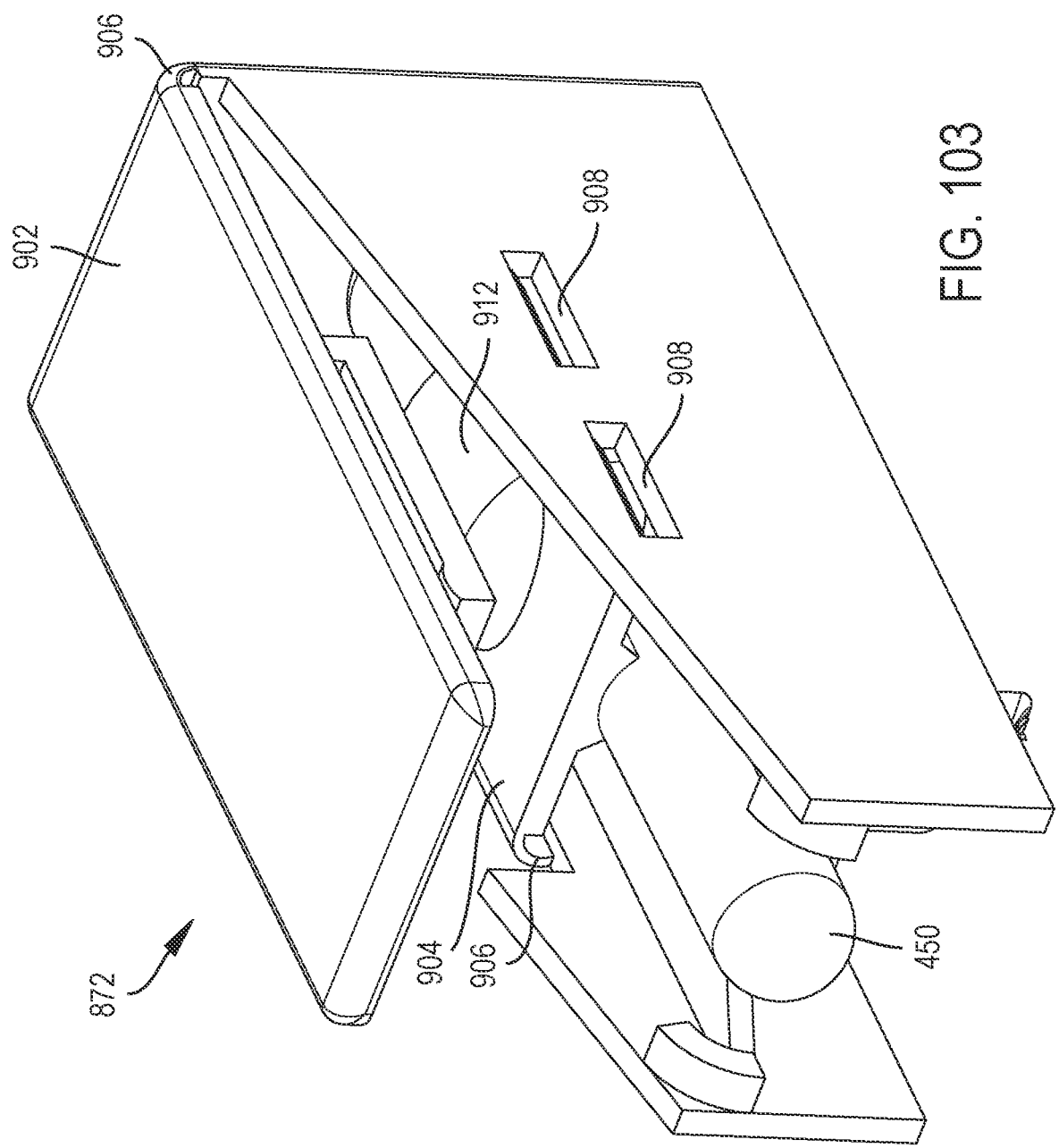
FIG. 103 depicts a view of the exemplary slide body of FIG. 102 after being transitioned to an assembly configuration in which foldable portion of the slide body have been bent and an example ampoule has been captured within a holster clamshell of the slide body.

Referring now to FIGS. 102-103, a view of the slide body 872 of the example delivery device 10 shown in FIGS. 98-99 is depicted. The slide body 872 may be constructed as a single monolithic component. This may help to minimize the number of components needed to construct a delivery device 10. The slide body 872 in the view depicted in FIG. 102 is shown in a molding configuration. The slide body 872 may be manipulated from the molding configuration into an assembly configuration for installation into a delivery device 10 during the manufacturing process. The slide body 872 is depicted in the assembly configuration in FIG. 103.

As shown, the slide body 872 may include a main portion 900 and one or more foldable section 902, 904. In the example embodiment, the slide body 872 includes two foldable sections 902, 904. The foldable sections 902, 904 may be connected to the main portion 900 of the slide body 872 via living hinges 906. These foldable sections 902, 904 may be displaced into their assembly configuration via bending of the living hinges 906. The main portion 900 of the slide body 872 may include notches 908 or other retention interfaces. The notches 908 may cooperate with latch projections 910 of one or more of the foldable section 902, 904 to hold the one or more foldable sections 902, 904 in the assembly configuration. The latch projections 910 may include a ramped face to facilitate displacement of the latch projections 910 into the notches 908 during assembly. In other delivery device 10 embodiments shown and described herein, housing components may similarly be constructed with foldable sections which may be displaced between a molding configuration an assembly configuration.

Foldable sections 902, 904 may allow for certain portions of a delivery device 10 to bend or move in a facile manner relative to other physically connected portions of the delivery device 10. Such foldable sections 902, 904 may not be latched into place during assembly. Due to the living hinge 906 connection, different portion of the same monolithic component may displace relative to one another, displace along different axes, or in different manners (e.g. translationally, rotationally).

Still referring primarily to FIGS. 102-103, in the molding configuration, the foldable sections 902, 904 may be positioned so as to facilitate molding of the slide body 872 in a single molding operation. Foldable sections 902, 904 may also be included in a slide body 872 so as to allow molding via a minimally complicated molding operation. That is, even in delivery device 10 embodiments where a slide body 872 (or other housing component) could be molded in a single molding operation, foldable sections 902, 904 may still be included as they may allow the mold or molding operation to be simplified.

Additionally, including one or more foldable section 902, 904 may allow for other components of a delivery device 10 to be placed into the slide body 872 (or other housing component). This may be done prior to manipulation of the slide body 872 into its assembly configuration where clearance or a pathway to insert these other components may not exist. In the example embodiment shown in FIGS. 102 and 103, the slide body 872 includes a holster 912 for supporting an ampoule 440 and its elastomeric housing 450 (only the elastomeric housing is visible in FIG. 103). The example holster 912 is constructed as a clamshell style retainer for the ampoule 440. In the molding configuration, the holster 912 may be in an open state. An ampoule 440 may be placed in one portion of the holster 912 clamshell while the slide body 872 is in the molding configuration. When the slide body 872 is folded into the assembly configuration, the holster 912 may be brought to a closed state in which the ampoule 440 is retained and locked within the slide body 872. In the example embodiment, this may be accomplished by displacing a foldable section 904 of the slide body 872 against the ampoule 440 and driving the latch projections 910 into the notches 908 of the main portion 900 of the slide body 872.

As shown, the holster 912 may also include a flow pathway projection 913 which includes a flow channel that communicates with the delivery sharp(s) 892. The elastomeric housing 450 may include a receptacle 917 (see, e.g., FIG. 105) which mates onto the projection 913. As the foldable section 904 is brought to the closed state the foldable section 904 may slightly compress the material of the elastomeric housing 450 aiding in sealing around the projection 913.

Still referring to FIGS. 102 and 103, the first foldable section 902 may include a pawl projection 880. Additionally, the first foldable section 902 may include a clip member 882. The clip member 882 may include a cantilevered tab 884 which extends toward the pawl projection 880. As will be explained in greater detail later in the specification, the pawl projection 880 and clip member 882 may cooperate with a portion of the base body 870 to direct displacement of the slide body 872 relative to the base body 870 as the delivery device 10 is transitioned form the storage state to the delivery state. The main portion 900 of the slide body 872 may include guide projections 886. The guide projections 886 may include a rounded surface which may be configured to slide against an abutting surface of the base body 870 when the delivery device 10 is assembled.

Figure 104:
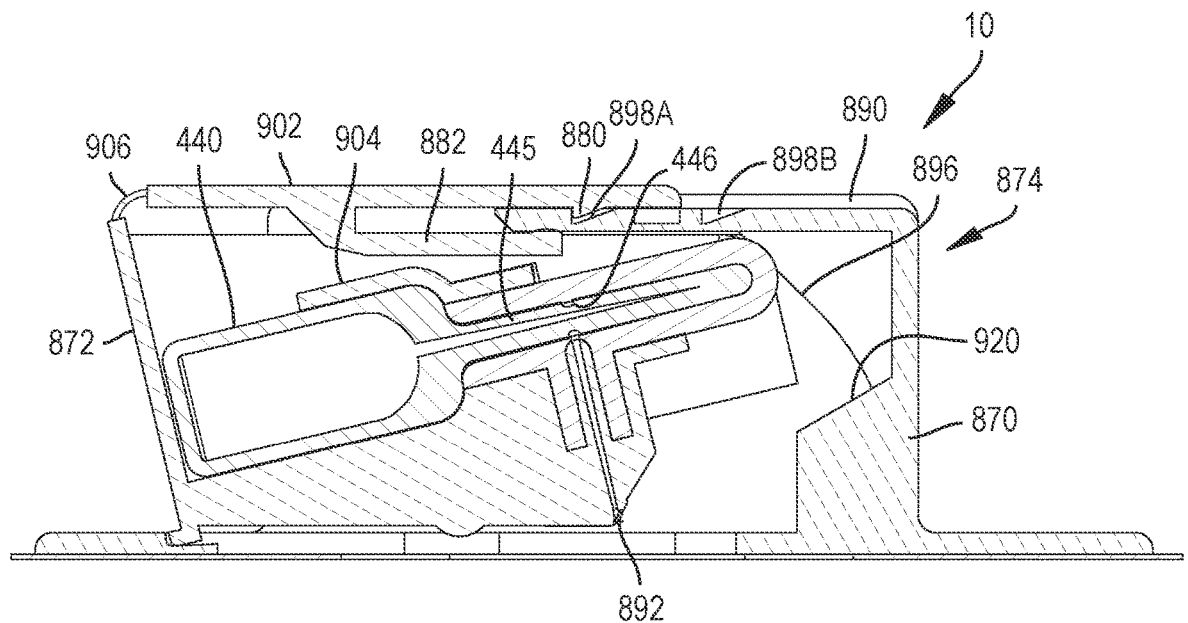
FIG. 104 depicts a cross-sectional view of an example delivery device embodiment where the delivery device is in a storage state.

Referring now to FIG. 104, a cross section of the example delivery device 10 shown in FIGS. 98-99 is depicted. The cross-section is taken along a longitudinal midplane of the example delivery device 10. The delivery device 10 is depicted in an assembled state with the slide body 872 folded into its assembly configuration and installed in the delivery device 10. The delivery device 10 is arranged in a storage or shipping state in FIG. 104. As shown, when the delivery device 10 is in the storage state, the microneedle(s) 892 may be disposed within the housing 874 of the delivery device 10.

A ratcheting wall 890 of the base body 870 may be captured between the clip 882 and the remainder of the first foldable section 902 of the slide body 872. The ratcheting wall 890 may include a number of ratchet interfaces 892. These ratchet interfaces 892A, B may be raised off the main surface of the ratchet wall 890 or recessed into the ratchet wall 890 as shown in FIG. 104. The pawl projection 880 may engage with a first ratchet interface 892A when the slide body 872 is in a first position corresponding to the delivery device 10 being in a storage state. This may help to hold the delivery device 10 in the storage state during shipping and preparation for use. Additionally, the pawl projection 880 may prevent the slide body 872 from being removed from the delivery device 10 as the pawl projection 880 may catch against ratcheting interface 892A. The base body 870 may also include a stop 922 (see, e.g., FIG. 98) which a tab 924 (see, e.g., FIG. 98) of the slide body 872 may contact to inhibit removal of the slide body 872.

Figure 105:
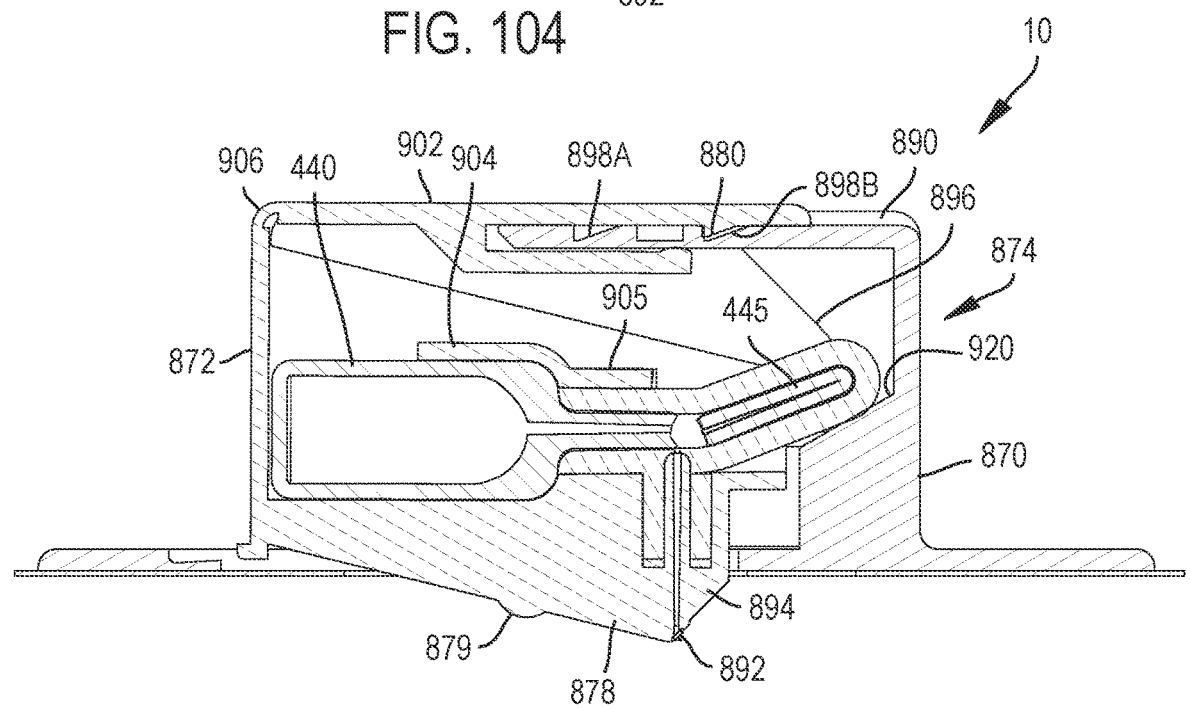
FIG. 105 depicts another cross-section view of an example delivery device embodiment where the delivery device is in a delivery state.

Referring now to FIG. 105, the slide body 872 may be displaced toward or into the base body 870 to transition the delivery device 10 from the storage state to the delivery state shown in FIG. 105. As the ratcheting wall 890 is captured between the clip 882 and the remainder of the first foldable section 902, the ratcheting wall 890 may constrain displacement of the first foldable section 902 to an axis substantially parallel to the ratcheting wall 890. The pawl projection 880 may pass out of the first ratchet interface 892A and engage a second ratcheting interface 892B when the slide body 872 has been displaced to a second position and the delivery device 10 is in the delivery state. The interaction of the pawl projection 880 and the second ratchet interface 892B may hold the delivery device 10 in the delivery state.

The base portion 870 may include a guide surface 896 against which the guide projections 886 (see FIG. 102) of the slide body 872 may ride as the slide body 872 is displaced. The guide surface 896 may direct displacement of the main portion 900 of the slide body 872 as the slide body 872 is driven to the second position. Thus the contour of the guide surface 896 may define the displacement path of the main portion 900 of the slide body 872. In the example embodiment, the guide surface 896 is a curved surface. As shown, when the slide body 872 is displaced from the first position to the second position, the main body 900 may displace into the base portion 870 and rotate such that the outlet assembly 894 and microneedle(s) 892 project out of the housing 874. The base body 870 may include a shelf 920 which extends into the interior of the housing 874. The neck portion 445 of the ampoule 440 may be driven into the shelf as the slide body 872 is moved to the second position. This may exert a breaking force on the frangible 446. As shown in FIG. 105, further advancement of the slide body 872 may cause the ampoule 440 to break at the frangible 446 of the ampoule 440. Once broken, pressure within the ampoule 440 may drive agent out of the ampoule 440, through the outlet assembly 894 and into an intradermal space (or other delivery destination depending on the type of delivery sharp) of a patient via the microneedle(s) 892.

The second foldable portion 904 may support the ampoule 440 against displacement relative to the slide body 872 as the slide body 872 is driven to the second position. Additionally, a segment 905 of the second foldable portion 904 may extend over a section of the neck 445 of the ampoule 440 which is upstream of the frangible 446. This may prevent breakage of the ampoule 440 in this region and help ensure that breakage occurs at the location of the frangible 446 as the slide body 872 is displaced to the second position.

In certain examples, the example delivery device 10 may include an ampoule 440 such as that shown and described in relation to FIGS. 90-97. In such embodiments, the delivery device 10 would also include an injection port 800 as shown in FIGS. 90-97. Thus, a second agent could be delivered through the delivery device 10 or the ampoule 440 could be repressurized if desired via the injection port 800.

Figure 106:
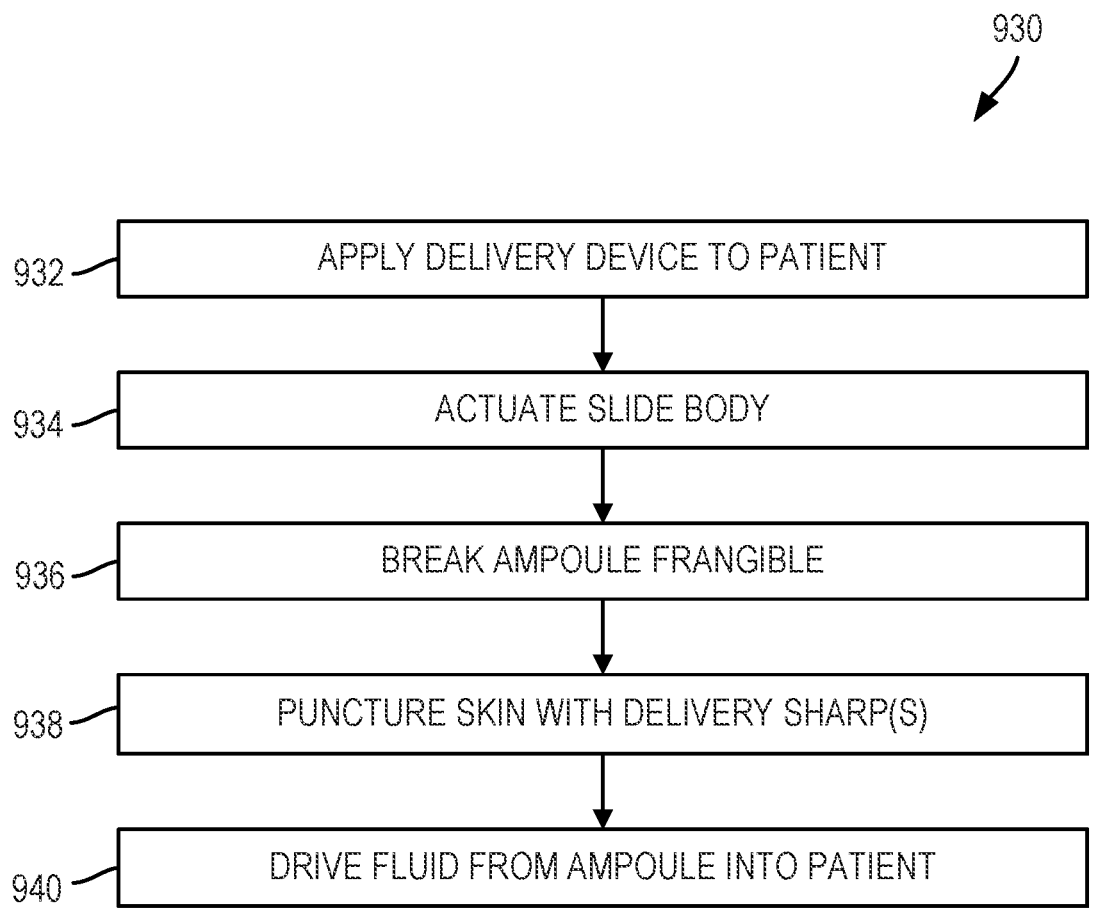
FIG. 106 depicts a flowchart detailing a number of example actions which may be executed to deliver fluid into a patient via a delivery device.

Referring now to FIG. 106, a flowchart 930 detailing a number of example actions which may be executed to deliver fluid from a delivery device to a patient is depicted. As shown, in block 932, a delivery device may be applied to the skin of a patient. In block 934, a slide body of the delivery device may be actuated. In block 936, the frangible of a pressurized ampoule contained in the delivery device may be broken. The delivery sharp(s) of the delivery device may puncture into the skin of the patient in block 938. In block 940, fluid from the ampoule may be driven into the patient via the pressure stored in the ampoule.

Figure 107:
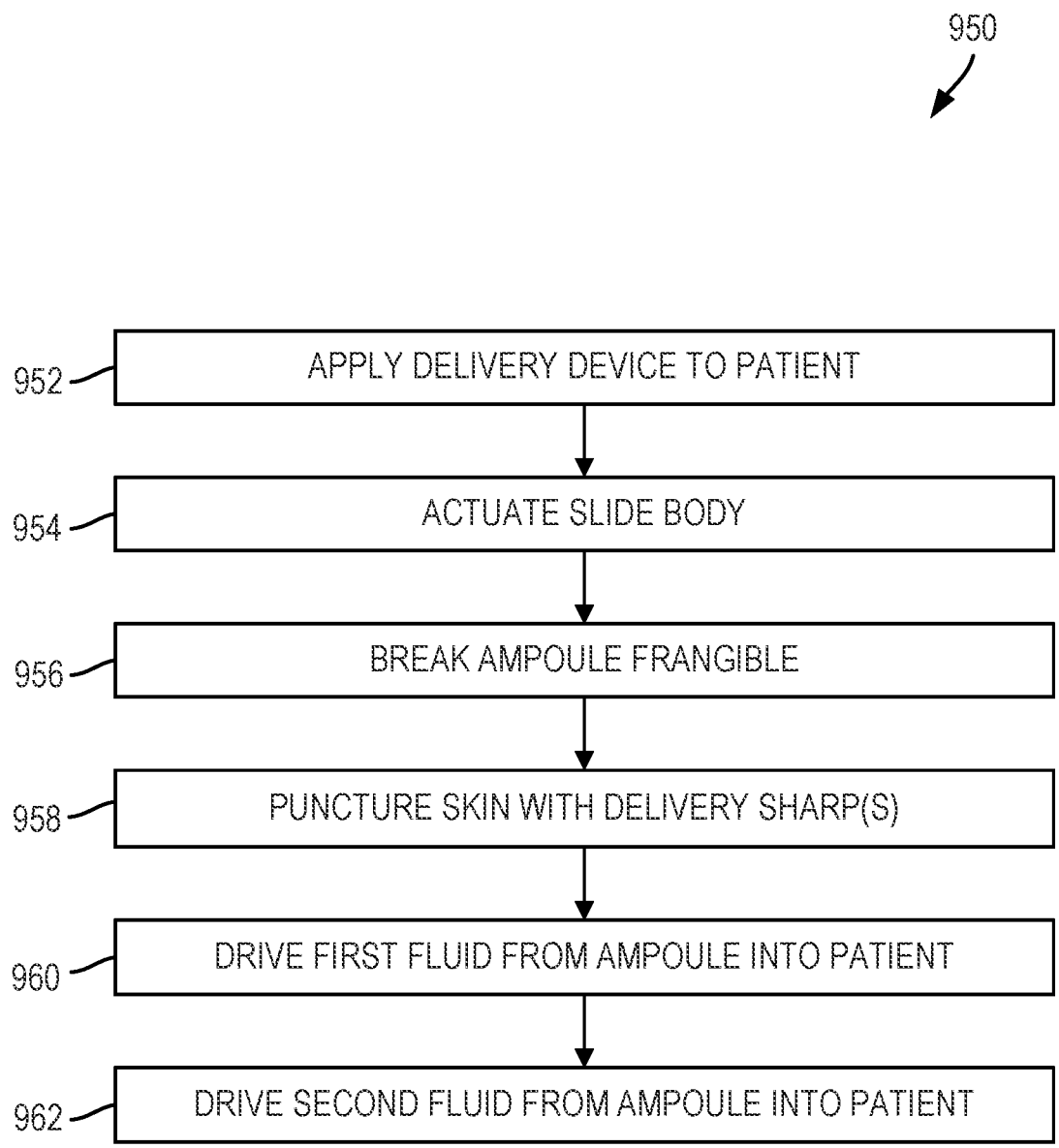
FIG. 107 depicts another flowchart detailing a number of example actions which may be executed to deliver fluid into a patient via a delivery device.

Referring now to FIG. 107, another flowchart 950 detailing a number of example actions which may be executed to deliver fluid from a delivery device to a patient is depicted. As shown, in block 952, a delivery device may be applied to the skin of a patient. In block 954, a slide body of the delivery device may be actuated. In block 956, the frangible of a pressure ampoule contained in the delivery device may be broken. The delivery sharp(s) of the delivery device may puncture into the skin of the patient in block 958. In block 960, a first fluid may be driven into the patient via the pressure. A second fluid may be driven into the patient in block 962. The first fluid may be an agent stored in the ampoule. The second fluid may be an agent which is administered via an injection port included in the delivery device. For example, this fluid may be delivered via an injection port 800 as shown and described in relation to FIGS. 90-97.

Alternatively, in certain embodiments, one of the first or second fluid may be a gas. This may be particularly useful in instance where the other of the first or second fluid is a vaccine. Gas may be introduced to the delivery device via a port such as injection port 800 (see FIGS. 90-97). In other examples, an ampoule of a delivery device may be pressurized to a degree that some gas may be delivered along with another agent contained in the ampoule. Other embodiments described herein may also deliver a gas as well as another agent (e.g. vaccine) to a patient. For example, when loading the reservoir portion 280 of the delivery device 10 described in FIG. 47, a liquid agent and a gas may be transferred into the reservoir portion 280. Each of these fluids may then be administered when delivery occurs. Similarly, a liquid agent and a gas may be loaded into the delivery device 10 described in relation to FIGS. 52-54 via port assembly 360. The reservoir portions of the delivery devices 10 shown in FIGS. 1-34, 55-65, and 66-67 may be loaded with a liquid agent and a gas. Likewise, the blister 652 reservoirs shown in FIGS. 35-42 may be filled with both a liquid and a gas. The reservoir 415 of the delivery device 10 shown in FIGS. 68-70 may also be filled with both a liquid agent and a gas via port assembly 400. Both a liquid agent and a gas may be delivered via the delivery device 10 shown in FIGS. 108-115 via access port 708.

Upon entry into the patient, the gas may aid in generating a space within the tissue to accommodate agent administered into the patient. For example, the gas may help to enlarge the area taken up by an agent depot delivered into the patient and/or increase the surface area of tissue which is exposed to the agent. In an intradermal delivery, the gas may encourage larger diameter blebs for a given volume of delivered agent. This may help to expose more cells which play a role in immune response to the agent when the agent is administered. This may be particular desirable intradermal injections due to the density of antigen presenting cells (e.g. macrophages and phagocytic immune cells such as dendritic or Langerhans cells). As a result, such gas delivery may aid in augmenting dose or injection sparing by helping to elevate the immunogenicity of the vaccination. Additionally, certain gases (e.g. carbon dioxide) have been observed to increase skin microcirculation which may aid in generating a robust immune response.

Figure 108:
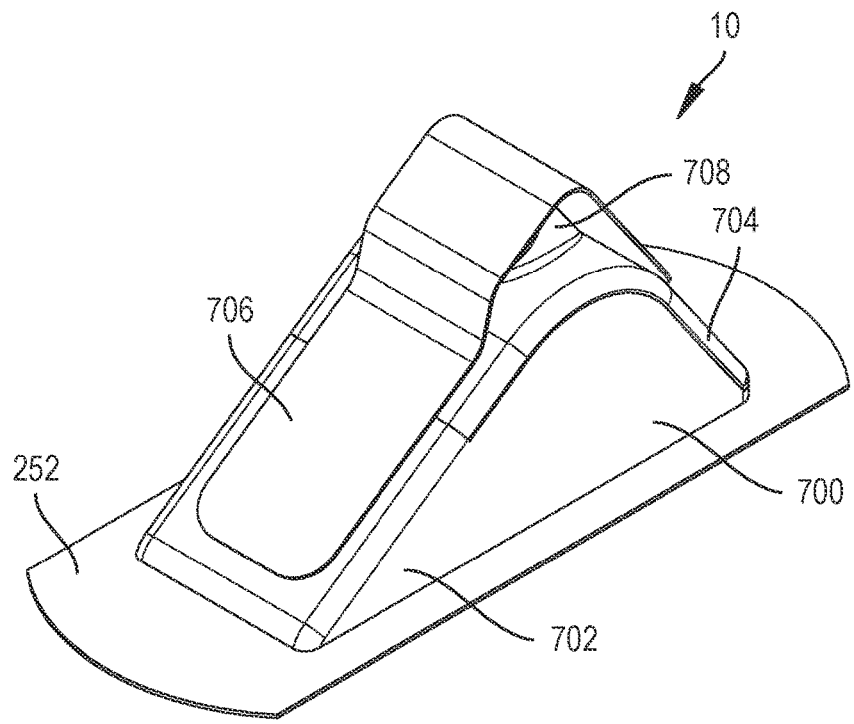
FIG. 108 depicts a perspective view of yet another embodiment of an example delivery device.
Figure 109:
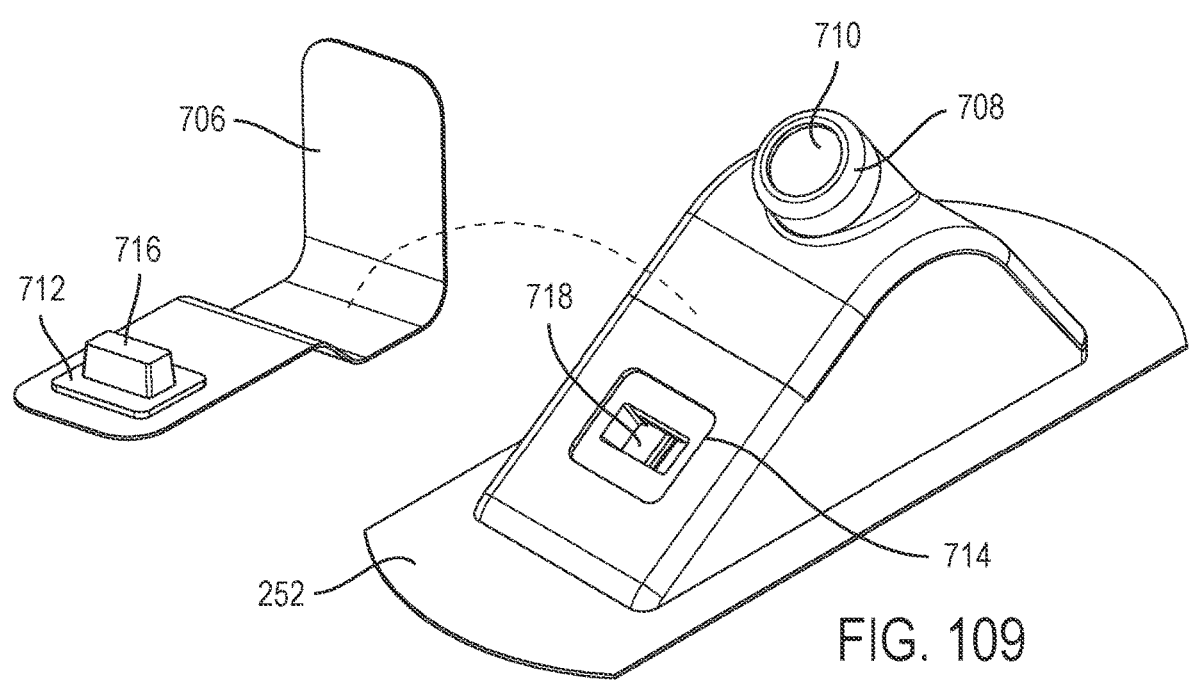
FIG. 109 depicts a perspective view of an example delivery device with a flexible strip and locking member removed.

Referring now to FIG. 108 and FIG. 109, another example embodiment of a delivery device 10 is depicted. As shown, the delivery device 10 may include a housing 700. The housing 700 may be mounted on a bandage 252 which may be used to secure the delivery device 10 to the skin of a user. The housing 700 may be generally triangular in shape with the point of the triangle most distal to the bandage 252 being rounded. Housings 700 having alternative shapes may also be used. The housing 700 may include a base portion 702 and a cover portion 704. The base 702 may be attached to the bandage 252. As shown, the cover portion 704 may couple to the base portion 702 to enclose internal components of the delivery device 10.

A flexible strip 706 of material may be coupled to the housing 700. The strip 706 may include one end which may be attached to the cover portion 704 and may include an opposing end which may be coupled to the base portion 702. As shown, the cover portion 704 may include an access port 708. Any suitable access port 708 may be provided. In the example embodiment, an access port 708 including a piercable septum 710 is shown. Alternatively, the access port 708 could, for example, include a luer connector, needleless connector, quick connect fitting, split septum, protective cover/cap, or combination thereof. The flexible strip 706 may extend over the access port 708 when the strip 706 is attached to the housing 700. Thus, the flexible strip 706 may act as a protective strip which prevents the access port 708 from coming into contact with detritus, fingers, etc. during storage and handling. The flexible strip 706 may also provide a visual indicator that the delivery device 10 has not been previously used.

As best shown in FIG. 109, a lock member 712 may be coupled to the flexible strip 706 in some embodiments. The lock member 712 may seat in a recess 714 defined in the base portion 702 of the housing 700. The lock member 712 may include a protuberance 716 which may extend through an aperture 718 in the recess 714. When in place within the recess 714, the protuberance 716 of the lock member 712 may extend into the interior of the housing 700 and prevent actuation of the delivery device 10. As the lock member 712 is coupled to the flexible strip 706, the lock member 712 may be extracted from the housing 700 when the flexible strip 706 is removed. In alternative embodiments, the lock member 712 need not be coupled to the flexible strip 706. Instead, the lock member 712 may be manually removed by the user in a separate operation and may include a grip feature, pull ring, interface for a removal tool, etc. to facilitate removal of the lock member 712. Once the lock member 712 is removed, an insertion stroke may commence and a delivery sharp 732 (see, e.g., FIG. 110) within the delivery device 10 may be deployed into the skin of a patient. In some embodiments, the insertion stroke may commence upon actuation of a button interface or the like after removal of the lock member 712.

Once the delivery sharp 732 is inserted, a fluid administration implement (e.g. syringe) may then be used to administer fluid into the patient via the access port 708. In some embodiments, fluid may be forced out the fluid administration implement and into the patient through the delivery sharp 732. Alternatively, the delivery device 10 may include and interior reservoir which may be filled by fluid loaded in from the fluid administration implement. For example, a spring biased syringe (see e.g. FIGS. 14-16, FIG. 47, FIG. 58) may be loaded via fluid loaded into the delivery device. Alternatively, a reservoir with an elastomeric wall (see, e.g. FIGS. 68-70) may be loaded with fluid from the fluid administration implement. Fluid may then be dispensed out of the reservoir of the delivery device 10 into the patient via the delivery sharp 732.

Figure 110:
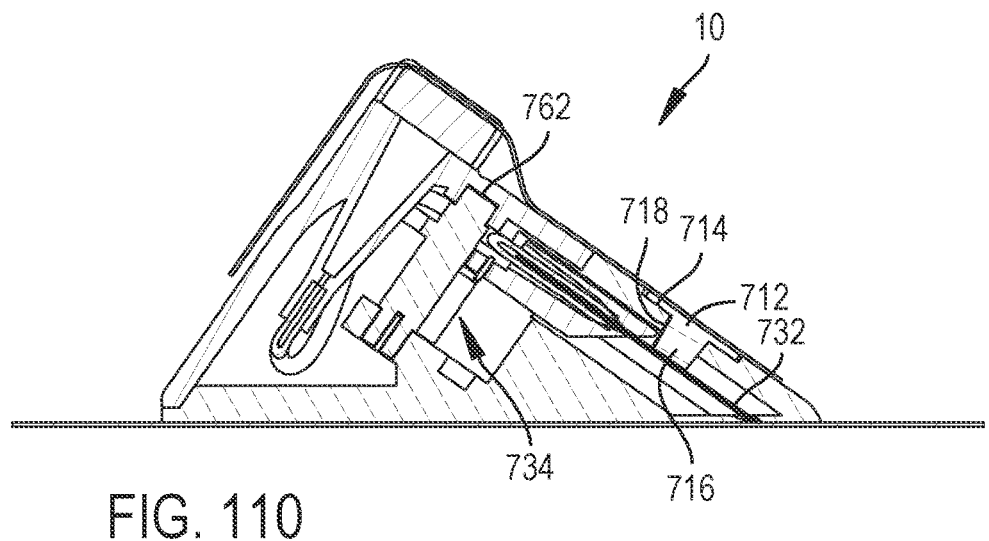
FIG. 110 depicts a cross-sectional view of an example delivery device in a storage state.
Figure 111:
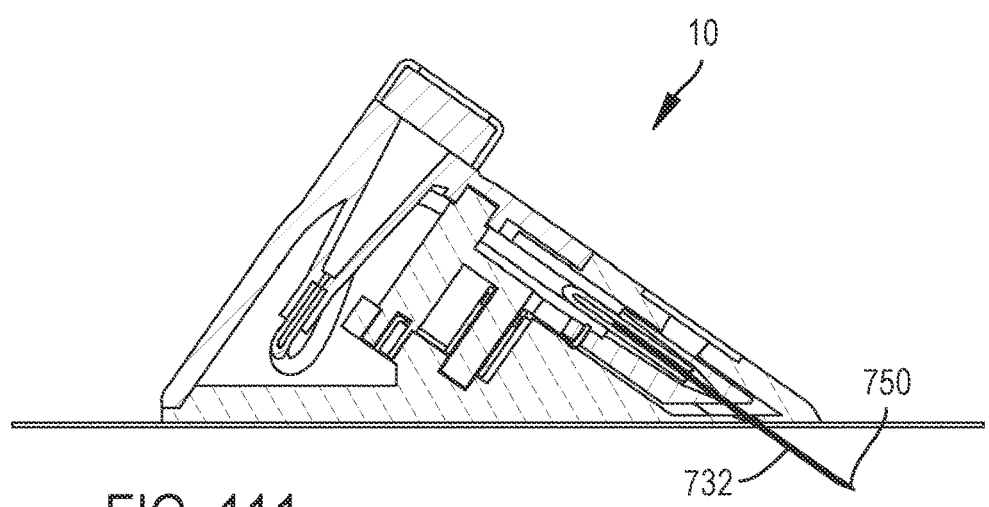
FIG. 111 depicts a cross-sectional view of a delivery device in which a delivery sharp of the delivery device has been extended to a first position.
Figure 112:
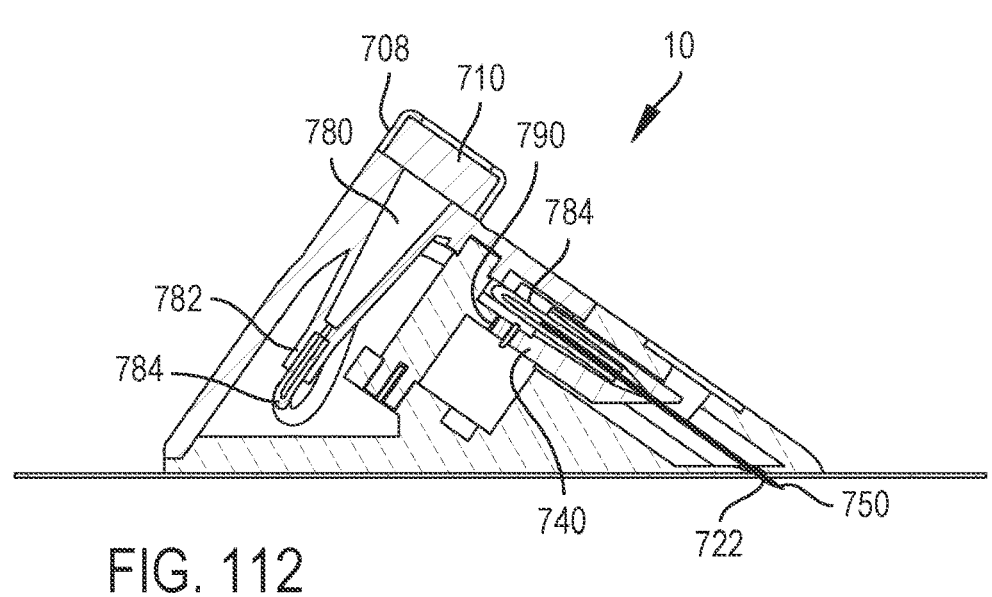
FIG. 112 depicts a cross-sectional view of a delivery device in which a delivery sharp has been retracted from a first position to a second position in which the delivery sharp extends a lesser distance from the housing than in the first position.

Referring now to FIGS. 110-112, a number of cross-sectional views of the example delivery device 10 depicted in FIGS. 108-109 are shown. FIGS. 110-112 depict a progression of views showing the example delivery device 10 transitioning through an actuation sequence which displaces the delivery sharp 732 into the body of a patient and positions the tip 750 of the delivery sharp 732 at a target destination in the patient. In some embodiments, and as shown in the example embodiment, a delivery device 10 may use a conventional delivery sharp 732 (e.g. a 30-gauge needle or smaller) to establish access to a shallow (e.g. epidermal, dermal, junctional areas between the epidermis and dermis or dermis and subcutis) delivery destination.

This shallow (e.g. intradermal) positioning may be achieved by starting from a deeper insertion of the delivery sharp 732. The delivery sharp 732 may be inserted into the patient and then withdrawn, for example, almost all the way out so as to locate the tip 750 of the delivery sharp 732 in a targeted shallow delivery location. Thus, the delivery sharp 732 may be advanced out of the housing 700 for a first portion of the actuation sequence and retracted in the opposing direction for a second, subsequent portion of the actuation sequence. This deep insertion and withdrawal may be accomplished via an insertion stroke which drives the delivery sharp 732 into the skin and then withdraws the delivery sharp 732 in a single fluid motion in certain embodiments. Thus the same delivery stroke may include a puncturing portion and a withdrawal portion.

Though embodiments described herein may target a shallow delivery destination, other embodiments may target deeper tissues. For example, in some embodiments, subcutaneous tissue may be targeted and the delivery sharp 732 may be advanced to an intramuscular location and withdrawn to the targeted subcutaneous tissue during the insertion stroke. In general, a delivery sharp 732 may be advanced to a first depth and withdrawn to a delivery destination at a second depth. The tissue or structure at the first depth and second depth may be the same or the tissue or structure at each depth may differ.

Still referring to FIGS. 110-112, in a storage state, the delivery sharp 732 of the delivery device 10 may be within the housing 700 of the delivery device 10. This may prevent inadvertent contact with the delivery sharp 732 and facilitate placement of the delivery device 10 on the skin. When actuated, an actuator assembly 734 of the delivery device 10 may drive the delivery sharp 732 from a storage state (see FIG. 110) to a first extended position (see FIG. 111). In the first extended position the delivery sharp 732 may project out of the delivery device 10 a maximum distance ("L"). In this position, the tip 750 of the delivery sharp 732 may extend into the patient at a depth which is greater than a final target depth. For an intradermal delivery device 10, the delivery sharp 732 may extend transcutaneously into the patient. In some examples, the tip 750 of the delivery sharp 732 may be in muscle or subcutaneous tissue for example. As the actuator assembly 734 of the delivery device 10 continues to drive the delivery sharp 732, the delivery sharp 732 may be withdrawn to a second extended position (see FIG. 112). The second extended position may be a final or a delivery position. In the second extended position, the delivery sharp 732 may extend from the delivery device 10 a distance which is less than in the first extended position. In the second extended position, the tip 750 of the delivery sharp 732 may extend a target distance from the housing 700 such that the tip 750 may be positioned at the target delivery depth (e.g. an intradermal location). Thus, when being withdrawn, the delivery sharp 732 may be withdrawn "L" less the target delivery depth "$D_r$" (e.g. 100-1500 microns, for example 500 or 600 microns). The target delivery depth may vary by embodiment, but may be below the stratum corneum.

By driving the delivery sharp 732 past a target location and reaching the target location on a withdrawal portion of the actuation sequence, the delivery sharp 732 may be reliably placed at a target penetration depth in a patient. Certain challenges related to precise positioning of the tip 750 may be avoided with such an approach. For example, elasticity of the skin (and variations thereof related to age, hydration state, location on the body, etc.) may not present a positioning challenge. Moreover, any bunching, bulging, wrinkling, or other deformation of the skin resulting from introduction of the delivery sharp 732 may be at least partially relieved during the withdrawal portion of the insertion stroke. This may facilitate delivery of fluid and may aid in minimizing pain associated with the injection. The withdrawal portion of the insertion stroke may also help to ensure that the skin is at an expected position. For example, in the event that the skin is pulled away from the bandage 252 (see, e.g., FIG. 108) during insertion into the skin, withdrawal of the delivery sharp 732 may help to pull the skin back into contact with the adhesive 252. Thus, the skin may be in a prescribed location helping to ensure that the tip 750 of the delivery sharp 732 is at the expected depth. In some embodiments, the delivery sharp 732 may have a treatment on its exterior surface which roughens the external face of the delivery sharp 732. This may aid in ensuring the skin is pulled back as the withdrawal portion of the insertion stroke occurs. Such an insertion sequence may also aid in minimizing any leaking of agent out of a patient during/after injection. This may be due to the outlet of the delivery sharp 732 reliably being inserted in its entirety into the patient regardless of any skin deformation at the puncture site. Additionally, such an insertion sequence may aid in establishing a seal between the tissue and the outer surface of the delivery sharp 732.

Referring primarily to FIG. 112, once the delivery sharp 732 is positioned in the second extended state, a user may introduce a fluid administration implement (e.g. syringe) to the access port 708. As shown, the example access port 708 includes a piercable septum 710 which may self-seal after being punctured. The access port 708 may be in fluid communication with the outlet of the delivery sharp 732. The cover portion 704 of the body may include a sharp receiving cavity 780 which in the example embodiment is depicted as a funnel cavity. Preferably this cavity 780 may have a minimal dead volume. The cover portion 704 may also define a conduit receptacle 782 which may communicate (e.g. via a connecting passage) with the sharp receiving cavity 780. A conduit 784 which extends from the conduit receptacle 782 into fluid communication with the delivery sharp 732 may be included. In the example, the conduit extends from the conduit receptacle 782 to an end of the delivery sharp 732 opposite the tip 750. A user may deliver fluid from the fluid administration implement into the delivery device 10 through the access port 708 and this fluid may be driven through the conduit and into the patient via the delivery sharp 732. The conduit 784 may be flexible and may include an amount of slack so as to allow the conduit 784 to spool out or displace as needed over the course of the insertion stroke.

Though the example embodiment includes an access port 708 through which agent may be introduced, delivery devices 10 which insert a delivery sharp 732 to a first depth and withdraw it to its target depth may receive agent from a pressurized ampoule 440, a spring loaded syringe like reservoir, or any other reservoir type. The outlet of a syringe like reservoir may be in fluid communication with the delivery sharp 732 via a conduit for example. Any spring loaded syringe type reservoir such as those described herein (see, e.g., FIGS. 55-65) may be included in such a delivery device 10. Similarly, a port 458 (see, e.g. FIGS. 78-79) in an elastomeric housing 450 (see, e.g. FIGS. 78-79) surrounding an ampoule 440 (see, e.g. FIGS. 78-79) may be plumbed into communication with a delivery sharp 732 via a conduit. The ampoule 440 may, for example, be broken via displacement of a neck 445 (see, e.g., FIG. 104) portion of the ampoule 440 into a rigid shelf defined in the housing or may be broken by driving a ram body 612 (see, e.g. FIG. 89) or other ramming element into the neck portion 445. Any arrangements described herein for breaking an ampoule 440 frangible 446 may be incorporated into a delivery device 10 including an insertion mechanism such as that described in FIGS. 108-115. Alternatively, a reservoir with an elastomeric wall (see, e.g. FIGS. 68-70) may be connected to the access port 708. Such a reservoir may communicate with the delivery sharp 732 via a conduit.

Figure 113:
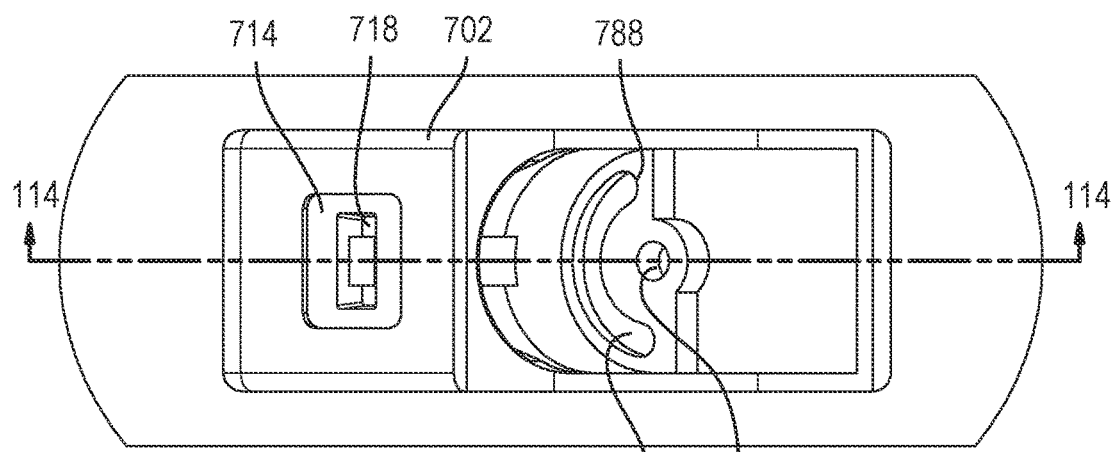
FIG. 113 depicts a top down plan view of an example delivery device with a sharp assembly and actuation assembly removed.
Figure 114:
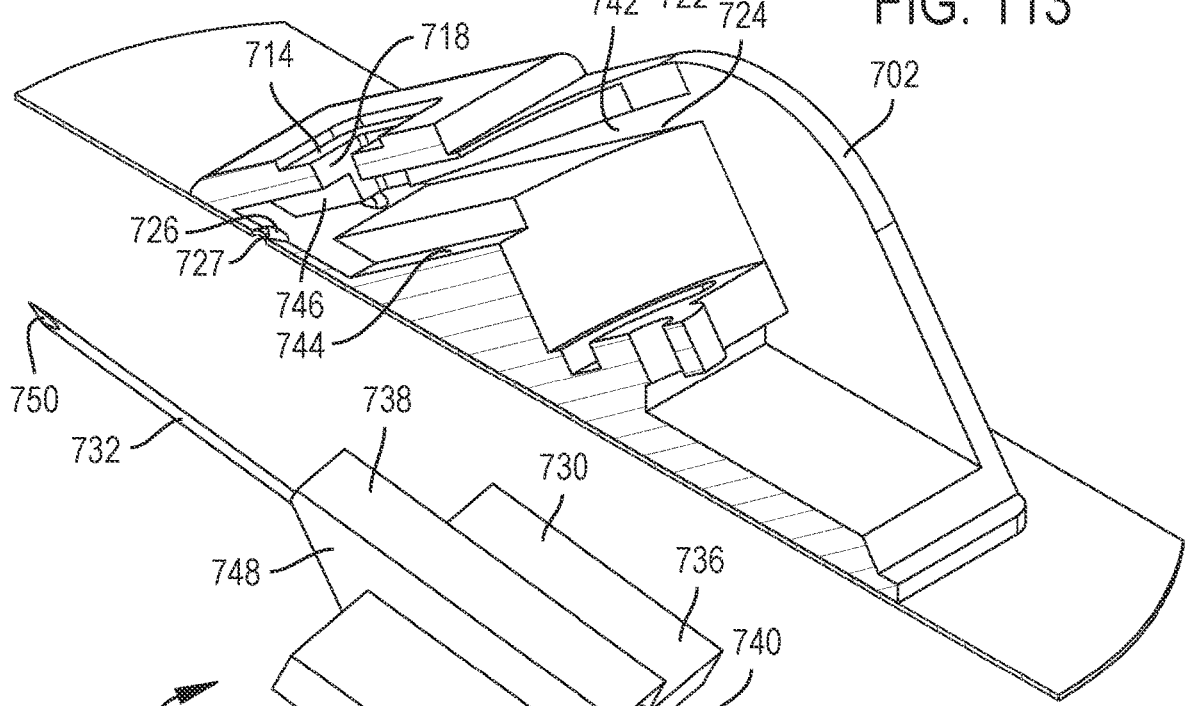
FIG. 114 depicts a cross-sectional view of the example delivery device of FIG. 113 taken at the indicated cut plane of FIG. 113.

Referring now to FIG. 113 and FIG. 114 (a cross-sectional perspective view taken at the indicated cut plane of FIG. 114), an example base portion 702 is depicted. As shown, the base portion 702 may include a pivotal bearing 720. The base portion 702 may also include a number of guides. In the example embodiment, the base portion 702 includes an arcuate guide track 722. The base portion 702 may also include a guide channel 724 which may be shaped so as to accept a sharp assembly 731. The sharp assembly 731 in the example embodiment includes the delivery sharp 732 and a sled 730 on which the delivery sharp 732 is borne. In other embodiments, a sharp assembly 731 may include a plurality of delivery sharps 732. Each of the delivery sharps 732 may be mounted on the sled 730 in, for example, a row. In the example embodiment, the guide channel 724 extends through the base portion 702 to a delivery sharp aperture 726 through which a delivery sharp 732 may extend to access a patient. As shown, the bandage 252 may also include an aperture 727. The bandage aperture 727 may preferably have a diameter only slightly larger (e.g. up to ~30% or 40%) than the outer diameter of the delivery sharp 732. This may aid in holding the skin in place at the puncture location during the insertion stroke.

As shown, the aperture 718 of the recess 714 extends through the wall of the base portion 702 to the guide channel 724. When the lock member 712 is installed within the recess 714, the protuberance 716 of the lock member 712 may obstruct passage of the sled 730 of the sharp assembly 731 along the guide channel 724 (see, e.g., FIG. 110). In certain examples, the delivery device 10 may be automatically actuated upon removal of the lock member 712.

Figure 115:
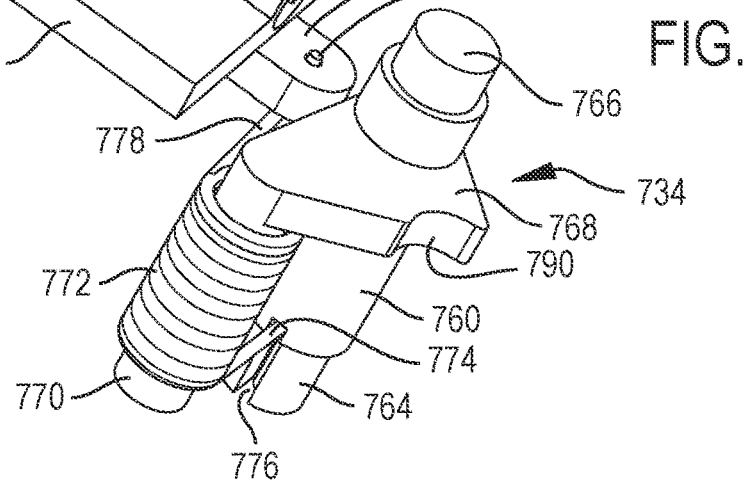
FIG. 115 depicts a perspective view of an example sharp assembly and example actuation assembly which may be included in a delivery device such as that shown in FIG. 113.

Referring now also to FIG. 115, a perspective view of a delivery sharp 732 bearing sled 730 and actuator assembly 734 are shown. In the example embodiment, the delivery sharp 732 is depicted as a 30-gauge needle (higher or lower gauge needles may also be used in alternative embodiments) which has an insertable length suitable for subcutaneous or intramuscular agent administration. The delivery sharp 732 may be made of a metal such as stainless steel though other metals, polymers, or any other suitable material may be used. In certain embodiments, a plurality of such delivery sharps 732 (e.g. two, three, four, or more) may be included. The delivery sharp(s) 732 may be rotationally clocked to a prescribed orientation when installed within the sled 730. In the example embodiment, the delivery sharp 732 is rotationally clocked such that the point 750 of the delivery sharp 732 is most proximal to the wall of the base portion 702 where the recess 714 is defined. This position may be referred to as a 12 o'clock position. It should be understood that the delivery sharp 732 may be rotationally clocked such that the point 750 of the delivery sharp 732 is in alternative rotational orientations (e.g. in a 6 o'clock position or any other o'clock position). Where multiple delivery sharps 732 are included, each delivery sharp 732 may be clocked to any desired rotational position. In some embodiments, each delivery sharp 732 may be clocked to the same position as at least one other delivery sharp 732. Alternatively, all delivery sharps 732 may be clocked to different positions. Use of multiple delivery sharps 732 may aid in distributing agent delivered to the patient over a large area at the target depth.

As shown, the sled 730 of the sharp assembly 731 includes two wing bodies 736 which flank a main body 738 in which the delivery sharp 732 may be mounted. The delivery sharp 732 may be coupled into the main body 738 via friction fit, adhesive, or in any other suitable manner. The sled 730 may also include a hitch portion 740 via which the sled 730 may be coupled to the actuator assembly 734. Any suitable linkage to couple the hitch portion 740 and actuator assembly 734 may be used. The guide channel 724 of the base portion 702 of the housing 700 may be shaped so as to accept the sled 730. The guide channel 724 may, for example, have wing receiving slots 742, a hitch receiving channel 744 and a main body receiving slot 746. The guide channel 724 may constrain movement of the sled 730 substantially to a direction parallel to the axis of the delivery sharp 732. Thus, the guide channel 724 may define the insertion angle of the delivery sharp 732 into the patient. This angle may be from 5° and 45° (though steeper and shallower angles are possible) in various embodiments. In some embodiments the angle may be 5°-15°. In some embodiments, the angle may be no greater than 35°. In the example embodiment, the guide channel 724 defines an insertion angle for the delivery sharp 732 at 35°. The end of the main body 738 of the sled 730 most proximal the tip or point 750 of the delivery sharp 732 may include an angled face 748 which may be roughly parallel to the face of the base portion 702 which is secured to the bandage 252 (see, e.g., FIG. 108). This face 748 may act as a stop which prevents the delivery sharp 732 from being deployed beyond a certain amount.

Still referring primarily to FIG. 115, the actuation assembly 734 may include a pivot pin 760. The pivot pin 760 may include a first end 764 which may seat within the pivotal bearing 720 of the base portion 702. The cover portion 704 of the housing 700 may include a second bearing 762 (see, e.g., FIG. 110) which may accept a second end 766 of the pivot pin 760. A boom plate 768 may extend from a portion of the pivot pin 760 proximal the second end 766. The boom plate 768 may support a guide pin 770 which may project from the boom plate 768. As the pivot pin 760 is rotated about its longitudinal axis, the guide pin 770 may be displaced along an arcuate path. The guide pin 770 may include an end opposite the boom plate 768 which rides within the arcuate guide track 722 of the base portion 702. The guide pin 770 may receive a bias member 772. The bias member 772 may couple to the pivot pin 760 as well as the hitch 740 of the sled 730. Thus the bias member 772 may double as the linkage coupling the sharp assembly 731 and the actuation assembly 734. In the example embodiment, the bias member 772 is depicted as a torque producing bias member. A torsion spring is shown in the exemplary embodiment. The torsion spring is disposed on the guide pin 770 such that the guide pin 770 extends through the central void of the torsion spring. The example bias member 772 includes a first arm 774 which may be assembled into a notch 776 defined in the first end 764 of the pivot pin 760. The exemplary bias member 772 also includes a second arm 778 which is coupled into an orifice 780 of the hitch 740.

The bias member 772 may be held in a stressed state when the delivery sharp 732 is within the delivery device 10. The lock member 712 may prevent the bias member 772 from transitioning to an unstressed state. As the pivot pin 760 is confined within the pivotal bearing 720 and second bearing 762, displacement of the pivot pin 760 may be constrained to rotation about the long axis of the pivot pin 760. When the bias member 772 is released (e.g. via removal of the lock member 712) and allowed to restore to a less stressed state, the bias member 772 may drive the guide pin 770 along an arcuate displacement path. The guide pin 770 may be displaced toward the sharp aperture 726 during displacement along a first portion of the arcuate displacement path and may be displaced away from the sharp aperture 726 as it displaces along a subsequent portion of the arcuate displacement path. The guide pin 770 may also be urged along the arcuate guide track 722 as displacement along the arcuate displacement path occurs. Since the bias member 772 in the example embodiment couples the guide pin 770 to the sled 730 via the hitch 740, movement of the guide pin 770 may cause the sharp assembly 731 to displace along the guide channel 724 of the base portion 702 in a reciprocating motion. This reciprocating motion of the sharp assembly 731 may occur without any reciprocating motion or doubling back of the guide pin 770 along its displacement path. The reciprocating motion of sharp assembly 731 may be driven via a single, continuous, fluid motion of the guide pin 770 in a single rotational direction (clockwise or counterclockwise depending upon the embodiment) along its arcuate displacement path.

As the guide pin 770 is urged to displace along the arcuate guide track 722 from a starting position, the guide pin 770 may reach a point at which it is closest to the delivery sharp aperture 726 of the base portion 702 (see, e.g., FIG. 111). The delivery sharp 732 may extend its maximum extent from the housing 700 (the first extended state) at this point. The arcuate guide track 722 may be asymmetric about the midplane (see cut plane 114-114 of FIG. 113) of the delivery device 10. As the guide pin 770 continues along the arcuate guide track 722, the guide pin 770 may become more distant from the delivery sharp aperture 726. Thus, the delivery sharp 732 may begin to withdraw from the skin. The guide track 722 may be shorter on the withdraw portion of the insertion stroke. Due to the asymmetry of the arcuate guide track 722, the delivery sharp 732 may be prevented from fully withdrawing into the housing 700 of the delivery device 10. In the example, the arcuate guide track 722 may include a terminus 788 which presents a stop that blocks further displacement of the guide pin 770 and defines an end of the displacement range of the guide pin 770 along its arcuate displacement path. The terminus 788 may be a rigid, non-compliant wall of the guide track 722. The insertion stroke may complete when the guide pin 770 contacts the stop presented by the terminus 788 of the arcuate guide track 722. The terminus 788 may be positioned such that the delivery sharp 732 may be at the target depth (the second extended position) in the skin when the guide pin 770 reaches the terminus 788. Thus, via urging of a single bias member 772, the sharp assembly 731 may be driven in a reciprocating motion along the guide channel 724 to advance the delivery sharp 732 to the first extended position and then partially retract the delivery sharp 732 to its target position. At this point, the delivery device 10 may be ready for administration of agent into the patient.

The bias member 772 may still be partially stressed when the delivery sharp 732 is in its target position. This may ensure that the sharp assembly 731 does not move after the insertion stroke completes. In the example embodiment, the boom plate 768 includes a nock 790. The nock 790 may at least partially receive the hitch 740 of the sled 730 (or potentially another portion of sharp assembly 731) when the delivery sharp 732 is in the second extended position. This may aid in holding the sharp assembly 731 in place during administration of agent to the patient. The hitch 740 is depicted as received within the nock 790 in FIG. 112.

Figure 116:
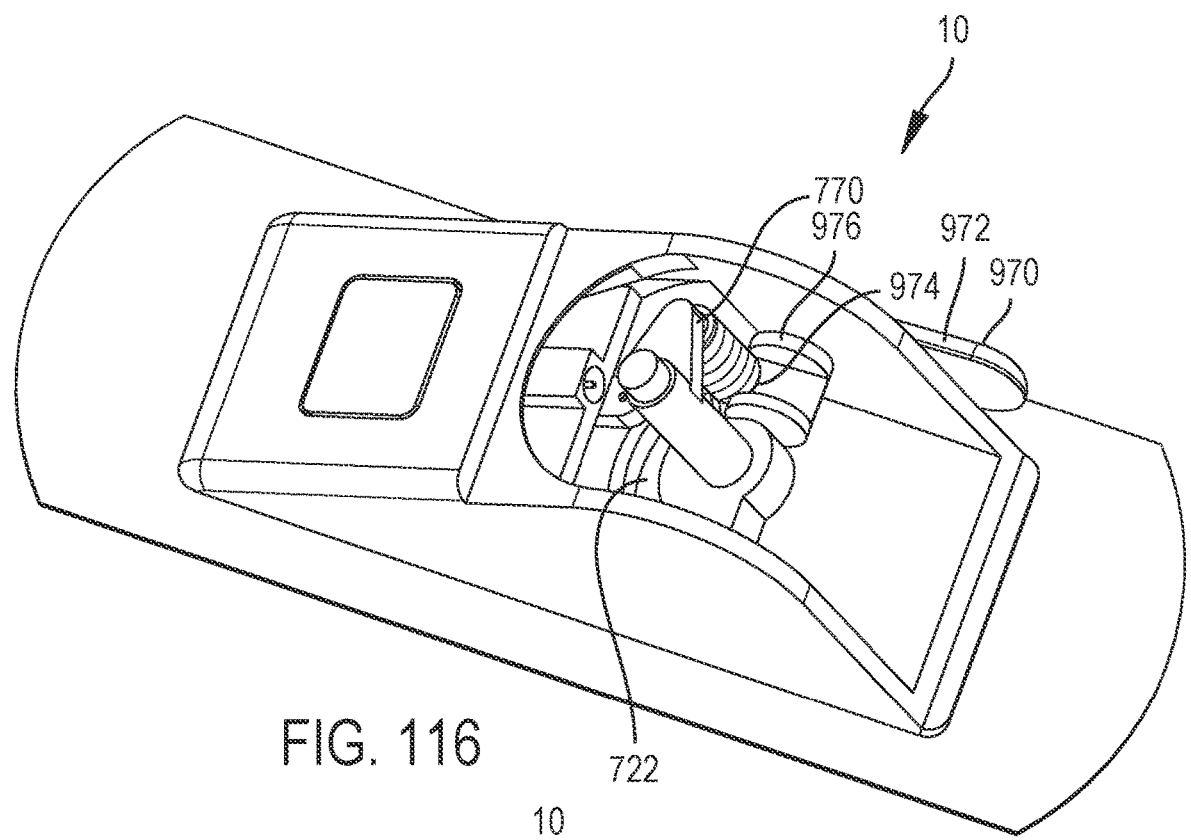
FIG. 116 depicts a perspective view of another example embodiment of a delivery device.
Figure 117:
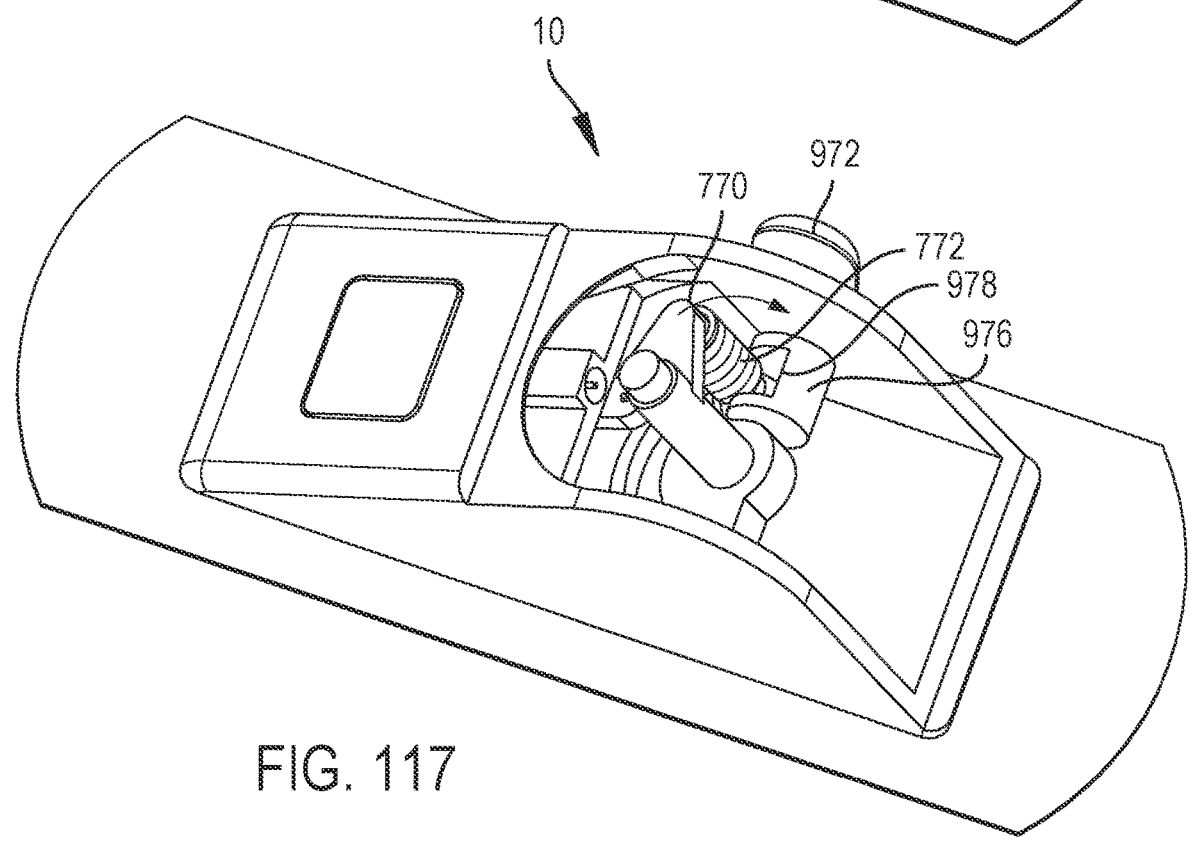
FIG. 117 depicts another perspective view of the delivery device in FIG. 116.

Referring now to FIGS. 116-117, in certain examples, the delivery device 10 may be arranged such that the delivery sharp 732 may be completely retracted into the housing 700 once delivery into the patient is complete. For example, the terminus 788 may be a displaceable barrier (e.g. pivotal). When injection is complete, the terminus 788 may be displaced (e.g. via interaction with a lever/button/knob accessible via the exterior of the housing 700) allowing the guide pin 770 to be displaced further away from the delivery sharp aperture 726. Thus, the delivery sharp 732 may be fully retracted into the delivery device 10 after infusion of fluid has completed.

As shown in FIGS. 116-117, an example delivery device 10 including a knob 970 is shown. Various components of the delivery device 10 have been hidden for sake of illustration. As shown, the knob 970 may include a lever 972, turnkey, dial, or other user-graspable feature which is accessible on the exterior of the delivery device 10. When the delivery device 10 is actuated, the guide pin 770 may displace along the guide track 722 and into contact with a stop surface 974 defined on a pin portion 976 of the knob 970 which extends into the delivery device 10. The stop surface 974 may act as the terminus 788 of the guide track 722 described above. Once delivery has completed, the knob 970 may be rotated to a stowing position (see FIG. 117). As shown, the pin portion 976 of the knob 970 may include a channel 978 recessed therein. This channel 978 may be sized to accept the guide pin 770. As shown, when the knob 970 has been rotated to the stowing position, the stop surface 974 may be rotated out of contact with the guide pin 770 and the channel 978 may be rotated into a position in which it may accept the pin 770. This may allow the bias member 772 to drive the guide pin 770 into the channel 978. As a result, the delivery sharp 732 may be further withdrawn and be located entirely within the delivery device 10. In turn, the delivery sharp 732 may be retracted into the delivery device 10 to stow the delivery sharp 732 out of potential contact with a user.

Figure 118:
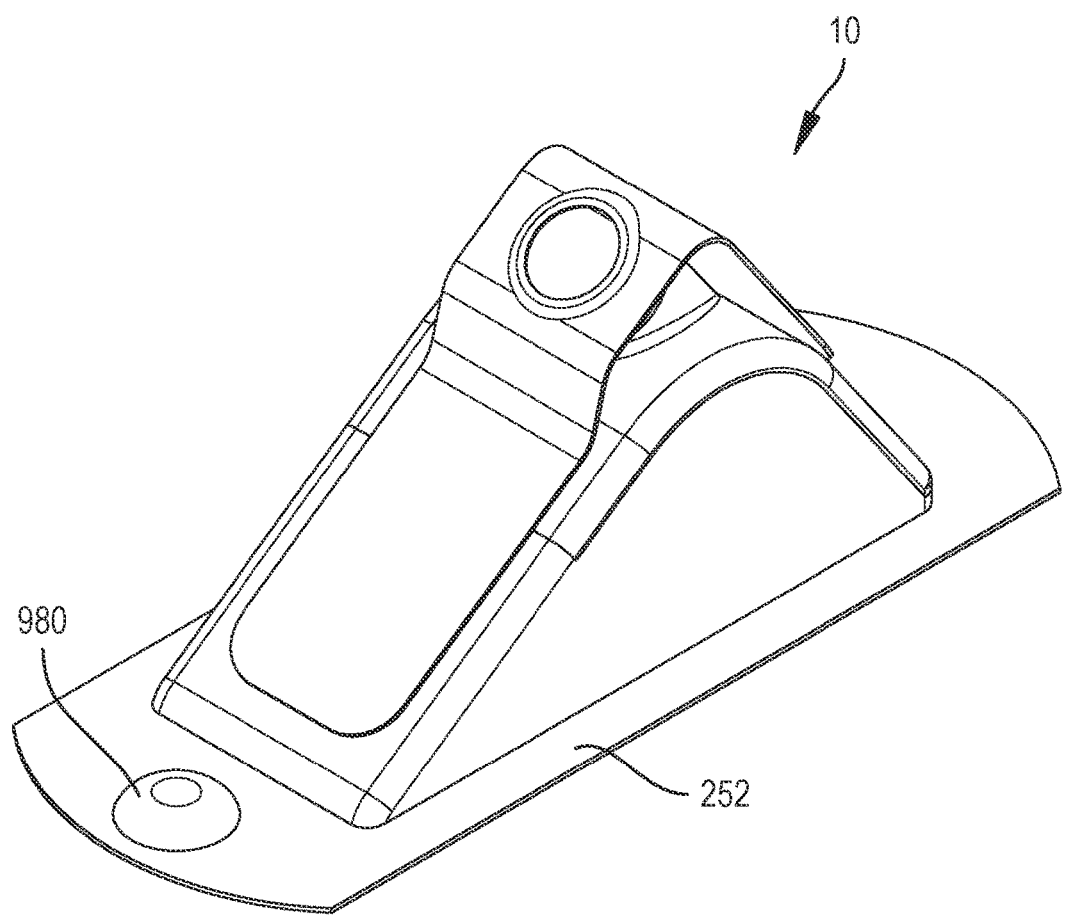
FIG. 118 depicts a perspective view of a delivery device having a bandage with a cover included therein.
Figure 119:
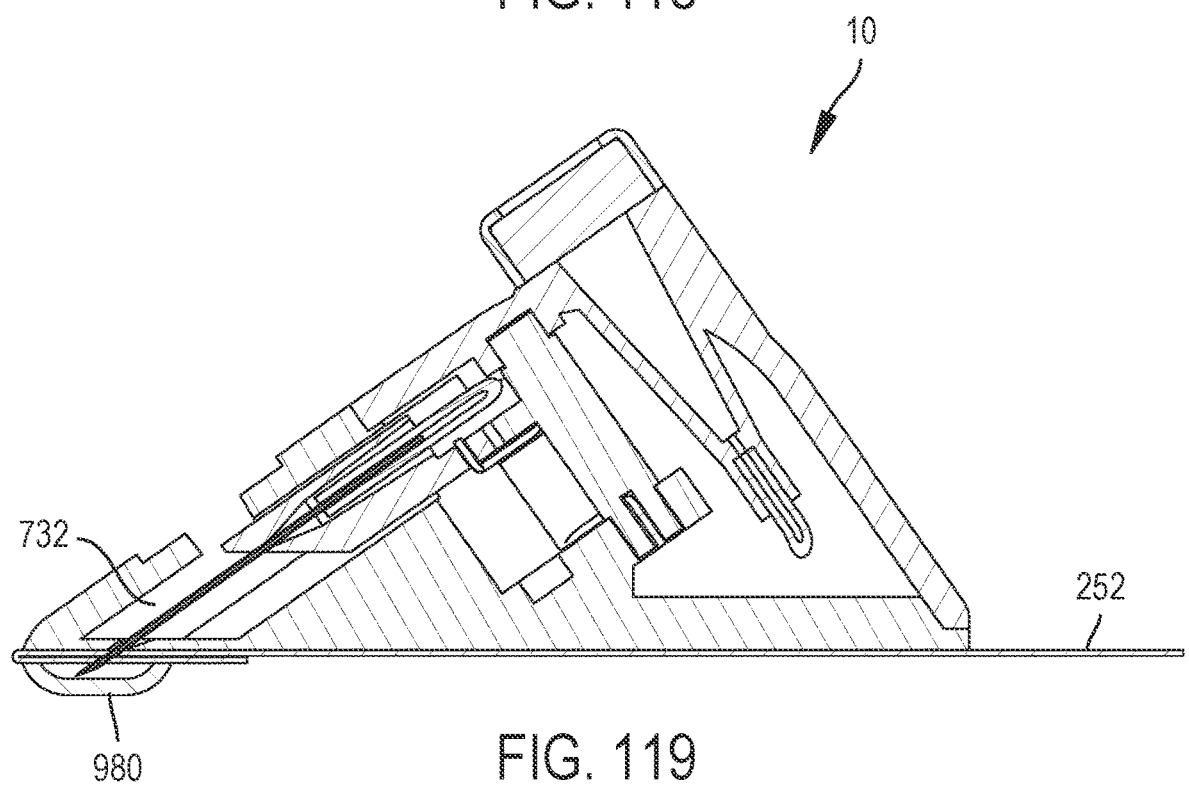
FIG. 119 depicts a cross-sectional view of a delivery device having a bandage with a cover, the bandage being folded such that the cover is positioned over the delivery sharps.

Referring now to FIGS. 118-119, a cross-section of an example delivery device 10, in certain examples, a sharp cover 980 may be included as part of the bandage 252 of a delivery device 10. Though the embodiment shown in FIGS. 118-119 is depicted as a delivery device 10 of the variety illustrated in FIGS. 108-115, such a sharp cover 980 may be included on the bandage 252 of any delivery device 10 described herein. As shown, the sharp cover 980 may be a resilient well which is included in a portion of the bandage 252 outside of the footprint of the housing of the delivery device 10. The portion of the bandage 252 including the sharp cover 980 may be flexible or connected to the remainder of the bandage 252 via a bendable region. Once the delivery device 10 has been used, the bandage 252 may be folded over such that the tip of the delivery sharp 732 is positioned within the well formed by the sharp cover 980. As the bandage 252 may be adhesive bearing, the bandage 252 may stick to itself when folded over. Thus, the sharp cover 980 may be coupled in place around the delivery sharp 732 preventing inadvertent contact with the delivery sharp 732. Though the sharp cover 980 is coupled in place via the adhesive of the bandage 252 in the example embodiments, in other embodiments, the sharp cover 980 may additionally or alternatively snap into place around the delivery sharp 732.

Figure 120:
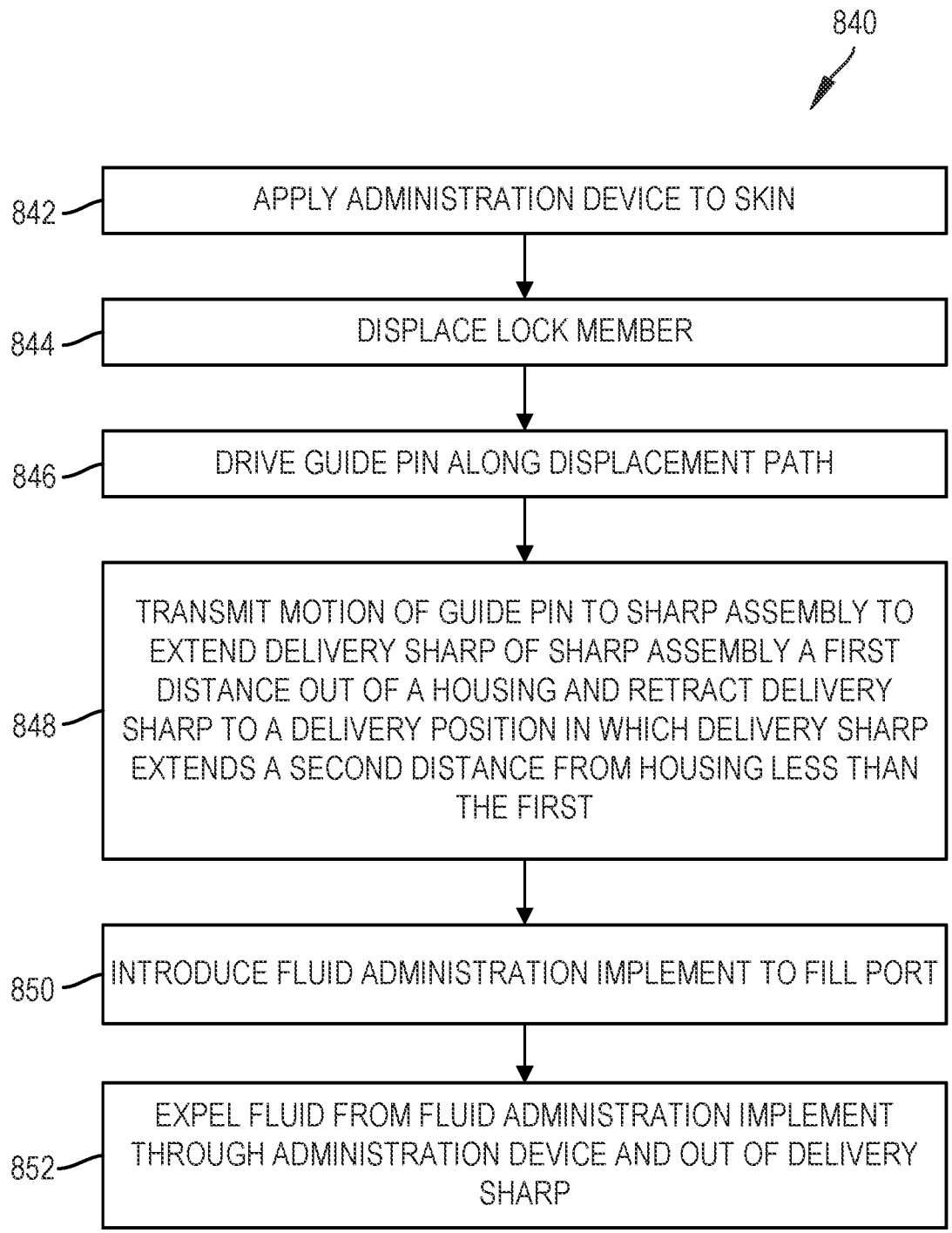
FIG. 120 depicts a flowchart detailing a number of example actions which may be executed to position a delivery sharp at a target delivery depth in a patient.

Referring now to FIG. 120, a flowchart 840 depicting a number of exemplary actions which may be executed to deliver fluid to a target depth in a patient are shown. As shown, in block 842, the delivery device 10 may be applied to a patient. In certain examples, the delivery device 10 may be adhered to the patient via an adhesive member. In block 844, a lock member may be displaced to a state in which it is disengaged. In some examples, the lock member may be removed from the delivery device 10. In block 846, a guide pin may be urged along a displacement path. Movement of the guide pin along the displacement path may occur in a single fluid motion. The guide pin may be acted on by a single bias member which displaces the guide pin in a single direction along an arcuate displacement path in various examples. The guide pin may be displaced along the displacement path until abutting a stop which halts movement of the guide pin. In block 848, motion of the guide pin may be transmitted to a sharp assembly of the delivery device 10 such the sharp assembly is displaced in a reciprocating motion. In the example detailed in FIG. 120, the sharp assembly may be displaced such that at least one delivery sharp of the sharp assembly is advanced a first distance out of a housing of the delivery device 10 and then retracted to a delivery position. In the delivery position, the at least one delivery sharp may extend a second distance from the housing which is less than the first. When the at least one delivery sharp is retracted to the second position the outlet(s) of the at least one delivery sharp may be at the target depth (e.g. intradermal) in a patient. In block 850, a fluid administration implement may be introduced into a fill port of the delivery device 10. Fluid may be expelled from the fluid administration implement, driven through the delivery device 10, and out of the at least one delivery sharp in block 852. In alternative embodiments, fluid from another reservoir such as a pressurized ampoule or a spring loaded syringe type reservoir may be delivered through the delivery sharp into the patient.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. An agent administration device comprising:
a housing;
a sharp assembly including a delivery sharp, the sharp assembly reciprocally displaceable along a guide channel of the housing;
an access port in fluid communication with the delivery sharp; and
an actuation assembly configured to drive the sharp assembly, via urging of a single bias member, from a storage state in which the delivery sharp is within the housing, through a first extended position in which the delivery sharp extends a maximum distance from the housing and to a partially retracted position in which the delivery sharp is stationary and extends a lesser distance from the housing.

2. The agent administration device of claim 1, wherein the guide channel defines an insertion angle of the delivery sharp.

3. The agent administration device of claim 1, wherein the access port includes a pierceable septum.

4. The agent administration device of claim 1, wherein the single bias member is a torsion spring.

5. The agent administration device of claim 1, wherein the maximum distance is sufficient to penetrate transcutaneously into a patient.

6. The agent administration device of claim 1, wherein the lesser distance corresponds to a penetration depth in a patient suitable for intradermal administration of agent.

7. The agent administration device of claim 1, wherein the agent administration device is configured to deliver an agent which includes at least one vaccine.

8. The agent administration device of claim 1, wherein the device further comprises a removable lock member configured to hold the sharp assembly in the storage state when installed in the device.

9. The agent administration device of claim 1, wherein the agent administration device further comprises a stowing assembly, and wherein when the sharp assembly is in the partially retracted position, the sharp assembly is configured to displace, via urging of the single bias member, from the partially retracted position to a further retracted position in which the delivery sharp is within the housing upon transition of the stowing assembly from a first state to a second state.

10. The agent administration device of claim 2, wherein the insertion angle is 5°-45°.

11. An agent administration device comprising:
a housing including a guide;
a sharp assembly including at least one delivery sharp, the sharp assembly reciprocally displaceable along the guide;

an access port in fluid communication with the delivery sharp; and an actuation assembly coupled to the sharp assembly and including a guide pin, the sharp assembly being displaced from a storage state to an administration state in which the at least one delivery sharp extends a target distance out of the housing as the guide pin displaces from a starting position to a stop in a single direction, the at least one delivery sharp extending a distance greater than the target distance as the guide pin is displaced along an intermediate portion of a displacement range of the guide pin between the starting position and the stop.

12. The agent administration device of claim 11, wherein the single direction is selected from a group consisting of a clockwise direction and a counterclockwise direction.

13. The agent administration device of claim 11, wherein the guide defines an insertion angle of the delivery sharp.

14. The agent administration device of claim 11, wherein the access port includes a pierceable septum.

15. The agent administration device of claim 11, wherein the distance greater than the target distance is a distance sufficient to penetrate transcutaneously into a patient.

16. The agent administration device of claim 11, wherein the target distance corresponds to a penetration depth in a patient suitable for intradermal administration of an agent.

17. The agent administration device of claim 11, wherein the agent administration device is configured to deliver an agent which includes at least one vaccine.

18. The agent administration device of claim 11, wherein the device further comprises a removable lock member configured to hold the sharp assembly in the storage state when installed in the device.

19. The agent administration device of claim 11, wherein the actuation assembly includes the guide pin, a bias member configured to assert a bias force on the guide pin, and a pivot pin pivotally retained in the housing and coupled to the guide pin.

20. The agent administration device of claim 11, wherein the access port is in fluid communication with the delivery sharp in the storage state, administration state, and any position therebetween.

21. The agent administration device of claim 11, wherein the stop is displaceable to a stowed position, the guide pin displacing a further amount in the single direction when the stop is displaced to the stowed position, the at least one delivery sharp retracting into the housing as the guide pin displaces the further amount.

22. The agent administration device of claim 13, wherein the insertion angle is 5°-45°.

23. An agent administration device comprising:
a housing;
a delivery sharp assembly reciprocally displaceable along a guide of the housing;
an actuation assembly having a single bias member, the delivery sharp assembly being driven, when the single bias member is released from a storage state, from a first position in which the delivery sharp assembly is within the housing, through an intermediate positon in which a delivery sharp of the delivery sharp assembly projects a maximum distance out of the housing and into a stationary delivery position in which the delivery sharp projects a lesser distance than the maximum distance; and
an access port in fluid communication with the delivery sharp assembly.

24. The agent administration device of claim 23, wherein the device further comprises a removable lock member configured to hold the delivery sharp assembly in the storage state when installed in the device.

25. The agent administration device of claim 23, wherein the lesser distance corresponds to a penetration depth in a patient suitable for intradermal administration of agent.

* * * * *